(12) United States Patent
Leonetti et al.

(10) Patent No.: US 9,279,113 B2
(45) Date of Patent: Mar. 8, 2016

(54) ENZYMES AND USES THEREOF

(75) Inventors: Jean-Paul Leonetti, Castelnau-le-Lez (FR); Jean-Michel Claverie, Cassis (FR); Pascale Joseph, Montpellier (FR); Lucie Roux, Nimes (FR)

(73) Assignee: DEINOVE, Paris (FR)

(*) Notice: Subject to any disclaimer, the term of this patent is extended or adjusted under 35 U.S.C. 154(b) by 138 days.

(21) Appl. No.: 13/884,087

(22) PCT Filed: Nov. 8, 2011

(86) PCT No.: PCT/EP2011/069669
§ 371 (c)(1),
(2), (4) Date: Jul. 10, 2013

(87) PCT Pub. No.: WO2012/062767
PCT Pub. Date: May 18, 2012

(65) Prior Publication Data
US 2013/0280786 A1    Oct. 24, 2013

Related U.S. Application Data

(60) Provisional application No. 61/411,167, filed on Nov. 8, 2010.

(30) Foreign Application Priority Data

Nov. 8, 2010 (EP) ..................... 10306221

(51) Int. Cl.
| | | |
|---|---|---|
| C12N 9/28 | (2006.01) | |
| C12N 15/00 | (2006.01) | |
| C12N 1/00 | (2006.01) | |
| C12N 1/21 | (2006.01) | |
| C12N 1/15 | (2006.01) | |
| C12N 1/16 | (2006.01) | |
| C12N 1/20 | (2006.01) | |
| C12P 19/14 | (2006.01) | |
| C12N 9/42 | (2006.01) | |
| C12N 9/18 | (2006.01) | |
| C12N 9/24 | (2006.01) | |
| C12N 9/34 | (2006.01) | |
| C12P 7/06 | (2006.01) | |
| C12N 9/16 | (2006.01) | |
| C12P 19/02 | (2006.01) | |
| C12P 39/00 | (2006.01) | |

(52) U.S. Cl.
CPC .. *C12N 9/42* (2013.01); *C12N 9/16* (2013.01); *C12N 9/18* (2013.01); *C12N 9/2402* (2013.01); *C12N 9/244* (2013.01); *C12N 9/248* (2013.01); *C12N 9/2417* (2013.01); *C12N 9/2428* (2013.01); *C12N 9/2437* (2013.01); *C12P 7/065* (2013.01); *C12P 19/02* (2013.01); *C12P 19/14* (2013.01); *C12P 39/00* (2013.01); *C12Y 301/01072* (2013.01); *Y02E 50/17* (2013.01)

(58) Field of Classification Search
None
See application file for complete search history.

(56) References Cited

FOREIGN PATENT DOCUMENTS

| WO | WO 95/34644 | 12/1995 |
| WO | WO 2009/063079 | 5/2009 |
| WO | WO 2010/094665 | 8/2010 |

OTHER PUBLICATIONS

Sang, H., Mechanisms of Development 121:1179-1186, 2004.*
Pizzut-Serin et al., FEBS Lett. 579:1405-1410, 2005.*
Appukuttan et al., Appl. Environmen. Microbiol. 72:7873-7878, 2006.*
GenBank Accession No. CP000359, "Deinococcus geothermalis DSM 11300, complete genome", Oct. 2007; 459 pages.*
Aiyer et al., Afr. J. Biotechnol. 4:1525-1529, 2005.*
Skov et al., J. Biol. Chem. 276:25273-25278, 2001.*
Database UniProt [Online] Accession No. Q1J0M2, Jun. 13, 2006, p. 1, XP-002668574.
Database UniProt [Online] Accession No. Q1J0F7, Jun. 13, 2006, pp. 1-2, XP-002653376.
Database UniProt [Online] Accession No. Q1IXJ3, Jun. 13, 2006, p. 1, XP-002668575.
Database UniProt [Online] Accession No. A8ZR50, Jan. 15, 2008, p. 1, XP-002668576.
Database EMBL [Online] Accession No. CP000358, "Deinococcus geothermalis DSM 11300 plasmid pDGE001, complete sequence" May 8, 2006, pp. 1-224, XP-002653378.
Joshi, H. et al. "Competition Triggers Plasmid-Mediated Enhancement of Substrate Utilisation in *Pseudomonas putida*" PLoS One, Jun. 2009, pp. 1-10, vol. 4, Issue 6.
Lee, J.-H. et al. "Characterization of a glycoside hydrolase family 42 β-galactosidase from *Deinococcus geothermalis*" Biotechnology Letters, 2011, pp. 577-583, vol. 33.
Jung, J.-W. et al. "Molecular Cloning and Characterization of Maltogenic Amylase from *Deinococcus geothermalis*" Korean Journal of Food Science and Technology, 2011, pp. 369-374, vol. 43, No. 3. Abstract Only.
Written Opinion in International Application No. PCT/EP2011/069669, May 21, 2012, pp. 1-13.

* cited by examiner

*Primary Examiner* — David J Steadman
(74) *Attorney, Agent, or Firm* — Saliwanchik, Lloyd & Eisenschenk

(57) ABSTRACT

The present invention relates to novel enzymes and the uses thereof. The invention also relates to methods of producing such enzymes, coding nucleic acid molecules, recombinant cells and methods of transforming biomass from such materials. The invention is particularly suited to degrade biomass and/or to improve biomass degradation, and to produce bioenergy products or recombinant proteins. This invention also relates to various applications of the enzymes in the field of paper industry, textile industry as well as in the chemical and medical fields.

11 Claims, 10 Drawing Sheets

Figures 1A, 1B, 2:
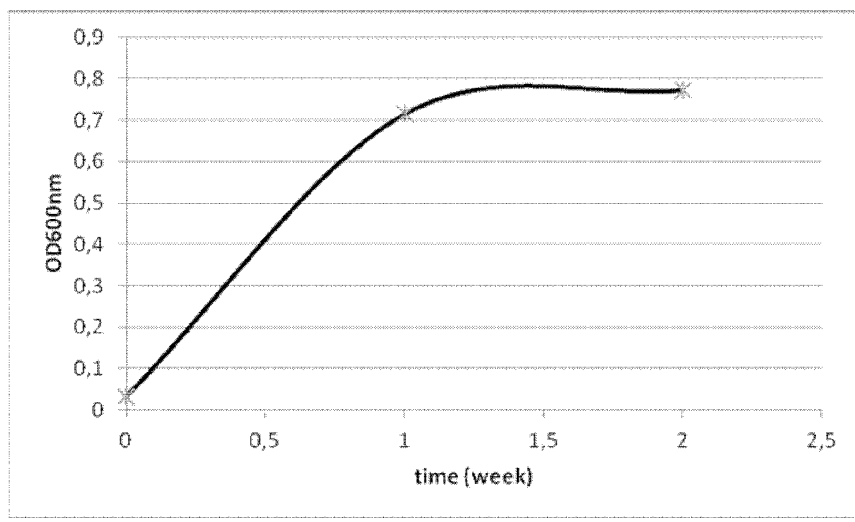

| Strains names | Number of days for observation of whatman paper degradation |
|---|---|
| D. cellulosilyticus DRH46 | 6 |
| D. geothermalis M1-3H | 9 |

| Strains names | Growth in the presence of starch as sole carbon source |
|---|---|
| D. geothermalis M23r-3A | ++ |
| D. geothermalis DRH38 | ++ |
| D. geothermalis MC2-2A | ++ |

| Strains names | Growth in the presence of xylan as sole carbon source | Xylanolytic activity U/mg |
|---|---|---|
| D. geothermalis MC3-4A | ++ | 10 |
| D. geothermalis DRH38 | ++ | 5 |
| D geothermalis DRH46 | ++ | nd |

Fig. 5A
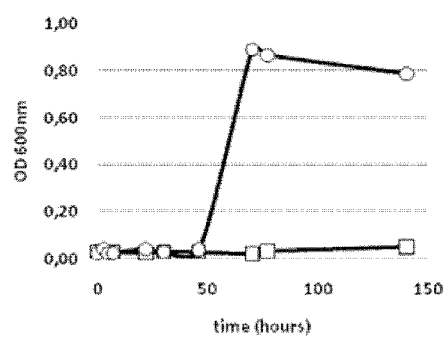
Fig. 5B
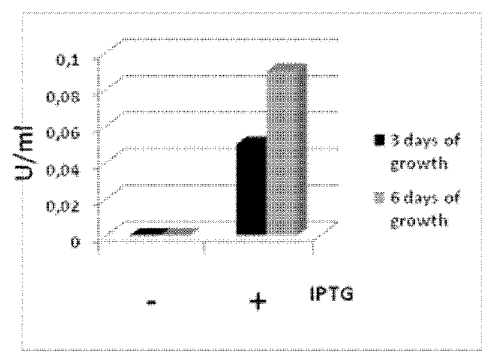
Fig. 6A
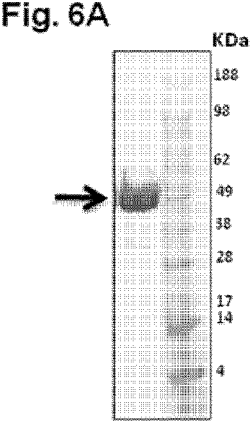
Fig. 6B
| | Protein concentration | α-amylase activity |
|---|---|---|
| | mg/ml | IU/mg |
| M23-3A | 1,3 | 22 |

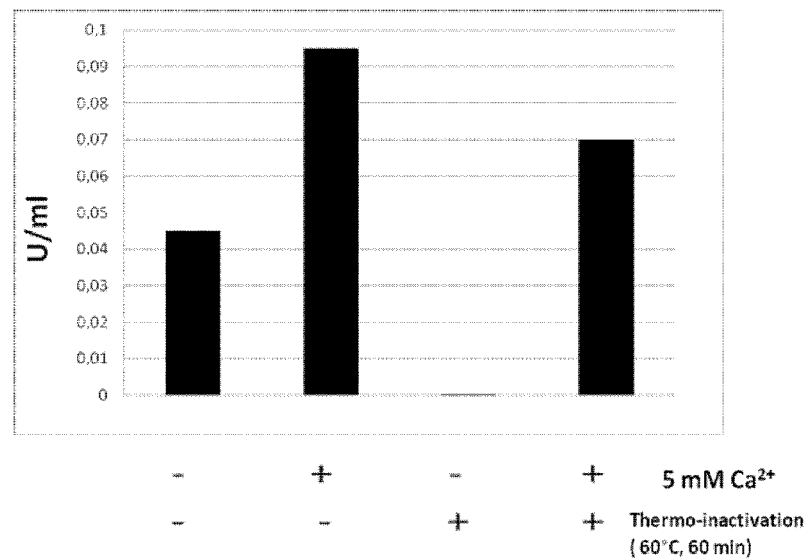
Fig. 7A
FIG. 7B
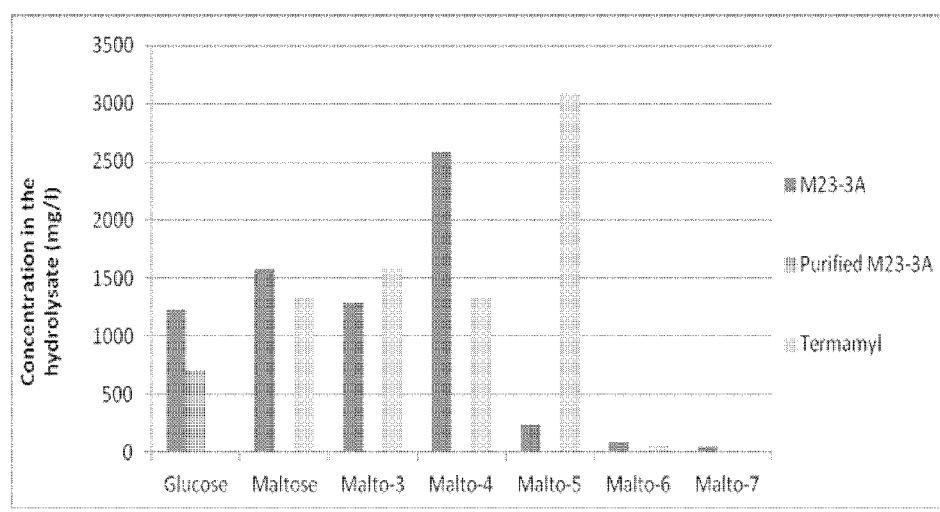

ENZYMES AND USES THEREOF

CROSS-REFERENCE TO RELATED APPLICATIONS

This application is the U.S. national stage application of International Patent Application No. PCT/EP2011/069669, filed Nov. 8, 2011, which claims the benefit of U.S. Provisional Patent Application No. 61/411,167, filed Nov. 8, 2010.

FIELD OF THE INVENTION

The Sequence Listing for this application is labeled "SeqList-replace.txt" which was created on Jun. 8, 2015 and is 232 KB. The entire contents of the sequence listing is incorporated herein by reference in its entirety.

The present invention relates to novel enzymes and the uses thereof. The invention also relates to methods of producing such enzymes, coding nucleic acid molecules, recombinant cells and methods of modifying biomass from such materials. The invention is particularly suited to degrade biomass and/or to improve biomass degradation, and to produce bioenergy products such as bioethanol or other valuable metabolites or proteins. This invention also relates to various applications of the enzymes in the field of paper industry, textile industry, resin industry as well as in the chemical and medical fields.

BACKGROUND OF THE INVENTION

The use of microorganisms to conduct modification of biomass for the production of bioenergy products or metabolites has been proposed in the art. Such process, ideally, would require two major types of activities: (i) a degradation activity, to transform biomass into fermentable sugars and (ii) a fermentation activity, to transform said sugars into bioenergy products or other valuable metabolites. So far, efforts have been directed mainly towards the identification of microorganisms having the ability to catalyze the fermentation step.

A monograph on the production of ethanol through fermentation with microorganisms was published under the title "Ethanol Fermentation Strains" by J. R. Hettenhaus, under the aegis of the United States Department of Energy and the National Renewable Energy Laboratory (Dec. 16, 1998). In this document, which summarizes the contributions made by participants in the study, it is pointed out that:
- only microorganisms similar to *Saccharomyces, Zymomonas* and *E. coli* can be used in existing equipment;
- in the short term, the increased fermentation of xylose and arabinose could be the main objective, it being specified however that it is of little interest to increase the converting efficacy of the other sugars of hexose or oligomer type;
- over the longer term, gains could be achieved regarding higher operating temperatures and combining of the steps of enzyme production, saccharification and hydrolysis.

Current industrial processes only allow the culture and growth of microorganisms for the fermentation and extraction of ethanol at temperatures in the region of 30° C., owing to the fragility of the industrial microorganisms (yeasts) used. They also entail major bioenergy costs to concentrate the ethanol after fermentation, since yeasts currently used for this fermentation cannot withstand ethanol concentrations above 100 g/l. Additionally, the fermentation of yeasts practically only uses C6 sugars, of glucose type.

The conversion of biomass using microorganisms has also been tested (Blumer-Schuette et al., 2008, Extremely thermophilic microorganisms for biomass conversion: status and prospects, Curr Opinion Biotechnol 19, pp. 210-217; Perez et al., 2002, Int Microbiol 5, pp 53-63). However, as reported in Mosier et al. (Bioresource Technology 96 (2005) 673-686), a pre-treatment of lignocellulosic biomass is required to alter the structure of cellulosic biomass to make cellulose more accessible to the enzymes that convert the carbohydrate polymers into fermentable sugars.

The industrial and efficient production of fermentable sugars (e.g., monomeric sugars) from raw (i.e., starch, lignocellulosic) biomass still remains a challenge. Various approaches have been proposed to exploit raw biomass, such as thermochemical methods, acid hydrolysis or enzymatic hydrolysis. Sun H et al (Appl Biochem Biotechnol. February 2010; 160(4):988-1003) discusses the use of non *Deinococcus* enzymes for the degradation of starch. Polizeli M L et al, and Collin T et al (Appl Microbiol Biotechnol. June 2005; 67(5):577-591; FEMS Microbiol Rev. January 2005; 29(1): 3-23) reviews the use of non *Deinococcus* enzymes for the degradation of xylan. Wilson D B et al (Curr Opin Biotechnol. June 2009; 20(3):295-299) discusses the use of non *Deinococcus* enzymes for the degradation of cellulose for biofuel applications.

These approaches, however, did not lead so far to the implementation of an effective and industrial enzymatic method of producing metabolites from biomass. Furthermore, due to the wide diversity of lignocellulosic biomass, with each having a specific composition of starch, cellulose, hemicellulose and lignin, there is a need for additional enzymes with improved activities.

Accordingly, there is a need for novel enzymes active in the modification of biomass. There is also a need in the art for a cost-effective and scalable process for the degradation of starch and lignocellulosic biomass into valuable products such as fermentable sugars or bioenergy products and metabolites.

Work conducted by the applicant has led to the surprising finding that strains of the genus *Deinococcus* exhibit remarkable properties for use in the transformation of biomass into metabolites, including bioenergy products (WO2009/063079). More particularly, the applicant has demonstrated that *Deinococcus* strains are able to catalyse or cause biomass degradation into fermentable sugars, and to produce metabolites from said sugars. Applicant has also demonstrated these strains are resistant to and active at elevated temperature, elevated ethanol concentrations, and within a wide range of pH values (PCT/EP2010/056600, presently unpublished). The applicants have further discovered that *Deinococcus* bacterium may degrade raw biomass, including starch, xylan or cellulose, which provides additional substantial advantages for biomass conversion and metabolite production (WO2010/094665). *Deinococcus*, as well as related bacteria, therefore open the path towards new and efficient bioenergy and metabolite production from biomass.

The present invention discloses novel enzymatic activities derived from *Deinococcus* and related bacteria. These enzymes are involved in energetic metabolism. They have been structurally characterized and exhibit distinct motifs or sequences, which confer on said proteins remarkable biological activities. These Deinococcal enzymes have the ability e.g., to hydrolyse the main constituents of biomass, including xylan, cellulose, and/or hemicelluloses or any lignocellulosic material under conditions suitable for an industrial process. Such enzymes had never been reported or isolated in the art and bring substantial improvements to the development of industrial processes of transforming biomass. The enzymes may be used as such, in purified or isolated form, or in a mixture of enzymes comprising at least one enzyme of this invention, in industrial processes. These enzymes also allow or favour the use of cheaper carbon source for fermentation and may be used in the production of metabolites, bioenergy products, or in the production (or over-expression) of recombinant proteins.

SUMMARY OF THE INVENTION

The present invention relates to novel enzymes, their manufacture and their uses. The invention also relates to nucleic acids encoding these enzymes, vectors, recombinant cells and their uses. The invention further relates to compositions and methods for modifying biomass and/or producing valuable products from biomass or derivatives thereof. More specifically, the invention relates to novel enzymes having the ability to transform starch and biomass or derivatives thereof into valuable products, including fermentable sugars, bioenergy products and other chemical compounds. The invention also relates to methods of producing valuable products and metabolites using such enzymes. The invention further relates to industrial, agricultural and health applications using enzymes of the invention.

The invention stems inter alia from the identification of enzymes having the unexpected and remarkable properties of transforming starch and biomass or derivatives thereof, with a view to obtaining compounds which can be used to produce bioenergy, ethanol in particular, and other alcohols and chemical compounds on an industrial scale and both economically and reliably.

An object of this invention thus relates to enzymes, wherein said enzymes are derived from a *Deinococcus* or a related bacterium and are involved in energetic metabolism.

A further particular object of this invention is an enzyme, wherein said enzyme derives from a *Deinococcus* or a related bacterium and has the ability to modify biomass into fermentable sugars, preferably at a temperature of 30° C. or more, even more preferably of 40° C. or more.

A further particular object of this invention is an enzyme, wherein said enzyme derives from a *Deinococcus* or a related bacterium and has the ability to hydrolyse xylan or cellulose, preferably at a temperature of 30° C. or more, even more preferably of 40° C. or more.

In a particular embodiment, the enzymes of the invention catalyze biomass modification and are selected, preferably, from amylases, glucosidases, cellulases, xylanases, pectinases, esterases, acetyl xylan esterases and glucuronidases.

In another particular embodiment, the enzymes catalyse sugar fermentation, particularly ethanol production by fermentation. Preferred and specific examples of such enzymes include acetaldehyde dehydrogenases, alcohol dehydrogenases, and pyruvate dehydrogenases.

Most preferred enzymes of the invention are of *Deinococcus* origin.

A further object of this invention is a polypeptide comprising all or part of any one of amino acid sequences SEQ ID NOs: 1 to 12, 27 to 41, 58, 60, 62, 64, 66, 68, 70 and 72. A further object of this invention is a composition comprising at least one enzyme as defined above. The composition may comprise additional enzymes, selected from enzymes of the invention or any other enzyme, preferably active in energetic metabolism. The composition may be used e.g., as a catalyst or starter. In a particular embodiment, the invention relates to a composition comprising a xylanase and at least one amylase, glucosidase or cellulase as defined above.

A further object of the invention is a nucleic acid coding an enzyme as defined above.

A further object of the invention is a vector comprising a nucleic acid as defined above.

The invention also relates to a recombinant cell containing at least one nucleic acid or vector as defined above, preferably a recombinant bacterium containing at least one nucleic acid or a vector as defined above.

The invention also relates to a *Deinococcus* bacterium which contains at least one nucleic acid or vector as defined above. The invention indeed allows the engineering of *Deinococcus* strains with improved capacity to process starch and lignocellulosic biomass, with the use of *Deinococcus* DNA only.

The invention also relates to an extract of a cell of the invention. Such an extract preferably exhibits the enzymatic activity.

The invention also relates to the use of an enzyme, or of a combination of enzymes, corresponding nucleic acid, vector, cell or cell extract as defined above for modifying biomass and/or producing metabolites, bioenergy products or proteins, or for processing wood, pulp, agricultural wastes, organic wastes, beverages, detergents, resins, textiles, health products and drugs.

The invention also relates to a method for modifying biomass, comprising exposing such biomass to an enzyme or to a combination of enzymes, corresponding nucleic acid, vector, cell or cell extract as defined above.

The invention also relates to a method for increasing biomass modification, the method comprising adding to the biomass an enzyme, or a combination of enzymes, corresponding nucleic acid, vector, cell or cell extract as defined above.

The invention also relates to a method for improving a catalytic rate of a chemical reaction, comprising adding to the reaction, an enzyme of the invention, or a combination of enzymes, corresponding nucleic acid, vector, cell or cell extract as defined above.

The invention also relates to a method for producing metabolites or bioenergy products, comprising exposing a carbon source, such as for example a biomass or constituents thereof, to an enzyme, or to a combination of enzymes, corresponding nucleic acid, vector, cell or cell extract as defined above. The method advantageously further comprises a step of collecting the metabolite or bioenergy product.

More generally these enzymes can be used to convert cheaper carbon source into fermentable sugar(s). In addition to the production of metabolites and bioenergy products as disclosed above, they can therefore be used as well for the production of any recombinant proteins. In particular, the enzymes of the invention can be used to engineer microorganisms, such as bacteria, having the ability to use cheap carbon sources, such as biomass, and to produce at low cost and/or high level any product from such engineered microorganism. In particular, a nucleic acid encoding a protein of industrial interest (such as enzymes, pharmaceutical proteins and the like) may be cloned and expressed in a bacterium, such as a *Deinococcus* bacterium, engineered to express an enzyme of the invention. Such a bacterium may therefore produce the recombinant protein using cheap carbon source. Such bacterium may also express the recombinant protein at high levels due to improved metabolic pathways.

LEGEND TO THE FIGURES

FIG. 1: DRH46 and M1-3H degrade Filter paper (A) and DRH46 exhibit a strong cellulolytic activity on CMC 1% (B).

FIG. 2: M23r-2A, DRH38 and MC2-2A grow rapidly in the presence of starch as sole carbon source.

Figures 3, 4:
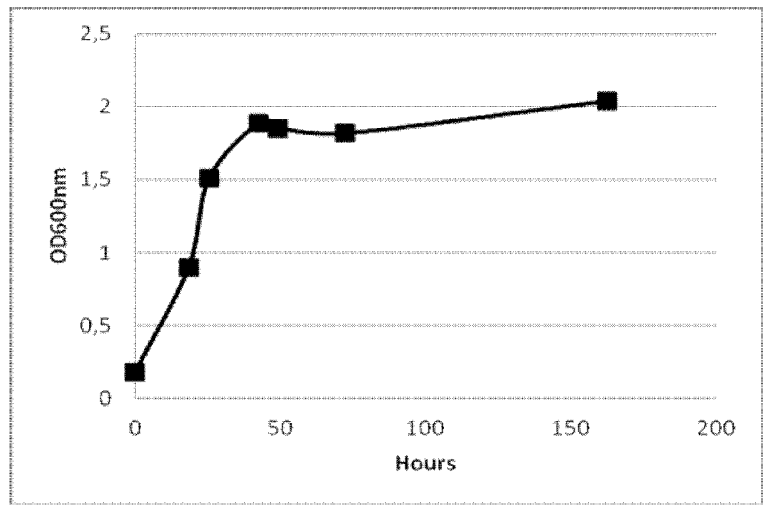

FIG. 3: M23r-2A exhibits a strong amylolytic activity on 0.5% starch as sole carbon source.

FIG. 4: MC3-4A, DRH38 and DRH46 grow rapidly on birchwood xylan as sole carbon source and encode strong xylanolytic enzymes.

FIG. 5: Amylase activity in the cell-free supernatant of *E. coli* expressing a *Deinococcus* alpha-amylase after growing cells in starch-containing defined minimal medium. (A) Growth of *E. coli* harboring the 6(His) tagged alpha-amylase cloned under an inducible IPTG promoter in the pETDEST42 vector. Circle and square denote growth in presence and absence of IPTG, respectively. (B) Recombinant 6(His) tagged Alpha-amylase activity was measured in the cell-free supernatant of the recombinant *E. coli*, after 3 and 6 days of growth in the presence or absence of IPTG.

FIG. 6: Purification and activity of a recombinant alpha-amylase derived from *D. geothermalis*. (A) Coomassie blue stained SDS-PAGE after purification of recombinant 6(His) tagged alpha-amylase by Nickel-affinity chromatography. The arrow shows a band corresponding to the purified alpha-amylase. (B) Activity of the purified enzyme.

FIG. 7: (A) Effect of $Ca^{2+}$ on the activity and stability of the recombinant alpha-amylase of SEQ ID NO: 3. (B) HPLC analysis of hydrolysis products is shown at 24 hours time point. Termamyl 120L was used as a reference enzyme.

Figure 8:
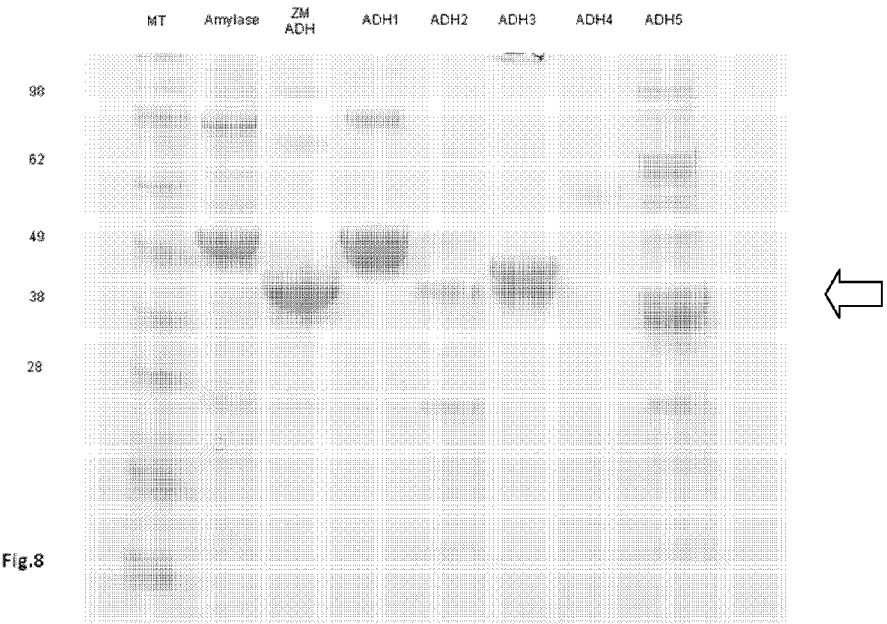

FIG. 8: Purification of recombinant enzymes of the invention derived from *D. geothermalis*. Coomassie blue stained SDS-PAGE after purification of recombinant 6(His) tagged enzymes by Nickel-affinity chromatography. The arrow shows a band corresponding to the purified enzymes.

Figure 9:
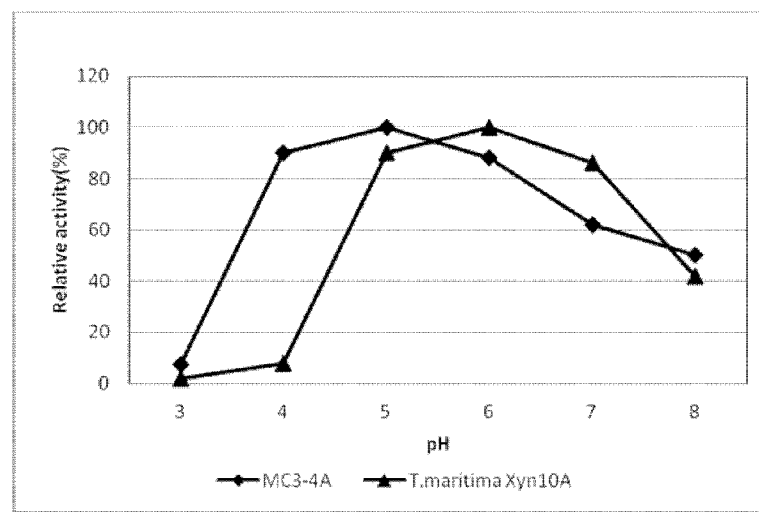

FIG. 9: Optimal pH of the recombinant xylanase from MC3-4A.

Figure 10:
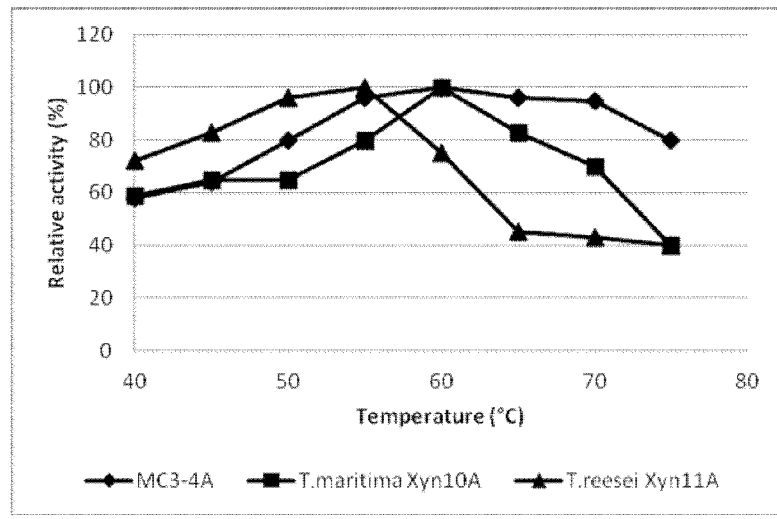

FIG. 10: Optimal temperature of the recombinant xylanase from MC3-4A.

Figure 11A:
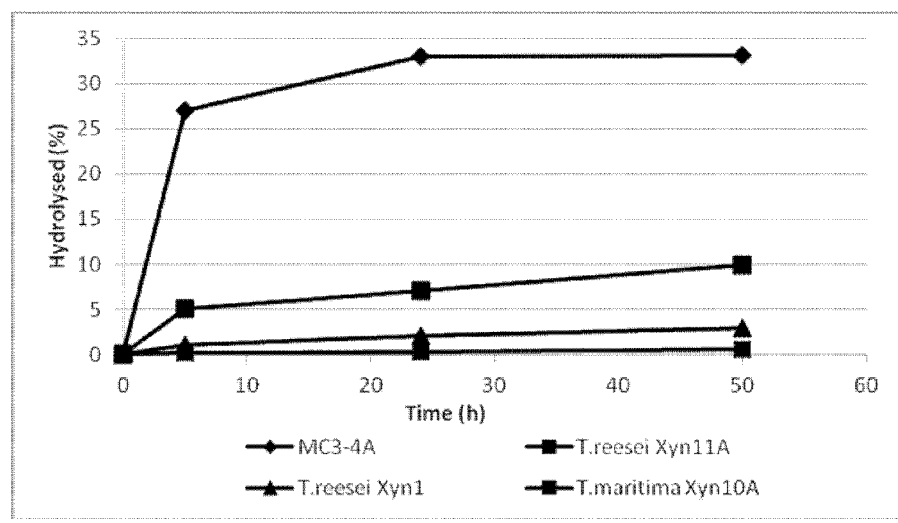
Figure 11:
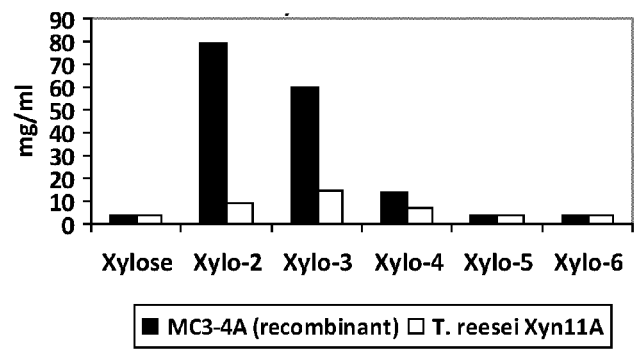
Figure 11:
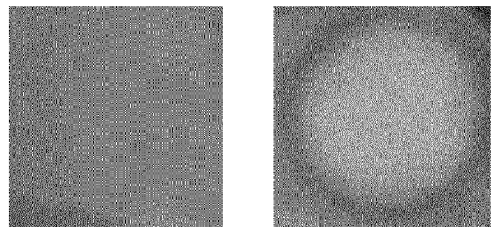

FIG. 11: Xylanolytic activity of *Deinococcus* endoxylanase MC3-4A. (A) Hydrolysis of arabinoxylan by *Deinococcus* endoxylanase MC3-4A. (B) Hydrolysis of arabinoxylan by the recombinant endoxylanase from strain MC3-4A. HPLC analysis of hydrolysis products (i.e., xylose, xylo-2, xylo-3, xylo-4, xylo-5 and xylo-6) is shown at 48 hours time point. *T. reesei* Xyn11A was used as a reference enzyme. (C) Xylan hydrolysis of the recombinant endoxylanase from *Deinococcus geothermalis* MC3-4A. 20 µg of purified enzyme was spotted onto minimum medium-agar plate containing 5% AZO birchwood Xylan (S-AXBL Megazyme); incubation at 37° C. 2 days. Left photograph: negative control=recombinant purified alpha amylase from *D. geo* M23-3A. Right photograph: recombinant purified endoxylanase from *D. geo* MC3-4A.

Figure 12:
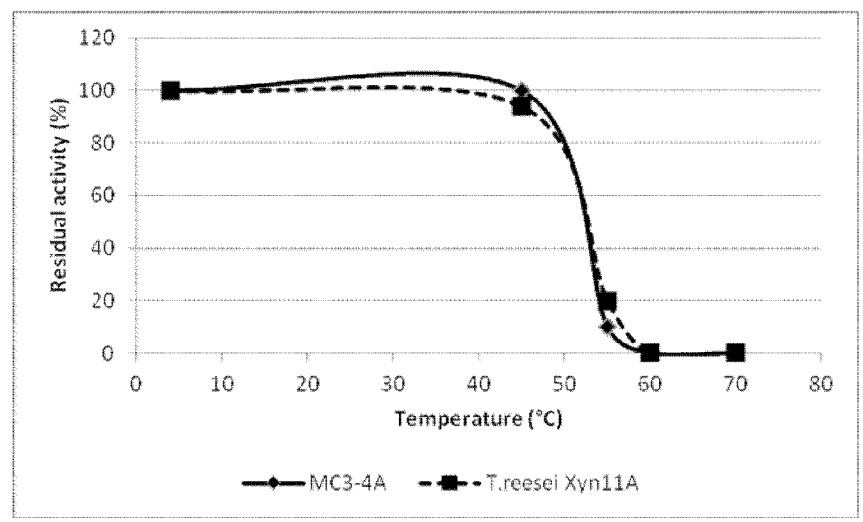

FIG. 12: Long term temperature stability (24 hours) of the recombinant endoxylanase from MC3-4A.

Figure 13:
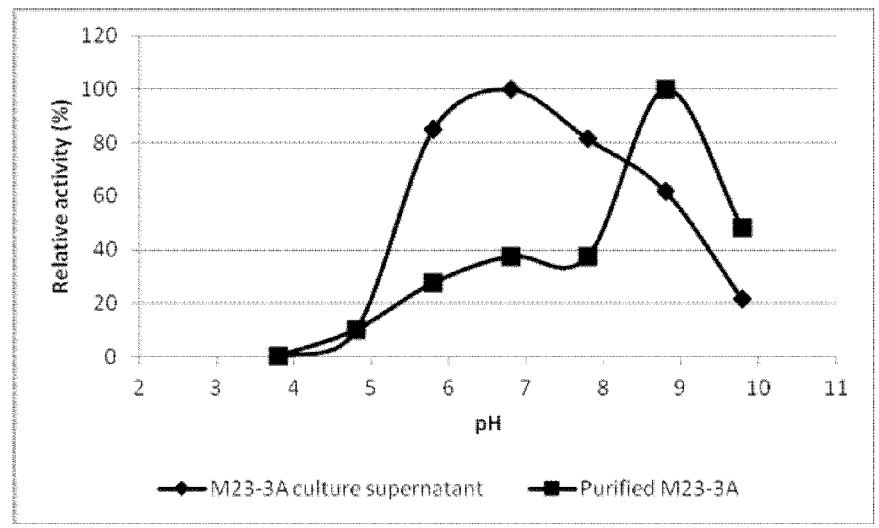

FIG. 13: pH optimum of the recombinant α-amylase and crude enzyme preparation from the strain M23-3A.

Figure 14:
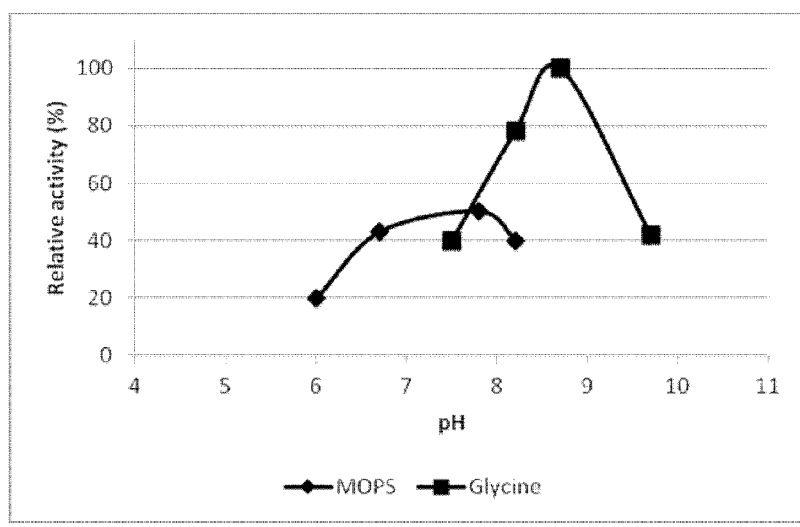

FIG. 14: Effect of buffer on pH optimum of the recombinant α-amylase from the strain M23-3A.

Figure 15:
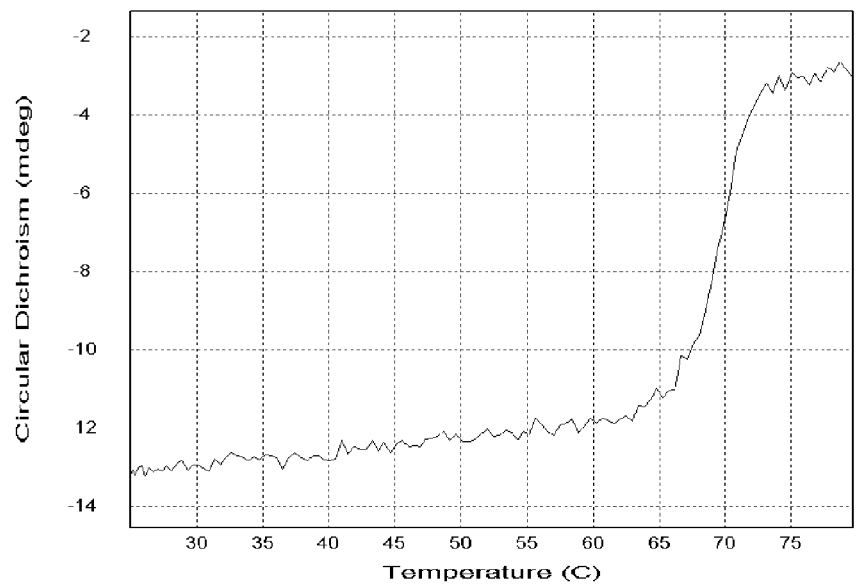

FIG. 15: Thermal stability of the recombinant M23-3A α-amylase.

Figure 16:
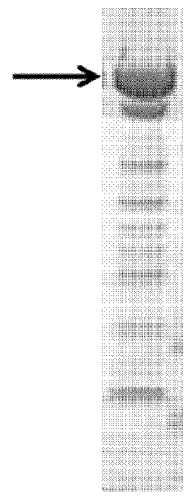

FIG. 16: Purification of the recombinant endocellulase derived from *Deinococcus* DRH-46. Coomassie blue stained SDS-PAGE after purification of recombinant 6(His) tagged endocellulase by Nickel-affinity chromatography. The arrow shows a band corresponding to the purified endocellulase.

Figure 17:
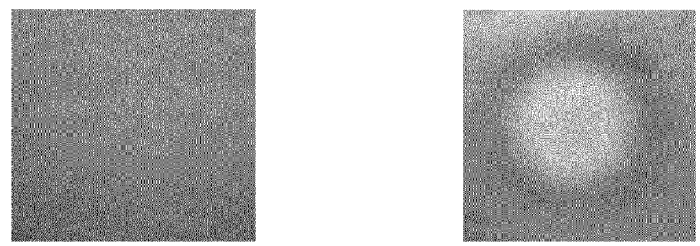

FIG. 17: Cellulose hydrolysis of the recombinant endocellulase from *Deinococcus* DRH-46. 10 µg of the purified enzyme was spotted onto minimum medium-agar plate containing 5% AZO Cellulose (S-ACMCL Megazyme; incubation at 37° C. 2 days. Left photograph: negative control=recombinant purified alpha amylase from *D. geo* M23-3A. Right photograph: recombinant purified endoxylanase from D. DRH46.

Figure 18:
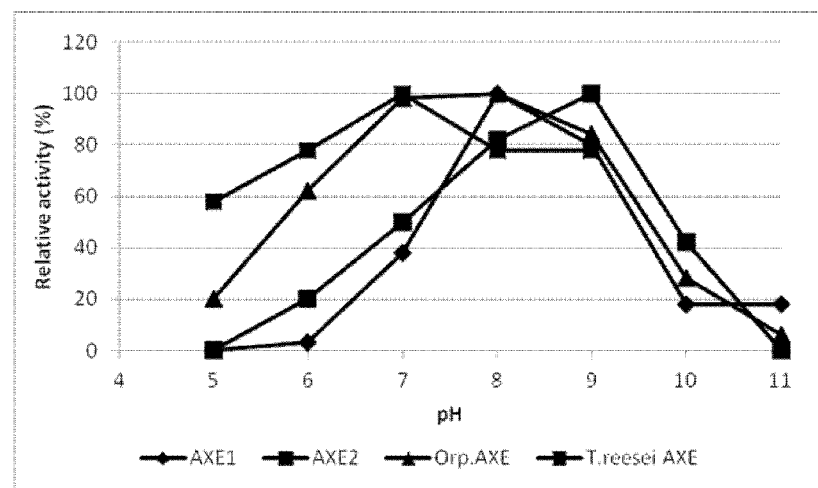

FIG. 18: pH optimum of the recombinant acetyl xylan esterase from strain DRH46.

DETAILED DESCRIPTION OF THE INVENTION

The invention relates, generally, to valuable enzymes derived from *Deinococcus* or related bacteria, which are involved in energetic metabolism, more preferably in biomass modification. These enzymes, which are preferably active at 30° C., even more preferably at 40° C. or more, can be used as such, alone or in combination(s), to cause or improve enzymatic reactions. These enzymes, or their coding nucleic acids, may also be used to create improved recombinant bacteria which may serve to cause or improve biomass conversion. Such bacteria may combine different enzymatic activities or biological properties.

The present disclosure will be best understood by reference to the following definitions:

"Within the context of the invention, the term "derived from a *Deinococcus* bacterium or related bacterium" in relation to an enzyme indicates that the enzyme has been isolated from such a bacterium, or that the enzyme comprises all or a biologically active part of the amino acid sequence of an enzyme isolated, purified or characterized from such a bacterium. The term "derived from a *Deinococcus* bacterium or related bacterium" further includes any recombinant, synthetic and/or optionally modified enzyme (e.g., modified chemically, enzymatically, physically) synthesized from a nucleic acid or amino acid sequence identified in a *Deinococcus* or a related bacterium.

"*Deinococcus* bacterium" designates any bacterium species of the genus *Deinococcus*. *Deinococcus* bacterium includes, without limitation, *D. cellulolysiticus, D. radiodurans, D. proteolyticus, D. radiopugnans, D. radiophilus, D. grandis, D. indicus, D. frigens, D. saxicola, D. maricopensis, D. marmoris, D. deserti, D. geothermalis, D. murrayi, D. aerius, D. aerolatus, D. aerophilus, D. aetherius, D. alpinitundrae, D. altitudinis, D. apachensis, D. aquaticus, D. aquatilis, D. aquiradiocola, D. aquivivus, D. caeni, D. claudionis, D. ficus, D. gobiensis, D. hohokamensis, D. hopiensis, D. misasensis, D. navajonensis, D. papagonensis, D. peraridilitoris, D. pimensis, D. piscis, D. radiomollis, D. roseus, D. sonorensis, D. wulumuqiensis, D. xibeiensis, D. xinjiangensis, D. yavapaiensis* and *D. yunweiensis*.

A bacterium or a bacterial strain "related" to *Deinococcus* designates a bacterium which (i) contains a 16S rDNA which, upon amplification using primers GTTACCCGGAAT-CACTGGGCGTA (SEQ ID NO: 26) and GGTATCTACG-CATTCCACCGCTA (SEQ ID NO: 25), generates a fragment of about 158 base pairs and/or (ii) resists a UV treatment of 4 $mJ/cm^2$. In a particular embodiment, *Deinococcus*-related bacteria are bacteria having a 16S rDNA molecule which is at least 70%, preferably at least 80% identical in sequence to a *Deinococcus* 16S rDNA sequence.

The term "purified" or "isolated", in relation to an enzyme or nucleic acid, indicates the enzyme or nucleic acid is not in its natural medium or form. The term "isolated" thus includes an enzyme or nucleic acid removed from its original environment, e.g., the natural environment if it is naturally occurring. For instance, an isolated enzyme is typically devoid of at least some proteins or other constituents of the cells to which it is normally associated or with which it is normally admixed or in solution. An isolated enzyme includes said enzyme naturally-produced contained in a cell lysate; the enzyme in a purified or partially purified form, the recombinant enzyme, the enzyme which is expressed or secreted by a bacterium, as well as the enzyme in a heterologous host cell or culture. In relation to a nucleic acid, the term isolated or purified indicates e.g., that the nucleic acid is not in its natural genomic context (e.g., in a vector, as an expression cassette, linked to a promoter, or artificially introduced in a heterologous host cell).

The term "energetic metabolism" designates all biological pathways and reactions that contribute to creating or stocking energy products or metabolites in a cell. These include, without limitation, pathways and reactions such as biomass processing, e.g., the degradation of polymers of biomass into fermentable sugars; and sugars fermentation into valuable metabolites or products. An enzyme involved in biomass processing includes, more preferably, an enzyme that modifies or degrades or hydrolyses materials such as, but not limited to, starch, xylan, cellulose; or any of the major components of lignocellulosic biomass, or any composition containing cellulose or hemicellulose, such as some by-products in industrial processing, or an enzyme that contributes to using pyruvate to generate metabolites or energy products in a cell.

The term "biomass" according to the invention typically designates any biological material. In particular, the term biomass includes unprocessed material of biological origin, including vegetal or animal biomass. Examples of biomass include, without limitation, forestry products, including mature trees unsuitable for lumber or paper production, pulp, recycled paper, organic waste, agricultural products, such as grasses, straw, crops and animal manure, and aquatic products, such as algae and seaweed. Examples of biomass include wood or vegetal material derived from numerous types of plants, including miscanthus, hemp, switchgrass, sugarbeet, wheat, barley, corn, rice, soy, canola, rapeseed, sorghum, sugarcane, peanut, cotton, lupine, and a variety of tree species, ranging from eucalyptus to oil palm, poplar, willow. Specific sources of biomass include, without limitation, plant residues, hardwood or softwood stems, cobs, straw, grass, leaves, seeds, paper, etc. (see for instance Sun et al., Bioresource Technology 83 (2002) 1-11). The term biomass also encompasses transformed biomass or secondary biomass, which essentially contains hydrolysed pre-treated biomass products. In a preferred embodiment, biomass according to the invention comprises any lignocellulosic material, for example, cellulose, hemicelluloses and/or xylan.

"Modifying" a biomass within the context of the present invention includes any modification thereof, including transformation, degradation, hydrolysis, conversion or processing of a biomass. The term "modifying" a biomass typically encompasses any modification of the biomass that results in the production of fermentable sugars, monomeric sugars, polymeric sugars, metabolites, resins and/or chemicals, or any other useful product. Modification also typically encompasses the hydrolysis of biological polymers of the biomass.

The term "fermentable sugar" designates, without limitation, carbohydrates having a basic composition $(CH20)_n$. Based on the number of carbons (e.g., 3, 4, 5, or 6), the oligosaccharide is a triose, (i.e., glycerol), tetraose, pentose (i.e., xylose), hexose (i.e., glucose), etc. Starch refers to a carbohydrate consisting of a large number of glucose units joined together by 1-4 and 1-6 glycosidic bonds. Starch is an energy storage molecule accumulated by many plants and bacteria, and starch molecules arrange themselves in the plant in semi-crystalline granules.

Furthermore, the inventors have also discovered that the enzymes of the invention such as amylases, cellulases and xylanases generate oligosaccharides which are composed of several molecules of the same or different sugar monomers. In a particular embodiment, the enzymes of the invention generate polymers comprising up to 15 monosaccharides. In a preferred embodiment, the enzymes of the invention generate small polymers such as di-, tri- and tetrasaccharides. Such polymers generated by the enzymes of the invention are particularly interesting for applications in resin industry (e.g., in fabrication of plastics, paints, varnishes, adhesives and other synthetic products).

Biomass Processing Enzymes

The present invention discloses the isolation and characterization of novel enzymes involved in biomass processing. More particularly, the invention provides novel enzymes which modify (or contribute to the modification of) biomass into fermentable sugars, at temperatures of preferably 30° C. or more, typically between 30 and 70° C. Preferred enzymes of the invention catalyze degradation of starch, xylan and/or cellulose into fermentable sugars. These enzymes exhibit novel structures and valuable biological activities. Other preferred enzymes of the invention catalyse ethanol production by fermentation of sugars. Examples of such enzymes include alcohol dehydrogenases, acetaldehyde dehydrogenases and pyruvate dehydrogenases. These enzymes represent the first functional enzymes involved in energetic metabolism isolated from *Deinococcus* bacteria. Because of their activity, structure and physicochemical properties, these enzymes represent novel valuable products for use in industrial degradation processes, in treating environmental pollutants, in bioenergy production, in pulp and paper industry, in textile industry, in resin industry as well as in the chemical and medical fields.

As mentioned, specific and preferred enzymes of this invention catalyze (or contribute to the catalysis of) the degradation of starch, xylan or cellulose into fermentable sugars. In this regard, preferred enzymes of this invention are selected from glucosidases, xylanases, amylases, cellulases, pectinases, esterases, acetyl xylan esterases and glucuronidases.

Xylanases are enzymes that catalyze the hydrolysis of xylan, a major component of hardwood and softwood hemicelluloses. Xylanases may be of different types, such as endoxylanases, glycoside hydrolases, beta-xylosidases, and alpha-L-arabinofuranosidases, depending on their substrate specificity and/or on the type of chemical bong they may cleave. The present invention discloses the isolation and characterization of novel, biologically active xylanases. The invention particularly discloses the isolation and characterization of endoxylanases, acetyl xylan esterases, alpha-glucuronidases, glycoside hydrolases, beta-xylosidases, and alpha-L-arabinofuranosidases, which represent particular objects of this invention. Specific examples of such enzymes are disclosed in the experimental section, and include polypeptides comprising all or an active part of any one of SEQ ID NOs: 6 to 12, 64, 66, 68 or 72.

Amylases are involved in the hydrolysis of polysaccharides, particularly starch. Starch is a carbohydrate consisting of a large number of glucose units joined together by 1-4 and 1-6 glycosidic bonds. The term "amylases" includes polypeptides having alpha-amylase, beta-amylase, glucoamylase, alpha-glucosidase or pullulanase (glycosyl hydrolase) activities. Alpha-amylases have the ability to hydrolyze internal alpha-1,4-glucosidic linkages in starch to produce smaller molecular weight malto-dextrins. Glucoamylases have ability to hydrolyse glucose polymers linked by a-1,4- and a-1,6-glucosidic bonds. Glucoamylases have the ability to release beta-D-glucose from glucans. Amylase polypeptides of the invention can be used to catalyze the hydrolysis of starch into sugars, such as glucose. The present invention discloses the isolation and characterization of novel, biologically active Deinococcal amylases. The invention particularly discloses the isolation and characterization of Deinococcal alpha-amylase and alpha-glucosidase, which represent particular objects of this invention. Specific examples of such enzymes are disclosed in the experimental section, and include polypeptides comprising all or an active part of any one of SEQ ID NOs: 3 to 5, 58 or 62.

Cellulases are enzymes that catalyze the hydrolysis of cellulose or hemicellulose, a major component of hardwood and softwood. Cellulases may be of different types, such as endoglucanases, endocellulases, cellobiohydrolases (CBH) or cellobiosidases, or β-Glucosidases (cellobiases; BGL). The present invention discloses the isolation and characterization of novel, biologically active Deinococcal cellulases. The invention particularly discloses the isolation and characterization of Deinococcal endoglucanases, cellobiohydrolases and β-Glucosidases, which represent particular objects of this invention. Specific examples of such enzymes are disclosed in the experimental section, and include polypeptides comprising all or an active part of e.g., SEQ ID NOs: 1, 2, 60 or 70.

Other specific and preferred enzymes of this invention catalyze (or contribute to the catalysis of) sugar fermentation, particularly ethanol production by fermentation. Particularly preferred enzymes catalyze (or contribute to the catalysis of) the conversion of pyruvate into ethanol. Examples of such enzymes include acetaldehyde dehydrogenases, alcohol dehydrogenases and pyruvate dehydrogenases. Alcohol dehydrogenases and acetaldehyde dehydrogenases are groups of dehydrogenase enzymes that occur in many organisms and facilitate the interconversion between alcohols and aldehydes or ketones. In bacteria, they participate in generation of useful alcohol groups during biosynthesis of various metabolites. In particular, they play an important part in the production of ethanol by fermentation. More specifically, pyruvate, resulting from glycolysis, is converted to acetaldehyde and carbon dioxide, and the acetaldehyde is then reduced to ethanol by an alcohol dehydrogenase and/or an acetaldehyde dehydrogenase. Acetaldehyde dehydrogenases also catalyse (or contribute to the catalysis of) the conversion of acetyl-CoA into acetaldehyde.

The invention particularly discloses the isolation and characterization of Deinococcal acetaldehyde dehydrogenases, which represent particular objects of this invention. Specific examples of such enzymes are disclosed in the experimental section, and include polypeptides comprising all or an active part of anyone of SEQ ID NOs: 27 to 31.

The invention also discloses the isolation and characterization of Deinococcal alcohol dehydrogenases, which represent particular objects of this invention. Specific examples of such enzymes are disclosed in the experimental section, and include polypeptides comprising all or an active part of anyone of SEQ ID NOs: 32 to 41.

Enzymes of the present invention are polypeptides, which may be naturally-occurring, recombinant and/or synthetic and, optionally modified (e.g., chemically, enzymatically, physically, etc.). The enzymes are preferably in isolated or purified form. The enzymes are advantageously functional at 30° C., or at higher temperatures. Preferred enzymes of the invention may be used at temperatures above 40° C., or even above 45° C., for instance. They are also active under stringent pH (e.g., between 3.5 and 9) or alcohol conditions.

In a preferred embodiment, enzymes of the present invention are polypeptides comprising an amino acid sequence selected from anyone of SEQ ID NOs: 1 to 12, fragments thereof comprising at least 15 contiguous amino acid residues; or functional variants thereof having xylanase, amylase or cellulase activity.

In another preferred embodiment, enzymes of the present invention are polypeptides comprising an amino acid sequence selected from anyone SEQ ID NOs: 27-31, fragments thereof comprising at least 15 contiguous amino acid residues; or functional variants thereof having acetaldehyde dehydrogenase activity.

In another preferred embodiment, enzymes of the present invention are polypeptides comprising an amino acid sequence selected from anyone SEQ ID NOs: 32-41, fragments thereof comprising at least 15 contiguous amino acid residues; or functional variants thereof having alcohol dehydrogenase activity.

Functional variants according to the invention retain an activity of the reference polypeptide. They typically also exhibit at least 50% amino acid sequence identity to the reference polypeptide, even more preferably at least 60%, 70%, 80% or 90%. The extent of sequence identity (homology) may be determined using any computer program and associated parameters, including BLAST 2.2.2 or FASTA version 3.0t78, with the default parameters. Preferred functional variants have a level of identity of at least 90% with the reference sequence, most preferably of at least 92, 95, or 97%.

In a preferred embodiment, functional variants comprise at most between 1 to 50, 1 to 40, 1 to 30, 1 to 25, 1 to 20, 1 to 15, 1 to 10, or 1 to 5 modified (e.g., deleted, substituted or inserted) amino acid residues as compared to the reference polypeptide.

Polypeptides according to the invention qualify as functional if they exhibit at least 20%, preferably at least 30% and more preferably at least 50% of an enzymatic activity of the reference polypeptide.

Preferred fragments of a polypeptide of this invention comprise at least about 10, 15, 20, 25, 40, 50 or even more preferably 60 contiguous amino acids of said polypeptide. Most preferred fragments are functional, either by themselves or when fused to or combined with another polypeptide. Also, the polypeptides of the invention may be used to create fusion or chimeric polypeptides having multiple activities.

An "active part" of a polypeptide more specifically designates a portion of that polypeptide which confers or exhibits an enzymatic activity of the entire polypeptide.

The active part may, for instance, confer substrate specificity or affinity, it may contain the catalytic site, or it may confer pharmacokinetics properties. An active part of a protein also designates a mature form of the protein (i.e., that does not contain a signal peptide at the N-terminal end of the protein).

In this regard, the enzymes of the invention include, for example:
  a mature form of endoxylanase of SEQ ID NO: 6 without signal peptide MKRSKTHLAVVGLGLLALLG-SCGQS (SEQ ID NO: 73);
  a mature form of alpha-amylase of SEQ ID NO: 3 without signal peptide MRRLPLLAALLASLAGAQA (SEQ ID NO: 74);
  a mature form of alpha-amylase of SEQ ID NO: 62 without signal peptide MKRFQKVGRSGALAVLTLAL-SACGVLKA (SEQ ID NO: 75).

Polypeptides of the invention may be produced by recombinant techniques, or they may be isolated or purified from natural sources, when naturally-occurring, or they may be artificially produced. The enzymes may be in soluble form, or on solid phase. In particular, they may be bound to cell membranes or lipid vesicles, or to synthetic supports such as glass, plastic, polymers, filter, membranes, e.g., in the form of beads, columns, plates and the like.

Enzymes of the invention may be expressed, derived, secreted, isolated, or purified from a *Deinococcus* or related bacterium. The enzymes may be purified by techniques known per se in the art, and stored under conventional techniques. The polypeptides may be further modified to improve e.g., their stability or activity. They may be used as such, in purified form, either alone or in combinations, to catalyse enzymatic reactions involved in the transformation of raw biomass into fermentable sugars. They may be used to supplement biological processes of transformation of biomass into fermentable sugars. For instance, they may be added into reactors containing microorganisms or enzymes, to supplement the activity. In a preferred embodiment, these enzymes are used to engineer improved microorganisms having novel biological activities. In other specific embodiments, the enzymes of the invention may be used in the production of bioenergy (such as bioethanol), in industrial biomass degradation processes, in bioenergy production, in pulp and paper industry (pulping, paper bleaching), in textile industry, in detergent industry, in resin industry as well as in the chemical and medical fields, as described below.

Nucleic Acid

A further object of the invention is a nucleic acid encoding an enzyme or polypeptide as defined above. A further object of the invention is a vector comprising a nucleic acid as defined above.

The term "nucleic acid" designates any type of nucleic acid, such as DNA, RNA, PNA, DNA-like or RNA-like material, which may be of recombinant, artificial and/or synthetic origin, single-stranded or double-stranded, and represent the sense or antisense strand. The term encompasses nucleic acids containing known analogues of natural nucleotides. The term also encompasses nucleic-acid-like structures with synthetic backbones.

Specific examples of such nucleic acids include nucleic acids comprising a sequence selected from any one of SEQ ID NOs: 13 to 24, 42 to 57, 59, 61, 63, 65, 67, 69 and 71. SEQ ID NOs: 13-24 contain a nucleic acid sequence encoding the proteins of SEQ ID NOs: 1-12, respectively. SEQ ID NOs: 42-56 contain a nucleic acid sequence encoding the proteins of SEQ ID NOs: 27-41, respectively. SEQ ID NO 57, 59, 61, 63, 65, 67, 69 and 71 contain a nucleic acid sequence encoding the proteins of SEQ ID NOs: 58, 60, 62, 64, 66, 68, 70 and 72, respectively. The nucleic acids of the invention can be in isolated or purified form, and made, isolated and/or manipulated by techniques known per se in the art, e.g., cloning and expression of cDNA libraries, amplification, enzymatic synthesis or recombinant technology. The nucleic acids can also be synthesized in vitro by well-known chemical synthesis techniques, as described in, e.g., Belousov (1997) Nucleic Acids Res. 25:3440-3444.

The invention also encompasses nucleic acids which hybridize, under stringent conditions, to a nucleic acid encoding an enzyme as defined above. Preferably, such stringent conditions include incubations of hybridization filters at about 42° C. for about 2.5 hours in 2×SSC/0.1% SDS, followed by washing of the filters four times of 15 minutes in 1×SSC/0.1% SDS at 65° C. Protocols used are described in such reference as Sambrook et al. (Molecular Cloning: a Laboratory Manual, Cold Spring Harbor Press, Cold Spring Harbor N.Y. (1988)) and Ausubel (Current Protocols in Molecular Biology (1989)).

The invention also encompasses nucleic acids encoding a polypeptide of the invention, wherein the sequence of said nucleic acids, or a portion of said sequence at least, has been engineered using optimized codon usage.

A specific embodiment of this invention resides in a polynucleotide encoding an enzyme as defined above, comprising a sequence selected from SEQ ID NOs: 1-12, 27-41, 58, 60, 62, 64, 66, 68, 70 and 72.

In another specific embodiment, the invention resides in a polynucleotide encoding an active part or a mature form (i.e., without signal peptide) of a polypeptide selected from SEQ ID NO: 1-12, 58, 60, 62, 64, 66, 68, 70 and 72.

A further specific embodiment of this invention resides in a polynucleotide comprising a sequence selected from anyone of SEQ ID NOs: 13-24, 42-57, 59, 61, 63, 65, 67, 69 and 71.

Nucleic acids of this invention may comprise additional nucleotide sequences, such as regulatory regions, i.e., promoters, enhancers, silencers, terminators, and the like that can be used to cause or regulate expression of an enzyme in a selected host cell or system.

A further aspect of this invention resides in a vector, such as an expression, cloning or reporter vector comprising a nucleic acid as defined above. Such vectors may be selected from plasmids, recombinant viruses, phages, episomes, artificial chromosomes, and the like. Many such vectors are commercially available and may be produced according to recombinant techniques well known per se in the art, such as the methods set forth in manuals such as Sambrook et al., *Molecular Cloning* (2d ed. Cold Spring Harbor Press 1989), which is hereby incorporated by reference herein in its entirety. A specific example of such a plasmid is described e.g., in US patent application No. 2003/0175977, which discloses an endogenous plasmid derived from a strain of *D. radiopugnans*, pUE30, which can be used as vector able to replicate autonomously in bacteria of genus *Deinococcus*, and which can be used to construct a shuttle vector also containing a plasmid able to replicate autonomously in *E. coli* and its derivatives, and able to replicate in a bacterium both of genus *Deinococcus* and of *E. coli*.

A further aspect of this invention resides in a host cell transformed or transfected with at least one nucleic acid or a vector as defined above. The nucleic acid (or the vector) may remain extrachromosomal, or become inserted in the genome, e.g., through homologous or heterologous recombination. The host cell may be any cell that can be genetically modified and, preferably, cultivated. The cell can be eukaryotic or prokaryotic, such as a mammalian cell, an insect cell, a plant cell, a yeast, a fungus, a bacterial cell, etc. Typical examples include bacteria (e.g., *E. coli, Deinococcus*, etc.). It should be understood that the invention is not limited with respect to any particular cell type, and can be applied to all kinds of cells, following common general knowledge. Transformation may be carried out using techniques known per se in the art, such as lipofection, electroporation, calcium phosphate precipitation, etc.

In yet another embodiment, the present invention includes a recombinant cell that contains at least one vector as defined above.

The invention also relates to a recombinant cell containing at least one nucleic acid or a vector as defined above.

The invention also relates to a *Deinococcus* or related bacterium which contains at least one nucleic acid or a vector as defined above. The invention indeed allows the engineering of *Deinococcus* strains with improved capacity to process starch and lignocellulosic biomass, with the use of *Deinococcus* DNA only.

The native profile of "wild type" cellulolytic and/or xylanolytic and/or amylolytic *Deinococcus* strains is not always optimal for degradation of cellulose, xylan, and starch. The identification and the replacement or the complementation of wild type strains with *Deinococcus* genes encoding enzymes, or sets of enzymes of the invention, allow an optimal processing of the biomass. We outline the minimal enzymes necessary for hydrolysis of cellulose and xylan and starch present in a genuine biomass substrates. The available data demonstrate the feasibility of the concept and illustrate the potential improvements obtainable by use of minimal enzyme cocktails for pre-treated lignocellulosic, hemicellulosic and starch-rich biomass substrates.

Methods of Use

The present invention provides methods using enzymes of the invention in various industrial, agricultural, biotechnological, chemical and medical areas. Indeed, due to their high catalytic efficiency, enzymes of the invention are much more advantageous in comparison with other known chemical and microbial catalysts since they have an increased catalytical rate. The enzymes of the invention may be used, for example, in biomass processing, in delignification and pulp bleaching, in biofuel production, in textile industry, in bakery industry, in pharmaceuticals, in resin industry, in organic synthesis, etc.

Biomass Modification and Bioenergy Production

The enzymes of the present invention can be used in methods for modification of a biomass or any lignocellulosic material comprising cellulose, hemicelluloses, lignin and/or xylan. In a particular embodiment, the biomass is a cellulose, starch or xylan-containing material of vegetal origin. The enzymes of the invention can be applied, for example, for the conversion of a biomass into fermentable sugars and/or monomeric sugars and/or polymeric sugars for the production of metabolites and/or energy products (e.g., biofuels) or chemicals from a biomass.

The invention also relates to the use of an enzyme, nucleic acid, vector or cell as defined above, or a combination thereof, for modifying biomass and/or producing metabolites or energy products.

The invention also relates to a method for modifying biomass, comprising exposing such biomass to an enzyme, nucleic acid, vector or cell as defined above, or to a combination thereof.

The invention also relates to a method for increasing biomass modification, the method comprising adding to the biomass an enzyme, nucleic acid, vector or cell as defined above, or a combination thereof.

The invention also relates to a method for producing metabolites or bioenergy products, comprising exposing a carbon source, e.g., a biomass or constituents thereof, to an enzyme, nucleic acid, vector or cell as defined above, or a combination thereof. The method may further comprise a step of isolating or recovering the metabolite or product. Examples of metabolites include, without limitation, organic acids and alcohols such as, preferably, formate, lactate, acetate, succinate, fumarate, pyruvate, propanol, mannitol and arabitol. Examples of energy products include biofuels such as, without limitation, ethanol, butanol or methanol.

In a particular embodiment, the carbon source is a xylan-containing biomass and the enzyme comprises at least a xylanase of the invention.

In another particular embodiment, the carbon source is a cellulose- or hemicellulose-containing biomass and the enzyme comprises at least a cellulase of the invention.

In a particular embodiment, the carbon source is a polysaccharide-containing biomass (e.g. starch-containing biomass) and the enzyme comprises at least an amylase of the invention.

In another embodiment, the carbon source is a pyruvate-containing material and the enzyme comprises at least an ADH, ACDH or PDH of the invention.

A particular object of the invention concerns a method for producing a biofuel (for example, bioethanol, biomethanol, biopropanol, biobutanol, etc.), comprising exposing a carbon source, e.g., a biomass or constituents thereof and/or a fermentable sugar, to an enzyme, nucleic acid, vector or cell as defined above, or a combination thereof, and recovering biofuel produced. More generally the enzymes of the invention can also be used to engineer microorganisms having the capacity to use cheaper carbon source. Such microorganisms may thus be used to produce any product of interest (e.g., proteins, RNAs, metabolites, etc.) at lower cost and/or improved levels. In this respect, the invention also relates to a method for producing a recombinant protein, comprising expressing said protein in a recombinant microorganism encoding at least one enzyme as defined above, or a combination thereof, and recovering the protein produced. Examples of such recombinant proteins include pharmaceutical proteins, or industrial enzymes such as for instance a lipase.

The invention also relates to a method of modifying starch, comprising exposing starch or a starch-containing material, to an enzyme, nucleic acid, vector, cell or cell extract as defined above.

The invention also relates to a method of modifying xylan, comprising exposing xylan or a xylan-containing material, to an enzyme, nucleic acid, vector, cell or cell extract as defined above.

The invention also relates to a method of modifying cellulose, comprising exposing cellulose or a cellulose-containing material, to an enzyme, nucleic acid, vector, cell or cell extract as defined above.

The method can be made in any suitable condition or environment allowing modification of the biomass to produce bioenergy products or metabolites. In this regard, the method can be performed in a reactor, in a fermentor, outdoor, in the presence of suitable nutrients or additives, if needed. The method is typically conducted at a temperature above 30° C., and in the presence of suitable substrates.

Pulp and Paper Industry

The enzymes of the invention may be used in many industrial processes, particularly in methods of producing a paper-making pulp in the paper industry.

In particular embodiments, the invention provides methods of pulping and methods of repulping, by using an enzyme of the invention.

In a specific embodiment, a method of the invention allows the chlorine-free bleaching of wood pulp prior to the paper-making process, by using, for example, a xylanase of the invention.

The present invention also provides methods of pulp or paper craft bleaching which may result in higher pulp yields and energy saving. Such methods may use, for example, a xylanase of the invention.

In another embodiment, the present invention also provides methods of modifying cellulosic fibers and improving the quality of paper by using, for example, a cellulase of the invention.

Textile Industry

The invention also provides methods of treating textiles using an enzyme of the invention. The enzymes can be applied during or after the weaving of textiles, or during the desizing stage or during additional fabric processing steps.

In particular embodiments, cellulases of the invention may be used in textile industry and in laundry detergents.

In another particular embodiment, an amylase of the invention may be used in detergent industry for preparation of detergent compositions, e.g., for use in clothing and dishwasher detergents in order to dissolve starches from fabrics and dishes.

Resin Industry

The enzymes of the invention may also be used in resin industry, in particular, for producing plastics, paints, varnishes, adhesives, etc. In this regard, a preferred enzyme which is used in resin industry to form plastics, paints, varnishes, adhesives and other synthetic products, is an amylase, cellulose or xylanase of the invention that is able to generate polymers of sugar, as described above. In this regard, the most efficient enzymes are able to generate polymers comprising up to 15 monosaccharides. preferably di-, tri- and tetrasaccharides.

Bakery Industry

In a particular embodiment, an enzyme of the invention (e.g., xylanase) may be used as the key ingredient in the dough conditioner or to improve the dough workability and absorption of water.

In another particular embodiment, amylase enzymes of the invention can be used in dough making, e.g., in bread making, in order to break down complex sugars such as starch (found in flour) into simple sugars, which are further converted into alcohol and $CO_2$. Thus, amylases of the invention can make the bread making process faster and more practical for commercial use. Amylases of the invention may also be used to add flavor to any alimentary product prepared from dough and containing a flour.

Medical Applications

Enzymes of the invention can also be used in the pharmaceutical field. For example, a cellulase of the invention may be used as a treatment for phytobezoars, which is a form of cellulose bezoar found in the human stomach. Amylases of the invention may be used for purposes of medical diagnosis.

In molecular biology, an amylase of the invention may be used, e.g., as an additional tool in the method of selecting for successful integration of a reporter construct, in addition to antibiotic resistance. For example, if reporter genes are flanked by homologous regions of the amylase gene, successful integration will disrupt the amylase gene and will prevent starch degradation that can be easily detectable through iodine staining.

The present invention also relates to the use of an enzyme, nucleic acid, vector or cell as defined in the present application, or a combination thereof, for all the above applications.

Because of their activity, structure and physicochemical properties, the enzymes of the invention represent novel and highly valuable products for use in various industrial, agricultural, chemical, biotechnological and medical areas. Such an enzyme, derived from a *Deinococcus* or a related bacterium, exhibits a higher catalytic activity compared to activity of other conventional enzymes applied by a skilled person in biomass degradation processes, in bioenergy production, in pulp and paper industry, in textile industry, in detergent industry, in bakery industry, as well as in the chemical and medical field.

The enzymes may be used either alone or in combinations. In this regard, the invention also relates to a composition comprising at least 2 enzymes as defined above. When used in combination, the enzymes may be combined simultaneously or sequentially. For instance, two or more enzymes may be combined in a composition, and the composition can be added to biomass or a carbon source, or a reactor, as mentioned above.

Alternatively, two or more enzymes may be added sequentially to said biomass, carbon source or reactor, to provide a combined enzymatic activity to the reaction. Similarly, nucleic acids, vectors or cells coding or expressing a combination of enzymes can be used. Also, instead of whole cells, an enzymatically active extract thereof may be used, such as a lysate or supernatant. Enzymes of the invention may further be combined with other enzymes known or disclosed or available in the art.

Depending on the conditions, the biomass or substrate can be contacted with a product of the invention alone or in combination with other enzymes or microorganisms. It should be understood that the precise amounts of enzyme or bacterium used initially in order to efficiently transform biomass into substantial bioenergy products or metabolites can be adjusted by the skilled artisan depending on the type of bacterium, the type of biomass, and the culture conditions.

In a particular embodiment, the method of the invention is performed in a reactor of conversion of biomass. By "reactor" is meant a conventional fermentation tank or any apparatus or system for biomass conversion, typically selected from bioreactors, biofilters, rotary biological contactors, and other gaseous and/or liquid phase bioreactors. The apparatus which can be used according to the invention can be used continuously or in batch loads.

In the reactor, to implement the method of the invention, at least one enzyme, bacterium or bacterial extract of the invention is used, whilst said reactor is arranged and supplied so that physicochemical conditions are set up and maintained therein so that said enzyme or bacterium is operational.

Depending on the bacterium used, the method may be conducted under aerobiosis, anaerobiosis or microaerobiosis.

Co-Cultures

A further aspect of the invention resides in microorganism co-cultures having improved properties. More specifically, the invention relates to co-cultures using *Deinococcus* bacteria, which co-cultures have improved enzymatic activities or physico-chemical properties. In a particular embodiment, the invention relates to a co-culture of at least two distinct microorganisms, wherein at least one of said microorganisms is a *Deinococcus* bacterium and at least one of said microorganisms is a prokaryotic or eukaryotic cell, wherein said at least two microorganisms are symbiotic to each other, and wherein said at least one *Deinococcus* bacterium exhibits an enzymatic activity according to the invention.

The prokaryotic or eukaryotic cell may be selected, e.g., from bacteria, yeasts, plant cells, fungi, and mammalian cells. Examples of yeasts include, without limitation, *Saccharomyces, Kluyveromyces, Schizosaccharomyces, Pichia*, etc. Examples of bacteria include *Deinococcus* bacteria, *Bacillus* sp., *E. Coli, Clostridium* sp., etc. Two microorganisms are considered symbiotic to each other when both require the other for its survival and growth. Co cultures of the invention may comprise more than 2 distinct microorganisms, such as 3 or 4. Also, co-cultures may be simultaneous or sequential, preferably simultaneous.

In this regard, a specific object of the invention is a culture of at least two distinct microorganisms, wherein at least one of said microorganisms is a *Deinococcus* bacterium and at least one of said microorganisms is a yeast, and wherein said at least one *Deinococcus* bacterium exhibits an enzymatic activity according to the invention.

These co-cultures offer improved range of enzymatic activities and represent valuable products for industrial processes.

Further aspects and advantages of the invention will be disclosed in the following examples, which illustrate the invention.

EXAMPLES

Materials and Methods
Selection Tests and Culture Media Composition

| 167 Thermus medium | |
|---|---|
| Tryptone | 1 G |
| Yeast extract | 1 G |
| Agar | 28 G |
| Nitrilotriacetic acid | 100 mg |
| $CaSO_4 \times 2\, H_2O$ | 40 mg |
| $MgCl_2 \times 6\, H_2O$ | 200 mg |
| 0.01M Fe citrate | 0.5 ml |
| Solution of trace elements (see below) | 0.5 ml |
| Phosphate buffer (see below) | 100 ml |
| $H_2O$ | 900 ml |
| Adjust to pH 7.2 with NaOH, autoclave at 121° C. for 15 min. autoclave the phosphate buffer separately and add to the medium | |

| Phosphate buffer | |
|---|---|
| $KH_2PO_4$ | 5.44 G |
| $Na_2HPO_4 \times 12\, H_2O$ | 43 G |
| $H_2O$ | 1000 Ml |
| Adjust to pH 7.2 | |

Composition of Minimum Medium
MOPS buffer 1× (ph7) containing: acid MOPS buffer 40 mM, $NH_4Cl$ 20 mM, KOH 10 mM, NaOH 10 mM, $CaCl_2$ 0.5 μM, $Na_2SO_4$ 0.276 mM, $MgCl_2$ 0.528 mM.
A solution of micronutriments (pH5): $(NH_4)_6(MO_7)_{24}$ 3 nM, $H_3BO_3$ 400 nM, $CoCl_2$ 30 nM, $CuSO_4$ 10, nM, $MnCl_2$ 250 nM, $ZnSO_4$ 10 nM.
Solution of vitamins, pH4.0, (1 μg/1 each): D-biotin, niacin, pyridoxal-HCl, thiamin-HCl, vitamin B12.
Source of phosphate: $K_2HPO_4$ 5.7 mM.
$FeCl_3$ 20 μM (prepared in a solution of sodium citrate then filtered).

Example 1

Identification of Enzymes with Cellulolytic Activity
(FIG. 1)

*Deinococcus* sp were inoculated on a minimal culture medium made up of a MOPS buffer solution at pH7 and filtered: acid MOPS buffer 40 mM (Sigma, France), $NH_4Cl$ 20 mM, KOH 10 mM, NaOH 10 mM, $CaCl_2$ 0.5 μM, $Na_2SO_4$ 0.276 mM, $MgCl_2$ 0.528 mM), a solution of micronutriments at pH5 ($(NH_4)_6(MO_7)_{24}$ 3 nM, $H_3BO_3$ 400 nM, $CoCl_2$ 30 nM, $CuSO_4$ 10 nM, $MnCl_2$ 250 nM, $ZnSO_4$ 10 nM), a solution of vitamins at pH4 (1 μg/L of D-biotin, niacin, pyridoxal-HCl, thiamin-HCl and vitamin B12), a solution of $K_2HPO_4$ at 5.7 mM as well as a solution of $FeCl_3$ at 20 μM in $NaH_2(C_3H_5O(COO)_3)$. A piece of whatman I filter was added as sole carbon source.
The bacteria were grown at 45° C. or 30° C. Filter paper degradation was monitored up to 28 days. Strains having the ability to grow under these conditions and to degrade the piece of whatman I filter paper have been isolated, and designated as cellulolytic.

Additionally the cell-free culture supernatants were tested for their ability to release glucose from carboxymethyl cellulose (CMC).
FIG. 1A shows strains DRH46 and M1-3H degrade filter paper. Furthermore, this degradation is correlated with a strong cellulolytic activity (FIG. 1B).
The corresponding enzymes have been characterized, and the amino acid sequences of these cellulolytic enzymes are described in the application:
a cellobiohydrolase (endocellulase processive) from M1-H3 is represented as SEQ ID NOs: 1 (partial sequence) and 60 (full-length natural variant);
two endoglucanases from DRH-46 are represented as SEQ ID NOs: 2 and 70, respectively.
The coding nucleic acid sequences have also been isolated, and represented in SEQ ID NOs: 13 (nucleotide sequence coding for the cellobiohydrolase of SEQ ID NO: 1), 14 (nucleotide sequence coding for the endoglucanase of SEQ ID NO: 2), 69 (nucleotide sequence coding for the endoglucanase of SEQ ID NO: 70) and 59 (nucleotide sequence coding for the full-length variant of cellobiohydrolase of SEQ ID NO: 1), respectively. These nucleic acids have been cloned into the pETDEST42 expression vector and recombinant bacteria containing said vectors have been produced and maintained.

Example 2

Identification of Enzymes with Amylolytic Activity

*Deinococcus* sp were inoculated on a minimal culture medium made up of a MOPS buffer solution at pH7 and filtered: acid MOPS buffer 40 mM (Sigma, France), $NH_4Cl$ 20 mM, KOH 10 mM, NaOH 10 mM, $CaCl_2$ 0.5 μM, $Na_2SO_4$ 0.276 mM, $MgCl_2$ 0.528 mM), a solution of micronutriments at pH5 ($(NH_4)_6(MO_7)_{24}$ 3 nM, $H_3BO_3$ 400 nM, $CoCl_2$ 30 nM, $CuSO_4$ 10 nM, $MnCl_2$ 250 nM, $ZnSO_4$ 10 nM), a solution of vitamins at pH4 (1 μg/L of D-biotin, niacin, pyridoxal-HCl, thiamin-HCl and vitamin B12), a solution of $K_2HPO_4$ at 5.7 mM as well as a solution of $FeCl_3$ at 20 μM in $NaH_2(C_3H_5O(COO)_3)$. Soluble starch from potatoes was added as sole carbon source at a final concentration of 0.5% (w/v).
The bacteria are grown in aerobiosis. The kinetic growth of strains grown at 45° C. in minimal defined medium containing starch was monitored by measuring $OD_{600nm}$ over 50 hours. Bacteria having the ability to grow under such conditions have been isolated, which are designated as amylolytic. In addition, the cell-free culture supernatants are tested either for their ability to release reducing sugar monomer (glucose) from starch by using DNS method or for their ability to release p-nitrophenol from p-nitrophenyl maltosaccharide by using the Ceralpha method (K-cera; Megazyme).
Our results show that strains M23r-2A, DRH38 and MC2-2A grow rapidly in the presence of starch as sole carbon source (FIG. 2). Furthermore, we show that this fast growth of M23r-2A is correlated with a strong amylolytic activity (FIG. 3).
Using M23r-2A, we have then been able to identify an alpha-amylase enzyme. The amino acid sequence of this enzyme, which is capable of degrading starch, is represented in SEQ ID NO: 3. Our results further show that the sequence of this enzyme is divergent from that of previously known amylases.
We have also identified from strain DRH38 a glucan 1,4-alpha-glucosidase or glucoamylase. The amino acid sequence of this enzyme, which is capable of degrading starch, is represented in SEQ ID NO: 4. Our results further show that the sequence of this enzyme is divergent from that of previously known amylases.

We have also identified from strain MC2-2A a glucan 1,4-alpha-glucosidase or glucoamylase. The amino acid sequence of this enzyme, which is capable of degrading starch, is represented in SEQ ID NO: 5. Our results further show that the amino acid sequence of this enzyme is divergent from that of previously known amylases.

The coding nucleic acid sequences have also been isolated, and represented in SEQ ID NOs: 15-17, respectively.

We have further identified from strain M23-3A another alpha amylase enzyme. The amino acid sequence of this enzyme is represented in SEQ ID NO: 62. The coding nucleic acid sequence has also been isolated, and represented in SEQ ID NO: 61. This nucleic acid has been cloned into the pETDEST42 expression vector and recombinant bacteria containing said vectors have been produced and maintained.

We have also identified from strain M23-3A a glucoamylase enzyme. The amino acid sequence of this enzyme, which is capable of degrading amylopectine and starch is represented in SEQ ID NO: 58. The results further show that the sequence of this enzyme is divergent from that of previously known amylases. The coding nucleic acid sequence has also been isolated and represented in SEQ ID NO: 57. This nucleic acid has been cloned into the pETDEST42 expression vector and recombinant bacteria containing said vectors have been produced and maintained.

Example 3

Identification of Enzymes with Xylanolytic Activity

*Deinococcus* sp were inoculated on a minimal culture medium made up of a MOPS buffer solution at pH7 and filtered: acid MOPS buffer 40 mM (Sigma, France), $NH_4Cl$ 20 mM, KOH 10 mM, NaOH 10 mM, $CaCl_2$ 0.5 µM, $Na_2SO_4$ 0.276 mM, $MgCl_2$ 0.528 mM), a solution of micronutrients at pH5 (($NH_4)_6(MO_7)_{24}$ 3 nM, $H_3BO_3$ 400 nM, $CoCl_2$ 30 nM, $CuSO_4$ 10 nM, $MnCl_2$ 250 nM, $ZnSO_4$ 10 nM), a solution of vitamins at pH4 (1 µg/L of D-biotin, niacin, pyridoxal-HCl, thiamin-HCl and vitamin B12), a solution of $K_2HPO_4$ at 5.7 mM as well as a solution of $FeCl_3$ at 20 µM in $NaH_2(C_3H_5O(COO)_3)$. Birch wood xylan was added as sole carbon source at a final concentration of 0.5% (w/v).

The bacteria are grown in aerobiosis. The kinetic growth of strains grown at 45° C. in minimal defined medium containing birchwood xylan were monitored by measuring $OD_{600\,nm}$ over 50 hours. Bacteria having the ability to grow under such conditions have been identified and isolated, which are designated as xylanolytic. In addition, the cell-free culture supernatants are tested for their ability to release reducing sugar monomer (xylose) from birchwood xylan. The amount of xylose liberated has been determined with DNS (3,5-dinitrosalicylic acid) as described previously (Miller G. L 1959). One unit was defined as the activity that produces 1 µmol of xylose per minute.

Our results show that strains MC3-4A, DRH38 and DRH46 grow rapidly on birchwood xylan as sole carbon source and encode strong xylanolytic enzymes (FIG. 4). The corresponding enzymes have been identified and characterized. These enzymes are:
an endoxylanase (endo-1,4-beta-glucanase), deriving from strain MC3-4A, having an amino acid sequence represented in SEQ ID NO: 6;
a glycoside hydrolase, derived from strain DRH-38, having an amino acid sequence represented in SEQ ID NO: 7;
a beta-xylosidase, derived from strain DRH-46, having an amino acid sequence represented in SEQ ID NO: 8; and
five distinct arabinofuranosidases, derived from strain DRH-46, having an amino acid sequence represented in SEQ ID NOs: 9-12 and 68, respectively.

The coding nucleic acid sequences have also been isolated, and represented in SEQ ID NOs: 18-24 and 67, respectively. These nucleic acids have been cloned into the pETDEST42 expression vector and recombinant bacteria containing said vectors have been produced and maintained.

Example 4

Identification of Enzymes with ACDH Activity

*Deinococcus* bacteria are grown at 45° C. or 30° C. The cell-free culture supernatants are tested according to the following protocol:
The tested reaction is as follows:

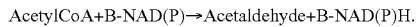

AcetylCoA+B-NAD(P)→Acetaldehyde+B-NAD(P)H.

The reaction is tested at 25° C., pH=8.5, A340 nm using Continuous Spectrophotometric Rate Determination. The following reagents are used (initial concentrations):
Reagent A: 100 mM Glycine/NaOH, pH 8.5;
Reagent B: 0.4 mM Acetyl CoA;
Reagent C: 1 mM β-Nicotinamide Adenine Dinucleotide, reduced in 10 mM NaOH (B-NADH);
Reagent D: Enzyme solution (cell crude extracts or purified protein);
Reagent E: BSA (Blank).

Protocol

Pipette (in µl) the following reagents into microplates:

|  | Test | Blank |
|---|---|---|
| Reagent A (Buffer) | 150 | 150 |
| Reagent B (AcetylCoA) | 75 | 75 |
| Reagent C (β-NADH) | 60 | 60 |

Shake the microplate and equilibrate to 25° C. Monitor the A340 nm until constant, using a suitably thermoregulated spectrophotometer. Then add:

| Reagent D (Enzyme Solution) | 15 µl |
|---|---|
| Reagent E (Blank) | 15 µl |

Immediately mix by inversion and record the increase in A340 nm for approximately 6 minutes. Obtain the ΔA340 nm/minute using the one to six minute range for both the Test and Blank.

The results show that tested strains DRH05 and M23r-2A exhibit substantial ACDH activities. The corresponding enzymes have been characterized, and the amino acid sequence of these ACDH enzymes is represented in SEQ ID NOs: 27-31, respectively.

The coding nucleic acid sequences have also been isolated, and represented in SEQ ID NOs: 42-46, respectively. These nucleic acids have been cloned into the pETDEST42 expression vector and recombinant bacteria containing said vectors have been produced and maintained.

Example 5

Identification of Enzymes with ADH Activity

*Deinococcus* bacteria are grown at 45° C. or 30° C. The cell-free culture supernatants are tested according to the following protocol:
The tested reaction is as follows:

Ethanol+B-NAD(P)→Acetaldehyde+B-NAD(P)H.

The reaction is tested at 25° C., pH=8.8, A340 nm using Continuous Spectrophotometric
Rate Determination. The following reagents are used (initial concentrations):
Reagent A: 50 mM Sodium Pyrophosphate Buffer, pH 8.8;
Reagent B: Ethanol or Butan-1-ol or others;
Reagent C: 15 mM B-Nicotinamide Adenine Dinucleotide Solution (B-NAD). Idem for B-NADP;
Reagent D: Enzyme solution (cell crude extracts or purified protein);
Reagent E: 10 mM Sodium Phosphate Buffer with 0.1% BSA, pH 7.5 at 25° C. (Blank) (Blank).
Protocol
Pipette (in μl) the following reagents into microplates:

|  | Test | Blank |
| --- | --- | --- |
| Reagent A (Buffer) | 130 | 130 |
| Reagent B (Alcohol) | 10 | 10 |
| Reagent C (β-NAD) | 150 | 150 |

Shake the microplate and equilibrate to 25° C. Monitor the A340 nm until constant, using a suitably thermoregulated spectrophotometer. Then add:

| Reagent D (Enzyme Solution) | 10 μl |
| --- | --- |
| Reagent E (Blank) | 10 μl |

Immediately mix by inversion and record the increase in A340 nm for approximately 6 minutes. Obtain the ΔA340 nm/minute using the one to six minute range for both the Test and Blank.

The results show that tested strains DRH05 and DRH46 exhibit substantial ADH activities. The corresponding enzymes have been characterized, and the amino acid sequence of these ADH enzymes is represented in SEQ ID NOs: 32-41, respectively.

The coding nucleic acid sequences have also been isolated, and represented in SEQ ID NOs: 47-56, respectively. These nucleic acids have been cloned into the pETDEST42 expression vector and recombinant bacteria containing said vectors have been produced and maintained.

Example 6

Production of Recombinant Enzymes

As mentioned in Example 2, a nucleic acid encoding the alpha-amylase derived from M23r-2A, comprising SEQ ID NO: 3, was cloned into the pETDEST42 vector according to conventional recombinant techniques. In the vector, the nucleic acid is cloned in frame with a 6(His) tag, to facilitate purification of the recombinant protein.

*E. coli* cells harboring the recombinant nucleic acid were prepared and grown in 4 liters of Luria Bertani medium. Induction of the alpha-amylase protein production was performed overnight at 30° C. in presence of 1 mM IPTG. After centrifugation of the culture, cells were resuspended in 50 mM Tris HCl buffer pH8, 300 mM NaCl, 5 mM Imidazole, 5% Glycerine, 0.5 mM PMSF, 1 mg/ml Lysozyme and disrupted by sonication. Cell debris were removed by centrifugation and the supernatant was collected and applied to a His-Trap affinity chromatography column (HisTrap™ HP column). Fractions containing recombinant alpha-amylase were eluted with buffer containing 300 mM imidazole, 300 mM NaCl, 50 mM Tris HCl pH8. Fractions containing recombinant alpha amylase were dialyzed against 50 mM pH8 Tris HCl, 50 mM NaCl, 5% glycerine.

The alpha-amylase derived from M23r-2A was purified to 90% homogeneity with a yield of 4 mg/l of culture. FIG. 6A shows the protein is correctly expressed, with a molecular weight of about 49 kDa.

In a similar manner, FIG. 8 shows recombinant ADHs of the invention (ADH1-5 are SEQ ID NO: 32-36, respectively) are correctly expressed and purified.

All the recombinant enzymes which are characterized in the examples below, were produced and purified as described above.

Example 7

Activity of the Recombinant Amylase of SEQ ID NO: 3

*E. coli* harboring a recombinant nucleic acid encoding an alpha-amylase-derived from M23r-2A, cloned into the pET-DEST42 vector, was grown in the presence or absence of 1 mM IPTG in defined minimal medium containing 0.5% starch as sole carbon source. Aliquot of cultures were taken at 3 and 6 days of growth to measure alpha-amylase activity in the supernatant culture after depletion of the cells by centrifugation.

The α-amylase activity was evaluated by using the Ceralpha method (K-cera 08/05, Megazyme) that employs as substrates, the defined oligosaccharide "non-reducing-end blocked p-nitrophenyl maltoheptoside (BNPG7) in the presence of excess levels of a thermostable α-glucosidase (which has no action on the native substrate due to the presence of the blocking group). On the hydrolysis of the oligosaccharide by endo-acting α-amylase, the excess of α-glucosidase give quantitative hydrolysis of the p-nitrophenyl maltosaccharide fragment to glucose and free p-nitrophenol.

Crude enzyme (cell-free supernatants culture) or purified alpha-amylase (purified from soluble cytoplasmic fraction without peptide signal following procedure example 6) were incubated 30 min at 45° C. with 109 μg BNPG7 substrate in 50 mM sodium phosphate buffer pH7 in the presence or absence of 2.5 mM $Ca^{2+}$. The reaction was stopped at room temperature by addition of 300 μl Tri sodium phosphate ($Na_3PO_4$) 1% solution pH11. The absorbance of solutions was next read at 400 nm. The reaction blank containing water instead of crude enzyme was treated as indicated above. P-nitrophenol (10 mM, Sigma Aldrich, N7660) was used to construct a standard curve.

One unit of activity is defined as amount of enzyme, in the presence of excess thermostable α-glucosidase, required to release one micromole of p-nitrophenol from BNPG7 in one minute under the assay condition described above. Protein concentration of the supernatant has been determined with the MicroBC assay (Interchim) as indicated by the supplier and with BSA as standard.

The results are depicted in FIGS. 5 and 6. As shown FIG. 5A, the recombinant cells are able to grow in the presence of starch, as sole carbon source, only upon induction of the enzyme. Furthermore, FIG. 5B confirms the alpha amylolytic activity of the protein on purified starch. FIG. 6A shows the protein is correctly expressed, with a molecular weight of about 49 kDa, and FIG. 6B shows the protein exhibits, in the tested condition, an activity above 20 IU/mg. These results therefore clearly demonstrate the recombinant enzyme is fully active and exhibits a strong amylase activity.

In addition, the α-amylase activity was also evaluated by using DNS method (Table 1A) testing the ability of the cell-free culture supernatants to release reducing sugar monomer (maltose) from starch.

TABLE 1A

| Enzyme name | Substrate: Starch soluble (ref. S9765; Sigma) pH 7, 45° C. | | |
|---|---|---|---|
| | U/ml | Concentration (mg/ml) | Activity (U/mg) |
| Purified alpha amylase cytoplasmic. (without Signal PeptidePS) | 40 | 1.3 | 30.8 |

Table 1A shows that the recombinant amylase of SEQ ID NO: 3, exhibits, in the tested conditions (45° C., pH=7), an activity above 30 U/mg thus confirming that the alpha-amylase recombinant enzyme is fully active and exhibits a strong amylolytic activity.

The activity of the recombinant alpha-amylase was also tested in other experimental conditions as detailed in Table 1B below.

TABLE 1B

| Protein for Strain | pH optimum | T optimum | main degradation products | specific activity U/mg | substrate | stability |
|---|---|---|---|---|---|---|
| M23-3A | 9 | ≤40° C. | glucose/maltose/ maltodextrins | 104 | p-np α-D-maltoheptaoside | 2 h, 60° C. |

Table 1B shows that the recombinant amylase of SEQ ID NO: 3, exhibits, in the tested conditions (540° C., pH=9), an activity above 100 U/mg thus confirming that the recombinant alpha-amylase is fully active and exhibits a strong amylolyticamyolytic activity.

Temperature Effect and $Ca^{2+}$ Effect

Thermal inactivation of enzymes was performed at 60° C. during one hour in water-bath in the presence of absence of 5 mM $Ca^{2+}$. The samples were next cooled on ice 5 minutes before performing the enzymatic assays as described above in the presence or absence of 5 mM $Ca^{2+}$. The remaining activity was measured at 45° C. pH7 as described above. The non-heated samples were taken as 100%.

The results are presented FIG. 7A. They show that the addition of 5 mM Ca2+ increases thermostability of the purified amylase, and that in the presence of calcium, the recombinant enzyme is active even after 1 hour treatment at 60° C. Furthermore, as shown in Table 1B above (last column), the recombinant alpha-amylase is still active even after 2 hours treatment at 60° C.

HPLC Analysis

In another experiment, gelatinized Sigma starch was used as substrate to determine the hydrolysis pattern of the strain M23-3A and the recombinant enzyme of SEQ ID NO: 3 from strain M23-3A. After 24 hours hydrolysis, hydrolysis products were analyzed by HPLC. The gelatinization of the substrate was performed at 88° C. for 90 min. After the gelatinization the starch suspension was tempered to 45° C. and buffer was added.

The hydrolysis was carried out in 100 mM HEPES buffer (pH 8.0) containing 5 mM $CaCl_2$. Volume of the samples was 1.0 ml. The substrate concentration was 2 w-% with gelatinized starch. Enzyme loading was 0.1 Ceralpha U/ml. The M23-3A culture supernatant was concentrated circa 20× prior to the analysis using Vivaspin 20 centrifugal concentrators (5000 MWCO PES) and buffer was changed to 100 mM HEPES (pH 8.0) containing 5 mM $CaCl_2$.

Ceralpha activity of the concentrated sample was determined in 100 mM HEPES buffer containing 5.0 mM $CaCl_2$ at pH 7.0. After 24 h of incubation at 45° C. the hydrolysis reactions were terminated by adding 100 μl of 1 M NaOH. Samples were centrifuged (15 min, 3000 rpm) and filtered (Syringe Filter Acrodisc, GHP/PF, 45 um, 25 mm, Pall Life Science). Hydrolysis products were analyzed by HPLC using CarboPac PA-1 guard and analytical columns.

As shown in FIG. 7B, the recombinant enzyme from M23-3A strain leads mainly to glucose products whereas reference enzyme Termamyl 120L is not able to lead to glucose.

pH Optimum

Dye-labelled and cross-linked starch was used as a substrate (Ceralpha, Amylazyme, Megazyme), and incubated during 20 min, at 45° C. with the following buffers:
  100 mM sodium acetate-acetic acid (pH range 3.8-5.8)
  100 mM MOPS-NaOH (pH range 6.8-7.8)
  100 mM Glycine-NaOH (pH range 8.8-10.8)
All the buffers contained 5 mM CaCl2.

Crude enzyme (M23-3A culture supernatant) showed the highest activity at pH 7.0, while the purified recombinant M23-3A showed the highest activity at pH 9.0 (as shown in FIG. 13) in glycine-NaOH buffer. In MOPS buffer, the optimum pH was around 8.0 (FIG. 14).

Buffer Effect

Ceralpha substrate activity of the enzyme was determined in different buffers. The substrate was dissolved in 50 mM sodium phosphate buffer pH 7.0. The enzyme was diluted either in:
  Distilled water
  50 or 100 mM HEPES buffer pH 7.0
  50 or 100 mM MOPS buffer pH 7.0
  Storage buffer: 50 mM Tris-HCl+50 mM NaCl+5% glycerol, pH 7.0 or pH 8.0

Highest activities were obtained when the enzyme was diluted in HEPES buffer (as shown in table 2 below).

TABLE 2

| Buffer | Activity (U/ml) |
|---|---|
| Water | 49.2 |
| 50 mM MOPS pH 7.0 | 34.8 |
| 100 mM MOPS pH 7.0 | 37.2 |
| 50 mM HEPES pH 7.0 | 60.9 |
| 100 mM HEPES pH 7.0 | 68.8 |

TABLE 2-continued

| Buffer | Activity (U/ml) |
| --- | --- |
| Storage buffer pH 7.0 | 35.4 |
| Storage buffer pH 8.0 | 10.8 |

Higher activities were obtained when 5 mM $CaCl_2$ was added to MOPS (pH 7.0) and sodium phosphate was excluded from the samples. In such conditions, the activity of the enzyme ranged from 118.3 U/ml to 69.6 U/ml depending on the dilution.

In 200 mM HEPES (pH 7.0) containing 10 mM $CaCl_2$, the activity of the enzyme was 170 U/ml.

Thermal Stability of the Purified M23-3A α-Amylase

Thermal stability of the purified M23-3A α-amylase was studied using circular dicroism spectroscopy. The spectra were recorded in 10 mM HEPES buffer (pH 7.0) in the presence of 5 mM $CaCl_2$. Protein concentration was 2.9 µM and wavelength 222 nm.

The results are presented FIG. 15. Apparent thermal transition temperature ($T_{1/2}$) of the enzyme was 69° C. According to CD spectra, the enzyme has a fold. These results therefore clearly demonstrate the recombinant enzyme is fully active and exhibits a strong amylase activity.

Example 8

Activity of the Recombinant Glucoamylase of SEQ ID NO: 58

*E. coli* cells harboring the recombinant nucleic acid encoding a glucoamylase of SEQ ID NO: 58 (derived from strain M23-3A), cloned into the pETDEST42 vector, were prepared and grown in 4 liters of Luria Bertani medium. Induction of the glucoamylase protein production was performed overnight at 30° C. in 4 liters of Luria Bertani medium in presence of 1 mM IPTG. After centrifugation of the culture, cells were resuspended in 50 mM Tris HCl buffer pH8, 300 mM NaCl, 5 mM imidazole, 0.5 mM PMSF, 1 mg/ml Lysozyme and disrupted by sonication. Cell debris were removed by centrifugation and the supernatant was collected and applied to a Cobalt His-Trap affinity chromatography column (HisTrap™ HP column). Fractions containing recombinant glucoamylase were eluted with buffer containing 50 mM Tris HCl buffer pH8, 50 mM imidazole, 300 mM NaCl. Fractions containing recombinant glucoamylase were subsequently desalted using Hi-trap Desalting column against 50 mM Tris HCl pH8 buffer 50 mM NaCl, 5% glycerine.

The glucoamylase derived from M23r-2A was purified to 90% homogeneity.

The glucoamylase activity was evaluated by using starch (Fluka 85649) as a substrate. Glucose released during the incubation was quantified with glucose kit (Roche 11448676) using glucose as a standard.

The reaction was performed at 60° C. during 10 min, in 20 mM sodium acetate buffer pH 5.0. One unit of activity was defined as amount of enzyme required to release one micromole of glucose from the substrate in one minute under the assay condition described above. The results are shown in the table 3 below:

TABLE 3

| | Activity pH 5.0 (U/ml) | Specific Activity pH 5.0 (U/mg) |
| --- | --- | --- |
| M23-3A | 26.5 | 35.1 |

Table 3 shows that the recombinant glucoamylase exhibits, in the tested conditions (60° C., pH=5), an activity of 35.1 U/mg.

These results demonstrate that the glucoamylase recombinant enzyme of SEQ ID NO: 58 is fully active and exhibits a strong amylolytic activity.

Example 9

Activity of the Endoglucanase of SEQ ID NO: 60

*E. coli* harboring a recombinant nucleic acid encoding endoglucanase of SEQ ID NO: 60, cloned into the pETDEST42 vector, are grown in the presence or absence of 1 mM IPTG in defined minimal medium containing cellulose as carbon source. Aliquot of cultures is taken at 3 and 6 days of growth to measure endoglucanase activity in the supernatant culture after depletion of the cells by centrifugation.

The enzyme activity is assayed at 50° C. based on initial reaction rates in a 10-min reaction period. The reaction mixtures (0.5 mL) contain 1% (wt/vol) of the substrate (e.g., Avicel PH-105, RAC, carboxymethyl cellulose) in a 50 mmol/L 2-N-morpholino-ethanesulfonic acid (MES) buffer (pH 6.0) containing 1 mmol/L $CaCl_2$. Enzyme concentration in the reactions is 2 µg/mL (~20 nmol/L), unless otherwise noted. The reactions are terminated by boiling for 5 min. After centrifugation, aliquots of the supernatants are assayed for the release of the reducing sugars.

Concentration of reducing sugars is determined by the 2,2'-bicinchoninate method (Waffenschmidt and Janeicke, 1987) with modifications described by Zhang et al. (Zhang and Lynd, 2005) and with glucose as the standard, where the reduced reaction temperature (75° C.) can generate more accurate results for the reducing sugar ends for mixed cellodextrins. One unit of activity is defined as the amount of enzyme that releases 1 µmol of reducing sugar end per min.

After the hydrolysis of RAC substrate by 20 µg/mL of purified enzyme for 6 h, the soluble cellodextrins are analyzed by using a high-performance liquid chromatography (HPLC) equipped with a Bio-Rad HPX-42A column and a refractive index detector at a flow rate of 0.4 mL/min.

Example 10

Activity of the Recombinant Endoxylanase of SEQ ID NO: 6

*E. coli* harboring a recombinant nucleic acid encoding endoxylanase of SEQ ID NO: 6, cloned into the pETDEST42 vector, were prepared and grown in Luria Bertani medium. Induction of the endoxylanase protein production was performed during 6 hours at 37° C. in 4 liters of Luria Bertani medium in presence of 1 mM IPTG. After centrifugation of the culture, cells were resuspended in 50 mM Phosphate buffer pH7.5, 300 mM NaCl, 5 mM Imidazole, 0.5 mM PMSF, 1 mg/ml Lysozyme and disrupted by sonication. Cell debris were removed by centrifugation and the supernatant was collected and applied to a Nickel His-Trap affinity chromatography column (HisTrap™ HP column). Fractions containing recombinant endoxylanase were eluted with buffer containing 50 mM Phosphate buffer pH7.5, 50 mM imidazole, 300 mM NaCl. Fractions containing recombinant endoxylanase were subsequently desalted using Hi trap Desalting column against 50 mM Tris HCl pH8 buffer, 50 mM NaCl, 5% glycerine. The endoxylanase derived from MC3-4A was purified to 90% homogeneity with a yield of 10 mg/l of culture.

The endoxylanase activity was evaluated by using DNS method testing the ability of the recombinant protein to release reducing sugar monomer (xylose) from xylan or other substrate. The reaction was performed at 55° C. in microplates: 50 µl of purified protein were added to 50 µl of 1% (w/v) birchwood xylan (Sigma, X0502) or wheat arabinoxylan (Megazyme) prepared in 50 mM Sodium citrate pH4.5. After 30 minutes of incubation at 55° C., the reaction was stopped by addition of 150 µl of DNS (3.5 Dinitrosalicylic acid) solution. Microplates were then incubated at 90° C. during 30 min and cooled at room temperature for few minutes.

The OD was then read at 540 nm. Standard curve of xylose (0.41 to 8.33 µmol/ml) was used to determine µmol/ml of xylose realized in the assays. In a control sample, the enzyme was replaced by appropriate buffer. One unit of the endoxylanase activity is defined as amount of enzyme required to release one micromole of xylose in one minute under the assay condition described above. The results are shown in tables 4 and 5 below.

TABLE 4

| | Substrate: Xylan birchwood 1%, pH 4.5, 55° C. | | |
|---|---|---|---|
| Enzyme name | U/ml | Concentration (mg/ml) | U/mg |
| Purified recombinant MC3-4A cytoplasmic (without PS) | 1280 | 2 | 640 |
| Xylanase thermomyces lanuginosus (reference enzyme) | 200 | 4 | 50 |

TABLE 5

| | Substrate: Wheat arabinoxylan 1%, pH 4.5, 55° C. | | |
|---|---|---|---|
| Enzyme name | U/ml | Concentration (mg/ml) | U/mg |
| Purified recombinant MC3-4A cytoplasmic (without PS) | 700 | 2 | 350 |
| Xylanase thermomyces lanuginosus (reference enzyme) | 30 | 4 | 7.5 |

Table 4 shows that the recombinant endoxylanase of SEQ ID NO: 6, exhibits, in the tested conditions (55° C., pH=4.5, xylan birchwood as substrate), the activity of 640 U/mg thus confirming that the recombinant enzyme is fully active. Furthermore, the activity of the recombinant endoxylanase enzyme is approximately 13-fold higher in comparison with the activity of the reference enzyme of *Xylanase thermomyces lanuginosus*.

Table 5 shows that the recombinant endoxylanase of SEQ ID NO: 6, exhibits, in the tested conditions (55° C., pH=4.5, wheat arabinoxylan as substrate), the activity of 350 U/mg thus confirming that the recombinant enzyme is fully active. Furthermore, the activity of the recombinant endoxylanase enzyme is approximately 47-fold higher in comparison with the activity of the reference enzyme of *Xylanase thermomyces lanuginosus*.

In another series of experiments, the recombinant endoxylanase activity was also compared to the activity of other reference enzymes such as *T. reesei* Xyn11A and *T. maritima* Xyn10A by using DNS method and Roth xylan as substrate. These assays were performed using 100 µl enzymes (dilutions from 1:500-1:8000) and 100 µl 1% Roth xylan in 500 mM Na-acetate pH 5.0.

The substrate used was 1% birch glucuronoxylan (Roth 7500) and the released xylo-oligosaccharides were quantified in a chromogenic reaction. The assay was performed on 96-well microtiter plates. A 4% stock of the substrate (in $H_2O$) was first prewarmed to the assay temperature (55° C.). 25 µl of the culture supernatants and 50 µl of McIlvaine buffer (pH 3-8) were pipetted to the wells. The plate was tempered for 5 min at 55° C. after which 25 µl of the prewarmed substrate was added. The reaction was performed at 55° C. during 10 minutes. The reaction was ended by adding 100 µl of DNS (dinitrosalisylic acid). The reaction mixture was pipetted into 96-well PCR plate, sealed with a folio seal and heated at a PCR block at 98° C. for 5 min and cooled on ice. 150 µl of the mixture was pipetted into a 96-well microtiter plate and the absorbance was measured at 540 nm. Enzyme zero and measurement zero were applied to all samples.

Pure xylose was used as a standard and the standards were treated similarly as the samples. The absorbances were converted to enzyme activity (U/ml) by using standard curve. In a control sample, the enzyme was replaced by appropriate buffer. One unit of the endoxylanase activity is defined as amount of enzyme required to release one micromole of xylose in one minute under the assay conditions described above. The results of these experiments are shown in table 6 below.

TABLE 6

| protein | Specific activity (U/mg) |
|---|---|
| MC3-4A | 607 |
| *T. reesei* Xyn11A | 343 |
| *T. maritima* Xyn10A | 32 |

Table 6 confirms that the specific activity of purified recombinant xylanase from MC3-4A (of 607 U/mg) is almost 2-fold better than that of *T. reesei* Xyn11A and 20-fold better that *T. maritima* Xyn10A.

Hydrolysis Optimum

The recombinant endoxylanase activity was also compared to the activity of the reference enzymes (i.e., *T. reesei* Xyn11A, *T. reesei* Xyn1 and *T. maritima* Xyn10A) in a test of hydrolysis of arabinoxylan. This assay was performed with wheat arabinoxylan (Megazymes) 5 g/l as substrate. Enzyme dose was 0.02 mg/g substrate. The reaction was performed at 55° C. at pH 5.0. Hydrolysis of arabinoxylan was evaluated at the following time points: 4 h, 24 h and 48 h as shown in FIG. 11A). Releasing of reducing sugars was determined with PAHBAH using xylose as standard. The rate of hydrolysis (w/w) was calculated as the mass of measured soluble xylose divided by the initial mass of arabinoxylan (calculated as xylose).

FIG. 11A shows that the experimental maximum of hydrolysis of arabinoxylan by the recombinant *Deinococcus* endoxylanase MC3-4A of the invention was above 33%. The results shown in FIG. 11A also demonstrate that the recombinant enzyme of the invention performs approximately 3-fold more efficiently than *T. reesei* Xyn11A, 11-fold more efficiently than *T. maritima* Xyn10A and 63-fold more efficiently than *T. reesei* Xyn1.

In another experiment, samples from 48 hours time point were examined by HPLC in order to analyze the arabinoxylan hydrolysis products. As shown in FIG. 11B, the recombinant enzyme from MC3-4A strain leads mainly to xylobiose and xylotriose products. The recombinant endoxylanase was also tested in xylan hydrolysis (FIG. 11C). Photographs of FIG.

11C show that the recombinant endoxylanase from *Deinococcus* MC3-4A strain clearly shows xylanolytic activity.

pH Optimum

Assays were performed in microtiter plates containing 50 µl McIlvaine buffer pH 3-8, 25 µl enzyme (20 µg/ml) and 25 µL 4% Roth xylan in H2O. The samples were then heated at 55° C. for 10 minutes. The reaction was stopped with 100 µl of DNS and incubated at 98° C. for 5 minutes. OD was read at 540 nm. The purified recombinant endoxylanase enzyme from strain MC3-4A showed the highest activity at pH 5.0. However, the activity of the recombinant endoxylanase remains high in a very broad range including for example pH 4.0, where the reference enzyme has almost no activity (as shown in FIG. 9).

Temperature Optimum

Assays were performed in microtubes containing 100 µl of the recombinant enzyme (final concentration 2% g/ml, *T. maritima* 16*g/ml) and 100µ 2% Roth xylan in 50 mM Na-acetate pH 5. The samples were heated at 55° C. for 10 minutes. The reaction was stopped with 200 µl of DNS and incubated at 98° C. for 5 minutes. OD was read at 540 nm. As shown in FIG. 10, the temperature optimum curve for the recombinant endoxylanase is very broad since at least 90% of its activity is retained in the temperature range between 55 and 70° C. In conclusion, the temperature optimum for the recombinant xylanase from MC3-4A is much broader than that of the reference enzymes *T. maritima* Xyn10A and *T. reesei* Xyn11A.

Thermal Stability of the Recombinant Endoxylanase

Temperature stability of the MC3-4A endoxylanase over 24 hours was studied. *T. reesei* Xyn11A was used as reference enzyme. Residual xylanase activity was then measured with arabinoxylan after incubation at different temperatures (i.e., 45° C., 55° C., 60° C. and 65° C.) for 24 hours. The results are presented in FIG. 12. The recombinant enzyme is still active after 24 hours of treatment at 55° C., the remaining activity being of approximately 20%. The results in FIG. 12 also show that the recombinant endoxylanase MC3-4A is more stable and more efficient that the reference xylanase from *T. reesei* Xyn11A.

Furthermore, thermal stability of the recombinant endoxylanase MC3-4A was also studied after 48 hours incubation in comparison with the reference enzyme *T. reesei* Xyn11A. The results are presented in table 7 below.

TABLE 7

| protein | Stability |
|---|---|
| MC3-4A | 48 h; 50° C. |
| T. reesei Xyn11A | 48 h; 45° C. |

Table 7 shows that the recombinant endoxylanase enzyme of the invention is still stable after 48 hours incubation at 50° C. contrary to the reference enzyme *T. reesei* Xyn11A, which is no more stable when the incubation temperature is higher than 45° C. All the above results demonstrate that the recombinant endoxylanase enzyme of SEQ ID NO: 6 is fully active and exhibits a strong xylanolytic activity.

Example 11

Identification of an Enzyme with Acetyl Xylan Esterase Activity

*Deinococcus* sp were inoculated on a minimal culture medium made up of a MOPS buffer solution at pH7 and filtered: acid MOPS buffer 40 mM (Sigma, France), $NH_4Cl$ 20 mM, KOH 10 mM, NaOH 10 mM, $CaCl_2$ 0.5 $Na_2SO_4$ 0.276 mM, $MgCl_2$ 0.528 mM), a solution of micronutriments at pH5 (($NH_4$)$_6$($MO_7$)$_{24}$ 3 nM, $H_3BO_3$ 400 nM, $CoCl_2$ 30 nM, $CuSO_4$ 10 nM, $MnCl_2$ 250 nM, $ZnSO_4$ 10 nM), a solution of vitamins at pH4 (1 µg/L of D-biotin, niacin, pyridoxal-HCl, thiamin-HCl and vitamin B12), a solution of $K_2HPO_4$ at 5.7 mM as well as a solution of $FeCl_3$ at 20 µM in $NaH_2(C_3H_5O(COO)_3)$. Acetylated xylan was added as carbon source.

The results obtained by the inventors show that DRH-46 strain grows in the presence of xylan. The inventors have been able to identify two acetyl xylan esterases (called herein: acetyl xylan esterase no 1 (AXE1) and acetyl xylan esterase no 2 (AXE2)). The amino acid sequences of these enzymes which are capable of degrading acetylated xylan are represented in SEQ ID NO: 64 and 66, respectively.

The coding nucleic acid sequences have also been isolated, and represented in SEQ ID NO: 63 and 65, respectively. These nucleic acids have been cloned into the pETDEST42 expression vector and recombinant bacteria containing said vectors have been produced and maintained.

*E. coli* harboring a recombinant nucleic acid encoding AXE1 or AXE2, cloned into the pETDEST42 vector, were prepared and grown in Luria Bertani medium. Induction of the AXE1 or AXE2 recombinant protein production were performed overnight at 30° C. in 4 liters of Luria Bertani medium in presence of 1 mM IPTG. After centrifugation of the culture, cells were resuspended in 50 mM Tris HCl buffer pH8, 300 mM NaCl, 5 mM Imidazole, 0.5 mM PMSF, 10 mg/ml Lysozyme and disrupted by sonication. Cell debris were removed by centrifugation and the supernatant was collected and applied to a Nickel His-Trap affinity chromatography column (HisTrap™ HP column). Fractions containing recombinant acetyl xylan esterase were eluted with buffer containing 200 mM imidazole, 300 mM NaCl, 50 mM Tris HCl buffer pH8.0, 10% Glycerine. Fractions containing recombinant acetyl xylan esterase were subsequently desalted using Hi trap Desalting column against 50 mM Tris HCl pH8 buffer 50 mM NaCl, 10% glycerine.

The acetyl xylan esterases AXE1 and AXE2 derived from DRH-46 were purified to 90% homogeneity.

The acetyl xylan esterase activity was evaluated by using acetylated xylo-oligomers substrate (Birke retentate), extracted with water from birch wood after steam treatment (in BFH Hamburg). The substrate was prepared in 50 mM sodium citrate buffer pH 5 (50 mg/ml).

The reaction was performed at 50° C.:30 µl of recombinant purified protein was added to 30 µl of substrate (acetylated xylo oligomer 50 mg/ml, DPn of 10). The assay was performed during 1 hour at pH7 at 50° C. The reaction was terminated by boiling the samples for 3 min. The samples were centrifuged and the acetic acid formed was determined enzymatically with Boehringer test combination kit 148261. Enzyme and measurement zero were applied. One unit of activity was defined as amount of enzyme required to release one micromole of acetic acid from the substrate in one minute under the assay condition described above. The results are shown in the table 8 below.

TABLE 8

| Sample | Specific activity (U/mg) at pH 7 |
|---|---|
| AXE1 | 0.16 |
| AXE2 | 0.1 |
| Orp. AXE | 0.03 |

Table 8 shows that the recombinant acetyl xylan esterase AXE1 and AXE2 exhibit, an activity 5 to 3-fold higher (respectively) in comparison with the activity of the reference enzyme of *Orpinomyces* sp. Acetyl xylan esterase.

pH Optimum

Assays were performed in microtiter plates containing 50 µl substrate (alpha-naphthyl acetate) and 50 µl of enzyme dilution in buffer. Then, ΔAbsorbance 235 nm with Varioskan was measured for 10 minutes. As shown in FIG. 18, the purified recombinant acetyl xylan esterase enzyme from strain DRH-46 showed the highest activity at pH 8 (AXE1) and pH8-9 (AXE2).

All the above results demonstrate that the recombinant acetyl xylan esterase enzymes of SEQ ID NO: 64 and 66 are fully active and exhibit a strong xylanolytic activity.

Example 12

Activity of the Recombinant Alpha-L-Arabinofuranosidase of SEQ ID NO: 68

*E. coli* harboring a recombinant nucleic acid encoding alpha L arabinofuranosidase of SEQ ID NO: 68 cloned into the pETDEST42 vector, were prepared and grown in Luria Bertani medium. *E. coli* culture was induced for recombinant protein production. The induction was performed during 5 hours at 30° C. in 4 liters of Luria Bertani medium in presence of 1 mM IPTG. After centrifugation of the culture, cells were resuspended in 50 mM Phosphate buffer pH7.4, 300 mM NaCl, 5 mM Imidazole, 0.5 mM PMSF, 1 mg/ml Lysozyme and disrupted by sonication. Cell debris were removed by centrifugation and the supernatant was collected and applied to a Nickel His-Trap affinity chromatography column (His-Trap™ HP column). Fractions containing recombinant alpha L arabinofuranosidase were eluted with buffer containing 300 mM imidazole, 300 mM NaCl, and 50 mM Phosphate pH7.4. Fractions containing recombinant alpha L arabinofuranosidase were subsequently desalted using Hi-trap Desalting column against 50 mM Phosphate pH7.4 buffer 50 mM NaCl, 10% glycerine. The alpha-L-arabinofuranosidase derived from DRH-46 was purified to 90% homogeneity.

The arabinofuranosidase activity was evaluated as described below.

The reaction was performed at 30° C. in microplates: 100 µl of purified proteins were added to 100 µl of substrate: 4-methyl umbelliferyl alpha-L-arabinofuranoside 0.01 mM (reference Sigma, ref: M9519) prepared in 50 mM sodium phosphate 50 mM pH7. In a control sample, the enzyme was replaced by appropriate buffer. Standard used was 4-methyl umbelliferone sodium salt (Sigma, ref: M1508) prepared in 50 mM sodium phosphate pH7.0 (0.0005 mM-5 mM). Fluorescence was read (excitation 355 nm, emission 460 nm) using BMG labtech Fluo. One unit of the alpha-L-arabinofuranoside activity is defined as amount of enzyme required to release 1 µmol of 4-methyl umbelliferone in 1 min. The results are shown in Table 9A below.

TABLE 9A

| Enzyme name | Substrate: 4-methyl umbelliferyl alpha L arabinofuranoside, pH 7, 30° C. U/mg |
|---|---|
| Alpha L arabinofuranosidase DRH46.61-237 | 1500 |
| Alpha L arabinofuranosidase *Aspergillus Niger* (Megazyme E-AFASE; reference enzyme) | 300 |

Table 9A shows that the recombinant alpha-L-arabinofuranosidase of SEQ ID NO: 68, exhibits, in the tested conditions, the activity of 1500 U/mg thus confirming that the recombinant enzyme is fully active. Furthermore, the activity of the recombinant alpha-L-arabinofuranosidase enzyme is 5-fold higher in comparison with the activity of the reference enzyme of *Aspergillus Niger* Megazyme E-AFASE.

The activity of the recombinant alpha-L-arabinofuranosidase was also tested in other experimental conditions as detailed in Table 9B below.

The substrate used was 2 mM p-nitrophenyl-alpha-L-arabinofuranoside (Sigma N-3641) in 50 mM sodium citrate buffer pH 5 and the colour formed by p-nitrophenyl released from the substrate is measure at 400 nm. The assay was performed on 96-well microtiter plates. The substrate was prewarmed to the assay temperature (50° C.). 10 µl of the culture supernatant was pipetted into the wells and the plate was tempered to 50° C. followed by 90 µl of the substrate. The plate was incubated in a thermal mixer (Eppendorf) for 10 min and the reaction was ended by adding 50 µl on 1M $Na_2CO_3$. The fainted color was measured by a spectrophotometer at 400 nm. Enzyme and measurement zero were applied. p-nitrophenol was used as a standard and the standards were treated similarly as the samples. The absorbances were converted to enzyme activities (U/ml) by utilizing the standard curve.

TABLE 9B

| Strain | Enzyme | pH optimum | T optimum | main degradation products | specific activity U/mg | substrate |
|---|---|---|---|---|---|---|
| DRH46 | α-L-arabinufuranosidase (DRH46.61_237) | 7 | 45° C. | arabinose | 24.3 | pnp-α-arabinofuranoside |
| *A. niger* (Megazyme) | | | 45-50° C. | | 7.7 | pnp-α-arabinofuranoside |
| *Bifidobacterium* sp. (Megazyme) | | | 40° C. | | 0.08 | pnp-α-arabinofuranoside |

Table 9B shows that the recombinant alpha-L-arabinofuranosidase of SEQ ID NO: 68, exhibits, in the tested conditions, the activity of 24.3 U/mg thus confirming that the recombinant enzyme is fully active.

Furthermore, the activity of the recombinant alpha-L-arabinofuranosidase enzyme is 3 to 303-fold higher in comparison with the activity of the reference enzyme of *Aspergillus Niger* or *Bifidobacterium* sp. respectively.

Stability: At 40° C. pH7, the enzyme keeps 70% of activity left at 24 h.

All the above results demonstrate that the recombinant alpha L arabinofuranosidase enzyme of SEQ ID NO: 68 is fully active and exhibit a strong xylanolytic activity.

Example 13

Activity of the Recombinant Endocellulase of SEQ ID NO: 70

*E. coli* harboring a recombinant nucleic acid encoding endocellulase, cloned into the pETDEST42 vector, were prepared and grown in Luria Bertani medium. *E. coli* culture was induced for recombinant protein production. The induction was performed overnight at room temperature in 4 liters of Luria Bertani medium in presence of 1 mM IPTG. After centrifugation of the culture, cells were resuspended in 50 mM Tris HCl buffer pH8, 50 mM NaCl, 10% Glycerine, 0.5 mM PMSF, 1 mg/ml Lysozyme and disrupted by sonication. Cell debris were removed by centrifugation and the supernatant was collected and applied to a Nickel His-Trap affinity chromatography column (HisTrap™ HP column). Fractions containing recombinant endocellulase were eluted with buffer containing 50 mM Tris HCl pH8, 200 mM imidazole, 50 mM NaCl. Fractions containing recombinant endocellulase were subsequently dialysed against 50 mM Tris HCl pH8 buffer, 50 mM NaCl, 10% glycerine.

The endocellulase derived from DRH-46 was purified to 90% homogeneity.

The substrate used to evaluate endocellulase activity is 2% carboxymethyl cellulose (CMC) (Sigma) dissolved into 50 mM NaAc buffer (pH 5). The assay is performed on 96-well microtiter plates. 50 µl of culture supernatant and 50 µl of substrate are mixed and incubated at 40° C. O/N. The reaction is terminated by adding 100 µl of DNS and heated at 98° C. for 10 min. After cooling the samples on ice the formed color was measured at 540 nm. Glucose was used as the standard and the standard curve was utilized for converting the absorbances into reducing sugars (g/l).

The results are shown in the table 10 below. Furthermore, FIG. 16 shows the protein is correctly expressed, with a molecular weight of about 88 kDa.

TABLE 10

| Sample | Specific activity (U/mg) pH 7 60° C. |
|---|---|
| Endocellulase | 11.15 |

Table 10 shows that the recombinant endocellulase enzyme of SEQ ID NO: 70 is fully active and exhibits a strong cellulolytic activity.

The recombinant endocellulase was also tested in AZO-cellulose hydrolysis (S-ACMCL Megazyme). Photographs of FIG. 17 show that the purified recombinant endocellulase from *Deinococcus* DRH-46 strain clearly shows cellulolytic activity.

All the above results clearly demonstrate the recombinant endocellulase is fully active and exhibits a strong cellulolytic activity.

Example 14

Identification of Enzymes with Alpha-Glucuronidase Activity

*Deinococcus* sp are inoculated on a minimal culture medium made up of a MOPS buffer solution at pH7 and filtered: acid MOPS buffer 40 mM (Sigma, France), $NH_4Cl$ 20 mM, KOH 10 mM, NaOH 10 mM, $CaCl_2$ 0.5 $Na_2SO_4$ 0.276 mM, $MgCl_2$ 0.528 mM), a solution of micronutriments at pH5 (($NH_4$)$_6$($MO_7$)$_{24}$ 3 nM, $H_3BO_3$ 400 nM, $CoCl_2$ 30 nM, $CuSO_4$ 10 nM, $MnCl_2$ 250 nM, $ZnSO_4$ 10 nM), a solution of vitamins at pH4 (1 µg/L of D-biotin, niacin, pyridoxal-HCl, thiamin-HCl and vitamin B12), a solution of K2HPO4 at 5.7 mM as well as a solution of FeCl3 at 20 µM in NaH2(C3H5O (COO)3). Alpha-glucuronoside is used as substrate.

The inventors have also been able to identify an alpha-glucuronidase enzyme. The amino acid sequence of this enzyme is represented in SEQ ID NO: 72. The coding nucleic acid sequence has also been isolated, and represented in SEQ ID NO: 71.

The invention claimed is:

1. An isolated polynucleotide comprising a nucleic acid encoding an alpha-amylase and a heterologous promoter, wherein the nucleic acid is operably linked to the heterologous promoter, and wherein the amino acid sequence of said alpha-amylase is selected from the group consisting of:
   a) an amino acid sequence having at least 90% sequence identity to the amino acid sequence of SEQ ID NO: 3,
   b) a fragment of the amino acid sequence of SEQ ID NO: 3, wherein the fragment has alpha-amylase activity, and
   c) the amino acid sequence of SEQ ID NO: 62.

2. A vector comprising the polynucleotide of claim 1.

3. A recombinant cell comprising the polynucleotide of claim 1, wherein said recombinant cell is a yeast, fungal or bacterial cell.

4. The recombinant cell of claim 3, wherein said recombinant cell is transformed or transfected with a vector comprising said polynucleotide.

5. The recombinant cell of claim 3, which is a *Deinococcus* bacterium.

6. A method for modifying biomass, comprising contacting the biomass with the recombinant cell of claim 3 to thereby modify the biomass.

7. A co-culture of at least two distinct microorganisms, wherein at least one of said microorganisms is the *Deinococcus* bacterium of claim 5 and at least one of said microorganisms is a prokaryotic or eukaryotic cell, wherein each of said at least two microorganisms requires the other microorganism(s) for its survival and growth.

8. The co-culture of claim 7, wherein at least one of said microorganisms is a yeast cell.

9. The isolated nucleic acid of claim 1, wherein the amino acid sequence of said alpha-amylase comprises an amino acid sequence having at least 90% sequence identity to the amino acid sequence of SEQ ID NO: 3.

10. The isolated nucleic acid of claim 1, wherein the amino acid sequence of said alpha-amylase comprises a fragment of the amino acid sequence of SEQ ID NO: 3, wherein the fragment has alpha-amylase activity.

11. The isolated nucleic acid of claim 1, wherein the amino acid sequence of said alpha-amylase comprises the amino acid sequence of SEQ ID NO: 62.

* * * * *

SEQUENCE LISTING

```
<160> NUMBER OF SEQ ID NOS: 75

<210> SEQ ID NO 1
<211> LENGTH: 403
<212> TYPE: PRT
<213> ORGANISM: Deinococcus sp.
<220> FEATURE:
<221> NAME/KEY: MISC_FEATURE
<223> OTHER INFORMATION: Cellobiohydrolase (CBH) derived from  M1-3H
      (partial sequence)
<220> FEATURE:
<221> NAME/KEY: misc_feature
<222> LOCATION: (394)..(398)
<223> OTHER INFORMATION: Xaa can be any naturally occurring amino acid

<400> SEQUENCE: 1

Met Lys Leu Gly Glu Asp Thr Thr Ala Pro Tyr Glu Phe Thr Val Asn
1               5                   10                  15

Ala Asp Pro Gly Leu Asn Gly Thr His Val Tyr Ser Ala Gln Ala Val
            20                  25                  30
```

```
Ala Gly Asp Ala Ala Gly Ile Ser Ala Pro Val Ser Val Gln Ile Arg
             35                  40                  45

Ile Ala Asp Thr Arg Thr Thr Glu Leu Leu Ser Asn Gly Asp Phe Ser
 50                  55                  60

Gln Gly Leu Asn Pro Trp Trp Thr Ala Gly Thr Ala Ala Ser Thr Thr
 65                  70                  75                  80

Gly Gly Glu Thr Cys Leu Asn Ile Thr Gln Pro Gly Ser Asn Pro Trp
                 85                  90                  95

Asp Val Leu Phe Gly Gln Gly Gly Val Gly Leu Asn Glu Gly Gly Thr
                100                 105                 110

Tyr Thr Leu Ser Phe Thr Ala Arg Ala Ala Gln Pro Thr Ser Phe Arg
            115                 120                 125

Thr Leu Leu Gln Phe Asp Gly Ala Pro Tyr Thr Asn Tyr Phe Val Gln
        130                 135                 140

Asp Ala Asp Val Thr Ser Gln Pro Lys Thr Phe Thr Ser Thr Phe Thr
145                 150                 155                 160

Met Ala Gln Pro Ser Asp Ala Lys Ala Ala Phe Gln Phe Gln Leu Gly
                165                 170                 175

Ala Arg Ala Ala Thr Thr Val Cys Phe Ser Arg Ile Ser Leu Thr Gly
            180                 185                 190

Pro Ala Phe Gly Ser Ala Val Pro Ala Pro Gly Ala Asp Asp Leu Lys
        195                 200                 205

Leu Val Arg Leu Asn Gln Thr Gly Tyr Leu Pro Asp Arg Pro Lys Leu
210                 215                 220

Ala Ala Leu Pro Phe Asp Ser Asp Arg Pro Leu Pro Trp Thr Leu Leu
225                 230                 235                 240

Asp Gly Thr Arg Thr Val Ala Ser Gly Val Thr Arg Val Phe Gly Ala
                245                 250                 255

Asp Ala Ala Ser Gly Glu His Val His Gln Val Asp Phe Ser Ala Val
            260                 265                 270

Thr Ala Pro Ala Asp Gly Leu Val Leu Asp Val Ala Gly Phe Arg Ser
        275                 280                 285

His Pro Phe Arg Ile Gly Arg Val Tyr Asp Gly Leu Lys Arg Asp Ala
290                 295                 300

Leu Ala Tyr Phe Tyr His Asn Arg Ser Gly Thr Pro Ile Lys Ala Lys
305                 310                 315                 320

Tyr Val Gly Asp Ala Trp Ala Arg Pro Ala Gly His Ala Gly Thr Ser
                325                 330                 335

Pro Asn Gln Gly Asp Thr Arg Val Ser Cys Phe Lys Gly Thr Asp Gln
            340                 345                 350

Ala Gly Asn Val Trp Pro Gly Cys Gly Tyr Glu Leu Asp Ala Ser Gly
        355                 360                 365

Gly Trp Tyr Asp Ala Gly Asp His Gly Lys Tyr Val Val Asn Gly Gly
370                 375                 380

Val Ser Val Trp Thr Leu Leu Asn Leu Xaa Xaa Xaa Xaa Ser Gly
385                 390                 395                 400

Ala Arg Ala
```

<210> SEQ ID NO 2
<211> LENGTH: 485
<212> TYPE: PRT
<213> ORGANISM: Deinococcus sp.
<220> FEATURE:
<221> NAME/KEY: MISC_FEATURE
<223> OTHER INFORMATION: Endoglucanase derived from DRH-46

<400> SEQUENCE: 2

```
Met His Lys Arg Thr Val His Leu Ala Leu Leu Thr Cys Ser Leu Leu
1               5                   10                  15

Ala Leu Thr Ala Cys Gly Thr Asn Thr Gln Val Asp Leu Ala Ser Ala
            20                  25                  30

Pro Pro Lys Ile Glu Pro Gly Phe Arg Pro Gln Ser Ala Thr Ala Ala
            35                  40                  45

Asp Val Trp Val Thr His Pro Asp Arg Ser Arg Leu Ile Ser Trp Asp
50                  55                  60

Gly Thr Lys Asn Phe Val Ser Asp Gly Asn Val Thr Pro Ser Thr Leu
65                  70                  75                  80

Thr Ile Asn Glu Ser Gln Thr Phe Gln Thr Met Glu Gly Phe Gly Ala
                85                  90                  95

Ser Leu Thr Asp Ser Ala Gly Trp Leu Met Trp Asn Lys Met Ser Ala
            100                 105                 110

Thr Gln Arg Asn Ser Leu Met Gln Ser Leu Phe Gly Phe Asn Asp Gly
            115                 120                 125

Asn Ala Gly Ile Ser Phe Leu Arg Ile Pro Leu Gly Gly Ser Asp Met
130                 135                 140

Ala Leu Ser His Tyr Thr Tyr Asn Asp Gly Ala Ala Asp Pro Asn Leu
145                 150                 155                 160

Thr Arg Phe Ser Ile Val His Asp Leu Thr Tyr Ile Val Pro Leu Ala
                165                 170                 175

Lys Gln Ala Lys Thr Ile Asn Ser Ser Leu Arg Tyr Met Gly Thr Pro
            180                 185                 190

Trp Ser Pro Pro Ala Trp Met Lys Thr Ser Gly Ser Leu Asn Ser Gly
            195                 200                 205

Lys Leu Lys Pro Glu His Tyr Gln Thr Tyr Ala Asn Tyr Leu Arg Lys
210                 215                 220

Thr Phe Asp Ala Tyr Asn Ala Gln Gly Val Lys Phe Asn Tyr Leu Ser
225                 230                 235                 240

Pro Gln Asn Glu Pro Gln Tyr Glu Pro Gly Ser Tyr Pro Gly Thr Lys
                245                 250                 255

Phe Glu Trp Tyr Asp Glu Leu Asn Phe Val Arg Gly His Leu Phe Asn
            260                 265                 270

Thr Met Asn Gly Thr Gly Val Lys Ile Leu Thr Leu Asp His Asn Trp
            275                 280                 285

Asp Leu Glu Trp Tyr Pro Arg Ala Val Leu Asn Glu Gly Ser Ala Tyr
290                 295                 300

Tyr Glu Gly Thr Ala Trp His Cys Tyr Ala Gly Asn Asn Ala Ala Met
305                 310                 315                 320

Ser Arg Val Arg Asp Ala Phe Pro Ser Lys Gly Val Tyr Leu Thr Glu
                325                 330                 335

Cys Ser Gly Gly Leu Trp Ala Thr Asn Phe Gly Asp Asn Met Lys Trp
            340                 345                 350

Asn Met Gln Asn Leu Phe Ile Gly Gly Thr Lys Asn Trp Ala Lys Thr
            355                 360                 365

Val Leu Phe Trp Ser Leu Ala Leu Asp Pro Ser Gly Gly Pro His Leu
370                 375                 380

Gly Gly Cys Ser Asn Cys Arg Gly Val Val Ser Ile Asn Gln Asn Gly
385                 390                 395                 400

Gly Ala Val Thr Phe Asn Glu Glu Tyr Tyr Ala Ile Ala His Phe Ala
```

```
                        405                 410                 415
Arg Phe Val Trp Pro Gly Ala Val Arg Ile Gly Thr Thr Asp Ser Ser
                420                 425                 430

Asp Gly Lys Phe Ile Gly Val Ala Phe Arg Asn Thr Asn Gly Ala Lys
            435                 440                 445

Ala Leu Val Val Leu Asn Gln Ser Asn Ser Thr Ala Thr Phe Lys Met
        450                 455                 460

Val Trp Asn Gly Lys Ser Ile Gln Gln Ser Leu Pro Ala Ser Gly Val
465                 470                 475                 480

Ala Thr Val Phe Trp
                485

<210> SEQ ID NO 3
<211> LENGTH: 485
<212> TYPE: PRT
<213> ORGANISM: Deinococcus sp.
<220> FEATURE:
<221> NAME/KEY: MISC_FEATURE
<223> OTHER INFORMATION: Alpha -amylase derived from M23r-2A

<400> SEQUENCE: 3

Met Arg Arg Leu Pro Leu Leu Ala Ala Leu Leu Ala Ser Leu Ala Gly
1               5                   10                  15

Ala Gln Ala Ser Pro Thr Leu Pro Ser Phe Glu Gly Gln Val Ile Tyr
            20                  25                  30

Gln Val Met Pro Asp Arg Phe Phe Asp Gly Asn Lys Ala Asn Asp Ala
        35                  40                  45

Gly Val Asp Arg Ser Asp Pro Arg Ala Trp His Gly Asp Leu Ala
    50                  55                  60

Gly Leu Thr Ala Lys Leu Pro Tyr Leu Arg Gln Leu Gly Ala Thr Ala
65                  70                  75                  80

Val Trp Leu Thr Pro Ile Tyr Arg Gln Gln Thr Ala Asn Ala Phe Gly
                85                  90                  95

Thr Ala Pro Tyr His Gly Tyr Trp Pro Ala Asp Phe Arg Asp Val Asp
            100                 105                 110

Pro His Phe Gly Thr Leu Ala Asp Phe Gly Phe Val Lys Ala Ala
        115                 120                 125

His Gly Ala Gly Leu Arg Val Val Leu Asp Gln Val Ile Asn His Tyr
    130                 135                 140

Gly Tyr Glu Ala Ala Val Lys Glu His Pro Ala Trp Phe Asn Gly
145                 150                 155                 160

Lys Ala Ala Cys Asp Ala Ser Gly Asn Lys Asp Val Asn Cys Pro Leu
                165                 170                 175

Ala Gly Leu Pro Asp Leu Lys Gln Ser Asn Pro Glu Val Arg Ala Leu
            180                 185                 190

Leu Leu Gly Asn Ala Asp Phe Trp Arg Gly Gln Gly Val Asp Gly Phe
        195                 200                 205

Arg Tyr Asp Ala Ile Lys Asn Val Glu Thr Pro Phe Leu Lys Glu Leu
    210                 215                 220

Leu Ala Arg Asp Arg Ala Ala Gly Thr Trp Thr Leu Gly Glu Trp Tyr
225                 230                 235                 240

Gly Ala Asp Thr Gly Thr Val Ala Asp Trp Gln Gln Ala Gly Phe Asp
                245                 250                 255

Ser Leu Phe Leu Phe Ser Leu Gln Gln Ala Met Gly Gln Ser Leu Met
            260                 265                 270
```

```
Gly Gly Gln Gly Leu Ser Arg Val Ala Ser Val Leu Ser Arg Gln Gly
            275                 280                 285

Glu Leu Pro Arg Pro Gly Glu Val Ala Leu Phe Leu Asp Asn His Asp
        290                 295                 300

Val Pro Arg Phe Ala Gln Gly Ser Leu Phe Glu Asp Gln Ala Gln Ala
305                 310                 315                 320

Arg Thr Arg Tyr Gly Leu Arg Ala Leu Met Thr Leu Lys Gly Val Pro
                325                 330                 335

Val Leu Trp Gln Gly Thr Glu Ile Ala Met Arg Gly Gly Pro Asp Pro
            340                 345                 350

Asp Asn Arg Arg Asp Met Arg Phe Glu Asn Glu Trp Thr Pro Ala Glu
        355                 360                 365

Arg Gln Val Phe Glu Thr Ala Arg Asp Ala Ile Ala Val Arg Gln Ala
370                 375                 380

Ser Arg Ala Leu Ser Ile Gly Thr Gln Lys Leu Leu Pro Thr Pro Ala
385                 390                 395                 400

Ser Leu Glu Asp Asp Leu Leu Leu Phe Thr Arg Glu Ala Gln Gly Glu
                405                 410                 415

Arg Val Leu Val Ala Trp His Asn Gly Arg Asn Arg Lys Thr Tyr Ser
            420                 425                 430

Leu Arg Leu Ser Ala Leu Gly Leu Lys Ala Glu Pro Gln Ala Val Thr
        435                 440                 445

Arg Ser Leu Phe Ala Gly Gln Asp Ala Lys Leu Ser Val Ser Gly Gly
    450                 455                 460

Trp Leu His Leu Ser Leu Pro Ala Glu Asp Ala Ala Gly Phe Gly Leu
465                 470                 475                 480

Gly Gly Ser Thr Arg
                485

<210> SEQ ID NO 4
<211> LENGTH: 951
<212> TYPE: PRT
<213> ORGANISM: Deinococcus sp.
<220> FEATURE:
<221> NAME/KEY: MISC_FEATURE
<223> OTHER INFORMATION: Glucan 1,4-alpha-glucosidase (glucoamylase)
      derived from DRH-38

<400> SEQUENCE: 4

Val Phe Val Gly Thr Gly His Lys Gly His Val Val Pro Gly Lys Ala
1               5                   10                  15

Val Val Ala Gly Gln Gly Val Arg Gln Asp Leu Leu Val His Val Pro
            20                  25                  30

Asp Val Gly Cys Ala Val Gly Val Val Asn Gly Gly Arg Asn Lys Lys
        35                  40                  45

Leu Val Leu Cys Gly Leu Arg Leu Ser Arg His Gly Arg Ser Pro Pro
    50                  55                  60

Gly Arg Ser Leu Met Arg Glu Gly Pro Gly Asn Phe Pro Lys Ile Arg
65                  70                  75                  80

Lys Lys Ser Arg Ala Ala Gly Lys Cys Leu Arg Gln Ala Arg Arg Gly
                85                  90                  95

Ala Gly Leu Arg His Pro Ala Cys Pro Ser Gly Ala Arg Gly His Ser
            100                 105                 110

Gln His His Gly Gly Ala Asp Arg His Ala Pro Ser Ile Pro Asn Gly
        115                 120                 125

Gly Leu Gly Gln Arg Ala Arg Arg Leu Ala Ser Asp Ala Ala His Pro
```

-continued

```
            130                 135                 140
Pro Pro Asp Pro Thr Arg Arg Gly Asp Met Ser Asp Ala Ser Ala Gln
145                 150                 155                 160

Asn Pro Pro Glu Gln Leu Leu Ala Ala Pro Gly Ser Pro Glu Leu Ile
                165                 170                 175

Ser Pro Ala Gln Gly Leu Ala Pro Gly Ala Pro Gly Leu Pro Pro Thr
                180                 185                 190

Trp Ala Ser Ser Asp Lys Asp Phe Val Thr Thr Ala Leu Gly Gly Ala
                195                 200                 205

Ser Arg Leu Trp Ala Thr Gly Gly His Gly Met Leu Asn Glu Val Tyr
        210                 215                 220

Trp Pro Ser Thr Gly Gln Pro Gln Ile Arg Asp Leu Thr Phe Tyr Leu
225                 230                 235                 240

Val Gly Ala Ala Gly Trp Val Asp Leu Arg Arg Val Arg Arg Tyr Gln
                245                 250                 255

Leu Ser Met Pro Lys Pro Tyr Leu Pro Leu Pro Thr Leu Leu His Gln
                260                 265                 270

Gly Asp Asp Tyr Gln Leu Met Leu Glu Val Leu Pro Asp Pro His Arg
                275                 280                 285

Asp Val Leu Leu Ile Arg Tyr Ala Leu Ser Gly Pro Tyr Arg Leu Ala
        290                 295                 300

Ile Val Leu Ala Pro His Leu Thr Ser Thr Gly His Asp Asn Ala Ala
305                 310                 315                 320

Trp Val Glu Gly Gln His Leu Leu Ala Val Ser Gly Asn Arg Ala Leu
                325                 330                 335

Ala Leu Leu Ser Ser Ser Arg Met Glu His Leu Ser Ala Gly Tyr Val
                340                 345                 350

Gly Val Ser Asp Gly Trp Gln Asp Leu His Gln His Gly Arg Leu Thr
                355                 360                 365

Trp Ser Tyr Glu Arg Ala Glu Asn Gly Asn Val Ala Leu Ser Ala Glu
        370                 375                 380

Leu Gln Asp Ala Ser Gly Leu Ala Leu Gly Phe Ala Glu Asn Val
385                 390                 395                 400

Thr Gly Ala Gln Gly Leu Ala Arg Ala Ser Leu Ala Glu Gly Asp Glu
                405                 410                 415

Pro Ala Arg Arg Ala Phe Leu Cys Ala Trp Glu Ala Trp Gly Ser Ala
                420                 425                 430

Leu Lys Leu Gly Gly Ser Thr Pro Glu Leu Glu Ala Glu Ala Leu Leu
        435                 440                 445

Ser Ala Thr Val Leu Lys Val His Glu Asp Arg Thr Tyr Pro Gly Ala
450                 455                 460

Leu Val Ala Ser Leu Ser Ile Pro Trp Gly Asp Ser Thr Asp Thr Leu
465                 470                 475                 480

Gly Gly Tyr His Leu Val Trp Pro Arg Asp Ala Thr Leu Ala Ala Phe
                485                 490                 495

Ala Leu Leu Ala Cys Asn Gln Arg Glu Asp Ala Arg Arg Val Leu Ala
                500                 505                 510

Trp Phe Ile Ala Asn Gln Ser Asp Gly His Trp Leu Gln Asn Tyr
                515                 520                 525

Tyr Pro Asp Gly Gln Asp Phe Trp His Gly Val Gln Leu Asp Glu Thr
                530                 535                 540

Ala Phe Pro Val Leu Leu Ala Ala Lys Leu Arg Glu Glu Gly Glu Pro
545                 550                 555                 560
```

Glu Leu Glu Gly Thr Arg Asp Met Val Arg Ala Leu Ala Phe Val
            565                 570                 575
Ala Arg Thr Gly Pro Thr Ser Asp Gln Asp Arg Trp Glu Glu Asn Gln
            580                 585                 590
Gly Val Asn Pro Phe Thr Leu Ala Val Ala Ile Ala Ala Leu Val Ala
            595                 600                 605
Gly Ser Gly Trp Leu Glu Glu Asp Glu Arg His Tyr Ala Leu Ser Leu
            610                 615                 620
Ala Asp Asp Trp Asn Glu Arg Leu Glu Ser Leu Cys Tyr Val Thr Gly
625                 630                 635                 640
Thr Pro Leu Cys Arg Glu Leu Gly Val Glu Gly Tyr Tyr Val Arg Leu
            645                 650                 655
Ala Pro Pro Asp Arg Asp Gly Thr Leu Thr Gly Gln Val Thr Leu Gln
            660                 665                 670
Asn Arg Gln Gly Lys Thr Val Glu Ala Ala Leu Val Ser Leu Asp
            675                 680                 685
Phe Ser Tyr Leu Pro Arg Leu Gly Leu Arg Ser Ala Leu Asp Pro Arg
            690                 695                 700
Ile Arg Asn Thr Val Lys Val Val Asp Gln Leu Leu Ala Gln Lys Thr
705                 710                 715                 720
Pro Thr Gly Ile Phe Tyr His Arg Tyr Asn Gly Asp Gly Tyr Gly Glu
            725                 730                 735
His Glu Asp Gly Ala Pro Tyr Asp Gly Ser Gly Met Gly Arg Leu Trp
            740                 745                 750
Pro Leu Leu Ser Gly Glu Arg Gly His Leu Ala Leu Gln Ala Gly Glu
            755                 760                 765
Asp Ala Thr Val Tyr Leu Asn Ser Leu Leu Arg Cys Ser Ser Pro Gly
            770                 775                 780
Gly Leu Leu Pro Glu Gln Val Trp Asp Gly Pro Leu Pro Glu Arg
785                 790                 795                 800
Gly Leu Phe Pro Gly Arg Pro Ser Gly Ser Ala Met Pro Leu Leu Trp
            805                 810                 815
Ala His Ala Glu Phe Leu Lys Leu Leu His Thr Ala Gln Thr Gly Arg
            820                 825                 830
Pro Ala Glu Leu Leu Arg Glu Val Glu Glu Arg Tyr Arg Gln Pro Leu
            835                 840                 845
Pro Ala Gln Ala Arg His Trp Arg Pro Ala Ala Pro Val Pro Glu Leu
            850                 855                 860
Glu Pro Gly Leu Leu Leu Leu Ile Glu Asp Asp Lys Pro Phe Leu Leu
865                 870                 875                 880
His Tyr Gly Phe Asp Gly Trp Gln Asn Pro Gln Asp Arg Pro Ala Leu
            885                 890                 895
Arg Leu Pro Phe Gly Leu Trp Gly Val Thr Phe Ser Pro Gly Glu Leu
            900                 905                 910
Arg Glu His His Thr Leu Asp Phe Thr Arg Lys Leu Ala Val Gly Trp
            915                 920                 925
Glu Gly Gln Asp His His Ile Arg Leu His Glu Gly Ala Pro Lys Ala
            930                 935                 940
Ser Leu Thr Ala Gln Asn Gly
945                 950

<210> SEQ ID NO 5
<211> LENGTH: 951

```
<212> TYPE: PRT
<213> ORGANISM: Deinococcus sp.
<220> FEATURE:
<221> NAME/KEY: MISC_FEATURE
<223> OTHER INFORMATION: Glucan 1,4-alpha-glucosidase (glucoamylase)
      derived from MC2-2A

<400> SEQUENCE: 5
```

Met Phe Val Gly Thr Gly His Lys Gly His Val Val Pro Gly Lys Ala
1               5                   10                  15

Val Val Ala Gly Gln Gly Val Arg Gln Asp Leu Leu Val His Val Pro
                20                  25                  30

Asp Val Gly Cys Ala Val Gly Val Asn Gly Gly Arg Asn Lys Lys
            35                  40                  45

Leu Val Leu Cys Gly Leu Arg Leu Ser Arg His Gly Arg Ser Pro Pro
50                  55                  60

Gly Arg Ser Leu Met Arg Gly Pro Gly Asn Phe Pro Lys Ile Arg
65                  70                  75                  80

Lys Lys Ser Arg Ala Ala Gly Lys Cys Leu Arg Gln Ala Arg Arg Gly
                85                  90                  95

Ala Gly Leu Arg His Pro Ala Cys Pro Ser Gly Ala Arg Gly His Ser
            100                 105                 110

Gln His His Gly Gly Ala Asp Arg His Ala Pro Ser Ile Pro Asn Gly
        115                 120                 125

Gly Leu Gly Gln Arg Ala Arg Arg Leu Ala Ser Asp Ala Ala His Pro
130                 135                 140

Pro Pro Asp Pro Thr Arg Arg Gly Asp Met Ser Asp Ala Ser Ala Gln
145                 150                 155                 160

Asn Pro Pro Glu Gln Leu Leu Ala Ala Pro Gly Ser Pro Glu Leu Ile
                165                 170                 175

Ser Pro Ala Gln Gly Leu Ala Pro Gly Ala Pro Gly Leu Pro Pro Thr
            180                 185                 190

Trp Ala Ser Ser Asp Lys Asp Phe Val Thr Thr Ala Leu Gly Gly Ala
        195                 200                 205

Ser Arg Leu Trp Ala Thr Gly Gly His Gly Met Leu Asn Glu Val Tyr
210                 215                 220

Trp Pro Ser Thr Gly Gln Pro Gln Ile Arg Asp Leu Thr Phe Tyr Leu
225                 230                 235                 240

Val Gly Ala Ala Gly Trp Val Asp Leu Arg Val Arg Arg Tyr Gln
                245                 250                 255

Leu Ser Met Pro Lys Pro Tyr Leu Pro Leu Pro Thr Leu Leu His Gln
            260                 265                 270

Gly Asp Asp Tyr Gln Leu Met Leu Glu Val Leu Pro Asp Pro His Arg
        275                 280                 285

Asp Val Leu Leu Ile Arg Tyr Ala Leu Ser Gly Pro Tyr Arg Leu Ala
290                 295                 300

Ile Val Leu Ala Pro His Leu Thr Ser Thr Gly His Asp Asn Ala Ala
305                 310                 315                 320

Trp Val Glu Gly Gln His Leu Leu Ala Val Ser Gly Asn Arg Ala Leu
                325                 330                 335

Ala Leu Leu Ser Ser Arg Met Glu His Leu Ser Ala Gly Tyr Val
            340                 345                 350

Gly Val Ser Asp Gly Trp Gln Asp Leu His Gln His Gly Arg Leu Thr
        355                 360                 365

Trp Ser Tyr Glu Arg Ala Glu Asn Gly Asn Val Ala Leu Ser Ala Glu

```
                370             375             380
Leu Gln Asp Ala Ser Gly Leu Ala Leu Gly Phe Ala Glu Asn Val
385                 390             395                 400

Thr Gly Ala Gln Gly Leu Ala Arg Ala Ser Leu Ala Glu Gly Asp Glu
                    405             410                 415

Pro Ala Arg Arg Ala Phe Leu Cys Ala Trp Glu Ala Trp Gly Ser Ala
                420             425             430

Leu Lys Leu Gly Gly Ser Thr Pro Glu Leu Glu Ala Glu Ala Leu Leu
            435             440             445

Ser Ala Thr Val Leu Lys Val His Glu Asp Arg Thr Tyr Pro Gly Ala
450                 455             460

Leu Val Ala Ser Leu Ser Ile Pro Trp Gly Asp Ser Thr Asp Thr Leu
465                 470             475             480

Gly Gly Tyr His Leu Val Trp Pro Arg Asp Ala Thr Leu Ala Ala Phe
                485             490             495

Ala Leu Leu Ala Cys Asn Gln Arg Glu Asp Ala Arg Arg Val Leu Ala
            500             505             510

Trp Phe Ile Ala Asn Gln Gln Ser Asp Gly His Trp Leu Gln Asn Tyr
            515             520             525

Tyr Pro Asp Gly Gln Asp Phe Trp His Gly Val Gln Leu Asp Glu Thr
            530             535             540

Ala Phe Pro Val Leu Leu Ala Ala Lys Leu Arg Glu Glu Gly Glu Pro
545                 550             555                 560

Glu Leu Glu Gly Thr Arg Asp Met Val Arg Arg Ala Leu Ala Phe Val
                565             570             575

Ala Arg Thr Gly Pro Thr Ser Asp Gln Asp Arg Trp Glu Glu Asn Gln
            580             585             590

Gly Val Asn Pro Phe Thr Leu Ala Val Ala Ile Ala Ala Leu Val Ala
            595             600             605

Gly Ser Gly Trp Leu Glu Glu Asp Glu Arg His Tyr Ala Leu Ser Leu
            610             615             620

Ala Asp Asp Trp Asn Glu Arg Leu Glu Ser Leu Cys Tyr Val Thr Gly
625             630             635                 640

Thr Pro Leu Cys Arg Glu Leu Gly Val Glu Gly Tyr Tyr Val Arg Leu
                645             650             655

Ala Pro Pro Asp Arg Asp Gly Thr Leu Thr Gly Gln Val Thr Leu Gln
                660             665             670

Asn Arg Gln Gly Lys Thr Val Glu Ala Ala Leu Val Ser Leu Asp
            675             680             685

Phe Ser Tyr Leu Pro Arg Leu Gly Leu Arg Ser Ala Leu Asp Pro Arg
690             695             700

Ile Arg Asn Thr Val Lys Val Val Asp His Leu Leu Ala Gln Lys Thr
705                 710             715                 720

Pro Thr Gly Ile Phe Tyr His Arg Tyr Asn Gly Asp Gly Tyr Gly Glu
                725             730             735

His Glu Asp Gly Ala Pro Tyr Asp Gly Ser Gly Met Gly Arg Leu Trp
            740             745             750

Pro Leu Leu Ser Gly Glu Arg Gly His Leu Ala Leu Gln Ala Gly Glu
            755             760             765

Asp Ala Thr Val Tyr Leu Asn Ser Leu Leu Arg Cys Ser Ser Pro Gly
            770             775             780

Gly Leu Leu Pro Glu Gln Val Trp Asp Gly Pro Pro Leu Pro Glu Arg
785                 790             795                 800
```

```
Gly Leu Phe Pro Gly Arg Pro Ser Gly Ser Ala Met Pro Leu Leu Trp
                805                 810                 815

Ala His Ala Glu Phe Leu Lys Leu Leu His Thr Ala Gln Thr Gly Arg
            820                 825                 830

Pro Ala Glu Leu Leu Arg Glu Val Glu Arg Tyr Arg Gln Pro Leu
        835                 840                 845

Pro Ala Gln Ala Arg His Trp Arg Pro Ala Ala Pro Val Pro Glu Leu
    850                 855                 860

Glu Pro Gly Leu Leu Leu Ile Glu Asp Asp Lys Pro Phe Leu Leu
865                 870                 875                 880

His Tyr Gly Phe Asp Gly Trp Gln Asn Pro Gln Asp Arg Pro Ala Leu
                885                 890                 895

Arg Leu Pro Phe Gly Leu Trp Gly Val Thr Phe Ser Pro Gly Glu Leu
            900                 905                 910

Arg Glu His His Thr Leu Asp Phe Thr Arg Lys Leu Ala Val Gly Trp
        915                 920                 925

Glu Gly Gln Asp His His Ile Arg Leu His Glu Gly Ala Pro Lys Ala
    930                 935                 940

Ser Leu Thr Ala Gln Asn Gly
945                 950

<210> SEQ ID NO 6
<211> LENGTH: 426
<212> TYPE: PRT
<213> ORGANISM: Deinococcus sp.
<220> FEATURE:
<221> NAME/KEY: MISC_FEATURE
<223> OTHER INFORMATION: Endoxylanase (endo-1,4-beta-glucanase) derived
      from MC3-4A

<400> SEQUENCE: 6

Met Lys Arg Ser Lys Thr His Leu Ala Val Val Gly Leu Gly Leu Leu
1               5                   10                  15

Ala Leu Leu Gly Ser Cys Gly Gln Ser Val Pro Gly Pro Glu Gln Asn
            20                  25                  30

Ala Ala Phe Tyr Thr Gly Lys Tyr Arg Asn Leu Phe Thr Glu Trp Ser
        35                  40                  45

Ile Ala Thr Glu Ala Gln Val Gln Ala Lys Leu Asp Ala Tyr Trp Glu
    50                  55                  60

Ser Leu Phe Ala Ser Thr Asp Asp Gln Arg Arg Val Tyr Tyr Pro Ala
65                  70                  75                  80

Gly Ser Asn Ala Asn Gly Pro Met Ala Tyr Val Ala Asp Ile Gly Ser
                85                  90                  95

Asn Asp Val Arg Thr Glu Gly Met Ser Tyr Gly Met Met Ile Ala Val
            100                 105                 110

Gln Met Asn Lys Gln Ala Glu Phe Asn Ala Leu Trp Asn Tyr Ala Lys
        115                 120                 125

Ser Lys Met Gln His Gln Ser Gly Pro Arg Ala Gly Tyr Phe Ala Trp
    130                 135                 140

His Thr Asp Phe Glu Gly Asn Ile Leu Asp Ala Asn Pro Ala Ser Asp
145                 150                 155                 160

Gly Glu Glu Tyr Phe Ala Thr Ala Leu Phe Phe Ala Ser His Arg Trp
                165                 170                 175

Gly Asp Gly Asn Gly Ile Tyr Asn Tyr Ser Ala Glu Ala Asn Asn Ile
            180                 185                 190
```

-continued

Leu Asn Thr Met Leu His Lys Glu Asp Met Asn Gly Val Val Asn
         195                 200                 205

Gly Val Thr Asn Met Phe Asp Arg Glu His Lys Gln Val Val Phe Val
    210                 215                 220

Pro Glu Gly Asp Asn Ala Ile Phe Thr Asp Pro Ser Tyr His Leu Pro
225                 230                 235                 240

Ala Phe Tyr Glu Leu Trp Ser Arg Trp Ala Thr Gly Trp Asn Gly Gln
                245                 250                 255

Gln Ala Val Asp Arg Lys Phe Trp Ala Glu Ala Ala Gln Val Ser Arg
            260                 265                 270

Asp Tyr Phe Gln Lys Ala Thr His Pro Glu Thr Gly Leu Ala Pro Asp
        275                 280                 285

Tyr Ala Glu Phe Asp Gly Thr Pro Lys Gly Pro Ala Trp Asn Pro Asp
    290                 295                 300

Ala Ala Asn Phe Arg Phe Asp Ala Trp Arg Thr Ala Val Asn Trp Ser
305                 310                 315                 320

Val Asp Gln Ala Trp Trp Gly Lys Asp Ser Arg Glu Thr Ala Leu Thr
                325                 330                 335

Asp Lys Leu Gln Ser Phe Phe Glu Arg Gln Gly Ile Gly Thr Tyr Val
            340                 345                 350

Asn Gln Tyr Thr Val Ser Gly Thr Pro Leu Pro Gly Ala Gly Arg Ser
        355                 360                 365

Thr Gly Leu Ile Ala Thr Asn Gly Ala Ala Ser Ile Ala Thr Asp Thr
    370                 375                 380

Pro Arg Ala Arg Gln Phe Thr Gln Glu Leu Trp Lys Leu Glu Pro Pro
385                 390                 395                 400

Thr Gly Lys Trp Arg Tyr Tyr Asp Gly Met Met Asn Phe Met Ser Leu
                405                 410                 415

Leu His Ala Ser Gly His Phe Arg Ile Tyr
            420                 425

<210> SEQ ID NO 7
<211> LENGTH: 426
<212> TYPE: PRT
<213> ORGANISM: Deinococcus sp.
<220> FEATURE:
<221> NAME/KEY: MISC_FEATURE
<223> OTHER INFORMATION: Glycoside hydrolase derived from DRH-38

<400> SEQUENCE: 7

Met Lys Arg Ser Lys Thr His Leu Ala Val Val Gly Leu Gly Leu Leu
1               5                   10                  15

Ser Leu Leu Gly Ser Cys Gly Gln Ser Val Pro Gly Pro Glu Gln Asn
            20                  25                  30

Ala Ala Phe Tyr Thr Gly Lys Tyr Arg Asn Leu Phe Thr Glu Trp Gly
        35                  40                  45

Ile Ala Thr Glu Ala Gln Val Gln Ala Lys Leu Asp Ala Tyr Trp Glu
    50                  55                  60

Ser Leu Phe Ala Ser Thr Asp Gln Arg Arg Val Tyr Tyr Pro Ala
65                  70                  75                  80

Gly Ser Asn Ala Asn Gly Pro Met Ala Tyr Val Ala Asp Ile Gly Ser
                85                  90                  95

Asn Asp Val Arg Thr Glu Gly Met Ser Tyr Gly Met Met Ile Ala Val
            100                 105                 110

Gln Met Asn Lys Gln Ala Glu Phe Asn Ala Leu Trp Asn Tyr Ala Lys
        115                 120                 125

Ser Lys Met Gln His Gln Ser Gly Pro Arg Ala Gly Tyr Phe Ala Trp
130                 135                 140

His Thr Asp Phe Glu Gly Asn Ile Leu Asp Ala Asn Pro Ala Ser Asp
145                 150                 155                 160

Gly Glu Glu Tyr Phe Ala Thr Ala Leu Phe Phe Ala Ser His Arg Trp
                165                 170                 175

Gly Asp Gly Asn Gly Ile Tyr Asn Tyr Ser Ala Glu Ala Asn Asn Ile
            180                 185                 190

Leu Asn Thr Met Leu His Lys Glu Asp Met Asn Gly Gly Val Val Asn
        195                 200                 205

Gly Val Thr Asn Met Phe Asp Arg Glu His Lys Gln Val Val Phe Val
210                 215                 220

Pro Glu Gly Asp Asn Ala Thr Phe Thr Asp Pro Ser Tyr His Leu Pro
225                 230                 235                 240

Ala Phe Tyr Glu Leu Trp Ser Arg Trp Ala Thr Gly Trp Asn Gly Gln
                245                 250                 255

Gln Ala Ala Asp Arg Lys Phe Trp Ala Glu Ala Ala Gln Val Ser Arg
            260                 265                 270

Asp Tyr Phe Gln Lys Ala Thr His Pro Glu Thr Gly Leu Ala Pro Asp
        275                 280                 285

Tyr Ala Glu Phe Asp Gly Thr Pro Lys Gly Pro Ala Trp Asn Pro Asp
290                 295                 300

Ala Ala Asn Phe Arg Phe Asp Ala Trp Arg Thr Ala Val Asn Trp Ser
305                 310                 315                 320

Val Asp Gln Ala Trp Trp Gly Lys Asp Ser Arg Glu Thr Ala Leu Thr
                325                 330                 335

Asp Lys Leu Gln Ser Phe Phe Glu Arg Gln Gly Ile Gly Thr Tyr Val
            340                 345                 350

Asn Gln Tyr Thr Val Ser Gly Thr Pro Leu Pro Gly Ala Gly Arg Ser
        355                 360                 365

Thr Gly Leu Ile Ala Thr Asn Gly Ala Ala Ser Ile Ala Thr Asp Thr
370                 375                 380

Pro Arg Ala Arg Gln Phe Thr Gln Glu Leu Trp Lys Leu Glu Pro Pro
385                 390                 395                 400

Thr Gly Lys Trp Arg Tyr Tyr Asp Gly Met Met Asn Phe Met Ser Leu
                405                 410                 415

Leu His Ala Ser Gly His Phe Arg Ile Tyr
            420                 425

<210> SEQ ID NO 8
<211> LENGTH: 554
<212> TYPE: PRT
<213> ORGANISM: Deinococcus sp.
<220> FEATURE:
<221> NAME/KEY: MISC_FEATURE
<223> OTHER INFORMATION: Beta-xylosidase derived from DRH-46

<400> SEQUENCE: 8

Met Thr Gln His Phe Leu Gln Asn Pro Ile Leu Arg Gly Phe Asn Pro
1               5                   10                  15

Asp Pro Ser Ile Leu Arg Val Gly Asn Asp Tyr Tyr Ile Ala Thr Ser
                20                  25                  30

Thr Phe Glu Trp Phe Pro Gly Val Gln Ile His His Ser Arg Asp Leu
            35                  40                  45

Val Asn Trp Arg Leu Leu Thr Arg Pro Leu Thr Arg Lys Ser Gln Leu

```
                50                  55                  60
Asp Met Arg Gly Asn Ser Asn Ser Ala Gly Ile Trp Ala Pro Cys Leu
65                  70                  75                  80

Thr His Asp Gly Glu Lys Phe His Leu Ile Tyr Thr Asp Val Lys His
                85                  90                  95

Trp Ser Thr Asn Gly Ser Phe Lys Asp Thr His Asn Tyr Leu Val Thr
                100                 105                 110

Ala Glu Asn Ile Glu Gly Pro Trp Ser Glu Pro Ile Tyr Leu Asn Ser
                115                 120                 125

Ser Gly Phe Asp Pro Ser Leu Phe His Asp Glu Asp Gly Arg Lys Trp
                130                 135                 140

Leu Ser Asn Met Leu Trp Asp His Arg Pro Gly His His Pro Phe Ala
145                 150                 155                 160

Gly Ile Val Leu Gln Glu Tyr Asp Pro Val Lys Gln Lys Leu Val Gly
                165                 170                 175

Pro Ile Lys Asn Ile Phe Thr Gly Thr Ser Leu Lys Val Thr Glu Gly
                180                 185                 190

Pro His Leu Tyr Arg Lys Asp Gly Tyr Tyr Tyr Leu Leu Thr Ala Glu
                195                 200                 205

Gly Gly Thr Thr Tyr Glu His Ala Val Thr Phe Ala Arg Ser Arg Asn
                210                 215                 220

Ile Asp Gly Pro Tyr Glu Val His Pro Gln Asn Pro Leu Leu Thr Ser
225                 230                 235                 240

Phe Gly His Pro Asp Ile Leu Val Gln Lys Ala Gly His Gly Ser Leu
                245                 250                 255

Val Glu Thr Gln Ser Gly Glu Trp Tyr Leu Ala His Leu Gly Gly Arg
                260                 265                 270

Pro Leu Glu Asp Met His Ala Ser Glu Arg His Cys Asn Leu Gly Arg
                275                 280                 285

Glu Thr Ser Leu Gln Lys Val Glu Trp Arg Glu Asp Gly Trp Pro Tyr
                290                 295                 300

Val Val Gly Gly Asn Phe Pro Ser Ala Gln Val Pro Val Ser Leu Leu
305                 310                 315                 320

Pro His Pro Phe Glu Pro Glu Pro Ala Ala Glu Asp Phe Ala Ser Gly
                325                 330                 335

Arg Leu Ser Ile His Trp Gln Thr Leu Arg Thr Pro Met Asp Glu Ser
                340                 345                 350

Trp Val Asn Phe Thr Glu Arg Pro Gly His Leu Arg Leu Val Gly Arg
                355                 360                 365

Glu Ser Pro Thr Ser Leu His His Gln Ser Leu Val Ala Arg Arg Leu
                370                 375                 380

Gln Ala Phe His Ala Glu Ala Gln Thr Thr Ile Glu Phe Asp Pro Asp
385                 390                 395                 400

Thr Phe Gln Gln Met Ala Gly Leu Ser Ala Tyr Tyr Asp Thr Ser Asn
                405                 410                 415

Trp Thr Phe Leu Met Val Thr Trp Asp Glu Arg Leu Gly Arg Cys Leu
                420                 425                 430

Lys Leu Gly Thr Cys Glu Asn Gly Arg Tyr Ser Glu Ser Gly Thr Pro
                435                 440                 445

Ile Ser Leu Pro Asp Gln Ala Val His Leu Gly Leu Arg Phe Ala His
                450                 455                 460

Glu Ser Tyr Gln Phe Tyr Phe Ser Leu Asp Gly Ala Gln Trp Thr Pro
465                 470                 475                 480
```

```
Phe Gly Pro Ala His Pro Ser Tyr Lys Leu Ser Asp Glu Tyr Cys Gly
                485                 490                 495

Gly Leu Ala Phe Thr Gly Thr Phe Ile Ala Leu Ser Ala His Asp Met
            500                 505                 510

Ser Gly Gln Arg Lys Ala Ala Asp Phe Ser Arg Phe Glu Tyr Arg Glu
        515                 520                 525

Phe Pro Val Leu Glu Gly Phe Leu Ser Ala Ser Phe Pro Ser Ser Gln
    530                 535                 540

Ala Asn Gln Pro Glu Pro Val Ala Asp Leu
545                 550

<210> SEQ ID NO 9
<211> LENGTH: 1222
<212> TYPE: PRT
<213> ORGANISM: Deinococcus sp.
<220> FEATURE:
<221> NAME/KEY: MISC_FEATURE
<223> OTHER INFORMATION: Arabinofuranosidase derived from DRH-46

<400> SEQUENCE: 9

Met His Gln His Gln Pro Thr Arg Ser Lys Lys Asn Ala Arg Ser
1               5                   10                  15

Arg Leu Ser Leu Ala Leu Ala Leu Ser Cys Ala Val Ser Leu Ala Ser
            20                  25                  30

Pro Val Phe Ala Ala Glu Glu Gly Leu Leu Leu His Tyr Thr Phe Asp
        35                  40                  45

Ser Thr Ser Gly Asn Thr Val Ala Asp Ser Ser Gly Asn Lys Lys Asp
    50                  55                  60

Gly Val Met Glu Gly Lys Ala Ser Trp Thr Ala Ala Gly Lys Ile Gly
65                  70                  75                  80

Gly Ala Ile Asp Leu Asp Gly Thr Ser Gly Phe Ile Arg Leu Pro Glu
                85                  90                  95

Ala Leu Leu Ala Glu Gln His Asp Leu Thr Ile Ala Thr Trp Val Lys
            100                 105                 110

Pro Asp Ala Leu Gly Thr Trp Ala Arg Val Phe Asp Phe Gly Ser Gly
        115                 120                 125

Thr Asp Asn Trp Met Phe Leu Thr Leu Asn Asp Phe Thr Asn Ala Thr
    130                 135                 140

Arg Phe Ala Val Leu Pro Lys Gly Ser Ser Glu Asn Leu Leu Thr Gly
145                 150                 155                 160

Pro Ala Phe Pro Gly Gly Asn Asp Trp His His Val Ala Val Val Ile
                165                 170                 175

Ser Gly Asn Thr Tyr Thr Leu Phe Ile Asp Gly Ile Gln Ser Ala Ser
            180                 185                 190

Val Ser Asn Met Gln Asn Phe Pro Val Lys Leu Gly Ala Thr Thr Gln
        195                 200                 205

Asn Tyr Ile Gly Lys Ser Gln Phe Glu Pro Asp Pro Leu Phe Asp Gly
    210                 215                 220

Lys Leu Asp Asp Phe Arg Ile Tyr Asn Arg Ala Met Asn Gly Glu Glu
225                 230                 235                 240

Leu Met Ala Leu Val Thr Ala Gly Met Thr Asp Ala Asp Ser Val Ser
                245                 250                 255

Tyr Ala Gln Lys Trp Leu Asn Leu Gly Asp Thr Ser Gln Gln Thr His
            260                 265                 270

Asp Leu Asn Leu Pro Thr Ser Gly Pro Ser Gly Thr Thr Ile Arg Trp
```

-continued

```
            275                 280                 285
Ala Ser Ser Asn Pro Ala Val Ser Ala Glu Gly Lys Val Thr Arg
            290                 295                 300
Pro Ala Lys Gly Gln Ser Asn Gln Thr Val Thr Leu Thr Ala Thr Leu
305                 310                 315                 320
Gln Lys Gly Thr Thr Thr Asp Thr Arg Thr Phe Asp Val Gln Val Trp
                        325                 330                 335
Ala Gln Gly Ala Thr Ala Tyr Thr Leu Asp Val Gln Ala Asp Gln Pro
                        340                 345                 350
Leu His Ala Ile Ser Pro Thr Leu Tyr Gly Ile Phe Phe Glu Asp Ile
                        355                 360                 365
Asn Tyr Ala Ala Asp Gly Gly Leu Tyr Ala Glu Leu Val Arg Asn Arg
                        370                 375                 380
Ser Phe Glu Phe Asp Pro Gln Leu Ser Gly Trp Ala Val Val Thr Asp
385                 390                 395                 400
Ala Gly Gly Ala Gly Lys Ala Ser Gly Gln Thr Glu Arg Pro Leu Asn
                        405                 410                 415
Glu His Asn Pro Gln Tyr Met Arg Leu Glu Val Thr Ala Ala Gly Ala
                        420                 425                 430
Gly Leu Ser Asn Ser Gly Phe Asp Gly Ile Ala Val Gln Lys Gly Ala
                        435                 440                 445
Ala Tyr Thr Phe Ser Val His Ala Arg Ser Thr Ser Pro Leu Ser Arg
            450                 455                 460
Pro Leu Thr Val Gln Leu Arg Gly Gln Gln Gly Glu Val Tyr Gly Arg
465                 470                 475                 480
Cys Glu Val Ser Gly Val Thr Ala Ala Trp Gln Lys Phe Thr Cys Thr
                        485                 490                 495
Leu Thr Ser Asn Thr Thr Asp Pro Ala Ala Ser Val Ala Leu Met Val
                        500                 505                 510
Asn Glu Val Ala Thr Val Asp Phe Asp Met Val Ser Leu Phe Pro Glu
            515                 520                 525
Gln Thr Trp Met Asn Arg Pro Glu Gly Leu Arg Glu Asp Leu Ala Gln
            530                 535                 540
Lys Leu Asp Asp Leu Gln Pro Gly Phe Leu Arg Phe Pro Gly Gly Cys
545                 550                 555                 560
Ile Val Glu Gly Gly Ser Phe Phe Asn Arg Tyr Arg Trp Lys Asn Thr
                        565                 570                 575
Ile Gly Asp Val Thr Glu Arg Glu Ile Gln Pro Asn Gln Trp Ala Ser
                        580                 585                 590
Gly Tyr Tyr Gln Thr Phe Gly Leu Gly Phe Gln Glu Tyr Phe Gln Leu
                        595                 600                 605
Ala Gln Asp Ile Gly Ala Glu Pro Leu Pro Ile Leu Tyr Ala Gly Gln
            610                 615                 620
Thr Ser Cys Thr Gly Thr Pro Asp Met Val Ala Leu Asp Asp Leu Gly
625                 630                 635                 640
Pro Tyr Ile Gln Asp Ala Leu Asp Leu Ile Glu Tyr Ala Asn Gly Asp
                        645                 650                 655
Ala Lys Thr Thr Gln Trp Gly Ala Leu Arg Ala His Gly His Pro
                        660                 665                 670
Glu Pro Phe Asn Met Lys Tyr Leu Gly Val Gly Asn Glu Leu Trp Gly
            675                 680                 685
Gln Asp Tyr Leu Asn Arg Tyr Glu Lys Phe Tyr Asp Val Leu Lys Gln
            690                 695                 700
```

```
Lys His Pro Glu Ile Gln Leu Val Leu Ser Ala Gly Ala Phe Pro Ser
705                 710                 715                 720

Asp Phe Asn Phe Gln Leu Ala Trp Asp Trp Val Lys Thr Gly Lys
            725                 730                 735

Ala Asp Leu Ile Asp Glu His Met Tyr Gln Ser Pro Gln Trp Phe Tyr
            740                 745                 750

Asp Asn Ala Thr Arg Tyr Asp Asn Tyr Asp Arg Lys Gly Pro Lys Val
            755                 760                 765

Phe Val Gly Glu Tyr Ala Ala His Gly Val Gly Lys Arg Asn Asn Leu
        770                 775                 780

Glu Ser Ala Leu Ala Glu Ala Phe Met Thr Gly Leu Glu Arg Asn
785                 790                 795                 800

Ser Asp Val Val His Met Ala Ser Phe Ala Pro Leu Leu Ala Lys Glu
                805                 810                 815

Asn Arg Thr Gln Trp Thr Thr Asp Leu Ile Trp Phe Asn Asn Gln Gln
                820                 825                 830

Val Tyr Ala Thr Pro Asn Tyr His Val Gln Gln Leu Phe Lys Gln His
            835                 840                 845

Leu Gly Gln Gln Val Leu Pro Thr Thr Leu Lys Lys Glu Val Gln Thr
        850                 855                 860

Gln Val Asn Ala Gln Pro Ile Thr Gly Ser Ile Leu Leu Gly Ser Ser
865                 870                 875                 880

Asn Thr Ala Val Gln Tyr Asp Val Lys Ile Thr Ala Gly Asp Gln
                885                 890                 895

Thr Val Lys Tyr Gly Asn Asp Phe Ser Asp Ala Thr Arg Ile Ser Asp
            900                 905                 910

Trp Asn Thr Tyr Arg Gly Asp Trp Ser Ile Glu Glu Gly Thr Leu Lys
            915                 920                 925

Gln Thr Ser Ala Ser Leu Thr Asp Ala Arg Leu Leu Leu Gly Gln Gly
        930                 935                 940

Glu Asp Trp Ser Asn Tyr Thr Leu Ser Leu Arg Ala Arg Lys Asp Ser
945                 950                 955                 960

Gly Ala Glu Gly Phe Leu Ile Gly Phe Gly Val Lys Asn Thr Ser Asp
                965                 970                 975

Tyr His Trp Trp Asn Leu Gly Gly Trp Gly Asn Thr Ser Thr Ala Val
            980                 985                 990

Glu Lys Ser Val Gly Gly Val Lys Thr Thr Ile Gly Asn Ala Thr Pro
        995                 1000                1005

Val Thr Ile Glu Thr Gly Arg Trp Tyr Asp Leu Arg Ile Glu Val
    1010                1015                1020

Gln Gly Asn His Ile Arg Leu Tyr Leu Asp Asn Lys Leu Ile His
    1025                1030                1035

Asp Ile Thr Asp Ala Pro Ser Ser Asn Gly Pro Leu Tyr Ser Val
    1040                1045                1050

Ser Asn Phe Asp Gln Lys Thr Gly Asp Ile Ile Leu Lys Val Val
    1055                1060                1065

Asn Thr Ser Gly Asn Thr Gln Ser Thr Gln Val Asn Leu Gln Gly
    1070                1075                1080

Val Lys Asp Leu Gln Pro Thr Ala Thr Leu Ile Glu Leu Thr Ser
    1085                1090                1095

Ala Ser Ala Leu Asp Glu Asn Ser Phe Ala Ala Pro Asp Gln Val
    1100                1105                1110
```

```
Lys Pro Val Thr Arg Thr Leu Gly Gly Ile Thr Arg Asn Phe Ser
    1115                1120                1125

His Asp Phe Pro Ala His Ser Val Thr Ile Leu Arg Leu His Thr
    1130                1135                1140

Gly Lys Gln Ala Val Ile Gly Ser Ile Glu Pro Val Ser Met Gln
    1145                1150                1155

Thr Gly Ile Gly Lys Arg Pro Val Leu Pro Glu Gln Val Thr Val
    1160                1165                1170

Lys Asn Thr Asp Gly Ser Thr Arg Thr Val Pro Val Lys Trp Gln
    1175                1180                1185

Gln Ile Asp Asp Val Gln Leu Ser Thr Pro Gly Ser Phe Arg Val
    1190                1195                1200

Glu Gly Ser Val Glu Gly Thr Tyr Leu Glu Ala Glu Ala Leu Val
    1205                1210                1215

Thr Val Thr Pro
    1220

<210> SEQ ID NO 10
<211> LENGTH: 496
<212> TYPE: PRT
<213> ORGANISM: Deinococcus sp.
<220> FEATURE:
<221> NAME/KEY: MISC_FEATURE
<223> OTHER INFORMATION: arabinofuranosidase derived from DRH-46

<400> SEQUENCE: 10

Met Lys Lys Ala Gln Ile Leu Leu Asp Thr His Arg Thr Ile Ser Glu
1               5                   10                  15

Ile Ser His Tyr Ile Phe Gly Gly Phe Ala Glu His Met Gly Arg Cys
                20                  25                  30

Ile Tyr Glu Gly Ile Tyr Asp Pro Gln Ser Pro Leu Ser Asp Glu Asn
                35                  40                  45

Gly Ile Arg Arg Asp Val Met Asp Ala Leu Lys Glu Leu Asn Phe Cys
            50                  55                  60

Ser Ile Arg Tyr Pro Gly Gly Asn Phe Val Ser Gly Tyr Asn Trp Glu
65                  70                  75                  80

Asp Gly Ile Gly Pro Arg Glu Asn Arg Pro Val Lys Arg Asp Leu Ala
                85                  90                  95

Trp Arg Ser Ile Glu Thr Asn Gln Phe Gly Thr Asp Glu Phe Met Lys
                100                 105                 110

Val Cys Ala Glu Leu Lys Thr Glu Pro Met Met Ala Val Asn Leu Gly
            115                 120                 125

Thr Gly Ser Ile Gln Asp Ala Ala Asn Ile Val Glu Tyr Cys Asn Leu
        130                 135                 140

Glu Gly Gly Thr His Tyr Ser Asp Leu Arg Ile Lys Asn Gly Ala Glu
145                 150                 155                 160

Lys Pro Tyr Gly Val Lys Phe Trp Cys Leu Gly Asn Glu Met Asp Gly
                165                 170                 175

Pro Trp Gln Val Gly Gln Leu Ser Ala Glu Asp Tyr Ser Lys Lys Ala
                180                 185                 190

Val Gln Ala Ala Lys Ala Met Lys Leu Ile Asp Pro Ser Ile Gln Leu
            195                 200                 205

Ile Ala Cys Gly Ser Ser Ser Ser Leu Met Asn Ser Tyr Pro Glu Trp
        210                 215                 220

Asp Arg Ile Val Leu Glu Glu Thr Trp Asp Gln Ile Asp Tyr Leu Ser
225                 230                 235                 240
```

Met His Tyr Tyr Ala Ser Asn Arg Glu Glu Asp Thr Ala Ser Tyr Leu
                245                 250                 255

Ala Tyr Thr Arg Glu Phe Glu Asp His Leu Gln Thr Leu Ala Ala Thr
            260                 265                 270

Ile Arg Tyr Val Lys Ala Lys Arg Ser Gln Lys Asp Val Phe Leu
        275                 280                 285

Ser Trp Asp Glu Trp Asn Val Trp Tyr Arg Glu Met Asn Gly Asn Gly
290                 295                 300

Glu Trp Gln Gln Ala Pro His Ile Leu Glu Glu Val Tyr Asn Leu Glu
305                 310                 315                 320

Asp Ala Leu Val Val Ala Gln Trp Met Asn Val Phe Leu Lys His Ser
                325                 330                 335

Asn Val Leu Lys Met Ala Ser Ile Ala Gln Val Val Asn Val Ile Ala
            340                 345                 350

Pro Ile Met Thr Arg Arg Asp Gly Met Phe Lys Gln Thr Ile Tyr Tyr
        355                 360                 365

Pro Phe Leu Val Phe Ser Lys His Ala Ser Gly Gln Ala Leu Ser Leu
    370                 375                 380

His Val Ala Ser Asp Gln Tyr Glu Thr Lys Lys His Gly Leu Val Asn
385                 390                 395                 400

Leu Leu Asp Ala Ser Ala Ser Phe Asp Ala Ser Gln Asn Glu Gly Ala
                405                 410                 415

Val Phe Leu Val Asn Arg Ser Gln Asp Glu Leu Glu Thr Glu Ile
            420                 425                 430

Val Phe Gln Gly Arg Val Pro Thr Ser Val Arg Val Ala His Gln Leu
        435                 440                 445

Ala Gly Ser Asp Pro Lys Ala His Asn Ser Phe Glu Glu Pro Glu Lys
    450                 455                 460

Leu Thr Leu Gln Thr Ile Glu Ala Gly Glu Ile Lys Asp Gly Lys Leu
465                 470                 475                 480

Val Leu Lys Leu Pro Ala Leu Ser Phe Ser Ala Val Val Leu Asp Tyr
                485                 490                 495

<210> SEQ ID NO 11
<211> LENGTH: 500
<212> TYPE: PRT
<213> ORGANISM: Deinococcus sp.
<220> FEATURE:
<221> NAME/KEY: MISC_FEATURE
<223> OTHER INFORMATION: Arabinofuranosidase derived from DRH-46

<400> SEQUENCE: 11

Met Thr Thr Pro Thr Asn Thr Thr His Leu Lys Ile Thr Thr Pro Ile
1               5                   10                  15

Gly Leu Ile Ser Pro Arg Phe Tyr Gly His Phe Ala Glu His Leu Ala
            20                  25                  30

Arg Cys Cys Tyr Asp Gly Leu Trp Val Gly Pro Ser Ser Ile Pro
        35                  40                  45

Asn Thr Arg Gly Trp Arg Asn Asp Leu Val Ser Ala Leu Gln Gln Met
    50                  55                  60

Pro Val Pro Met Ile Arg Trp Pro Gly Gly Cys Tyr Ala Asp His Tyr
65                  70                  75                  80

His Trp Arg Asp Gly Ile Gly Gln Arg Thr Pro Arg Leu Gly Ile Ser
                85                  90                  95

Cys Gly Thr Arg Val Thr Asp Thr Asn Glu Leu Gly Thr His Glu Phe

```
            100                 105                 110
Met Asp Leu Cys Glu Leu Leu Gln Ser Glu Ala Tyr Leu Ala Gly Asn
        115                 120                 125

Met Ala Ser Gly Ser Val Gln Glu Met Cys Asp Trp Leu Glu Tyr Thr
130                 135                 140

Ser Gly Thr Ala Asp Thr Val Thr Arg Glu Arg Gln Lys Asn Gly
145                 150                 155                 160

Arg Lys Asp Pro Trp Asp Val Lys Leu Trp Gly Val Gly Asn Glu Ser
                165                 170                 175

Trp Asp Cys Gly Gly Arg Tyr Asp Ala Lys Thr Tyr Ala Ala Glu Phe
                180                 185                 190

Lys Arg Tyr Gly Val Met Met Lys His Val Asp Pro Ser Val Glu Leu
                195                 200                 205

Val Ala Val Gly Asn Asp Glu Val Ala Ala Arg Ala Asp His Met
        210                 215                 220

Glu Thr Phe Trp Asn Glu Ile Phe Met Glu His Ile Gln Asp His Ile
225                 230                 235                 240

Asp Leu Ile Asp His Leu Ser Val His Thr Tyr Trp Ile Asp Gly Gly
                245                 250                 255

Ala Glu Thr Gly Phe Ser Glu Glu Asn Tyr Tyr Thr Leu Leu Ala Glu
                260                 265                 270

Ala Asp Thr Thr Glu Glu Ala Ile Val Arg Ala Lys Arg Thr Ile Asp
                275                 280                 285

Lys Tyr Val Arg Gly Arg Lys Asn Ile Lys Val Ala Met Asp Glu Tyr
                290                 295                 300

Gly Val Trp His Pro Glu Thr Arg Pro Trp Gly Pro Gly Pro His Asp
305                 310                 315                 320

Asp Ser Arg Pro Asn Asn Phe Glu Gln Ala Asn Thr Leu Arg Asp Ala
                325                 330                 335

Leu Ser Val Gly Ile Ala Leu Glu Gly Phe His Arg Gln Ala Asn Ile
                340                 345                 350

Leu Gly Leu Ala Asn Leu Ala Gln Ile Val Asn Val Leu Gln Ser Val
                355                 360                 365

Ala Met Thr Glu Gly Glu Lys Met Phe Leu Thr Pro Thr Tyr His Ala
        370                 375                 380

Leu Lys Leu His Glu His His Ile Gly Ala Thr Ser Cys His Val Glu
385                 390                 395                 400

Val Gln Thr Asp Arg Val Phe Lys Met Pro Arg Val Thr Ala Thr Ala
                405                 410                 415

Ser Gln Lys Asp Gly Asn Thr Asn Leu Thr Leu Ile Asn Arg His Ile
                420                 425                 430

Ser Glu Glu Ser Gln Ile Met Leu Tyr Asp Leu Pro Glu Thr Leu Leu
                435                 440                 445

Ser Ala Gln Leu Leu Ser Gly Pro Ala Pro Asp Ala Thr Asn Thr Tyr
        450                 455                 460

Asp Gln Pro Glu Arg Ile Ser Leu Gln Pro Leu Asp Val Tyr Lys Glu
465                 470                 475                 480

Asp Asn Thr Trp Lys Leu Thr Leu Pro Pro His Ser Met Ala Thr Leu
                485                 490                 495

Arg Phe Ser Arg
            500

<210> SEQ ID NO 12
```

```
<211> LENGTH: 350
<212> TYPE: PRT
<213> ORGANISM: Deinococcus sp.
<220> FEATURE:
<221> NAME/KEY: MISC_FEATURE
<223> OTHER INFORMATION: Arabinofuranosidase derived from DRH-46

<400> SEQUENCE: 12
```

Met Phe Arg Ser Met Leu Phe Arg Leu Leu Cys Leu Ile Leu Leu Val
1               5                   10                  15

Val Ser Gly Gly Ala Ser Ala Gln Gly Lys Thr Phe Gln Asn Pro Leu
            20                  25                  30

Leu Val Phe Ala Gly Ala Asp Pro His Ile Val Phe His Asp Gly Trp
        35                  40                  45

Tyr Tyr Met Thr Tyr Thr Thr Gly Arg Asp Ile Gln Ile Arg Lys Ser
    50                  55                  60

Arg Ser Leu Ala Thr Leu Asp Gln Ala Glu Met Lys Val Val Phe Gln
65                  70                  75                  80

Pro Glu Gly Glu Ala Ser Cys Cys His Val Trp Ala Pro Glu Phe His
                85                  90                  95

Leu Leu Glu Gly Pro Ser Gly Lys Arg Trp Tyr Ile Tyr Tyr Thr Ala
            100                 105                 110

Gly Pro Lys Asp Cys Cys Ala His Gln Arg Met Tyr Val Ala Glu Ser
        115                 120                 125

Ala Thr Glu Asp Pro Met Gly Pro Tyr Thr Phe Lys Gly Lys Ile Ala
    130                 135                 140

Asp Pro Arg His Asp Phe Trp Ala Ile Asp Ala Ser Val Val Gln Thr
145                 150                 155                 160

Arg Asp His Leu Tyr Leu Val Tyr Ser Gly Thr Pro Glu Asp Phe Met
                165                 170                 175

Pro His Glu Lys Pro Gln His Leu Tyr Ile Ala Glu Met Ala Asn Pro
            180                 185                 190

Trp Thr Leu Lys Ser Glu Arg Val Glu Ile Ser Ser Pro Thr Phe Ile
        195                 200                 205

Trp Glu Arg Met Gly Gly Pro Val Asn Glu Gly Pro Val Ala Leu Tyr
    210                 215                 220

His Asn Asp Gln Ile Phe Leu Ala Phe Ser Gly Ser Gly Cys Trp Thr
225                 230                 235                 240

Asp Asp Tyr Ser Leu Gly Leu Leu Lys Ala Ser Ala Asn Ala Asp Leu
                245                 250                 255

Leu Asn Pro Ala Ser Trp Thr Lys Leu Pro Glu Pro Val Leu Glu Arg
            260                 265                 270

Asn Asp Ala Gly Gln Val Tyr Gly Pro Gly His Asn Gly Phe Phe Lys
        275                 280                 285

Ser Pro Asp Gly Thr Glu Asp Trp Val Val Tyr His Ala Asn Pro Ala
    290                 295                 300

Pro Gly Gln Gln Cys Gly Glu Ser Arg Val Ala Arg Ala Gln Lys Ile
305                 310                 315                 320

Thr Trp Asp Gln Ser Gly Met Pro Val Phe Gly Glu Ala Val Pro Leu
                325                 330                 335

Trp Thr Asp Leu Pro Leu Pro Ser Gly Asp Pro Gly Ala Pro
            340                 345                 350

```
<210> SEQ ID NO 13
<211> LENGTH: 1209
<212> TYPE: DNA
```

<213> ORGANISM: Deinococcus sp.
<220> FEATURE:
<221> NAME/KEY: misc_feature
<223> OTHER INFORMATION: Cellobiohydrolase (CBH) derived from M1-3H (partial sequence)
<220> FEATURE:
<221> NAME/KEY: misc_feature
<222> LOCATION: (1179)..(1192)
<223> OTHER INFORMATION: n is a, c, g, or t

<400> SEQUENCE: 13

```
gtgaaactcg gcgaggacac gaccgccccg tacgagttca cggtgaacgc cgaccctggc      60
ctgaacggca cgcacgtcta ctccgcgcag gcggtggcgg cgacgcggc cgggatctcc      120
gcgccggtca gcgtgcagat ccgcatcgcg gacacccgca ccaccgaact gctcagcaac     180
ggggacttca gccagggcct gaaccccctgg tggactgccg aacggccgc cagcacgacc      240
ggcggtgaga cctgcctgaa catcacgcag ccgggcagca accccctggga cgtgctgttc     300
gggcagggcg gcgtgggcct gaacgagggc ggcacgtaca ccctgagctt cacggcgcgc      360
gccgcgcagc ccacgtcgtt caggacgctg ctgcagttcg acggcgcgcc gtacaccaac      420
tacttcgtgc aggacgcgga cgtgaccagc cagccgaaga ccttcacgtc cacgttcacg      480
atggcgcagc ccagtgacgc gaaggccgcg ttccagttcc agctgggcgc cagggccgcc      540
acgaccgtgt gcttcagccg catttcactg actggcccgg ccttcggcag cgccgtgccc      600
gccccgggtg cggacgacct gaagctggtg cggctcaacc agaccgggta cctgccggac      660
cggccgaaac tggcggccct gccgttcgac tcggaccggc cgctgccgtg gactctgctg      720
gacggcacgc gcacggtcgc cagtggccgtg acccgcgtgt cggcgcgga cgccgcgtcc      780
ggcgagcacg tgcatcaggt ggacttcagt gccgtgaccg cccggccga cgggctggtg      840
ctggacgtcg cggggtttccg cagccaccccg ttccggatcg ggcgcgtgta cgacggcctg      900
aaacgcgacg cgctggcgta cttctaccac aaccgcagcg gcacgcccat caaggcgaag      960
tacgtcgggg acgcctgggc gcgcccggcc ggtcacgccg ggaccagccc gaaccagggg     1020
gacacgcgcg tcagctgctt caagggcacc gatcaggccg ggaacgtctg gcccggctgc     1080
gggtacgaac tggacgccag cggcggctgg tacgacgccg gggatcacgg gaagtacgtc     1140
gtgaacggcg gcgtgagcgt ctggacgctg ctgaacctnn nnnnnnnnn nncgagcggg     1200
gcgcgcgcc                                                              1209
```

<210> SEQ ID NO 14
<211> LENGTH: 1455
<212> TYPE: DNA
<213> ORGANISM: Deinococcus sp.
<220> FEATURE:
<221> NAME/KEY: misc_feature
<223> OTHER INFORMATION: Endoglucanase derived from DRH-46

<400> SEQUENCE: 14

```
atgcacaaac gaacggtcca ccttgcccctt ctgacctgca gcctgcttgc cctcacagcc      60
tgtggaacaa acacccaggt tgatctggct tctgcccctc caaagatcga gcccggtttc      120
cgaccccagt cggccacagc cgcggatgtg tgggtgaccc acccggaccg cagtcgcctg      180
atctcgtggg atggcacaaa gaacttcgtt tcagacggca atgtgacccc ctccaccctg      240
accatcaacg aaagccagac ctttcagacc atggaagggt ttggtgcttc tctgaccgat      300
tcagcagggt ggctgatgtg gaacaaaatg agcgccactc agcgcaacag cctgatgcaa      360
agtctgttcg ggttcaatga tgggaatgcc gggatcagct tcctgcgcat tcctctgggc      420
```

```
ggaagtgaca tggccctcag ccactacacc tacaacgatg gggcagccga tccaaacctc    480
acccggttct ccatcgtcca tgatctgacc tacattgtcc ccctggcgaa acaggcaaag    540
accatcaact ccagccttcg ctacatgggc acccccctgga gccctccggc ctggatgaag    600
accagtggaa gcctcaacag tggcaaactg aaacccgagc actaccagac ctacgccaat    660
tacctgcgca agacctttga tgcctacaat gcccagggg tgaagttcaa ttacctgtct    720
cctcagaacg agccgcaata cgaaccgggc agttacccag gcaccaaatt cgaatggtac    780
gacgaattga actttgtgag gggccaccct cttcaacacca tgaacggcac cggagtgaag    840
attttgaccc tggaccacaa ctgggatctg aatggtacc ccagagccgt actgaacgag    900
ggatcggcct actacgaagg caccgcctgg cactgttacg cagggaacaa cgctgccatg    960
agcagggtgc gagacgcctt tcccagcaaa ggcgtttacc tgaccgagtg ctctggggga   1020
ctctgggcca ccaactttgg ggacaacatg aagtggaaca tgcaaaacct cttcattgga   1080
ggcaccaaga actgggccaa aacggtcttg ttctggagcc ttgcccttga tccctccgga   1140 ggccccatc tgggaggatg ctccaactgc aggggagtgg tcagcatcaa ccagaatggc   1200
ggggcagtga ccttcaacga agagtattac gccattgcac actttgcccg tttcgtgtgg   1260
cccggtgccg tgcgcattgg caccacggat tccagcgacg aaaattcat cggggtggcc   1320 ttcaggaaca ccaatggcgc aaaagccctg gtggtcctca accagagcaa cagcacagcc   1380
accttcaaaa tggtctggaa cggcaagtcc atccagcaga gtttgcccgc ctctggagtg   1440
gccacggttt tctgg                                                    1455

<210> SEQ ID NO 15
<211> LENGTH: 1458
<212> TYPE: DNA
<213> ORGANISM: Deinococcus sp.
<220> FEATURE:
<221> NAME/KEY: misc_feature
<223> OTHER INFORMATION: alpha-amylase derived from M23r-2A

<400> SEQUENCE: 15
atgcgccgcc ttccctcct cgccgcgctg ctcgcctcgc tggcaggcgc gcaggcctcc     60
cccaccctcc cgtccttcga ggggcaggtg atctatcagg tgatgcctga ccggtttttt    120
gacgggaaca aggcgaacga cgcaggggtc gaccgctcgg acccacgtgc ctggcacggc    180
ggcgatctgg cgggcctcac ggccaaactg ccctacctcc ggcagctggg ggcgacggcg    240
gtatggctga cgccaatcta ccggcagcag acggccaacg ccttcggtac cgccccctac    300
cacggctact ggcccgccga cttccgcgac gtggacccac atttcgggac actggccgat    360
tttgtcggtt tcgtcaaggc ggcacacggg gcggggctgc gcgtggtcct cgatcaggtg    420
atcaaccatt acggctacga ggcggcgcg gtcaaggaac acccggcctg gttcaatggg    480
aaagcagcgt gcgacgcttc cggcaacaag gacgtgaact gcccactggc gggcctgccg    540
gacctcaagc agtcgaaccc cgaggtcagg gcgctgctgc tgggcaacgc cgacttctgg    600
cgggggcagg gggtggatgg tttccgctac gacgcgatca agaacgtgga gacgcccttt    660
ctgaaagagc tgttggcacg cgaccgtgcc gccgggacgt ggacgctggg cgagtggtac    720
ggggcagaca ccgggacggt ggcgactgg cagcaggcc ggttcgacag tctcttcctc    780
ttcagcctgc aacaggcgat ggggcagagc ctgatgggcg gcagggcct cagccgggtg    840 gcgagcgtgc tgaccgcca aggcgagctg ccacgccccg cgaggtggc cctctttctg    900 gacaaccacg atgtcccgcg ctttgcccag ggcagcctgt tcgaggacca ggcccaggcc    960
```

-continued

| | |
|---|---|
| cgcacccgct acggcctgcg tgcgctgatg accctgaagg gcgtgccggt gctctggcag | 1020 |
| ggcactgaga ttgccatgcg cggcggtccc gaccccgata accgccgcga tatgcgcttc | 1080 |
| gagaacgagt ggacccctgc cgagcgccag gtcttcgaga cggcccggga cgccatcgcc | 1140 |
| gtccgccagg ccagccgggc cctcagcatc gggacccaga agctgctccc cacacccgcc | 1200 |
| tccctggaag acgacctgct cctcttcaca cgcgaggcgc aggggggagcg cgtgctggtc | 1260 |
| gcctggcaca acggcaggaa ccgcaagacg tacagcctcc gcctgagcgc cctgggactg | 1320 |
| aaagcggagc cgcaggccgt cacccgcagc ctcttcgccg gcaggacgc caagctcagc | 1380 |
| gtgagcgggg gctggctgca cctgagtctg cctgcggagg acgcggcagg atttgggctg | 1440 |
| gggggaagca cccggtaa | 1458 |

<210> SEQ ID NO 16
<211> LENGTH: 2853
<212> TYPE: DNA
<213> ORGANISM: Deinococcus sp.
<220> FEATURE:
<221> NAME/KEY: misc_feature
<223> OTHER INFORMATION: Glucoamylase from DRH-38

<400> SEQUENCE: 16

| | |
|---|---|
| gtgttcgtcg gtaccggtca caaaggtcac gtcgtacccg gcaaggcggt ggtagcgggc | 60 |
| cagggcgtcc gccaggatct tctcgtacac gtgcccgatg tggggtgcgc cgttggcgta | 120 |
| gtcaatggcg gtcgtaataa aaaactcgtt ctgtgtggac tcaggctgtc tcgtcatggc | 180 |
| cgctccccgc ctggccggtc cctgatgaga aagggccag gcaacttccc aaagatacgg | 240 |
| aaaaaatcac gcgccgcagg aaagtgtctg agacaagcgc ggcgtggtgc tgggctgagg | 300 |
| caccccgcct gccccctcagg tgcgcggggc cattcgcagc atcacggcgg tgctgaccgt | 360 |
| catgccccca gtataccgaa tgggggggctg gccagcgggg cgcgtagact cgcctcagac | 420 |
| gcagcccatc ccccaccaga ccccacaagg agaggcgaca tgagtgacgc ttccgctcag | 480 |
| aacccccccag aacagctcct ggcagcccca ggttccccgg aactgatttc tcccgcccag | 540 |
| ggcctggccc ccggtgcccc cggcctgccc ccaacctggg cgagcagcga caaggacttc | 600 |
| gtgacgacgg ccctgggggg cgcgtcccga ctgtgggcga ccggtggcca cggaatgctg | 660 |
| aacgaagtgt attggccctc caccgggcag ccacagattc gtgacctgac cttttatctg | 720 |
| gtggggggcg ccggctgggt ggacctgagg cgggtgaggc gctaccagct gtccatgcca | 780 |
| aagccgtacc tgcccctccc gaccctgctg caccaggggg acgactacca gctcatgctg | 840 |
| gaggtgctgc ccgatccaca ccgcgacgtg ctgctgatcc gctacgccct gagcggtccc | 900 |
| tatcgccttg cgatcgtgct ggctccccac ctcacctcca ccgggcatga caacgccgcc | 960 |
| tgggtcgagg gtcagcacct gctggcgtg tccgggaacc gcgcgctcgc gctgctgtcg | 1020 |
| agcagccgga tggaacacct gagcgctggg tacgtgggag tttcggacgg ctggcaggac | 1080 |
| ttgcaccagc atgggcgcct cacctggagc tacgagcggg cggaaaacgg caacgtggcc | 1140 |
| ctcagtgccg agctgcagga tgcctccggg cttctggcac tgggttttgc ggaaaacgtg | 1200 |
| acgggtgcgc agggcctggc ccgcgccagc ctcgcggaag gggacgagcc tgcccgccgc | 1260 |
| gccttttttgt gcgcctggga agcctggggc agcgccctca agctcggcgg ctccacgccc | 1320 |
| gagctggagg ccgaggccct cctcagcgcg acggtcctca aggtgcacga ggaccgcacc | 1380 |
| tatcccggcg cgctggtcgc cagcctcagc attcccctggg gagacagcac cgacacgctg | 1440 |
| ggcggctacc accttgtctg gccgcgcgac gcgacgctgg cggcctttgc tctgctcgcc | 1500 |

-continued

```
tgcaatcagc gtgaggacgc gcgccgggtg ctggcgtggt tcatcgccaa ccagcagtcc    1560
gacggccact ggctccagaa ctactatcca gacggtcagg acttttggca cggcgtgcag    1620
ctcgacgaga cggcctttcc ggtgctgctg ccgccaagc tgcgcgagga gggcgagccg     1680
gagctggagg gcactcgcga catggtgcgc gcgcgcttg cctttgtggc ccgcaccggt     1740
cccaccagtg accaggaccg ctgggaggag aaccagggg taaacccctt tacgttggcg     1800
gtcgcgattg ccgcgctggt ggcggggtca ggctggttgg aggaggacga cgccactat     1860 gccctcagcc tggcggatga ctggaacgag cggctggaaa gcctctgcta cgtgaccggc    1920
acgccgctgt gccgtgagct gggggtggag ggctactacg tgcggctggc gcccctgac    1980 cgcgacggca ccctcaccgg ccaggtgacg ctccaaaacc gccaaggcaa aacggtggag    2040
gcagcggcgt tggtcagtct ggattttct tatctgccgc gactgggcct gcgttcggcg     2100
ctcgatccac gcattcgcaa caccgtgaag gtggtggatc agctgctggc ccaaaagacg    2160
ccgaccggca tcttctacca ccgctacaac ggcgatggct acggcgaaca cgaggacggg    2220
gcgccctacg acggctccgg aatggggcgg ttgtggccgc tgctgagcgg cgagcgtggc    2280
cacctggcgc ttcaggcggg cgaggacgcc accgtctacc tcaacagcct gctgcgctgc    2340
tctagccccg gcggcctgct gcccgagcag gtctgggacg gccacccct gcccgaacgc    2400 ggcctctttc ccgggcggcc cagcggcagc gcgatgccgc tgctgtgggc gcacgctgaa    2460
tttctgaagc tgctgcacac cgcgcagacg ggccgccccg ccgaactgtt gcgcgaggtg    2520
gaggaacgct accgccagcc tcttcctgcc caggctcgcc actggcgccc gccgcaccg    2580 gtgcccgaac tcgaacccgg cctgctgctg ctgatcgagg atgacaagcc tttcctgctg    2640
cactacggct ttgatggctg gcaaaacccc caggaccgcc cagccctgcg cctcccctt     2700 ggcctgtggg gtgtcacctt cagtccgggc gaactgcgcg agcaccacac cctcgacttc    2760
acgcgcaagc tggcggtggg ttgggagggg caggaccatc acatccggct ccatgagggc    2820
gcgcccaagg cgtccctgac cgcgcagaac ggg                                 2853
```

<210> SEQ ID NO 17
<211> LENGTH: 2853
<212> TYPE: DNA
<213> ORGANISM: Deinococcus sp.
<220> FEATURE:
<221> NAME/KEY: misc_feature
<223> OTHER INFORMATION: Glucoamylase from MC2-2A

<400> SEQUENCE: 17

```
gtgttcgtcg gtaccggtca caaaggtcac gtcgtacccg caaggcggt ggtagcgggc      60 cagggcgtcc gccaggatct tctcgtacac gtgcccgatg tggggtgcgc cgttggcgta    120
gtcaatggcg tcgtaataa aaaactcgtt ctgtgtggac tcaggctgtc tcgtcatggc     180
cgctccccgc ctggccggtc cctgatgaga ggagggccag gcaacttccc aaagatacgg    240
aaaaaatcac gcgccgcagg aaagtgtctg agacaagcgc ggcgtggtgc tgggctgagg    300 cacccccgcct gcccctcagg tgcgcggggc cattcgcagc atcacggcgg tgctgaccgt    360 catgcccca gtataccgaa tgggggctg ggccagcggg cgcgtagact cgcctcagac      420
gcagcccatc ccccaccaga ccccacaagg agaggcgaca tgagtgacgc ttccgctcag    480
aaccccccag aacagctcct ggcagcccca ggttccccgg aactgatttc tcccgcccag    540
ggcctggccc ccggtgcccc cggcctgccc caacctggg cgagcagcga caaggacttc     600
gtgacgacgg ccctgggggg cgcgtcccga ctgtgggcga ccggtggcca cggaatgctg    660
```

```
aacgaagtgt attggccctc caccgggcag ccacagattc gtgacctgac cttttatctg    720
gtggggcgg ccggctgggt ggacctgagg cgggtgaggc gctaccagct gtccatgccc    780
aagccgtacc tgccccttcc taccctgctg caccaggggg acgactacca gctcatgctg    840
gaggtgctgc ccgatccaca ccgcgacgtg ctgctgatcc gctacgccct gagcggtccc    900
tatcgcctgg cgatcgtgct ggcgccccac ctcacctcca ccggacatga caacgccgcc    960
tgggtcgagg tcagcacct gctggcggtg tccgggaacc gcgcgctcgc gctgctgtcg   1020
agcagccgga tggaacacct gagcgccggg tacgtgggag tttcggacgg ctggcaggac   1080
ttgcaccagc atgggcgcct cacctggagc tacgagcggg cggaaaacgg caacgtggcc   1140
ctcagtgccg agctgcagga tgcctccggg cttctggcac tgggctttgc ggaaaacgtg   1200
acgggtgcgc agggcctggc ccgcgccagc ctcgcggaag gggacgagcc tgcccgccgc   1260
gccttttgt gcgcctggga agcctgggc agcgccctca agctcggcgg ctccacgccc   1320
gagctggagg ccgaggccct cctcagcgcg acggtcctca aggtgcacga ggaccgcacc   1380
tatcccggcg cgctggtcgc cagcctcagc attccctggg gagacagcac cgacacgctg   1440
ggcggctacc accttgtctg gccgcgcgac gcgacgctgg cggcctttgc tctgctcgcc   1500
tgcaatcagc gtgaggacgc gcgccgggtg ctggcgtggt tcatcgccaa ccagcagtcc   1560
gacggccact ggctccagaa ctactatcca gacggtcagg acttttggca cggcgtgcag   1620
ctcgacgaga cggcctttcc ggtgctgctg ccgccaagc tgcgcgagga gggcgagccg   1680
gagctggagg gcactcgcga catggtgcgc cgcgcgcttg cctttgtggc ccgcaccggt   1740
cccaccagtg accaggaccg ctgggaggag aaccaggggg taaacccctt tacgttggcg   1800
gtcgcgattg ccgcgctggt ggcggggtca ggctggttgg aggaggacga gcgccactat   1860
gccctcagcc tggcggatga ctggaacgag cggctggaaa gcctctgcta cgtgaccggc   1920
acgccgctgt gccgtgagct gggggtggag ggctactacg tgcggctggc gccccctgac   1980
cgcgacggca ccctcaccgg ccaggtgacg ctccaaaacc gccaaggcaa aacggtggag   2040
gcagcggcgt tggtcagtct ggattttcct tatctgccgc gactgggcct gcgttcggcg   2100
ctcgatccac gcattcgcaa caccgtgaag gtggtggatc acctgctggc ccaaaagacg   2160
ccgaccggca tcttctacca ccgctacaac ggcgatggct acggcgaaca cgaggacggg   2220
gcgcccacg acggctccgg aatgggcgg ttgtggccgc tgctgagcgg cgagcgtggc   2280
cacctggcgc ttcaggcggg cgaggacgcc accgtctacc tcaacagcct gctgcgctgc   2340
tctagccccg gcgccctgct gcccgagcag gtctgggacg gccacccct gcccgaacgc   2400
ggcctcttc ccgggcggcc cagcggcagc gcgatgccgc tgctgtgggc gcacgctgaa   2460
tttctgaagc tgctgcacac cgcgcagacg ggccgcccg ccgaactgtt gcgcgaggtg   2520
gaggaacgct accgccagcc tcttcctgcc caggctcgcc actggcgccc cgccgcaccg   2580
gtgcccgaac tcgaacccgg cctgctgctg ctgatcgagg atgacaagcc tttcctgctg   2640
cactacggct ttgatggctg gcaaaacccc caggaccgcc cagccctgcg cctcccttt    2700
ggcctgtggg gtgtcacctt cagtccgggc gaactgcgcg agcaccacac cctcgacttc   2760
acgcgcaagc tggcggtggg ttgggagggg caggaccatc acatccggct ccatgagggc   2820
gcgcccaagg cgtccctgac cgcgcagaac ggg                                2853
```

<210> SEQ ID NO 18
<211> LENGTH: 1281
<212> TYPE: DNA
<213> ORGANISM: Deinococcus sp.

```
<220> FEATURE:
<221> NAME/KEY: misc_feature
<223> OTHER INFORMATION: Arabinofuranosidase derived from DRH-46

<400> SEQUENCE: 18
atgaagcgca gcaagactca tctagccgtc gtcggccttg ccttcttgc cttgctcggc      60
tcatgcggcc agtccgttcc gggaccagag cagaacgcag cgttttacac cgggaagtac    120
cgcaaccctct tcacggagtg gagcattgcc acggaagcgc aggtgcaggc caaactcgac   180
gcgtactggg agagcctctt tgccagcacg gacgaccagc ggcgcgtcta ctaccctgcc   240
gggagcaacg cgaacggccc catggcgtac gtcgccgaca tcggcagcaa cgacgtccgg   300
accgagggta tgagctacgg catgatgatc gccgttcaaa tgaacaagca ggcagagttc   360
aatgccctgt ggaactacgc caagagcaag atgcagcacc agtcgggacc tcgtgccgga   420
tactttgcct ggcatacaga ctttgagggc aacatccttg atgcaaaccc tgccagtgac   480
ggagaagagt atttcgccac ggcgctcttt ttcgcgtctc accgttgggg tgacggcaac   540
gggatttaca actacagtgc cgaggcgaac aacatcctca caccatgct gcacaaggag   600
gacatgaacg cggggttgt gaatgggtt accaacatgt cgaccggga gcacaagcag     660
gtggtgttcg ttccggaagg agataacgcc atcttcacgg acccctccta ccacctgccc   720
gccttctacg agctgtggag ccgctgggcg accggctgga acggccagca ggctgtcgac   780
cgcaagttct gggctgaagc cgcccaggtc agccgcgact acttccagaa ggccacccac   840
cccgaaacgg gcctagcgcc tgactatgcg gagttcgacg gcaccccccaa gggacctgcg   900
tggaaccctg acgccgccaa cttccgtttc gacgcctggc gcaccgccgt caactggtct   960
gtggaccagg cctggtgggg caaggacagc cgtgagaccg cgctgacaga caagctgcaa  1020
agtttcttcg agagacaggg cattggtacc tacgtcaacc agtacacggt cagcggcacc  1080
ccgctgccgg gcgcgggccg ctccaccggt ctgatcgcca ccaacggtgc tgcgtctatc  1140
gctaccgaca ccccgcgtgc tcgacaattc acgcaggaac tctggaagct cgagccgccc  1200
accgggaagt ggcggtacta cgacggaatg atgaacttca tgtccctgct tcacgccagc  1260
ggtcacttcc ggatctacta a                                              1281

<210> SEQ ID NO 19
<211> LENGTH: 1278
<212> TYPE: DNA
<213> ORGANISM: Deinococcus sp.
<220> FEATURE:
<221> NAME/KEY: misc_feature
<223> OTHER INFORMATION: Arabinofuranosidase derived from DRH-46

<400> SEQUENCE: 19
atgaagcgca gcaagactca tctagccgtc gtcggccttg ccttctttc cttgctcggc      60
tcatgcggcc agtccgttcc gggaccagag cagaacgcag cgttttacac cgggaagtac    120
cgcaaccctct tcacggagtg gagcattgcc acggaagcgc aggtgcaggc caaactcgac   180
gcgtactggg agagcctctt tgccagcacg gacgaccagc ggcgcgtcta ctaccctgcc   240
gggagcaacg cgaacggccc catggcgtac gtcgccgaca taggcagcaa cgacgtccgg   300
accgagggta tgagctacgg catgatgatc gccgttcaaa tgaacaagca ggcagagttc   360
aatgccctgt ggaactacgc caagagcaag atgcagcacc agtcgggacc tcgtgccgga   420
tactttgcct ggcatacaga ctttgagggc aacatccttg atgcaaaccc tgccagtgac   480
ggagaagagt atttcgccac ggcgctcttt ttcgcgtctc accgttgggg tgacggcaac   540
```

-continued

```
gggatttaca actacagtgc cgaggcgaac aacatcctca acaccatgct gcacaaggag      600
gacatgaacg gcggggttgt gaatggggtt accaacatgt tcgaccggga gcacaagcag      660
gtggtgttcg ttccggaagg agataacgcc accttcacgg acccctccta ccacctgccc      720
gccttctacg agctgtggag ccgctgggcg accggctgga acggccagca ggctgccgac      780
cgcaagttct gggctgaagc cgcccaggtc agccgcgact acttccagaa ggccacccac      840
cccgaaacgg gcctagcgcc tgactatgcg gagttcgacg gcaccccaa gggacctgcg      900 tggaaccctg acgccgccaa cttccgtttc gacgcctggc gcaccgccgt caactggtct      960
gtggaccagg cctggtgggg caaggacagc cgtgagaccg cgctgacaga caagctgcaa     1020
agtttcttcg agagacaggg cattggtacc tacgtcaacc agtacacggt cagcggcacc     1080
ccgctgccgg gcgcgggccg ctccaccggt ctgatcgcca ccaacggtgc tgcatctatc     1140
gctaccgaca ccccgcgtgc tcgacaattc acgcaggaac tctggaagct cgagccgccc     1200
accgggaagt ggcggtacta cgacggaatg atgaacttca tgtccctgct tcacgccagc     1260
ggtcacttcc ggatctac                                                    1278
```

<210> SEQ ID NO 20
<211> LENGTH: 1662
<212> TYPE: DNA
<213> ORGANISM: Deinococcus sp.
<220> FEATURE:
<221> NAME/KEY: misc_feature
<223> OTHER INFORMATION: Arabinofuranosidase derived from DRH-46

<400> SEQUENCE: 20

```
atgacccagc acttcctgca aaaccccatc ctgcggggat tcaatccaga ccccagcatc       60
ctgcgtgtcg caacgactga ctacatcgcc acctcgacct tgaatggtt tcccggcgtg      120 cagatccacc actcccgcga cctggtgaac tggaggctcc tcacccgccc actcacccgc      180
aagtcacaac tggacatgcg cggcaacagc aacagtgccg catctgggc ccctgcctg      240 acccacgacg gtgaaaagtt ccacctgatc tacaccgacg tgaagcactg gtccaccaat      300 ggctcttca aggacaccca caactacctg gtgaccgccg agaacatcga gggcccctgg      360
agtgaaccca tttacctgaa ttccagcggc tttgacccca gcctctttca tgacgaagac      420
ggcaggaaat ggctctccaa catgctgtgg gaccaccgcc ccggacacca ccccttcgca      480
ggcattgtgc tgcaggaata cgatcctgta aagcaaaaac tggttggacc catcaaaaac      540
atcttcacgg gcacctccct gaaagtcacc gaaggtcccc acctgtaccg caaagacggt      600
tactactacc tgctcaccgc agaaggggga accacctacg agcacgccgt cacccttcgca      660 cgttccagaa acattgatgg tccttacgaa gtgcaccctc aaaatcccct gctgacctcc      720
ttcgggcacc ccgacattct ggtgcagaag gccgacacg gttccctggt ggaaacccag      780
agtggcgaat ggtaccttgc ccacctgggc ggacggcctc tggaagacat gcatgcctcc      840
gagcgccact gcaacctggg ccgcgaaacc tccctgcaga aagtcgagtg gcgtgaagac      900
ggctggccct acgtggtcgg cggcaacttc ccagtgcac aggtcccggt gtccctcctt      960
ccccatcctt ttgaacctga gcctgcagca gaggatttg cctcaggccg actgagcatc     1020
cactggcaga ccctgcgcac cccgatggat gaaagctggg tcaacttcac agagcgtccc     1080
ggtcacctca ggctggtcgg gcgggaatcc cccacctccc tgcaccacca gagcctggtt     1140
gcacgccgcc tgcaggcttt ccatgccgag gcccagacca ccatcgaatt tgatcctgac     1200
accttccagc agatggccgg actgagcgcc tactacgaca ccagcaactg gaccttcctg     1260
```

-continued

| | |
|---|---|
| atggtcacct gggatgaaag gctcggacgc tgcctgaaac tggggacctg cgaaaacggc | 1320 |
| aggtacagcg aatctggcac ccccatctcc ctgcccgatc aggccgtgca cctgggactg | 1380 |
| cgcttcgccc acgaaagcta ccagttttac ttctcacttg atggtgcaca gtggaccccc | 1440 |
| tttggacccg cccaccccag ttacaaactg tctgacgagt actgcggcgg actggcattc | 1500 |
| acgggaacct tcattgcgct ctctgcccat gacatgtccg gccagcgaaa agcagccgac | 1560 |
| ttcagccgat tcgagtaccg cgaattccct gtcctggaag gcttcctgag tgcctctttc | 1620 |
| ccctccagcc aggcaaacca gcccgaaccc gtagcagacc tc | 1662 |

<210> SEQ ID NO 21
<211> LENGTH: 3666
<212> TYPE: DNA
<213> ORGANISM: Deinococcus sp.
<220> FEATURE:
<221> NAME/KEY: misc_feature
<223> OTHER INFORMATION: Arabinofuranosidase derived from DRH-46

<400> SEQUENCE: 21

| | |
|---|---|
| atgcatcaac atcaaccaac ccgctccaaa aagaaaaacg cccgctcaag gctcagcctt | 60 |
| gcacttgctc tgtcctgtgc tgtgtctctg gcctctcccg tcttcgctgc agaagaagga | 120 |
| ctgttgcttc actacacctt tgacagcacc tctggaaaca ccgtcgcaga cagttctggg | 180 |
| aacaaaaaag atggtgttat ggaaggaaaa gccagctgga ccgcagcggg caagattgga | 240 |
| ggggccatcg atctggatgg aacctccggg ttcatccgtc tgccagaggc cctgcttgca | 300 |
| gagcaacatg acctcaccat tgccacctgg gtgaagcctg atgccctggg cacctggggcc | 360 |
| aggtgtttg attttgggtc cgggaccgac aactggatgt tcctgaccct gaacgacttc | 420 |
| accaatgcca cccgctttgc tgttcttccc aaaggcagca gtgaaaacct gctgaccgga | 480 |
| ccggctttcc cgggaggcaa tgactggcac catgtggcgg tggtgatttc aggcaacacg | 540 |
| tacaccctgt tcatcgatgg catccagtca gcaagtgtca gcaacatgca gaattttccc | 600 |
| gtgaaactgg ggccaccac ccagaattac atcgggaaat cccagtttga acctgatcct | 660 |
| ctctttgatg gcaaactcga tgatttccgc atctacaacc gggccatgaa tggtgaggaa | 720 |
| ctgatggccc tggtcactgc aggcatgacc gacgccgaca gcgtgtccta tgctcaaaaa | 780 |
| tggctgaatc tgggagacac ctcccagcag acccacgacc tgaacctgcc cacctctgga | 840 |
| ccttccggga ccaccatccg ctgggcctct tcaaatcccg cagtggtcag tgcagaaggc | 900 |
| aaagtcaccc gtccggcaaa aggccagagc aaccagaccg tgaccctgac agccacctc | 960 |
| cagaaaggca ccaccacga cacacgcact tttgatgtgc aggtctgggc tcaggggggcc | 1020 |
| acggcgtaca cgctggatgt gcaggcagac cagcccctgc atgccatcag tccgaccctg | 1080 |
| tacgggattt ctttgaaga catcaactac gccgcagatg ggggtctgta cgcggagctg | 1140 |
| gtgcgcaacc gttcctttga attcgatccg cagctgagtg gtgggctgt ggtcacggac | 1200 |
| gctggagggg caggaaaggc cagtggtcag actgaacgcc cctcaatga gcacaatcct | 1260 |
| caatacatgc gtctggaggt tacggctgcg ggtgcaggac tgtccaattc tggatttgat | 1320 |
| ggcattgccg ttcagaaagg tgcagcctac acctttcgg tgcatgcccg ctcgacctct | 1380 |
| cccctctcca gaccccctcac cgttcagctc agagggcaac aaggcgaggt gtatgggagg | 1440 |
| tgtgaagttt caggtgtgac tgcagcctgg cagaaattca cctgcaccct gacctcgaac | 1500 |
| accaccgatc ctgcggccag tgtggcgttg atggtgaatg aagttgccac ggtggacttt | 1560 |
| gacatggtct ccctcttccc cgagcagacc tggatgaacc gtccagaagg cctgagggaa | 1620 |

| | |
|---|---|
| gacctggccc agaagcttga tgacctgcaa ccgggcttcc tgcgctttcc tggcgggtgc | 1680 |
| attgtggagg gaggttcctt cttcaaccgc taccgctgga aaaacaccat cggggacgtg | 1740 |
| actgaacggg aaatccagcc gaaccagtgg gccagtggct actaccagac cttcgggctc | 1800 |
| gggttccaag agtacttcca gcttgcacag gacatcgggg ccgaacccct tcccatcctt | 1860 |
| tatgcaggcc agacctcctg cacgggcact ccagacatgg tggccctcga tgaccttggg | 1920 |
| ccctacattc aggacgcact cgacctgatc gagtatgcca atggggacgc gaaaaccacc | 1980 |
| cagtggggtg ccctccgggc tgcgcacggt caccctgagc ctttcaacat gaagtatctc | 2040 |
| ggggtgggaa atgaattgtg gggccaggat tacctgaacc gctatgagaa attctacgac | 2100 |
| gtgctcaagc aaaaacaccc cgaaatccag ctggtgctga gcgcagggc tttcccttcg | 2160 |
| gatttcaatt ttcagctggc ctgggactgg gtgaagaaaa ccggcaaagc cgacctgatc | 2220 |
| gacgagcaca tgtaccagtc tccccagtgg ttttatgaca atgccacccg ttacgacaat | 2280 |
| tatgaccgca aagggccaaa agtcttcgtg ggtgaatatg ccgcccacgg ggtgggcaaa | 2340 |
| cgcaacaacc tggaaagtgc cctggcagaa gcggccttca tgaccggact ggagcgcaat | 2400 |
| tcagatgtgg tgcacatggc ctccttcgct cctctgctgg ccaaagagaa ccgcacccag | 2460 |
| tggaccaccg acctgatctg gttcaacaac cagcaggtgt acgccacccc caactatcat | 2520 |
| gtgcagcagc ttttcaagca acatctgggc cagcaggttc tgcccaccac cctgaaaaaa | 2580 |
| gaggtccaga cccaggtgaa tgcacagccc atcacgggtt ccatcctgct gggatcatcg | 2640 |
| aacactgcgg tgcagtatga cgatgtgaaa atcaccgctg agaccagac ggtgaagtac | 2700 |
| gggaatgatt tctcagatgc cacccgaatc tccgactgga acttaccg gggagactgg | 2760 |
| agcattgaag aaggcaccct gaaacagacc agtgcaagcc tcaccgatgc cagactcctg | 2820 |
| ctcgggcagg gagaggactg gagcaactac accctcagcc tgagggcacg caaagacagt | 2880 |
| ggtgcagaag gcttcctgat tggctttggg gtgaagaaca ccagcgatta ccactggtgg | 2940 |
| aacctgggcg ggtgggggaa cacctccacg gcagtgaaaa atcggtggg tggggtcaaa | 3000 |
| accaccatcg gaaatgccac cccggtgacc atcgaaaccg gacgctggta cgacctgagg | 3060 |
| attgaggtgc agggcaacca catccgcctg tacctggaca caaaactgat tcacgacatc | 3120 |
| accgatgccc cgtccagcaa tggtcccctc tacagtgtca gcaattttga ccagaaaaca | 3180 |
| ggagacatca ttctgaaggt ggtcaacacc tccggaaaca cccagagcac ccaggtgaac | 3240 |
| ctgcaagggg tgaaagacct gcaacccaca gccaccctga ttgaactcac ctccgcttct | 3300 |
| gccctcgacg agaattcctt tgctgcacca gatcaggtca aacctgtgac gcgcaccctg | 3360 |
| ggtggcatca cccggaattt cagtcatgac ttcccggccc actccgtgac catcctgagg | 3420 |
| ctgcacaccg gcaagcaagc ggtcatcggg tccattgagc ctgtcagcat gcaaacaggc | 3480 |
| atcgggaaac gtccggtgct tcctgaacag gtgaccgtga aaaacaccga cgggtccacc | 3540 |
| cgcacggttc ctgtaaaatg gcagcagatc gatgacgtcc agctcagcac ccctggctct | 3600 |
| ttcagggtgg agggcagcgt ggaaggaaca tacctggagg cagaagctct ggtgaccgtc | 3660 |
| accccct | 3666 |

<210> SEQ ID NO 22
<211> LENGTH: 1488
<212> TYPE: DNA
<213> ORGANISM: Deinococcus sp.
<220> FEATURE:
<221> NAME/KEY: misc_feature
<223> OTHER INFORMATION: Arabinofuranosidase derived from DRH-46

<400> SEQUENCE: 22

```
atgaaaaaag cccagattct tcttgacacc cacagaacca tcagcgaaat cagccactac      60
atctttggtg gattcgccga gcacatgggc cgctgcatct acgagggcat ctacgacccc     120
caaagccctc tgagcgacga gaacggcatc cgcaggatg tgatgacgc cctgaaggaa      180
ctcaatttct gttccatccg ttaccccggg ggcaacttcg tgtcagggta caactgggaa     240
gacggaattg gccccaggga aaaccgcccg gtcaagcgcg atctggcctg gaggagcatc     300
gaaaccaacc agtttggcac ggatgaattc atgaaggtct gcgctgaact gaaaaccgaa     360
cccatgatgg ccgtgaacct gggcaccgga agtattcagg acgcggccaa catcgtcgaa     420
tactgcaacc tcgaaggcgg cacccattac agcgacctgc gcatcaaaaa cggtgctgaa     480
aaaccttatg gtgtgaagtt ctggtgtctg gggaacgaga tggatggtcc ctggcaggtg     540
ggacagcttt ctgcagagga ttacagtaag aaagccgtgc aggctgcaaa ggccatgaag     600
ctgatcgatc cttccattca actgattgcc tgcggttcct cctccagcct catgaactcc     660
taccccgagt gggaccgcat cgtgctgaaa gagacctggg accagatcga ttacctctcg     720
atgcactact atgccagcaa ccgggaggag gacactgcca gttacctcgc ctataccgt       780
gaattcgaag accacctgca aaccctggcc gccaccatcc gttacgtgaa agccaagaaa     840
cgcagccaga aagacgtgtt cctctcctgg gatgaatgga acgtctggta ccgcgaaatg     900
aacggcaacg gcgagtggca gcaggccccc cacatcctgg aagaggtcta caaccttgaa     960
gatgcgctgg tggtggccca gtggatgaat gtcttcctga agcacagcaa tgtgctgaag    1020
atggcctcca tcgcacaggt tgtcaatgtg atcgctccca tcatgaccag acgggatggc    1080
atgttcaaac agaccatcta ttatcctttc ctggtgttca gcaaacacgc ttctggtcag    1140
gcgctcagcc tgcatgtggc ctccgaccag tacgagacga aaaaacacgg cctcgtgaac    1200
ctgctcgatg ccagtgccag ttttgatgcc agccagaacg aaggggctgt ttttctggtc    1260
aaccgcagcc aggatgaaga actcgaaacc gaaatcgtct ttcagggccg tgttcccact    1320
tccgtgcgcg tggcccacca gcttgctggc agcgacccca agcccacaa ctccttcgag    1380
gagcctgaaa agctcaccct gcagacgatt gaagcagggg agatcaaaga cggcaaactc    1440
gtgctgaagc ttcctgcccct gtcctttcg gcagtggtgc tggactac               1488
```

<210> SEQ ID NO 23
<211> LENGTH: 1500
<212> TYPE: DNA
<213> ORGANISM: Deinococcus sp.
<220> FEATURE:
<221> NAME/KEY: misc_feature
<223> OTHER INFORMATION: Arabinofuranosidase derived from DRH-46

<400> SEQUENCE: 23

```
atgacaacac caaccaacac cacccacctg aaaatcacca ccccccattgg cctgatctct     60
ccacgtttct atggccactt cgcagaacac cttgcccgct gctgttatga cggcctctgg    120
gttgggcctt cgtccagcat tcccaacacc aggggctgga ggaatgatct ggtgtctgcc    180
ctgcagcaga tgcctgttcc catgatccgc tggcccgggg ggtgttacgc agaccactac    240
cactggagag atggcatcgg gcagcgcacc cccaggctgg catctcctg cggcacccgc    300
gtgacggaca ccaacgaact gggcacccat gaattcatgg acctgtgtga gctgctgcaa    360
tctgaagcct atctggccgg aaacatggcc tcaggcagcg tgcaggagat gtgtgactgg    420
ctggaataca ccagtggcac tgcagacacc accgtcaccc gtgaacgcca agaacggc      480
```

```
agaaaagacc cctgggatgt gaaactctgg ggcgtgggca acgaaagctg ggactgcggt      540
gggcgttacg atgcaaagac ctatgctgca gaattcaagc gttatggcgt gatgatgaag      600
catgtggacc cctcggtgga actcgttgct gtcggaaacg atgaggtggc cgctgcccgt      660
gcagaccaca tggagacctt ctggaacgag atcttcatgg agcacatcca ggaccacatc      720
gacctgatcg atcacctgtc ggtgcacacc tactggattg atggggcgc agaaacaggt       780 ttctcggagg agaattatta caccctgctg gcggaggcgg acaccaccga ggaagcgatt      840
gtgcgggcca aacgcaccat cgacaaatac gtcagaggac gcaagaacat caaggtggcc      900
atggatgaat acggggtgtg gcacccagaa acccgcccct gggtcctggg ccctcatgat      960
gacagtcgcc ccaacaactt cgagcaggcc aacaccctgc gggatgccct ctccgtgggg     1020
attgcccttg agggcttcca cagacaggcg aacatcctgg tcttgccaa cctggcacag      1080 attgtgaatg tcctgcaaag cgtcgccatg accgaagggg agaagatgtt cctgaccccc     1140
acctaccacg ccctgaagct gcacgagcac cacatcgggg cgaccagctg tcatgtggag     1200
gttcagacag atcgggtctt caagatgccc cgtgtgaccg ccaccgccag ccagaaagac     1260
ggcaacacca acctcaccct catcaaccgc cacatcagcg aagaaagcca gatcatgctg     1320
tatgacctgc ctgaaacccct gctgtctgcc cagctcctct ctggccctgc gccagacgcc     1380
accaacactt atgaccagcc agaacggatc tcattgcagc ctctggacgt gtacaaagag     1440
gacaacacct ggaagctgac tctgcccccg cacagcatgg ccaccctccg tttctccaga     1500
```

<210> SEQ ID NO 24  
<211> LENGTH: 1050  
<212> TYPE: DNA  
<213> ORGANISM: Deinococcus sp.  
<220> FEATURE:  
<221> NAME/KEY: misc_feature  
<223> OTHER INFORMATION: Arabinofuranosidase derived from DRH-46

<400> SEQUENCE: 24

```
atgtttcgtt ccatgctttt tcgcctgctc tgcctgatcc tgcttgtcgt ctctggaggc       60
gcatctgccc agggcaaaac cttccagaac ccgctgctgg tgtttgcggg tgcagaccca      120
cacatcgttt ttcatgacgg ctggtattac atgacctaca ccacaggtcg agacatccag      180
atccgcaaat ccagaagcct ggccacccctg gaccaggcag agatgaaagt ggtgtttcag      240
cccgaagggg aagcgtcctg ctgccacgtc tgggctcccg agttccacct gctggagggt      300
ccttcaggca agcgctggta catctattac accgctggtc cgaaagactg ctgtgcccat      360
cagcgcatgt acgttgccga gagtgccact gaggacccca tgggaccccta caccttcaaa      420 ggcaagattg ccgatcccag acacgacttc tgggccattg atgcttctgt ggtgcaaacc      480
agagaccacc tgtatctggt gtacagcgga acccctgaag acttcatgcc ccacgagaaa      540
ccccagcacc tgtacatcgc agaaatggcg aaccccctgga ccctgaaaag cgaacgggtg      600
gagatttcct ccccgacttt catctgggag cgcatgggtg gcccggtgaa cgaaggacct      660
gtggcgcttt atcacaacga ccagattttt ctggctttct caggcagtgg atgctggacc      720
gatgattaca gtctgggcct cctgaaggcc agtgcaaatg cagaccttt gaatcctgct       780 tcatggacca aactgcccga gcctgtcctg aacgcaatac gccgggca ggtgtatggc        840 cctggtcaca acggattttt caagtctcca gatggcaccg aagactgggt ggtgtaccac      900
gccaaccctg ctccgggcca gcagtgtggt gaatctcgcg tggcccgtgc ccagaagatc      960
acctgggacc agagcggcat gccggtgttt ggagaagccg ttccctctg gaccgatctg      1020
```
cctttgccct caggtgatcc cggcgcaccc    1050

<210> SEQ ID NO 25
<211> LENGTH: 23
<212> TYPE: DNA
<213> ORGANISM: Artificial
<220> FEATURE:
<223> OTHER INFORMATION: Primer 16S

<400> SEQUENCE: 25
ggtatctacg cattccaccg cta    23

<210> SEQ ID NO 26
<211> LENGTH: 23
<212> TYPE: DNA
<213> ORGANISM: Artificial
<220> FEATURE:
<223> OTHER INFORMATION: Primer 16S

<400> SEQUENCE: 26
gttacccgga atcactgggc gta    23

<210> SEQ ID NO 27
<211> LENGTH: 475
<212> TYPE: PRT
<213> ORGANISM: Deinococcus sp.
<220> FEATURE:
<221> NAME/KEY: MISC_FEATURE
<223> OTHER INFORMATION: AcDH derived from Deinococcus geothermalis
      DRH05

<400> SEQUENCE: 27

```
Met Thr Thr Thr Leu Thr Arg Val Pro Leu Leu Ile Gly Gly Gln Ala
1               5                  10                  15

Val Gln Thr Glu Ala Gln Asp Thr Val Phe Asn Pro Leu Asn Gly Glu
            20                  25                  30

Ala Leu Tyr His Val Ala Gln Ala Asp Gly Glu Ala Leu Arg Arg Ala
        35                  40                  45

Ile Ala Ser Ala Gln Ala Ala Phe Ala Ala Tyr Arg Gln Trp Pro Ala
    50                  55                  60

His Arg Arg Ala Glu Ala Leu Arg Arg Ala Ser Ala Leu Leu Ala Glu
65                  70                  75                  80

Arg Ala Asp Leu Phe Ala Arg Thr Ile Ala Thr Glu Ala Gly Lys Pro
                85                  90                  95

Leu Lys Ala Ala Arg Val Glu Val Ala Arg Ser Val Glu Asn Leu Gly
            100                 105                 110

Phe Ala Ala Asp Glu Ala Ala Gln Leu Ala Gly Gln Gly Ile Pro Leu
        115                 120                 125

Asp Ala Ser Arg Phe Gly Glu Gly Arg Leu Gly Phe Thr Leu Arg Glu
    130                 135                 140

Pro Arg Gly Val Ile Ala Ala Ile Ser Pro Phe Asn Phe Pro Leu Asn
145                 150                 155                 160

Leu Ala Leu His Lys Val Gly Pro Ala Leu Ala Gly Gly Asn Thr Val
                165                 170                 175

Ile Leu Lys Pro Ala Pro Gln Thr Pro Leu Thr Ala His Leu Ile Gly
            180                 185                 190

Glu Leu Val Gln Asp Ala Gly Phe Pro Ala Gly Ala Leu Asn Val Leu
        195                 200                 205

His Gly Gly Ala Glu Leu Gly Ala Ala Leu Thr Ala Ala Pro Glu Ile
    210                 215                 220
```

Ala Leu Val Thr Phe Thr Gly Ser Pro Gln Val Gly Glu Ala Ile Lys
225                 230                 235                 240

Arg Gly Ser Gly Leu Lys Pro Val Val Leu Glu Leu Gly Asn Asn Ser
            245                 250                 255

Ala Asn Leu Val Asp Ala Asp Ser Asp Val Glu Leu Ala Ala Arg Lys
            260                 265                 270

Leu Ala Ala Val Ser Phe Ala Tyr Gln Gly Gln Val Cys Ile His Pro
            275                 280                 285

Gln Arg Leu Ile Val His Ala Asp Val Tyr Asp Ala Phe Lys Ala Thr
            290                 295                 300

Phe Leu Glu Ala Ser Arg Ala Leu Val Val Gly Asp Pro Leu Asp Glu
305                 310                 315                 320

Gln Thr Asp Val Gly Pro Leu Ile Asn Pro Ala Ala Leu Thr Arg Leu
            325                 330                 335

Gln Ser Trp Ile Gln Glu Ala Leu Asp Leu Gly Gly Arg Leu Leu Leu
            340                 345                 350

Gly Gly Thr Pro Gln Gly Asn Leu Leu Pro Pro Thr Val Leu Glu Asp
            355                 360                 365

Val Pro Glu Glu Ala Arg Leu Val Cys Glu Gly Ala Phe Gly Pro Val
370                 375                 380

Val Val Leu Ser Arg Ala Ala Ser Trp Thr Asp Ala Ile Ala Ala Ala
385                 390                 395                 400

Asn Arg Ser Arg Tyr Gly Leu Gln Thr Gly Val Phe Thr Arg Asn Leu
            405                 410                 415

Gln His Ala Leu Glu Ala Val Arg Gly Ile Glu Ala Gly Gly Val Ile
            420                 425                 430

Val Asn Asp Pro Ser Thr Phe Arg Val Asp Gln Met Pro Tyr Gly Gly
            435                 440                 445

Ile Lys Glu Ser Gly Phe Gly Arg Gly Gly Thr Arg Ser Ala Leu Glu
            450                 455                 460

Glu Leu Thr Tyr Leu Lys Thr Val Val Leu Ser
465                 470                 475

<210> SEQ ID NO 28
<211> LENGTH: 485
<212> TYPE: PRT
<213> ORGANISM: Deinococcus sp.
<220> FEATURE:
<221> NAME/KEY: MISC_FEATURE
<223> OTHER INFORMATION: AcDH derived from Deinococcus geothermalis
      DRH05

<400> SEQUENCE: 28

Met Thr Pro Asp Pro Gln His Pro Glu Lys Thr Ala Ser Asp Ser Gly
1               5                   10                  15

His Arg Pro Phe Ala Thr Val Asn Pro Tyr Thr Gly Glu Thr Leu Cys
            20                  25                  30

Glu Phe Pro Phe Leu Thr Thr Glu Glu Ala Leu Ala Ala Val Glu Arg
            35                  40                  45

Ala His Gln Ala Phe Gly Thr Trp Arg Arg Pro Val Glu Asp Arg
50                  55                  60

Ala Ala Ile Met Arg Arg Ala Ala Glu Leu Met Leu Glu Arg Arg Asp
65                  70                  75                  80

Glu Leu Ala Arg Leu Val Thr Leu Glu Met Gly Lys Leu Ile Arg Glu
            85                  90                  95

Ser Gly Leu Glu Val Glu Leu Ala Ala Ser Ile Leu Lys Tyr Tyr Gly
            100                 105                 110

Glu Lys Gly Pro Glu Phe Leu Arg Pro Gln Pro Leu Glu Val Glu Gly
        115                 120                 125

Gly Glu Ala Ala Ile Val Asn Glu Pro Leu Gly Val Leu Leu Gly Ile
    130                 135                 140

Gln Pro Trp Asn Phe Pro Leu Tyr Gln Val Ala Arg Phe Ala Ala Pro
145                 150                 155                 160

Tyr Leu Val Val Gly Asn Thr Ile Leu Leu Lys His Ala Glu Ser Cys
                165                 170                 175

Pro Gln Thr Ala Leu Ala Leu Glu Gln Leu Phe Cys Asp Ala Gly Val
            180                 185                 190

Pro Glu Gly Val Tyr Thr Asn Val Phe Leu Lys Ile Ser Asp Val Glu
        195                 200                 205

Pro Val Val Ala His Pro Ala Val Gln Gly Val Ser Leu Thr Gly Ser
    210                 215                 220

Glu Arg Ala Gly Ala Ser Val Ala Glu Ile Ala Gly Arg His Leu Lys
225                 230                 235                 240

Arg Cys Val Leu Glu Leu Gly Gly Ser Asp Pro Phe Ile Val Leu Asp
                245                 250                 255

Ala Pro Asp Leu Gln Arg Thr Leu Arg Ala Ala Val Ile Gly Arg Met
            260                 265                 270

Ala Asn Thr Gly Gln Ser Cys Val Ala Ala Lys Arg Phe Ile Val Met
        275                 280                 285

Asp Glu Leu Tyr Asp Ala Phe Val Ala Gly Leu Ala Gln Ala Phe Gly
    290                 295                 300

Ser Leu Lys Pro Gly Asp Pro Ala Asp Pro Ala Thr Thr Leu Gly Pro
305                 310                 315                 320

Leu Ser Ser Glu Arg Ala Ala Arg Asp Leu Leu Ala Gln Val Gln Asp
                325                 330                 335

Ala Val Glu Lys Gly Ala Thr Val Val Thr Gly Gly Gly Arg Pro Asp
            340                 345                 350

Leu Pro Gly Ala Phe Val Glu Pro Thr Leu Leu Thr Gly Val Lys Pro
        355                 360                 365

Gly Met Arg Ala Phe Ser Glu Glu Leu Phe Gly Pro Val Ala Val Val
    370                 375                 380

Tyr Arg Ile Ser Ser Asp Glu Glu Ala Val Ala Leu Ala Asn Ser Ser
385                 390                 395                 400

Ser Tyr Gly Leu Gly Gly Ala Val Phe Cys Ser Asp Leu Gln Arg Ala
                405                 410                 415

Arg Ala Val Ala Asp Gln Leu Asp Ser Gly Met Val Trp Ile Asn His
            420                 425                 430

Pro Thr Ser Ser Gln Ala Asn Leu Pro Phe Gly Gly Val Lys Arg Ser
        435                 440                 445

Gly Tyr Gly Arg Glu Leu Asp Arg Leu Gly Ile Phe Glu Phe Thr Asn
    450                 455                 460

Arg Lys Leu Val Arg Thr Leu Pro Ala Ser Arg Ser Gly Gly Gln Ala
465                 470                 475                 480

Ala Gln Val Val Gly
                485

<210> SEQ ID NO 29
<211> LENGTH: 503
<212> TYPE: PRT

```
<213> ORGANISM: Deinococcus sp.
<220> FEATURE:
<221> NAME/KEY: MISC_FEATURE
<223> OTHER INFORMATION: AcDH derived from Deinococcus geothermalis
      DRH05

<400> SEQUENCE: 29
```

| | | | | | | | | | | | | | | |
|---|---|---|---|---|---|---|---|---|---|---|---|---|---|---|
| Met | His | Ser | Gly | Arg | Ser | Trp | Ser | Asp | Val | Trp | Arg | Gln | Val | Thr | Ala |
| 1 | | | | 5 | | | | | 10 | | | | | 15 | |

| Leu | Val | Pro | Glu | Ala | Ala | Leu | Pro | Asp | Gly | Thr | Leu | Arg | Ser | Val | Trp |
|---|---|---|---|---|---|---|---|---|---|---|---|---|---|---|---|
| | | | 20 | | | | | 25 | | | | | 30 | | |

| Gly | Glu | Ser | Trp | Gln | Gly | Lys | Gly | Thr | Pro | Arg | Gln | Thr | Phe | Ser | Pro |
|---|---|---|---|---|---|---|---|---|---|---|---|---|---|---|---|
| | | | 35 | | | | | 40 | | | | | 45 | | |

| Asn | Asp | Gly | Ala | Ala | Leu | Thr | Arg | Pro | Leu | Glu | Leu | Gly | Arg | Ala | Asp |
|---|---|---|---|---|---|---|---|---|---|---|---|---|---|---|---|
| 50 | | | | | 55 | | | | | 60 | | | | | |

| Val | Gly | Thr | Val | Leu | Glu | Ala | Cys | Thr | Arg | Thr | His | Glu | Thr | Trp | Ser |
|---|---|---|---|---|---|---|---|---|---|---|---|---|---|---|---|
| 65 | | | | | 70 | | | | | 75 | | | | | 80 |

| Ala | Thr | Asp | Leu | Asp | Glu | Arg | Arg | Arg | Val | Ser | Ala | Ala | Leu | Asp |
|---|---|---|---|---|---|---|---|---|---|---|---|---|---|---|
| | | | | 85 | | | | | 90 | | | | | 95 |

| Ala | Ile | Ala | Ala | Gln | Arg | Glu | Leu | Phe | Ala | Ala | Leu | Leu | Ala | Trp | Glu |
|---|---|---|---|---|---|---|---|---|---|---|---|---|---|---|---|
| | | | 100 | | | | | 105 | | | | | 110 | | |

| Ile | Gly | Lys | Pro | Leu | Arg | Gln | Ala | Leu | Ala | Glu | Val | Asp | Arg | Thr | Val |
|---|---|---|---|---|---|---|---|---|---|---|---|---|---|---|---|
| | | | 115 | | | | | 120 | | | | | 125 | | |

| Asp | Gly | Val | Arg | Trp | Tyr | Ile | Asp | Glu | Ile | Glu | Gly | Met | Leu | Ala | Gly |
|---|---|---|---|---|---|---|---|---|---|---|---|---|---|---|---|
| | 130 | | | | | 135 | | | | | 140 | | | | |

| Arg | Arg | Pro | Leu | Gly | Val | Val | Ser | Asn | Ile | Ala | Ser | Trp | Asn | Tyr | Pro |
|---|---|---|---|---|---|---|---|---|---|---|---|---|---|---|---|
| 145 | | | | | 150 | | | | | 155 | | | | | 160 |

| Leu | Ser | Val | Leu | Val | His | Ala | Met | Leu | Val | Gln | Ala | Leu | Ser | Gly | Asn |
|---|---|---|---|---|---|---|---|---|---|---|---|---|---|---|---|
| | | | | 165 | | | | | 170 | | | | | 175 | |

| Ala | Val | Leu | Ala | Lys | Ser | Pro | Ser | Ala | Gly | Gln | Ala | Ser | Val | Thr |
|---|---|---|---|---|---|---|---|---|---|---|---|---|---|---|
| | | | 180 | | | | | 185 | | | | | 190 | |

| Leu | Ala | Val | Ala | Leu | Ala | Arg | Arg | Ala | Gly | Val | Pro | Leu | Ser | Leu | Val |
|---|---|---|---|---|---|---|---|---|---|---|---|---|---|---|---|
| | | | 195 | | | | | 200 | | | | | 205 | | |

| His | Gly | Ser | Gly | Gly | Thr | Val | Gly | Glu | Ala | Leu | Ala | Thr | Ala | Pro | Glu |
|---|---|---|---|---|---|---|---|---|---|---|---|---|---|---|---|
| | 210 | | | | | 215 | | | | | 220 | | | | |

| Val | Ala | Ala | Val | Ala | Phe | Val | Gly | Gly | Arg | Ala | Thr | Gly | Gln | Val | Leu |
|---|---|---|---|---|---|---|---|---|---|---|---|---|---|---|---|
| 225 | | | | | 230 | | | | | 235 | | | | | 240 |

| Gly | Glu | Arg | Leu | Arg | Gly | Gln | Pro | Gln | Arg | Val | Met | Leu | Glu | Met | Glu |
|---|---|---|---|---|---|---|---|---|---|---|---|---|---|---|---|
| | | | | 245 | | | | | 250 | | | | | 255 | |

| Gly | Val | Asn | Pro | Tyr | Gly | Leu | Trp | Asn | Phe | Ser | Asp | Trp | Glu | Arg | Phe |
|---|---|---|---|---|---|---|---|---|---|---|---|---|---|---|---|
| | | | 260 | | | | | 265 | | | | | 270 | | |

| Glu | Gln | His | Val | Arg | Ser | Gly | His | Asp | Tyr | Ala | Lys | Gln | Arg | Cys | Thr |
|---|---|---|---|---|---|---|---|---|---|---|---|---|---|---|---|
| | | 275 | | | | | 280 | | | | | 285 | | | |

| Val | Tyr | Pro | Arg | Phe | Val | Val | Gln | Arg | Glu | Leu | Phe | Pro | Gln | Phe | Leu |
|---|---|---|---|---|---|---|---|---|---|---|---|---|---|---|---|
| | 290 | | | | | 295 | | | | | 300 | | | | |

| Glu | His | Tyr | Leu | Arg | Ala | Val | Ser | Gln | Val | Arg | Val | Gly | His | Pro | Leu |
|---|---|---|---|---|---|---|---|---|---|---|---|---|---|---|---|
| 305 | | | | | 310 | | | | | 315 | | | | | 320 |

| Leu | Asp | Thr | Asp | Glu | Ala | Pro | Leu | Ser | Ser | Gly | Pro | Leu | Ile | His | Glu |
|---|---|---|---|---|---|---|---|---|---|---|---|---|---|---|---|
| | | | 325 | | | | | 330 | | | | | 335 | | |

| Arg | Lys | Val | Arg | Asp | Leu | Arg | Leu | Arg | Met | Gln | Glu | Ala | Thr | Gly | Leu |
|---|---|---|---|---|---|---|---|---|---|---|---|---|---|---|---|
| | | | 340 | | | | | 345 | | | | | 350 | | |

| Gly | Ala | Val | Pro | Leu | His | Ala | Gly | Thr | Leu | Glu | Asn | Ala | Arg | Leu | Glu |
|---|---|---|---|---|---|---|---|---|---|---|---|---|---|---|---|
| | | | 355 | | | | | 360 | | | | | 365 | | |

| Pro | Glu | Gln | Pro | Gln | Glu | Ala | Tyr | Leu | Ala | Pro | Gln | Leu | Leu | Leu | His |
|---|---|---|---|---|---|---|---|---|---|---|---|---|---|---|---|
| | 370 | | | | | 375 | | | | | 380 | | | | |

```
Pro Pro Ser Arg Ser Arg Leu Tyr Arg Glu Glu Pro Phe Gly Pro Val
385                 390                 395                 400

Asp Thr Val Val Ile Val Asp Arg Pro Glu Asp Leu Val Arg Glu Met
                    405                 410                 415

Asn Val Ser Arg Gly Ser Leu Val Ala Thr Leu Ala Thr Asp Asp His
                420                 425                 430

Thr Phe Ala Gln Glu Leu Thr Pro Gln Ile Gln Ala Phe Lys Val Gly
            435                 440                 445

Val Asn Ala Leu Arg Ser Arg Gly Asp Arg Asp Glu Pro Phe Gly Gly
        450                 455                 460

Ala Gly Ala Ser Trp Trp Gly Pro Tyr Leu Gly Gly Glu His Leu Val
465                 470                 475                 480

Arg Ala Val Thr Ala Gly Pro Ala Gly Glu Thr Leu His Gly Asn Phe
                485                 490                 495

Gly Pro Val Trp Arg Ser Thr
                500
```

<210> SEQ ID NO 30
<211> LENGTH: 525
<212> TYPE: PRT
<213> ORGANISM: Deinococcus sp.
<220> FEATURE:
<221> NAME/KEY: MISC_FEATURE
<223> OTHER INFORMATION: AcDH derived from Deinococcus geothermalis DRH05

<400> SEQUENCE: 30

```
Met Thr Ser Thr Leu Met Glu Gly Phe Leu Pro Phe Thr His Glu Pro
1               5                   10                  15

Tyr Phe Asn Phe Ala Gln Glu Asp Val Ala Gln Lys Gln Arg Glu Ala
                20                  25                  30

Tyr Arg Gln Val Arg Glu Lys Tyr Val Gly Arg Ser Phe Pro Met Met
            35                  40                  45

Leu Cys Gly Lys Pro Val Glu Gly Glu Asp Thr Phe Glu Val His Asn
        50                  55                  60

Pro Ala Asp Thr Arg Glu Thr Val Trp Arg Phe Pro Lys Ala Ser Pro
65                  70                  75                  80

Ala Gln Leu Glu Gln Ala Ile Ala Cys Ala Lys Ala Ala Phe Glu Glu
                85                  90                  95

Trp Arg Phe Ser Asp Pro Leu Gln Arg Ala Ala Ile Phe Lys Arg Ala
                100                 105                 110

Ala Glu Leu Leu Arg Thr Arg Met Glu Phe Asn Ala Val Met Gly
            115                 120                 125

Leu Glu Asn Gly Lys Asn Trp Ala Glu Ala Asp Gly Glu Ile Ala Glu
        130                 135                 140

Cys Val Asp His Phe Glu Val Phe Ala Arg Glu Thr Leu Arg Trp Ala
145                 150                 155                 160

Gln Gly Lys Pro Val Tyr Pro Met Pro Asp Glu His Val Thr Met Val
                165                 170                 175

Tyr Glu Pro Ile Gly Val Val Ala Val Ile Ser Pro Trp Asn Phe Pro
            180                 185                 190

Ala Ala Ile Pro Leu Gly Met Ser Leu Gly Ala Ile Ala Ala Gly Asn
        195                 200                 205

Thr Val Val Trp Lys Pro Ala Ser Glu Thr Pro Leu Ser Ser Leu Leu
    210                 215                 220
```

Leu Val Glu Leu Leu Phe Glu Ala Gly Leu Pro Arg Asn Val Ile Gln
225                 230                 235                 240

Phe Leu Thr Gly Thr Asp Glu Val Leu Gly Asp Pro Leu Val Asp His
            245                 250                 255

Lys Asp Ile Arg Met Ile Ala Phe Thr Gly Ser Lys Glu Ile Gly Cys
            260                 265                 270

Arg Ile Met Glu Arg Ala Ala Lys Val Gln Pro Gly Gln Lys Trp Leu
        275                 280                 285

Lys Arg Val Met Ala Glu Met Gly Gly Lys Asp Pro Thr Val Val Cys
    290                 295                 300

Ala Asp Ala Asp Leu Asp Asp Ala Ala Arg Gly Ile Val Gln Ala Ala
305                 310                 315                 320

Phe Gly Tyr Ser Gly Gln Lys Cys Ser Ala Cys Ser Arg Val Ile Ala
            325                 330                 335

Glu Asp Ser Val Tyr Asp Glu Leu Leu Asp Lys Val Val Arg Leu Thr
            340                 345                 350

Arg Glu Leu Lys Val Gly Leu Pro Glu Glu Asn Ala Pro Leu Gly Pro
        355                 360                 365

Val Ile His Glu Asp Ser Ala Asn Arg Ile Leu Ala Ser Ile Glu Arg
    370                 375                 380

Gly Lys Lys Thr Ala His Leu Val Leu Gly Gly Glu Arg Ala Asp Ser
385                 390                 395                 400

Gly Gly Arg Glu Gly Gly Tyr Leu Gln Pro Thr Ile Phe Ala Asp Val
            405                 410                 415

Asp Pro Arg Asp Pro Leu Phe Gln Glu Ile Phe Gly Pro Val Leu
        420                 425                 430

Ser Phe Thr Arg Ala Arg Asp Trp Arg His Ala Ile Asp Leu Ala Asn
    435                 440                 445

Asp Ser Glu Tyr Gly Leu Thr Ala Ala Phe Tyr Ser Arg Asp Pro Gln
    450                 455                 460

Lys Ile Ala Glu Ala Arg Arg Leu Ile His Val Gly Asn Leu Tyr Val
465                 470                 475                 480

Asn Arg Lys Cys Thr Gly Ala Leu Ser Gly Thr His Ala Phe Gly Gly
            485                 490                 495

Tyr Gly Met Ser Gly Thr Asn Ala Lys Val Gly Gly Pro Asp Tyr Leu
            500                 505                 510

Phe Trp Phe Leu Gln Thr Lys Thr Val Ala Gln Lys Tyr
        515                 520                 525

<210> SEQ ID NO 31
<211> LENGTH: 292
<212> TYPE: PRT
<213> ORGANISM: Deinococcus sp.
<220> FEATURE:
<221> NAME/KEY: MISC_FEATURE
<223> OTHER INFORMATION: AcDH derived from Deinococcus M23r-2A
<220> FEATURE:
<221> NAME/KEY: misc_feature
<222> LOCATION: (23)..(160)
<223> OTHER INFORMATION: Xaa can be any naturally occurring amino acid

<400> SEQUENCE: 31

Met Thr Arg Lys Leu Lys Ala Ala Ile Ile Gly Ser Gly Asn Ile Gly
1               5                   10                  15

Thr Asp Leu Met Ile Lys Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa

```
                    35                  40                  45
Xaa Xaa Xaa Xaa Xaa Xaa Xaa Xaa Xaa Xaa Xaa Xaa Xaa Xaa
         50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa Xaa
145                 150                 155                 160

Val Val Gly Gly Ala Ala Lys Gly Lys Ala Ile Ile Val Leu Asn Pro
                165                 170                 175

Ala Glu Pro Pro Leu Met Met Arg Asp Thr Val Tyr Thr Leu Ser Glu
            180                 185                 190

Leu Ala Asp Glu Asp Ala Ile Ala Arg Ser Val Glu Arg Met Ala Ser
            195                 200                 205

Asp Val Gln Ala Tyr Val Pro Gly Tyr Arg Leu Lys Gln Lys Val Gln
210                 215                 220

Phe Asp Arg Ile Glu Ser Asp Arg Pro Ile Arg Ile Pro Gly Val Gly
225                 230                 235                 240

Met Ser Met His Gly Leu Lys Thr Ser Ile Phe Leu Glu Val Glu Gly
                245                 250                 255

Ala Ala His Tyr Leu Pro Ala Tyr Ala Gly Asn Leu Asp Ile Met Thr
            260                 265                 270

Ser Ala Gly Leu Arg Thr Ala Glu Ser Met Ala Glu Arg Met Leu Glu
        275                 280                 285

Ala Ala His Ala
        290

<210> SEQ ID NO 32
<211> LENGTH: 452
<212> TYPE: PRT
<213> ORGANISM: Deinococcus sp.
<220> FEATURE:
<221> NAME/KEY: MISC_FEATURE
<223> OTHER INFORMATION: ADH derived from Deinococcus geothermalis
      DRH05

<400> SEQUENCE: 32

Met His Gly Gly Phe Gly Cys Asp Thr Gly Arg Glu Pro Tyr Ala Ala
 1               5                  10                  15

Pro Pro Ile Arg Arg Ser Thr Leu Ser Val His Pro Lys Thr Leu Gln
            20                  25                  30

His Glu Thr Leu Phe Thr Ile Glu Ala Thr Pro Val Lys Phe Gly Pro
        35                  40                  45

Gly Ala Ala Ala Asp Ala Gly Trp Glu Ala Ala Arg Leu Gly Ile Arg
    50                  55                  60

Arg Ala Phe Val Val Leu Asp Pro Arg Leu Ala Gln Gly Glu Ala Ala
65                  70                  75                  80

Arg Gly Val Leu Glu Asn Leu Arg Ala Ala Gly Ile Asp Leu Val Val
                85                  90                  95
```

```
Phe Thr Asp Ile Arg Ile Glu Pro Asp Leu Ala Ser Leu Glu Arg Ala
            100                 105                 110

Thr Ala Ala Ala Arg Glu Ala Lys Pro Asp Gly Phe Ile Ala Leu Gly
        115                 120                 125

Gly Gly Ser Thr Ile Asp Thr Ala Lys Val Ala Asn Leu Leu Thr Thr
130                 135                 140

His Gly Gly Lys Val Met Asp Tyr Val Asn Pro Ile Gly Gly
145                 150                 155                 160

Arg Ala Leu Pro Gly Pro Leu Arg Pro Leu Ala Ile Pro Thr Thr
                165                 170                 175

Ala Gly Ser Gly Ser Glu Ala Thr Thr Val Ala Ile Leu Asp Leu Pro
            180                 185                 190

Asp Leu Gly Val Lys Ser Gly Ile Ser His Arg Tyr Leu Arg Pro Ala
        195                 200                 205

Gln Ala Ile Val Asp Pro Glu Leu Thr Arg Thr Ala Pro Ser Ser Val
    210                 215                 220

Ile Ala Ser Ala Gly Leu Asp Val Val Cys His Ala Ala Glu Ser Phe
225                 230                 235                 240

Leu Ser Arg Pro Tyr Thr Thr Arg Pro Arg Pro Val Thr Pro Ala Glu
                245                 250                 255

Arg Pro Pro Tyr Gln Gly Ser Asn Pro Val Ala Asp Leu Trp Ser Ala
            260                 265                 270

Gln Ala Leu Arg Tyr Gly Gly Gln Tyr Leu Arg Arg Ala Val Ala Asp
        275                 280                 285

Pro Asp Asp Val Glu Ala Arg Gly Phe Met Met Leu Ser Ala Thr Met
    290                 295                 300

Ala Gly Val Gly Phe Gly Ser Ala Gly Val His Ile Pro His Ala Cys
305                 310                 315                 320

Ala Tyr Pro Ile Ala Gly Leu Arg His Ser Tyr His Ala Pro Asp Tyr
                325                 330                 335

Pro Gln Asp His Ala Phe Val Pro His Gly Phe Ser Val Ile Val Thr
            340                 345                 350

Ala Pro Ala Ala Phe Arg Phe Thr Phe Asp Ala Asp Pro Ala Lys His
        355                 360                 365

Val Tyr Ala Ala Ser Leu Leu Thr Gly Glu Ala Tyr Glu Glu Asp Asp
370                 375                 380

Arg Glu Ala Leu Pro Ser Ala Leu Leu Glu Leu Met Arg Asp Val Gly
385                 390                 395                 400

Ala Pro Ser Gly Val Ala Glu Leu Gly Tyr Gly Glu Ala Asp Leu Pro
                405                 410                 415

Ala Leu Val Ala Gly Ala Leu Lys Gln Gln Arg Leu Leu Ala Val Ala
            420                 425                 430

Pro Arg Thr Pro Thr Ala Gln Asp Leu Glu Gly Ile Leu Arg Glu Ser
        435                 440                 445

Met His Asn Gly
        450

<210> SEQ ID NO 33
<211> LENGTH: 342
<212> TYPE: PRT
<213> ORGANISM: Deinococcus sp.
<220> FEATURE:
<221> NAME/KEY: MISC_FEATURE
<223> OTHER INFORMATION: ADH derived from Deinococcus geothermalis DRH05
```

<400> SEQUENCE: 33

```
Met Ala Gln Ser Arg Pro Ser Leu Pro Glu Pro Gln Arg Pro Glu His
1               5                   10                  15

Phe Arg Ala Leu Arg Ala Val Lys Asp Glu Thr Gly Val Arg Pro Glu
            20                  25                  30

Phe Gln Thr Leu Thr Leu Ala Asp Leu Pro Glu Gly Glu Val Leu Val
        35                  40                  45

Arg Val Thr His Ser Ser Leu Asn Tyr Lys Asp Gly Leu Ala Val Ala
    50                  55                  60

Gly Arg Pro Gly Val Leu Lys Ala Tyr Pro Met Thr Pro Gly Ile Asp
65                  70                  75                  80

Leu Ala Gly Thr Val Val Glu Asp Gln Thr Gly Thr Tyr Arg Pro Gly
                85                  90                  95

Asp Ala Val Leu Leu Thr Gly Trp Gly Ile Gly Glu Arg Gln Asp Gly
            100                 105                 110

Gly Tyr Ala Glu Tyr Ala Arg Val Lys Ala Ala Trp Leu Val Pro Leu
        115                 120                 125

Pro Glu Gly Thr Asp Ala Gln Trp Ala Met Ser Val Gly Thr Ala Gly
    130                 135                 140

Phe Thr Ala Met Leu Ala Val Met Ala Leu Glu His Gly Val Thr
145                 150                 155                 160

Pro Gly Ser Gly Glu Val Leu Val Thr Gly Ala Ala Gly Gly Val Gly
                165                 170                 175

Ser Thr Ala Val Ala Leu Leu Ala Ala Ala Gly His Ser Val Thr Ala
            180                 185                 190

Ser Thr Gly Arg Arg Glu Glu Glu Asp Tyr Leu Arg Ser Leu Gly Ala
        195                 200                 205

Ala Asn Ile Ile Gly Arg Glu Glu Leu Pro Ala Leu Lys Arg Pro Leu
    210                 215                 220

Glu Lys Glu Arg Trp Ala Gly Val Val Asp Ser Val Gly Gly Asp Thr
225                 230                 235                 240

Leu Ala Gly Ala Leu Ala Ser Thr Arg Thr His Gly Ala Val Ala Ala
                245                 250                 255

Cys Gly Leu Ala Gly Gly Ser Gly Leu Asn Thr Thr Val Phe Pro Phe
            260                 265                 270

Ile Leu Arg Gly Val Asn Leu Leu Gly Ile Asp Ser Val Thr Cys Pro
        275                 280                 285

Thr Glu Arg Arg Arg Ala Ala Trp Ala Arg Leu Ala Arg Asp Leu Pro
    290                 295                 300

Ala Ala Lys Leu Ala Gly Val Thr Gln Leu Arg Pro Leu Ser Asp Val
305                 310                 315                 320

Pro Ala Leu Ala Gln Glu Ile Leu Ala Gly Arg Val Arg Gly Arg Thr
                325                 330                 335

Val Ile Asp Val Thr Arg
            340
```

<210> SEQ ID NO 34
<211> LENGTH: 379
<212> TYPE: PRT
<213> ORGANISM: Deinococcus sp.
<220> FEATURE:
<221> NAME/KEY: MISC_FEATURE
<223> OTHER INFORMATION: ADH derived from Deinococcus geothermalis DRH05

<400> SEQUENCE: 34

```
Met Lys Ala Val Ile Tyr Asn Gly Pro Arg Asp Val Arg Val Val Asp
1               5                  10                  15

Val Ala Asp Pro Gln Ile Glu Gln Pro Thr Asp Val Leu Val Lys Ile
            20                  25                  30

Thr Ser Thr Asn Ile Cys Gly Ser Asp Leu His Met Tyr Glu Gly Arg
        35                  40                  45

Thr Asp Ile Glu Cys Gly Arg Val Gly His Glu Asn Leu Gly Glu
    50                  55                  60

Val Val Glu Ile Gly Arg Ala Val Tyr Arg Ile Lys Val Gly Asp Lys
65                  70                  75                  80

Val Cys Leu Pro Phe Asn Ile Gly Cys Gly Phe Cys Arg Asn Cys Glu
                85                  90                  95

Lys Gly Leu Thr Gly Ala Cys Leu Thr Val Ala Pro Gly Gln Ala Gly
                100                 105                 110

Ala Ala Tyr Gly Phe Ala Asp Met Gly Pro Phe Gln Gly Gly Gln Ala
            115                 120                 125

Gln Tyr Leu Arg Val Pro Phe Gly Asp Phe Asn Cys Leu Lys Leu Pro
        130                 135                 140

Glu Asp Ala Ala Glu Lys Glu Asp Asp Tyr Val Met Leu Ala Asp Ile
145                 150                 155                 160

Phe Pro Thr Gly Trp His Ala Thr Arg Leu Ala Asn Leu Met Pro Gly
                165                 170                 175

Glu Ser Val Ala Ile Tyr Gly Ala Gly Pro Val Gly Leu Met Ala Ala
            180                 185                 190

Tyr Ser Ala Met Ile Gln Gly Ala Arg Gln Val Ile Val Asp Arg
        195                 200                 205

His Lys Asp Arg Leu Lys Leu Ala Glu Gln Ile Gly Ala Ile Ala Val
    210                 215                 220

Asn Asp Ala Glu His Asp Pro Val Glu Gln Ile Met Glu Leu Thr Asn
225                 230                 235                 240

Gly Arg Gly Thr Asp Lys Gly Cys Glu Cys Val Gly Trp Gln Cys His
                245                 250                 255

Asp His Gly Gly His Glu Ile Pro Asn Leu Thr Met Asn Asn Leu Val
            260                 265                 270

Lys Thr Thr Arg Ala Thr Gly Gln Ile Gly Val Val Gly Val Phe Val
        275                 280                 285

Pro Gln Asp Pro Lys Ser Pro Asp Asp Leu Met Lys Arg Gly Gln Ile
        290                 295                 300

Ala Phe Asp Ile Gly Asn Phe Phe Lys Gly Leu Arg Met Gly Ser
305                 310                 315                 320

Gly Gln Ala Asn Val Lys Ala Tyr Asn Arg Glu Leu Arg Asp Leu Ile
            325                 330                 335

His Ala Asp Arg Ala Lys Pro Ser Phe Leu Val Ser His Arg Leu Pro
        340                 345                 350

Leu Glu Gln Ala Pro Asp Ala Tyr Lys Asn Phe Asp Asn Arg Ile Asp
        355                 360                 365

Gly Trp Thr Lys Val Ile Leu Lys Pro Asn Glu
    370                 375

<210> SEQ ID NO 35
<211> LENGTH: 405
<212> TYPE: PRT
<213> ORGANISM: Deinococcus sp.
<220> FEATURE:
<221> NAME/KEY: MISC_FEATURE
```

<223> OTHER INFORMATION: ADH derived from Deinococcus geothermalis DRH05

<400> SEQUENCE: 35

```
Met Lys Ala Leu Val Trp Gln Gly Ile Asn Arg Val Gly Val Glu Arg
1               5                   10                  15

Val Pro Asp Pro Thr Ile Leu Gln Pro Thr Asp Ala Ile Val Arg Val
            20                  25                  30

Thr Ala Thr Ala Ile Cys Gly Ser Asp Leu His Leu Leu Asp Gly Tyr
        35                  40                  45

Ile Pro Ser Met Val Lys Gly Asp Ile Leu Gly His Glu Phe Met Gly
    50                  55                  60

Glu Val Val Glu Val Gly Ser Ala Val Arg Arg Ile Arg Val Gly Asp
65                  70                  75                  80

Arg Val Ile Val Pro Phe Pro Ile Ala Cys Gly Lys Cys Trp Tyr Cys
                85                  90                  95

Gln His Gly Leu Thr Ser Leu Cys Asp Asn Ser Asn Pro Asn Pro Lys
            100                 105                 110

Leu Ala Glu Thr Leu Trp Gly Tyr Ala Gly Ala Gly Ile Tyr Gly Tyr
        115                 120                 125

Ser His Ile Thr Gly Gly Tyr Ala Gly Gly Gln Ala Gln Phe Ala Arg
    130                 135                 140

Thr Val Tyr Ala Asp Ala Asn Leu Tyr Pro Val Pro Glu Gly Leu Thr
145                 150                 155                 160

Asp Glu Gln Val Leu Phe Leu Thr Asp Ile Leu Pro Thr Gly Tyr Met
                165                 170                 175

Ala Ala Glu His Ser Asn Ile Gln Pro Gly Asp Val Val Thr Val Phe
            180                 185                 190

Gly Ala Gly Pro Val Gly Leu Phe Thr Val Met Ser Ala Phe Leu Leu
        195                 200                 205

Gly Ala Gly Arg Val Ile Ser Ile Asp Arg Phe Asp Asp Arg Leu Lys
    210                 215                 220

Leu Ala Arg Gln Leu Gly Ala Glu Thr Ile Asn Tyr Glu Ala Asp Asn
225                 230                 235                 240

Val Phe Glu Arg Leu Lys Glu Leu Thr Gly Gly Arg Gly Pro Asp Ser
                245                 250                 255

Val Val Asp Ala Val Gly Met Glu Ser His Gly Thr Gly Leu Gly Gly
            260                 265                 270

Ile Tyr Asp Ala Val Lys Gln Thr Thr Arg Val Leu Glu Thr Glu Arg
        275                 280                 285

Pro His Ala Leu Arg Ala Ala Ile Met Ala Cys Arg Lys Gly Gly Thr
    290                 295                 300

Val Ser Val Pro Gly Val Tyr Gly Gly Leu Ala Asp Lys Ile Pro Val
305                 310                 315                 320

Gly Ala Leu Met Asn Lys Gly Leu Thr Leu Arg Thr Gly Gln Thr His
                325                 330                 335

Val His Arg Tyr Leu Asp Thr Leu Thr Gln His Ile Leu Arg Gly Asp
            340                 345                 350

Ile Asp Pro Thr Val Ile Ile Thr His Arg Leu Ser Leu Asp Glu Ala
        355                 360                 365

Pro Arg Gly Tyr Gln Leu Phe Lys His Lys His Asp Gly Cys Ile Lys
    370                 375                 380

Cys Val Leu Asp Pro Trp Ala Asp Pro Lys Glu His Ala Pro Thr Ser
385                 390                 395                 400
```

```
Pro Gln Pro Glu Thr
            405

<210> SEQ ID NO 36
<211> LENGTH: 329
<212> TYPE: PRT
<213> ORGANISM: Deinococcus sp.
<220> FEATURE:
<221> NAME/KEY: MISC_FEATURE
<223> OTHER INFORMATION: ADH derived from Deinococcus geothermalis DRH05

<400> SEQUENCE: 36

Met Ser Glu Ser Met Lys Ala Ile Val Val Glu Arg Leu Gly Pro Pro
1               5                   10                  15

Asp Val Met Glu Val Arg Glu Leu Pro Val Pro Gln Pro Gly Pro Gly
            20                  25                  30

Glu Val Arg Leu Lys Val Glu Ala Val Gly Ile Asn Phe Ala Asp Val
        35                  40                  45

Leu Ala Val Ala Gly Glu Tyr Leu Thr Arg Thr Arg Leu Pro Tyr Thr
50                  55                  60

Pro Gly Met Glu Phe Ala Gly Ile Val Asp Ala Leu Gly Glu Gly Val
65                  70                  75                  80

Thr Gly Val Gln Val Gly Gln Arg Val Ala Leu Ala Gly Arg Gly
                85                  90                  95

Gly Leu Ala Glu Tyr Ala Ile Ser Pro Ala Ala Ala Leu Ile Arg Val
            100                 105                 110

Pro Asp Ser Phe Ser Ala Ala Gln Ala Ala Ala Phe Pro Val Ser Tyr
        115                 120                 125

Phe Thr Ala Tyr His Gly Leu Lys Thr Leu Gly His Gly Lys Glu Gly
130                 135                 140

Glu Trp Val Leu Val Gln Ala Ala Gly Ala Leu Gly Thr Ala Ser
145                 150                 155                 160

Ile Gln Leu Ala Lys Ala Leu Gly Met Asn Val Ile Ala Met Ala Ser
                165                 170                 175

Thr Glu Glu Lys Leu His Ile Ala Arg Asp Leu Gly Ala Asp Val Thr
            180                 185                 190

Leu Leu Gln Asp Asp Pro Asp Arg Val Gln Lys Val Arg Asp Ala Ala
        195                 200                 205

Gly Gly Lys Gly Val Pro Leu Ile Leu Glu Val Ile Gly Gly Lys Arg
210                 215                 220

Phe Gln Glu Ser Leu Asp Met Ala Ala Asn Arg Gly Arg Ile Ile Val
225                 230                 235                 240

Ile Gly Asn Ala Ser Arg Glu Gln Ala Asn Leu Arg Pro Val Glu Leu
                245                 250                 255

Met Lys Arg Asn Leu Thr Val Thr Gly Leu Trp Leu Thr Ser Leu Met
            260                 265                 270

Gly Asp Gln Glu Ala Thr Arg Glu Ala Ala Glu Thr Leu Thr Gln Leu
        275                 280                 285

Val Ala Ser Gly Gln Val Thr Pro Gln Val Gly Pro Thr Tyr Pro Leu
290                 295                 300

Lys Asp Ser Ala Arg Ala Phe Gln Asp Ile Leu Asp Arg Lys Thr Thr
305                 310                 315                 320

Gly Lys Val Ile Ile Glu Pro Gln Arg
                325

<210> SEQ ID NO 37
```

```
<211> LENGTH: 325
<212> TYPE: PRT
<213> ORGANISM: Deinococcus sp.
<220> FEATURE:
<221> NAME/KEY: MISC_FEATURE
<223> OTHER INFORMATION: ADH derived from Deinococcus geothermalis DRH05

<400> SEQUENCE: 37
```

| | | | | | | | | | | | | | | |
|---|---|---|---|---|---|---|---|---|---|---|---|---|---|---|
| Met | Ser | His | Ala | Val | Leu | Val | Glu | Gln | His | Gly | Gly | Pro | Glu | Val | Leu |
| 1 | | | | 5 | | | | | 10 | | | | | 15 |
| Ser | Trp | Arg | Glu | Thr | Pro | Leu | Pro | Val | Pro | Gly | Pro | Gly | Gln | Val | Arg |
| | | | | 20 | | | | 25 | | | | | 30 | |
| Val | Arg | Val | Ser | Ala | Thr | Ser | Val | Asn | Tyr | Ala | Asp | Ile | Gln | Ala | Arg |
| | | 35 | | | | | 40 | | | | | 45 | | |
| Arg | Gly | Gly | Tyr | Asp | Ala | Gly | Gly | Lys | Leu | Pro | Phe | Thr | Pro | Gly | Leu |
| | 50 | | | | | 55 | | | | | 60 | | | | |
| Asp | Ala | Cys | Gly | Thr | Val | Asp | Ala | Leu | Gly | Glu | Gly | Val | Thr | Gly | Leu |
| 65 | | | | | 70 | | | | | 75 | | | | | 80 |
| Arg | Val | Gly | Glu | Arg | Val | Ala | Cys | Phe | Pro | Leu | Gly | Gly | Ser | Tyr | Ala |
| | | | | 85 | | | | | 90 | | | | | 95 | |
| Thr | His | Val | Leu | Ala | Pro | Ala | His | Leu | Thr | Phe | Pro | Leu | Glu | Asn | Asn |
| | | | 100 | | | | | 105 | | | | | 110 | | |
| Val | Pro | Asp | Ala | Ala | Ala | Ala | Ser | Leu | Thr | Ala | Leu | Val | Thr | Ala | Tyr |
| | | 115 | | | | | 120 | | | | | 125 | | | |
| Asn | Val | Val | Thr | Tyr | Ala | Gly | Arg | Leu | Gln | Arg | Gly | Glu | Thr | Val | Leu |
| | 130 | | | | | 135 | | | | | 140 | | | | |
| Ile | His | Ala | Ser | Ala | Gly | Gly | Val | Gly | His | Leu | Ala | Val | Gln | Ile | Ala |
| 145 | | | | | 150 | | | | | 155 | | | | | 160 |
| Arg | Glu | Gln | Gly | Ala | Gly | Gln | Val | Val | Gly | Val | Val | Gly | Ser | Asp | Ala |
| | | | | 165 | | | | | 170 | | | | | 175 | |
| Arg | Val | Asp | Phe | Leu | Arg | His | Leu | Gly | Val | Asp | Glu | Val | Val | Asn | Arg |
| | | | 180 | | | | | 185 | | | | | 190 | | |
| His | Arg | Glu | Asp | Phe | Val | Gly | Arg | Val | Asn | Ala | Leu | Thr | Glu | Gly | Arg |
| | | | 195 | | | | | 200 | | | | | 205 | | |
| Gly | Ala | Asp | Leu | Ile | Leu | Asp | Ser | Ile | Gly | Gly | Thr | Thr | Thr | Glu | Arg |
| 210 | | | | | 215 | | | | | 220 | | | | | |
| Gly | Phe | Thr | Cys | Leu | Ala | Pro | Phe | Gly | Arg | Leu | Val | Ile | Tyr | Gly | His |
| 225 | | | | | 230 | | | | | 235 | | | | | 240 |
| Ala | Gly | Arg | Gln | Pro | Ala | His | Leu | Pro | Ser | Pro | Leu | His | Arg | Gln |
| | | | | 245 | | | | | 250 | | | | | 255 |
| Ser | Arg | Ala | Val | Ile | Gly | Tyr | Ser | Ser | Gly | His | His | Arg | Gln | Ala | Arg |
| | | | 260 | | | | | 265 | | | | | 270 | | |
| Pro | Gln | Val | Val | Arg | Asp | Ala | Ala | Ala | Ala | Phe | Ala | Leu | Ala | Ala |
| | | 275 | | | | | 280 | | | | | 285 | | | |
| Ser | Gly | Ala | Val | Arg | Ile | His | Val | Ala | Ala | Glu | Phe | Pro | Leu | Met | Glu |
| | 290 | | | | | 295 | | | | | 300 | | | | |
| Ala | Ala | Arg | Ala | His | Ala | Leu | Val | Glu | Ser | Gly | Glu | Ile | Asn | Gly | Arg |
| 305 | | | | 310 | | | | | 315 | | | | | | 320 |
| Val | Leu | Leu | Thr | Val |
| | | | | 325 |

```
<210> SEQ ID NO 38
<211> LENGTH: 359
<212> TYPE: PRT
<213> ORGANISM: Deinococcus sp.
<220> FEATURE:
<221> NAME/KEY: MISC_FEATURE
```

<223> OTHER INFORMATION: ADH derived from Deinococcus geothermalis DRH05

<400> SEQUENCE: 38

| | | | | | | | | | | | | | | | |
|---|---|---|---|---|---|---|---|---|---|---|---|---|---|---|---|
| Met | Thr | Ser | Pro | Asp | Ser | Ser | Leu | Ser | Ser | Arg | Ile | Ser | Val | Leu | His |
| 1 | | | | 5 | | | | | 10 | | | | | 15 | |
| Gly | Ile | Arg | Asp | Leu | Arg | Trp | Glu | Thr | Arg | Glu | Val | Pro | Ala | Pro | Gly |
| | | | 20 | | | | | 25 | | | | | 30 | | |
| Pro | Arg | Glu | Val | Arg | Val | Arg | Val | Arg | Val | Gly | Val | Cys | Gly | Ser | |
| | | 35 | | | | | 40 | | | | | 45 | | | |
| Asp | Val | His | Tyr | Tyr | Thr | His | Gly | Arg | Ile | Gly | Ser | Phe | Val | Val | Glu |
| | 50 | | | | | 55 | | | | | 60 | | | | |
| Ala | Pro | Leu | Ile | Leu | Gly | His | Glu | Val | Met | Gly | Val | Val | Asp | Ala | Val |
| 65 | | | | | 70 | | | | | 75 | | | | | 80 |
| Gly | Glu | Gly | Val | Thr | His | Val | Arg | Pro | Gly | Asp | Arg | Val | Ala | Leu | Glu |
| | | | | 85 | | | | | 90 | | | | | 95 | |
| Pro | Gly | Val | Pro | Cys | Arg | Arg | Cys | Ala | Phe | Cys | Lys | Arg | Gly | Glu | Tyr |
| | | | 100 | | | | | 105 | | | | | 110 | | |
| Asn | Leu | Cys | Pro | Asp | Met | Thr | Phe | Met | Ala | Thr | Pro | Pro | Val | His | Gly |
| | | 115 | | | | | 120 | | | | | 125 | | | |
| Ala | Leu | Gly | Glu | Tyr | Val | Leu | Trp | Pro | Asp | Phe | Ala | Phe | Leu | Leu | |
| | 130 | | | | | 135 | | | | | 140 | | | | |
| Pro | Asp | Arg | Ile | Ser | Asp | Asp | Ala | Gly | Ala | Leu | Leu | Glu | Pro | Leu | Ala |
| 145 | | | | | 150 | | | | | 155 | | | | | 160 |
| Val | Gly | Ile | Trp | Ala | Ala | Arg | Lys | Gly | Asp | Val | Arg | Pro | Gly | Gln | Ser |
| | | | | 165 | | | | | 170 | | | | | 175 | |
| Val | Ala | Val | Phe | Gly | Ala | Gly | Pro | Ile | Gly | Cys | Thr | Thr | Leu | Gln | Ala |
| | | | 180 | | | | | 185 | | | | | 190 | | |
| Ala | Lys | Ala | Ala | Gly | Ala | Thr | Thr | Leu | Ile | Ala | Val | Asp | Leu | Glu | Asp |
| | | 195 | | | | | 200 | | | | | 205 | | | |
| Phe | Arg | Leu | Asp | Leu | Ala | Arg | Lys | Val | Gly | Ala | Thr | His | Thr | Ile | Asn |
| | 210 | | | | | 215 | | | | | 220 | | | | |
| Ala | Arg | Asn | Glu | Asp | Pro | Val | Ala | Arg | Ile | Arg | Glu | Ile | Thr | Arg | Gly |
| 225 | | | | | 230 | | | | | 235 | | | | | 240 |
| Asp | Leu | Pro | Ile | Ser | His | Ala | Gly | Val | Asp | Val | Ala | Phe | Glu | Thr | Ala |
| | | | | 245 | | | | | 250 | | | | | 255 | |
| Gly | Ser | Leu | Pro | Thr | Thr | Arg | Met | Ser | Leu | Ala | Ala | Pro | Arg | Pro | Gly |
| | | | 260 | | | | | 265 | | | | | 270 | | |
| Gly | Thr | Thr | Val | Leu | Val | Gly | Leu | Pro | Pro | Asp | Ser | Glu | Val | Ser | Leu |
| | | 275 | | | | | 280 | | | | | 285 | | | |
| Asp | Ile | Val | Ser | Ala | Ala | Ser | Arg | Glu | Val | Ser | Ile | Arg | Gly | Val | Phe |
| | 290 | | | | | 295 | | | | | 300 | | | | |
| Arg | Tyr | Ala | Asn | Cys | Tyr | Pro | Ala | Ala | Ile | Ala | Leu | Val | Glu | Ser | Gly |
| 305 | | | | | 310 | | | | | 315 | | | | | 320 |
| Ala | Val | Asp | Leu | Asp | Val | Leu | Val | Thr | His | Arg | Tyr | Pro | Phe | Asp | Gln |
| | | | 325 | | | | | 330 | | | | | 335 | | |
| Thr | Pro | Glu | Ala | Phe | Ala | Phe | Ala | Asp | Arg | Glu | Lys | Arg | Ala | Ser | Met |
| | | | 340 | | | | | 345 | | | | | 350 | | |
| Lys | Val | Met | Ile | Asp | Val | Gly | | | | | | | | | |
| | | | 355 | | | | | | | | | | | | |

<210> SEQ ID NO 39
<211> LENGTH: 324
<212> TYPE: PRT
<213> ORGANISM: Deinococcus sp.
<220> FEATURE:

<221> NAME/KEY: MISC_FEATURE
<223> OTHER INFORMATION: ADH derived from Deinococcus geothermalis DRH05

<400> SEQUENCE: 39

Met Arg Ala Leu Ile Cys Thr Ala Phe Ala Glu Pro Glu Ala Leu Thr
1               5                   10                  15

Val Gln Thr Val Pro Asp Pro Thr Pro Gly Pro Gly Glu Val Val Leu
            20                  25                  30

Asp Val Gln Ala Ala Gly Val Asn Tyr Pro Asp Ala Leu Met Val Met
        35                  40                  45

Gly Gln Tyr Gln Val Lys Pro Pro Leu Pro Phe Thr Pro Gly Ala Glu
    50                  55                  60

Ala Ala Gly Val Ile Ala Ala Val Gly Glu Gly Val Thr His Leu Arg
65                  70                  75                  80

Pro Gly Gln Arg Ala Val Ala Phe Thr Gly Thr Gly Ala Phe Ala Glu
                85                  90                  95

Gln Leu Leu Ala Pro Ala Ser Val Val Met Pro Leu Pro Asp Gly Leu
            100                 105                 110

Glu Leu Glu Val Ala Ala Gly Leu Pro Leu Ala Tyr Gly Thr Ser Met
        115                 120                 125

His Ala Leu Ala Asp Arg Ala Gln Leu Gln Ala Gly Glu Thr Leu Leu
    130                 135                 140

Val Leu Gly Ala Ala Gly Gly Val Gly Leu Ala Ala Val Met Ile Gly
145                 150                 155                 160

Lys Ala Leu Gly Ala Arg Val Ile Ala Ala Ser Ser Glu Glu Lys
                165                 170                 175

Leu Lys Leu Cys Arg Glu His Gly Ala Asp Glu Thr Leu Asn Tyr Ala
            180                 185                 190

Ala Glu Asn Leu Arg Glu Arg Leu Lys Thr Leu Thr Gly Gly Gln Gly
        195                 200                 205

Pro Asp Val Ile Phe Asp Pro Val Gly Gly Asp Leu Ala Glu Pro Ala
    210                 215                 220

Phe Arg Ser Ile Gly Trp Gly Gly Arg Tyr Leu Val Val Gly Phe Ala
225                 230                 235                 240

Gly Gly Glu Ile Pro Lys Leu Pro Leu Asn Leu Pro Leu Leu Lys Gly
                245                 250                 255

Ala Ser Leu Val Gly Val Phe Trp Gly Glu Phe Ala Arg Arg Asp Pro
            260                 265                 270

Pro Ala Asn Ala Arg Asn Met Ala Arg Leu Leu Ser Trp Val Ala Glu
        275                 280                 285

Gly Lys Val Arg Pro Leu Val Ser Glu Arg Tyr Ser Leu Glu Arg Ala
    290                 295                 300

Pro Glu Ala Leu Arg Ala Leu Leu Ser Arg Arg Val Thr Gly Lys Val
305                 310                 315                 320

Val Val Thr Pro

<210> SEQ ID NO 40
<211> LENGTH: 305
<212> TYPE: PRT
<213> ORGANISM: Deinococcus sp.
<220> FEATURE:
<221> NAME/KEY: MISC_FEATURE
<223> OTHER INFORMATION: ADH derived from Deinococcus DRH46

<400> SEQUENCE: 40

Met Thr Ser His Ala Ile Val Phe His Val Tyr Gly Asp Pro Asp Val

```
  1               5                  10                 15
Leu Gln Leu His Thr Phe Pro Val Pro Glu Pro Ser Ala Asn Gln Val
                20                 25                 30

Leu Val Arg Ile Arg Ala Ala Gly Val Gln Pro Phe Asp Val Gln Phe
                35                 40                 45

Arg Lys Gly Leu Met Ala Glu Arg Tyr Pro Ala Ser Phe Pro Gln Lys
                50                 55                 60

Ile Gly Asn Glu Phe Ala Gly Thr Val Glu Lys Ile Gly Asp Glu Val
 65                 70                 75                 80

Thr Arg Phe Lys Ser Gly Asp Ala Val Leu Gly Trp Val Val Leu Ala
                85                 90                 95

Ala Tyr Ala Glu His Val Leu Val Ser Glu Ala Thr Leu Thr His Lys
                100                105                110

Pro Pro Gln Met Pro Trp Glu Glu Ala Gly Ala Leu Thr Ala Ser Gly
                115                120                125

Gln Thr Ala Leu Thr Ala Leu Asp Ala Leu Gln Val Gly Pro Glu Asp
                130                135                140

Val Leu Leu Val His Ala Ala Gly Gly Val Gly Ser Phe Ala Val
145                 150                155                160

Gln Leu Ala Lys Ala Arg Gly Ala Arg Val Ile Gly Thr Ala Ser Pro
                165                170                175

Gly Asn His Ala Tyr Leu Gln Ser Leu Gly Thr Glu Pro Val Ser His
                180                185                190

Gly Glu Gly Leu Ala Glu Arg Val Leu Glu Leu Ala Pro Gln Gly Val
                195                200                205

Thr Ala Ser Leu Val Ala Val Gly Asn Glu Glu Ala Leu Arg Val Ser
                210                215                220

Leu Lys Val Thr Lys Asn Pro Glu Ser Ile Arg Thr Leu Ala Phe His
225                 230                235                240

Pro Leu Ala Arg Gln Leu Gly Ile Ala Trp Val Gly Ser Glu Arg Ser
                245                250                255

Leu Glu Arg Leu Glu Gln Leu Val Gln Phe Tyr Glu Lys Gly Gln Leu
                260                265                270

Lys Val His Ile Gln Glu Ala Phe Pro Leu Lys Asp Ala Ala Lys Ala
                275                280                285

His Arg Val Met Glu Lys Gly His Val Arg Gly Lys Leu Val Leu Leu
                290                295                300

Pro
305

<210> SEQ ID NO 41
<211> LENGTH: 342
<212> TYPE: PRT
<213> ORGANISM: Deinococcus sp.
<220> FEATURE:
<221> NAME/KEY: MISC_FEATURE
<223> OTHER INFORMATION: ADH derived from Deinococcus DRH46

<400> SEQUENCE: 41

Met Gln Ala Val Ala Leu Thr Arg Arg Gly Asn Ile Asp Ala Leu Glu
 1               5                  10                 15

Pro Ile Arg Leu Pro Ile Ser Glu Pro Gln Ala Gly Glu Val Leu Val
                20                 25                 30

Arg Ile Arg Ala Val Ala Leu Asn His Leu Asp Val Trp Val Arg Lys
                35                 40                 45
```

```
Gly Val Ala Ser Pro Lys Leu Pro Leu Pro His Leu Leu Gly Ser Asp
    50                  55                  60
Ile Ala Gly Glu Val Ala Ala Met Gly Pro Gly Val Glu Gly Leu Ser
65                  70                  75                  80
Glu Gly Thr Lys Val Met Leu Asn Pro Gly Val Ser Cys Gly His Cys
                85                  90                  95
Glu Arg Cys Leu Ser Gly His Asp Asn Leu Cys Arg His Tyr Gln Ile
            100                 105                 110
Leu Gly Glu His Arg Trp Gly Gly Tyr Ala Gln Tyr Ile Ser Ile Pro
        115                 120                 125
Arg Thr Asn Val Leu Pro Met Pro Glu Gly Leu Asp Phe Val Glu Ala
    130                 135                 140
Ala Ser Val Pro Leu Ser Ala Leu Thr Ala Tyr Gln Met Val Phe Asp
145                 150                 155                 160
Arg Ala Gln Leu Lys Pro Trp Glu Thr Val Leu Ile Leu Ala Ala Ala
                165                 170                 175
Ser Gly Val Ser Val Asn Leu Ile Gln Leu Cys Lys Leu Val Gly Ala
            180                 185                 190
Lys Val Ile Ala Val Ala Ser Thr Pro Glu Lys Gln Ala Leu Ala Leu
        195                 200                 205
Lys Leu Gly Ala Asp His Val Ile Gly Ser His Glu Asp Gln Ala Gln
    210                 215                 220
Ala Val Lys Ala Leu Thr Ala Gly Glu Gly Ala Asp Val Val Phe Asp
225                 230                 235                 240
His Thr Gly Ala Asp Asn Trp Gln Arg Ser Leu Lys Ser Leu Lys Trp
                245                 250                 255
Gly Gly Arg Leu Val Thr Cys Gly Ala Thr Ser Gly His Glu Ala Val
            260                 265                 270
Thr Pro Leu Asn Trp Val Phe Phe Lys Gln Leu Ser Ile Leu Gly Ser
        275                 280                 285
Thr Met Gly Ser Lys Ala Asp Leu His Lys Ile Gln Lys Phe Val Gln
    290                 295                 300
Glu Gly Lys Leu Arg Pro Val Val Gly His Val Leu Asp Phe Ala Gln
305                 310                 315                 320
Ala Arg Glu Ala His Gly Leu Leu Glu Ser Arg Gln Ala Leu Gly Lys
                325                 330                 335
Val Val Leu Arg Val Pro
            340

<210> SEQ ID NO 42
<211> LENGTH: 1428
<212> TYPE: DNA
<213> ORGANISM: Deinococcus sp.
<220> FEATURE:
<221> NAME/KEY: misc_feature
<223> OTHER INFORMATION: AcDH derived from Deinococcus geothermalis
      DRH05

<400> SEQUENCE: 42
atgaccacca cgctgacccg cgtgcccctc ctgatcggcg gtcaggccgt acagacggag      60
gcacaggaca ccgtcttcaa tcccttgaac ggggaggcgc tctatcatgt tgcccaggcg     120
gacggggaag cgctgcgccg ggcgattgcg tctgctcagg ccgcttttgc ggcttaccgc     180
cagtggcccg ctcaccgccg ggcagaagct ctgcgccgcg cttcggcatt gctggccgag     240
cgggccgacc tttttgcccg caccatcgcc accgaggcag gcaaacccct caaggcggct     300
```

```
cgcgttgaag tggcgcgcag cgttgagaac ttgggttttg ctgccgatga ggccgcccaa      360
ctggccggcc agggaattcc gctggacgcc agccgcttcg gggaaggtcg cctaggtttc      420
acgttgcgag agccgcgcgg cgtcatcgcg gcaatcagtc cctttaactt cccgctgaat      480
ctcgcgctgc acaaggtcgg cccagcactg gcgggcggca acaccgtcat tttgaaaccc      540
gccccgcaga cccccctgac tgcccacctg atcggggaac tggtccaaga tgccggtttt      600
cccgctggtg cgttgaacgt gctgcatggc ggcgctgagc tgggcgcagc cttgacggcg      660
gcccccgaga tcgccctggt gaccttcacc ggcagcccac aggtggggga ggcgatcaag      720
cgcggcagcg gcctcaagcc agtggtcctg gagctgggca caacagtgc caacctagta       780 gatgctgaca gtgacgtgga gcttgctgcg cgcaagctgg ccgccgtcag ctttgcctac      840
caggggcagg tctgcattca tccgcagcgc ctgatcgtcc acgccgatgt ctatgacgcc      900
ttcaaggcca cttttctgga ggccagccgc gccctggttg tcggtgatcc cctcgacgag      960
cagaccgatg tgggaccgct gatcaaccca gccgccctga cccgacttca gagctggatt     1020
caggaggcgc tggacctggg cggccggttg ctgctgggcg gcacacccca ggggaacctc     1080
cttccgccga ctgtcctaga ggacgtgccc gaggaggccc ggctggtttg cgaggaagcc     1140
tttggccgtg tggtggtgct ctcgcgtgct gcgagttgga cagacgcaat cgcggccgcc     1200
aaccgcagcc gctacggtct ccagactggt gtgtttaccc gcaacctcca gcatgccctg     1260
gaggcggtgc gcggcattga ggcaggcgga gtgatcgtga tgaccccag caccttccgg       1320 gtggaccaga tgccctacgg gggcatcaag gagagcggct cgggcgtga ggggactcgc       1380 agcgctctgg aggaactgac gtatctcaaa accgtggttc tcagctga                  1428
```

<210> SEQ ID NO 43
<211> LENGTH: 1458
<212> TYPE: DNA
<213> ORGANISM: Deinococcus sp.
<220> FEATURE:
<221> NAME/KEY: misc_feature
<223> OTHER INFORMATION: AcDH derived from Deinococcus geothermalis
      DRH05

<400> SEQUENCE: 43

```
atgaccctg acccccagca ccctgagaag accgccagcg attccggcca ccgtcccttt        60
gccaccgtca atccctacac cggtgagacc ctgtgtgaat ttccgtttct gaccaccgag      120
gaggccctcg ccgccgtaga gcgcgcgcat caggcgttcg gtacctggcg ccggcggccc     180
gtcgaggacc gcgcggcgat catgcgccgt gcggcggagc tgatgctgga acgcgggac      240 gaactcgccc gcctggtgac gctggagatg ggcaagctga tccgcgagag tggcctggag    300
gtcgagctgg ccgccagcat cctcaagtac tacggcgaga aggggccaga atttctacgc    360
ccgcaacccc tggaggtgga gggggcgag gcggccatcg tgaacgaacc gctgggcgtg     420
ctgttgggca tccagccctg gaacttcccg ctctaccagg tggcccgctt cgccgcgccg    480
tatctggtgg tgggcaacac catcctgctc aagcacgccg agagctgccc gcagacggcc    540
ctggcgcttg aacagctctt ctgcgacgcg ggtgtgccgg aaggcgttta caccaacgtt    600
tttctcaaga tcagcgatgt tgagccggtg gtcgcccacc ccgccgtgca gggcgtgtcc    660
ctcaccggca gcgaacgcgc gggcgcgagc gtggccgaga tcgccgggcg gcacctcaag    720
cgctgtgtgc tggaactggg cggcagcgac cccttcatcg tgctcgacgc accggatctc    780
cagcggaccc tccgagccgc cgtgatcggg cgaatggcca caccggcca gagctgcgtg    840 gcggccaagc ggttcatcgt gatggacgag ctctacgacg cgtttgtggc cgggctggct    900
```

```
caggcattcg gcagcctgaa accgggcgac cccgcggacc ccgcgaccac cctcggcccg    960
ctgtcctccg agcgagcggc gcgggatcta ctcgcacagg tgcaggacgc ggtggagaaa   1020
ggggcgacgg tggtgacggg cggcggacgt cccgaccttc ccggcgcctt tgtggagcca   1080
accctcctca caggcgtgaa gccgggcatg cgcgcctttt cggaagagtt gtttggcccg   1140
gtcgcggtgg tctaccgcat ctccagtgac gaggaagccg tggctctcgc caactcgtca   1200
agctacggac tggggggggc ggtgttttgc agcgaccttc agcgggcgcg ggcggtagca   1260
gaccagctgg acagcggcat ggtctggatc aaccatccca cctcgtcgca ggcgaacctg   1320
cccttcggcg gggtcaaacg ctctggttac gggcgagaac tcgatcgcct gggcatcttc   1380
gagttcacca accgcaagct ggtgcgaacg ctccctgcat ccagaagcgg gggccaggct   1440
gcccaggtgg tgggctga                                                1458

<210> SEQ ID NO 44
<211> LENGTH: 1512
<212> TYPE: DNA
<213> ORGANISM: Deinococcus sp.
<220> FEATURE:
<221> NAME/KEY: misc_feature
<223> OTHER INFORMATION: AcDH derived from Deinococcus geothermalis
      DRH05

<400> SEQUENCE: 44
atgcatagcg gcagaagctg gtccgacgtt tggcggcagg tcacggccct cgttcccgaa     60
gcagcgctgc cggacggcac cctgcgctcc gtgtggggg agagctggca ggggaagggc    120
accccgcgcc agacctttc tcccaacgac ggggccgcgc tcacccgccc cctggagctg    180
ggccgggcgg acgtggggac tgtgctggaa gcctgcaccc gcacccacga gacctggtcc    240
gccaccgacc tcgacgaacg ccgccgccgg gtgagcgcgg ccctggacgc catcgccgcg    300
cagcgggaac tgttcgcggc gctgctcgcc tgggagatcg gcaagccgct gcgtcaggcc    360
ctcgccgagg tggaccgcac cgtggacggg gtgcgctggt acatagacga aatcgagggg    420
atgctcgccg gacgccgccc gctggggggtc gtgagcaaca tcgcctcctg gaattatccc    480
ctctcggtgc tggtgcacgc gatgctcgtg caggccctga gcgcaatgc cgtcctcgcc    540 aagtcgccca gcgcgggcgg acaggcgagc gtgaccctgg cggtggcgct ggcgcggcgg    600
gccggggtcc cgctctcgct cgtgcacggt tctggtggga cggtgggcga ggcgctggcg    660
accgcgccgg aggtgcggc ggtggctttt gtgggggggcc cgccaccgg gcaggtgctg    720 ggcgaacgcc tgcgcggtca gccccagcgg gtgatgctgg agatggaggg ggtcaacccc    780
tacggcctct ggaacttcag cgactgggag cgcttcgagc agcacgtgcg ctccggccac    840
gactacgcca gcagcgctg caccgtctac cccgctttg tcgtccagcg cgagctgttt    900
ccgcagtttc tggagcacta cctgcgggcg gtttcgcagg tgcgggtggg gcatcccctg    960
ctcgacacgg acgaggcccc gctcagctcc ggccccctca tccacgagcg caaggtgcgg   1020
gacctgcgct tgcggatgca ggaggcgacc gggctggggg ccgtgccgct ccatgcgggc   1080
acgctggaga acgcacgcct ggagccggag cagccgcagg aggcatatct cgctccgcag   1140
ctcctgctgc atccaccctc gcgctcacgg ctctaccggg aagaacccctt cggcccagtg   1200 gataccgtgg ttatcgtgga ccgccccgaa gacctcgtgc gggagatgaa cgtctcgcgc   1260
ggcagcctgg tggcgaccct ggcaaccgac gaccacacct tcgcccagga gctcaccccg   1320
cagattcagg ctttcaaggt cggcgtgaac gccctgcgct cacgcggtga ccgtgacgaa   1380
```

```
ccctttggcg gcgcggggc ctcctggtgg ggaccgtacc tgggcggcga gcacctcgtg      1440
cgggcggtca cggcgggccc ggcgggtgag acgctgcacg caacttcgg cccggtctgg      1500 aggagcacgt ga                                                         1512

<210> SEQ ID NO 45
<211> LENGTH: 1578
<212> TYPE: DNA
<213> ORGANISM: Deinococcus sp.
<220> FEATURE:
<221> NAME/KEY: misc_feature
<223> OTHER INFORMATION: AcDH derived from Deinococcus geothermalis
      DRH05

<400> SEQUENCE: 45
atgaccagca cgttgatgga gggcttcctc ccatttacgc atgagccgta cttcaacttt        60
gctcaggaag acgtggcgca aaagcagcgc gaggcctacc ggcaggtgcg cgaaaaatac       120
gtaggccgca gcttcccgat gatgctgtgt ggcaaacctg tggagggcga ggacaccttc       180
gaggttcaca cccggcgga cacccgcgag acggtctggc gcttcccgaa ggcctcgccc        240
gcgcaactgg agcaagccat tgcctgcgcc aaagccgcct ttgaggagtg gcgtttcagt       300
gacccgctgc agcgcgcggc catcttcaag cggcggcgg agctgctgcg cacccggcgg       360
atggagttca cgcagtcat gggcctcgag aacggcaaga actgggccga ggcggacggc       420
gagatcgccg agtgcgtaga ccacttcgag gtcttcgccc gcgagacgct gcggtgggcg       480
caggggaagc cggtctaccc gatgcccgac gagcacgtga cgatggtgta cgagccgatc       540
ggcgtcgtcg cggtgattag cccctggaat ttcccggcgg cgattccgct gggcatgagc       600
ctaggcgcga tcgcggcggg caacaccgtg gtgtggaaac ccgcctccga cgcccctc        660 agcagcctgc tgctggtgga gctgctcttc gaggcgggcc tgccgcgcaa cgtcattcaa       720
tttctgaccg gtacggacga ggtgctgggt gatccgctgg tcgaccacaa agacatccgc       780
atgatcgcct ttaccggctc caaggagatt ggctgccgca tcatggagcg cgcggcgaag       840
gtgcagccag ggcaaaaatg gctcaagcgc gtgatggccg agatgggcgg caaggacccc       900
acggtggtct gcgccgacgc cgatctggac gacgccgcac ggggcatcgt gcaggcggcc       960
ttcgggtatt cgggccaaaa gtgcagcgcg tgcagccggg tgattgccga ggacagcgtg      1020
tatgacgagc tgctggacaa ggtcgtgcgg ctcacccgcg aactgaaggt cggcttgccg      1080
gaggagaatg ccccctcgg cccggtcatc cacgaggaca gcgcaaaccg catcctggcc      1140
tctatcgaac ggggcaagaa aacgcccat ctggtgctgg gcggcaacg cgctgacagc      1200 gggggccgcg agggcggcta cctccagccc accatcttcg cggacgtgga cccacgcgat      1260 ccctctttc aggaggagat tttcgggccg gtgctgagct ttacccgggc gcgcgactgg       1320
cggcacgcga tcgacctcgc caacgactcg gagtacggcc tgaccgccgc tttctatagc      1380
cgcgatcccc aaaagattgc ggaggctcgg cgcctgatcc acgtcggcaa cctgtatgtc      1440
aaccgcaagt gcaccggcgc cctgtcgggt acccacgcct tcggcggcta cggcatgagc      1500
ggcacgaacg ccaaggtggg cggccccgat tacctcttct ggttcctcca gacaaagacg      1560
gtggcacaga agtactga                                                    1578

<210> SEQ ID NO 46
<211> LENGTH: 606
<212> TYPE: DNA
<213> ORGANISM: Deinococcus sp.
<220> FEATURE:
<221> NAME/KEY: misc_feature
```

<223> OTHER INFORMATION: AcDH derived from Deinococcus M23r-2A
<220> FEATURE:
<221> NAME/KEY: misc_feature
<222> LOCATION: (69)..(210)
<223> OTHER INFORMATION: n is a, c, g, or t

<400> SEQUENCE: 46

| | | | | | | |
|---|---|---|---|---|---|---|
| atgacccgca | agctcaaggc | cgccatcatc | ggcagcggca | acatcggcac | agatctgatg | 60 |
| atcaagatnn | nnnnnnnnnn | nnnnnnnnnn | nnnnnnnnnn | nnnnnnnnnn | nnnnnnnnnn | 120 |
| nnnnnnnnnn | nnnnnnnnnn | nnnnnnnnnn | nnnnnnnnnn | nnnnnnnnnn | nnnnnnnnnn | 180 |
| nnnnnnnnnn | nnnnnnnnnn | nnnnnnnnnn | gtggtgggtg | gtgcagccaa | gggcaaggcc | 240 |
| atcatcgtgc | tcaaccctgc | agagccaccg | ctgatgatgc | gcgacaccgt | ttacacgctg | 300 |
| agcgagctgg | cggacgagga | tgcgatcgcc | aggtccgtag | agcgcatggc | ttcagatgtg | 360 |
| caggcctatg | tacccggcta | tcgactcaaa | cagaaggtgc | agtttgatcg | catcgagagc | 420 |
| gacaggccga | tccgcattcc | cggcgtgggt | atgagcatgc | atgggttgaa | gacctccatc | 480 |
| tttttggaag | tggaaggtgc | tgcgcattac | ctgcccgcct | acgcaggcaa | cctggacatc | 540 |
| atgaccagcg | ccggcctgcg | caccgctgag | tccatggccg | agcgaatgct | cgaagccgca | 600 |
| cacgcc | | | | | | 606 |

<210> SEQ ID NO 47
<211> LENGTH: 1359
<212> TYPE: DNA
<213> ORGANISM: Deinococcus sp.
<220> FEATURE:
<221> NAME/KEY: misc_feature
<223> OTHER INFORMATION: ADH derived from Deinococcus geothermalis DRH05

<400> SEQUENCE: 47

| | | | | | | |
|---|---|---|---|---|---|---|
| atgcacggcg | ggttcggatg | cgatactggc | cgggaaccct | acgcagctcc | ccccattcgg | 60 |
| aggtctacct | tgtccgtcca | tccgaaaacg | ctccagcatg | aaaccctctt | taccattgag | 120 |
| gccacacccg | ttaagttcgg | cccaggtgcc | gccgccgatg | cgggctggga | ggctgcgcgg | 180 |
| ctgggaatcc | ggcgggcctt | tgtcgtcctc | gacccgaggc | tcgcgcaggg | cgaggcagcg | 240 |
| cgcggtgtgt | tggagaacct | gcgcgcgcg | ggcatagatc | tggtggtctt | cacggacatc | 300 |
| cgtatcgaac | cggacctcgc | cagcctggaa | cgggcgacgg | cagcggcgcg | ggaggccaag | 360 |
| ccggatggct | tcatcgcgct | gggggcggc | tcgaccatcg | acactgccaa | ggtcgccaat | 420 |
| ctgctgacca | cgcacggcgg | gaaggtgatg | gactacgtga | acccgcccat | cggtggcggg | 480 |
| cgcgcgctgc | ctggtccgct | gcggcccctg | ctggcgattc | ccaccaccgc | cggttcggga | 540 |
| tcggaggcga | ctacggtggc | gattctcgat | ctgcccgacc | tgggggtcaa | aagcggtatc | 600 |
| agccaccgct | atctgcgccc | cgcacaggcc | atcgtggatc | cgaacttac | ccgcacagcg | 660 |
| cccagcagcg | tgattgcctc | agcgggtcta | gacgtggtct | gccacgccgc | cgagagcttc | 720 |
| ctgagccgcc | cctataccac | ccgtccgcgt | cccgtgaccc | ccgctgagcg | gcctccctat | 780 |
| cagggcagca | atccggtggc | ggatctgtgg | tcagctcaag | ccctgcgcta | tggcggccag | 840 |
| tatctccgcc | gtgcggtcgc | agaccccgac | gacgtggagg | cgcgcggttt | catgatgctc | 900 |
| tcggcgacga | tggcaggcgt | gggctttggt | tcggcgggcg | tgcacattcc | gcacgcctgt | 960 |
| gcctacccca | tcgcgggtct | gcgccacagc | taccacgcgc | ccgattatcc | ccaggaccat | 1020 |
| gctttcgttc | cgcacggctt | cagtgtgatc | gtgaccgctc | ctgccgcctt | ccgcttcacc | 1080 |
| ttcgatgccg | accccgctaa | acacgtgtac | gcggcgagcc | tcctgaccgg | agaagcgtat | 1140 |

| | |
|---|---:|
| gaagaggatg accgcgaggc ccttccgagc gccttgctcg agctgatgcg cgacgtaggt | 1200 |
| gcaccgagcg gcgtggccga actcggctac ggagaggccg acctgcccgc gctggtggcg | 1260 |
| ggggcgttaa aacagcagcg cctcctggcc gtcgcgcccc ggaccccgac ggcgcaagac | 1320 |
| ctggaaggca tcttgcggga gtccatgcac aacgggtag | 1359 |

<210> SEQ ID NO 48
<211> LENGTH: 1029
<212> TYPE: DNA
<213> ORGANISM: Deinococcus sp.
<220> FEATURE:
<221> NAME/KEY: misc_feature
<223> OTHER INFORMATION: ADH derived from Deinococcus geothermalis DRH05

<400> SEQUENCE: 48

| | |
|---|---:|
| atggcccagt cacgcccaag tttgcccgag cctcaacgtc ccgaacactt tcgtgccctg | 60 |
| cgcgccgtca aggacgagac cggcgtgcgg cctgagtttc agaccctcac tcttgccgat | 120 |
| ctgccggaag gcgaggtgct ggtgcgtgtc acccactcca gcctgaacta caaagacggc | 180 |
| ctggcggtcg cgggcagacc cggtgtgctt aaggcttacc cgatgacgcc cggcattgac | 240 |
| ctggcgggga ccgttgtgga ggaccagacc gggacgtacc ggccgggcga cgcagtcctg | 300 |
| ctgaccggct ggggcattgg cgagcgtcag gacgggggat acgccgagta cgcgcgggtg | 360 |
| aaggcagcct ggttggtgcc gctcccggaa ggaaccgacg cgcagtgggc catgagcgtg | 420 |
| ggtacggcgg gcttcacggc gatgctggcg gtgatggccc tggaggaaca cggcgtcacc | 480 |
| cccgggagcg gcgaggtgct ggtgacgggt gcggcgggcg gtgtgggcag cactgccgtc | 540 |
| gctctgcttg ccgccgccgg ccattccgtc accgccagca cgggccgccg cgaggaggag | 600 |
| gactatctgc gctccctcgg tgccgccaac atcattggcc gtgaggaatt gcccgcgctg | 660 |
| aagcggccgc tggaaaagga acgctgggcg ggcgtggtcg acagtgtggg ggggataccc | 720 |
| ttggccggtg cgctcgcgag cacccgtacc cacggcgcgg ttgcggcctg cgggctggcc | 780 |
| ggtggcagcg ggctcaacac cacggttttt cccttcatcc tgcggggcgt gaacttgctt | 840 |
| gggatcgact cggtgacctg ccccaccgag cggcgccgcg cggcctgggc aaggctagcg | 900 |
| cgcgacctgc ccgccgccaa actcgcaggt gtgacgcagc ttcgccccct cagcgacgta | 960 |
| cccgcgctcg cgcaggagat tctggcgggg cgggtgcggg gccggaccgt gatcgacgtg | 1020 |
| acccgctga | 1029 |

<210> SEQ ID NO 49
<211> LENGTH: 1140
<212> TYPE: DNA
<213> ORGANISM: Deinococcus sp.
<220> FEATURE:
<221> NAME/KEY: misc_feature
<223> OTHER INFORMATION: ADH derived from Deinococcus geothermalis DRH05

<400> SEQUENCE: 49

| | |
|---|---:|
| atgaaagctg tcatttacaa cggaccgcgt gatgttcgcg ttgtcgacgt ggccgacccc | 60 |
| cagattgagc aacccacaga tgtgctggtg aaaatcacga gtaccaacat ctgcggttcc | 120 |
| gacctgcaca tgtacgaggg ccgcaccgac atcgagtgcg ggcgggtgct gggcatgaa | 180 |
| aacctgggtg aagtggtgga aatcggccgg gcggtgtacc gcattaaggt gggtgacaag | 240 |
| gtctgtctgc cgtttaatat cggctgtggc ttctgccgta actgcgaaaa ggggttgact | 300 |
| ggagcctgcc tgacggtggc gccgggtcag gccggggctg cctacgggtt tgccgacatg | 360 |
| ggcccgtttc agggtggaca ggcccagtac ttgcgggtgc ccttcggtga tttcaactgc | 420 |

```
ctgaagctcc ccgaggacgc cgccgagaaa gaggacgact atgtgatgct ggccgacatt      480
tttccgacgg gctggcacgc cacgcggctc gccaatctga tgcccggcga gagcgtcgcg      540
atttacgggg cgggaccagt ggggctgatg gcggcctact ccgccatgat tcagggggcc      600
cggcaagtca tcgtggtcga ccgccacaag gatcgcctga agctggccga acagatcgga      660
gcgattgctg tcaacgacgc cgaacacgac ccggtcgaac agatcatgga actgacgaac      720
ggccggggga ccgataaggg ctgtgaatgt gtgggctggc agtgccacga ccacggggga      780
catgagatcc ccaacctgac catgaacaat ctggtgaaga ccactcgcgc caccgggcag      840
atcggcgtgc tgggtgtctt cgttccgcag gatccgaaat cgccgacga cctgatgaag       900 cgtggtcaga ttgccttcga catcggcaat ttcttcttca agggcctgcg gatgggttcg      960
gggcaagcca acgtgaaggc gtataaccgg gagttgcgcg acctgattca cgctgatcgt     1020
gccaagccat cattcctggt gtcgcaccgc ctgccgctgg aacaggcccc cgacgcatac     1080
aaaaacttcg ataaccgcat agacggctgg acgaaggtga tcctcaaacc caacgagtag     1140
```

<210> SEQ ID NO 50
<211> LENGTH: 1218
<212> TYPE: DNA
<213> ORGANISM: Deinococcus sp.
<220> FEATURE:
<221> NAME/KEY: misc_feature
<223> OTHER INFORMATION: ADH derived from Deinococcus geothermalis DRH05

<400> SEQUENCE: 50

```
atgaaggcgc tggtgtggca gggcatcaac cgggtgggag tggagcgcgt tcccgatccc       60
acgattctcc aacccaccga cgccatcgtg cgcgtgaccg cgaccgcgat ctgcggctcg      120
gacctgcacc tgctcgacgg ctacatcccg agcatggtga agggcgacat cctcgggcac      180
gagttcatgg gcgaggtggt ggaggtcggc tccgcagtcc ggcgcatccg ggtcggggac      240
cgggtgattg tgcccttttcc gatcgcctgc ggcaaatgct ggtactgcca gcacggcctg      300
acctcgctgt gtgacaactc caaccccaac cccaagcttg cggagacgct gtggggctac      360
gccggcgccg gcatctacgg ctactcgcac atcacagggg gatacgcggg cggccaagcg      420
cagtttgccc gcaccgtcta cgccgacgcc aacctctatc cggtgcccga gggcctgacc      480
gacgagcagg tgctcttcct gaccgacatc ctccccaccg gctacatggc cgccgaacac      540
agcaacatcc agccgggcga cgtggtgacg gtatttgggg cagggccagt tggcctcttc      600
acggtcatga gcgccttcct gctgggagca ggacgggtga tctcgattga ccgcttcgac      660
gaccgcttga agctcgcgcg ccagctgggc gccgagacga tcaactacga ggcggacaat      720
gtctttgagc gcctgaagga actgaccggc gggcgtggcc ccgacagcgt agtgacgcg      780 gtgggcatgg agtcgcacgg caccggccta ggcggcatct acgacgccgt caagcagacc      840
acccgcgtgc tggaaacaga gcgccccac gccctgcgcg ccgcgatcat ggcctgccgc      900
aagggaggca ccgtcagcgt gccgggagta tacggcggcc tagcggacaa gatcccagtg      960
ggcgccttga tgaacaaggg ccttaccctg cgcaccgggc aaacccacgt tcaccgctat     1020
cttgataccc tgacccaaca catcctgcgc ggcgacatcg accccaccgt gatcatcacc     1080
caccgcctga gcctggacga ggcgccgcgg ggctaccagc tgttcaagca caagcacgac     1140
ggctgcatca agtgtgtgct cgacccctgg gccgatccca aggagcacgc gccgacgtcg     1200
cctcagccgg agacctga                                                   1218
```

<210> SEQ ID NO 51
<211> LENGTH: 990
<212> TYPE: DNA
<213> ORGANISM: Deinococcus sp.
<220> FEATURE:
<221> NAME/KEY: misc_feature
<223> OTHER INFORMATION: ADH derived from Deinococcus geothermalis DRH05

<400> SEQUENCE: 51

| | | | | | |
|---|---|---|---|---|---|
| atgagcgaat | ccatgaaagc | catcgtggtg | aacgcctcg | gccctcccga | cgtgatggag | 60 |
| gtgcgtgagc | tgcccgtgcc | ccagcccggc | cccggcgagg | tgcggctgaa | ggtggaggcc | 120 |
| gtcggcatca | acttcgcgga | cgtgctggcg | gtcgcgggcg | agtacctgac | gcggacgcgc | 180 |
| cttccctaca | cgcctggcat | ggagtttgcc | ggcatcgtgg | acgcattggg | cgagggcgtg | 240 |
| acgggcgttc | aggtgggcca | gcgggtcgcg | gcgctcgccg | gacgcggggg | cctggccgag | 300 |
| tacgccatct | cccctgccgc | cgcgctcatc | cgggtaccgg | acagcttcag | cgccgcccag | 360 |
| gccgcggcct | ttccggtgtc | gtacttcacg | gcgtaccacg | ggttgaagac | gctgggccac | 420 |
| gggaaggaag | gcgagtgggt | gctggtgcag | gcagcagcgg | gagcgctggg | cacggcctcg | 480 |
| atccaactgg | caaaagcgct | ggggatgaac | gtcattgcga | tggcgagcac | tgaggagaaa | 540 |
| ctccacattg | cccgcgatct | cggcgctgac | gtgactctcc | tccaggacga | ccccgaccgc | 600 |
| gtgcagaagg | tgcgggatgc | ggcgggggc | aagggggtgc | ccctgattct | ggaggtcatc | 660 |
| ggcggcaaga | ggttccaaga | aagcctcgac | atggctgcca | accggggccg | catcatcgtg | 720 |
| atcggcaacg | ccagccgcga | gcaggccaac | ctgcgtccgg | ttgaactgat | gaagcgcaac | 780 |
| ctcacggtga | ctggtctgtg | gctcacctcg | ctgatggggg | atcaggaggc | cacccgcgag | 840 |
| gcggcgaaa | cgctgaccca | actcgtcgcc | agcggccagg | tcacaccaca | ggtcggaccg | 900 |
| acctacccccc | tcaaagacag | cgcccgcgcc | ttccaggaca | tcctcgaccg | caagacgacc | 960 |
| gggaaggtga | tcatcgagcc | ccagcgctaa | | | | 990 |

<210> SEQ ID NO 52
<211> LENGTH: 978
<212> TYPE: DNA
<213> ORGANISM: Deinococcus sp.
<220> FEATURE:
<221> NAME/KEY: misc_feature
<223> OTHER INFORMATION: ADH derived from Deinococcus geothermalis DRH05

<400> SEQUENCE: 52

| | | | | | |
|---|---|---|---|---|---|
| atgtcccacg | ccgtcctggt | tgagcagcac | ggcggccccg | aagtcttgtc | ctggcgagaa | 60 |
| actcccctgc | cggtgcccgg | cccggggccag | gtgcgcgtcc | gggtcagcgc | gaccagcgtg | 120 |
| aactacgcgg | acatccaggc | gcggcgaggc | ggctacgacg | cgggggggcaa | gctgcccttc | 180 |
| acacccggcc | tggacgcctg | cggcacggtg | gacgcgctgg | gggaggggt | gaccggcctg | 240 |
| cgggtggggg | aacgggttgc | ctgcttcccg | ctggcggaa | gttacgccac | ccacgttctt | 300 |
| gctccggccc | acctcacctt | cccgctggag | aacaacgtgc | cggacgccgc | agccgccagc | 360 |
| ctcaccgcgc | tggtcacggc | ctacaacgtc | gtgacgtatg | cgggcaggct | gcaaagggt | 420 |
| gagacggtgc | tgatccatgc | gtcgcggggg | gggtggggc | atctggcggt | gcagatcgcg | 480 |
| cgggagcagg | gagcgggcca | agtggtcggc | gtcgtgggca | gtgacgcccg | cgtcgacttt | 540 |
| ctgcggcatc | tcggtgtgga | cgaggtggtg | aaccggcacc | gcgaggattt | cgtagggcgc | 600 |
| gtgaacgccc | tgacgagggg | gcgtggggcg | gacctgattc | tggactctat | cggtggaacc | 660 |
| acgaccgagc | gcggctttac | ctgtctggcc | cccttcgggc | ggctggtgat | ctacgggcac | 720 |

```
gcgggcaggc agcccgccca cctgccttcg ccgccccttc accggcagag ccgcgcggtg    780
atcggctaca gcagcggcca ccaccgccag gcccggccgc aagtggtccg ggacgcggcg    840
gccgccgcct ttgccttggc ggcgagcggg gctgtccgca ttcacgtcgc ggcggaattt    900
cccctgatgg aagcagccag ggcacacgcg ctggtggagt cgggcgagat caacggacgg    960
gtgctgctga cggtctag                                                 978
```

<210> SEQ ID NO 53
<211> LENGTH: 1080
<212> TYPE: DNA
<213> ORGANISM: Deinococcus sp.
<220> FEATURE:
<221> NAME/KEY: misc_feature
<223> OTHER INFORMATION: ADH derived from Deinococcus geothermalis DRH05

<400> SEQUENCE: 53

```
atgacttccc cggattcctc tttgtcttcc cgcatcagcg ttttgcatgg catccgcgac    60
ctgcgctggg agacgcgcga ggtccccgcg cccggcccgc gcgaggtccg cgtgcgtgtg    120
cggcgggtgg gcgtgtgcgg cagcgacgtg cactactaca cccatggccg gatcggctct    180
tttgtggtgg aggcgccgct gatcctcggc catgaggtaa tgggcgtggt ggacgcggtg    240
ggcgagggcg tcacccacgt ccggcctggc gaccgggtgg cgctggaacc tggtgtgccg    300
tgccgccgct gcgctttctg taagcgcggc gagtacaacc tctgccccga catgaccttt    360
atggcgaccc cgcccgtcca cggcgcgctc ggtgaatacg tgctttggcc cgacgacttt    420
gcgtttctgc tgcctgaccg catcagtgac gacgcgggcg cctcctcga accgctcgcg    480 gtcgggatct gggccgcgcg caagggcgac gtgcgtcctg ggcaaagcgt ggcggtcttt    540
ggcgccggtc ccatcggctg caccaccctt caagccgcca aggcggccgg ggccaccacc    600
ctcattgctg ttgatctgga agacttccgg ctcgacctgg cgagaaaggt aggggccacc    660
cacaccatca cgcccgcaa cgaggacccc gtcgctcgca ttcgcgagat cacgcgcggc    720
gacctgccga tctcccacgc cggagtggat gtggcctttg agacggcagg gagcctcccc    780
accactcgca tgagcctcgc cgcgccccgc ccaggcggca ccactgtgtt ggtgggcctg    840
ccgcccgact ccgaagtcag cctcgacatc gtctcggcag ccagccgcga ggtgagcatc    900
cggggtgttt ccgctatgc gaactgctat ccggcggcca ttgcgctggt ggagagcggc    960
gcggtggacc tcgacgtgct tgtcacccac cgctatccct tgaccagac ccccgaagct    1020 tttgcgttcg ctgaccgtga gaaacgcgcc agcatgaagg tcatgatcga tgtcggctga  1080
```

<210> SEQ ID NO 54
<211> LENGTH: 975
<212> TYPE: DNA
<213> ORGANISM: Deinococcus sp.
<220> FEATURE:
<221> NAME/KEY: misc_feature
<223> OTHER INFORMATION: ADH derived from Deinococcus geothermalis DRH05

<400> SEQUENCE: 54

```
atgcgcgccc tgatctgcac cgcttttgcc gaacccgaag ccctcaccgt ccagactgtt    60
cccgatccca cccccggccc cggcgaggtg gtgttggacg tgcaggcggc aggtgtgaac   120
tatcccgacg ccttgatggt gatggggcag taccaggtga aacctcctct ccccttcaca   180
cctggtgcgg aggctgctgg ggtgatcgcg gcgtaggcg agggcgtcac acacctgcgg   240 cctgccagc gtgcagtggc cttaccgga acgggcgcct ttgcagaaca gctcctcgcc   300
ccggcctcgg tcgtgatgcc gctgcccgat ggcctagaac tggaggtggc ggcaggcctg   360
```

```
ccgctggcct acggcacctc gatgcacgcg ctggcggacc gggcacagct ccaagcaggc    420
gagacgctgc tcgtgctggg cgcggcgggc ggcgtgggcc tggcggcggt gatgatcggc    480
aaggcgctgg gggcgcgggt gatcgcggcg gcgagcagcg aggagaaact gaagctgtgc    540
cgcgaacacg gggcggacga gaccctcaac tacgccgccg agaacctgcg tgagcgcctg    600
aaaacattga cggaggcca gggaccggac gtgatcttcg acccggtggg gggcgacctc    660
gcggaacccg ccttccgctc gatcggctgg ggcgggcgct atctggtggt gggtttcgcg    720
gggggcgaga ttccgaagct gccgctgaac ctgccgcttc tcaagggcgc ctcgctggtg    780
ggcgtatttt gggcgagtt cgcgcggcgt gacccgcctg ccaacgcgcg gaacatggcg    840
cggctgctga gctgggtggc ggaaggcaag gtcaggccgc tcgtcagcga gcgctattcg    900
ctggagcgcg cccccgaggc cctgcgcgcg ctgctcagcc gccgggtgac cgggaaggtg    960
gtggtcacgc cttga                                                    975

<210> SEQ ID NO 55
<211> LENGTH: 915
<212> TYPE: DNA
<213> ORGANISM: Deinococcus sp.
<220> FEATURE:
<221> NAME/KEY: misc_feature
<223> OTHER INFORMATION: ADH derived from Deinococcus DRH46

<400> SEQUENCE: 55
atgaccagcc atgccattgt gttccatgtg tacggagacc cagatgtcct tcaattgcac     60
acatttcctg ttccagaacc ctctgcgaat caggttctgg tgaggatcag ggcggcaggg    120
gtgcaacctt tgacgtgca gtttcgcaag ggcctgatgg ccgaacgtta ccagcctca    180 tttccccaga gatcggcaa cgagtttgct ggcacagtcg aaaaaattgg agatgaggtc    240
acccgattca gtctggaga tgctgtgctg ggatgggtgg ttcttgccgc ctacgccgag    300
catgtgctgg tttcagaagc cacccctcacc cacaaacccc cccagatgcc ctgggaagag    360
gcaggagccc tgaccgcttc tggtcagacc gccctcaccg ccctggacgc tttgcaggtg    420
gggccagaag atgtgctctt ggtccatgcc gctgcaggag gggtgggaag ttttgcagtg    480
caactggcaa agccagagg ggccagggtg attggcacag caagtcctgg caaccacgca    540
tacctgcaaa gcctggggac agaacccgtg agccacggag aaggtctggc ggaaagggtg    600
ctggaactcg ccccacaggg ggtgacagct tcacttgttg ctgtcggcaa cgaagaggca    660
ctgagggttt ccttgaaggt gacaaagaac cccgaaagca tccgaacact ggcctttcat    720
ccgctggcaa gacaacttgg cattgcctgg gtgggatcgg aacgttccct ggaacgtctg    780
gagcaactgg tgcagttta cgagaagggc cagttgaaag tccacattca ggaggctttc    840
cccctgaaag atgctgcaaa agcacaccgg gtcatggaga aggacatgt gaggggaaaa    900 ctggtgctcc ttccc                                                    915

<210> SEQ ID NO 56
<211> LENGTH: 1026
<212> TYPE: DNA
<213> ORGANISM: Deinococcus sp.
<220> FEATURE:
<221> NAME/KEY: misc_feature
<223> OTHER INFORMATION: ADH derived from Deinococcus DRH46

<400> SEQUENCE: 56
atgcaagctg ttgcactcac cagacggggc aacattgacg cccttgaacc catccgcctg     60
```

| | |
|---|---|
| cccatttcag agcctcaagc tggagaagtc ctggtgcgca tccgtgcagt ggccctcaac | 120 |
| cacctggatg tgtgggtgcg caagggggtc gccagcccga aacttcccct gccacacctg | 180 |
| ctcggctcag acattgcggg agaggtggct gcaatgggtc caggggttga aggtttgtca | 240 |
| gagggcacaa aagtgatgct gaacccgggc gtatcctgcg ccactgcga acgctgcctc | 300 |
| agtggacacg acaacctgtg ccgccactac caaattctcg gggaacaccg ctggggaggg | 360 |
| tatgcccagt acatcagcat cccgagaacc aatgtgctgc ccatgccaga gggccttgac | 420 |
| tttgtagagg ccgcctctgt cccctgtcg gccctcaccg cttaccagat ggtgttcgac | 480 |
| cgtgcacagc tgaaaccctg gaaaccgtc ctgatcctgg cggcggcaag tggggtcagc | 540 |
| gtcaacctga tccagctctg caaactggtg ggtgcaaaag tcatcgctgt ggccagcacc | 600 |
| cctgaaaagc aggccctggc actgaaactt ggtgcagatc acgtgatcgg ttcacatgaa | 660 |
| gaccaggctc aggccgtcaa agccctgact gcaggagaag gggcagacgt ggtgtttgac | 720 |
| cacaccggag cggacaactg gcaacgcagc ctgaaaagcc tgaagtgggg aggccgtctg | 780 |
| gtcacctgtg gggcaaccag tggacatgaa gccgtgaccc ccctcaactg ggtgttttc | 840 |
| aagcagctca gcatcctggg ttccaccatg ggctccaaag cagacctcca caaaattcag | 900 |
| aagtttgtgc aagaaggaaa actcaggcct gtggtgggcc atgttctgga ctttgctcag | 960 |
| gcaagagagg cccatgggct tctggaatcc aggcaggctc tgggcaaggt ggttttgagg | 1020 |
| gtcccg | 1026 |

<210> SEQ ID NO 57
<211> LENGTH: 2382
<212> TYPE: DNA
<213> ORGANISM: Deinococcus sp.
<220> FEATURE:
<221> NAME/KEY: misc_feature
<223> OTHER INFORMATION: Glucoamylase derived from M23-3A

<400> SEQUENCE: 57

| | |
|---|---|
| atgcgtgacg cttcggccaa gaaccctccc gaacagcccc tttcagaccc aggtccccg | 60 |
| gcgcagggcc tggccccgg cgccccggc ctgccgccga cctggtcgag cagcgacaag | 120 |
| gacttcgtga caacggccct gggcggtgcg tcccgggtgt gggccactgg cggccacggg | 180 |
| atgctgaacg aggtgtactg gccctccacc ggccagccgc agattcgtga cctgaccttc | 240 |
| tatctggtgg gggagtcggg ctgggtggac ctggggcggg tccagcgtta ccagatctcg | 300 |
| gtgcccaaac cgtacctgcc gctgcctacc ctgctgcacc agggggacga ctaccagttg | 360 |
| atgctggagg tgctgcctga cccgcaccgc gacgtgctgc tgattcgcta cgctctgagc | 420 |
| ggcccttacc gcctggtggt tgtgctggcg ccccacctca cctccactgg cacgacaac | 480 |
| gccgctgggc tcgaggggca gcacctgctg cggtgtccg gcaaccgcgc gctcgcactc | 540 |
| ttggcgagta gcccgctggc ccacctcagc gccggatacg taggcttctc cgacggctgg | 600 |
| caggatctga accagcatgg gtgcctcacc tggagttacc aacgcgccga gaacggcaac | 660 |
| gtggccctca gcgccgatct tcaggacgct tcgggattgc tggcgctggg ctttgcggaa | 720 |
| aacgtgacgg gcgcgcaggg tctggcgcgg gccagccttg cggaagggga cgagcccgcc | 780 |
| cgccgcgcct ttttgtacgc ctgggaagcc tgggggcagcg cgctcaagct cggcggctcc | 840 |
| acgcccgagc tggaggccga ggccctcctc agcgcgacgg tcctcaaggt acacgaagac | 900 |
| cgcacctatc cggcgcgct ggttgccagc ctcagcattc cttggggaaa caccaccgac | 960 |
| acgctgggcg gctatcacct cgtctggcca cgtgacgcga cgctggcggc ttttgccctg | 1020 |

```
ctggcctgca accagcctga ggatgcgcgc cgggtgctgg cgtggttcat tgccaaccag    1080
cagcccgacg gccactggct ccagaactac tatccggacg gtcaggactt ctggcacggc    1140
gttcagctcg acgagacggc ctttccggtg ctgctggccg ccaaactgcg tgaggagggc    1200
gagccagaac tggagggcac ccgcgacatg gtgcgccggg cgcttgcctt cgtggcccgt    1260
accggtccca ccagcgacca ggaccgctgg gaggagaacc aggggtgaa cccttcacg     1320 ctggcggtcg cgattgccgc actggtggcg ggctcaggct ggctggaaga aaacgaacgc    1380
cactacgtcc tcagcctggc agacgactgg aatgagcggc tagaaagtct ttgctacgtg    1440
actggcaccc cgctgtgccg cgagctgggg gtgcagggc actacgtgcg gctggccccg     1500
cctgaccgcg acggcaccct tactggccag gtgaccctcc agaatcgtca ggggaagacg    1560
gtcgaggcgt cggcgctggt cagcctggat ttctcgtact tgccgcgtct gggcctgcgt    1620
tcggcgctgg acccgcgcat ccgcgacacc gtgaaggtgg tggatcacct gctggcccaa    1680
aagacgccaa cgggcacctt ctaccaccgc tacaacggcg acggctacgg cgaacatgag    1740
gatggcgcgc cctacgacgg cttcggggtt gggcggctgt ggccgctgct gaacggcgag    1800
cgcggtcacc tcgcactgca ggcgggcgag gacgcctccc tctacctcga cagcctgctg    1860
cgctgcgccg gtcctggcgg tctgctgcct gagcaggtct gggacggccc acccattccc    1920
gaacgagggc tcttcccggg gcgccccaat ggcagcgcaa tgcctctgct gtgggcgcac    1980
gccgagtttt tgaagctgct gcacactgcg cagacgggcc gccctgctga gctgctgcgc    2040
gaggtggagg aacgctaccg tcagcctctc cccgctcagg cccgccactg gcgtcccgcc    2100
gcgccggtcc ccgaactcga acccggcctg ctcctgctga tcgaggacga caagcctttc    2160
ttgctgcatt acgggtttga tggctggcaa atccccagg accgccaggc cctacgcctc    2220
cccttcggcc tgtggggcgt caccttagc cccggcgaac tgggacagca ccacaccctc    2280
gatttcaccc gccagctggc ggcgggttgg gagggacagg accatcacat ccggctacac    2340
gagcgcgctc ccaaggtgtc cctgaccgcg cagaacgggt aa                      2382
```

<210> SEQ ID NO 58
<211> LENGTH: 792
<212> TYPE: PRT
<213> ORGANISM: Deinococcus sp.
<220> FEATURE:
<221> NAME/KEY: MISC_FEATURE
<223> OTHER INFORMATION: Glucoamylase derived from M23-3A

<400> SEQUENCE: 58

Met Arg Asp Ala Ser Ala Lys Asn Pro Pro Glu Gln Pro Leu Ser Asp
1               5                   10                  15

Pro Gly Pro Pro Ala Gln Gly Leu Ala Pro Gly Ala Pro Gly Leu Pro
            20                  25                  30

Pro Thr Trp Ser Ser Ser Asp Lys Asp Phe Val Thr Thr Ala Leu Gly
        35                  40                  45

Gly Ala Ser Arg Val Trp Ala Thr Gly His Gly Met Leu Asn Glu
    50                  55                  60

Val Tyr Trp Pro Ser Thr Gly Gln Pro Gln Arg Asp Leu Thr Phe Tyr
65                  70                  75                  80

Leu Val Gly Glu Ser Gly Trp Val Asp Leu Gly Arg Val Gln Arg Tyr
                85                  90                  95

Gln Ile Ser Val Pro Lys Pro Tyr Leu Pro Leu Pro Thr Leu Leu His
            100                 105                 110

Gln Gly Asp Asp Tyr Gln Leu Met Leu Glu Val Leu Pro Asp Pro His

-continued

```
            115                 120                 125
Arg Asp Val Leu Leu Ile Arg Tyr Ala Leu Ser Gly Pro Tyr Arg Leu
        130                 135                 140
Val Val Val Leu Ala Pro His Leu Thr Ser Thr Gly His Asp Asn Ala
145                 150                 155                 160
Ala Trp Val Glu Gly Gln His Leu Leu Ala Val Ser Gly Asn Arg Ala
                165                 170                 175
Leu Ala Leu Leu Ala Ser Ser Pro Leu Ala His Leu Ser Ala Gly Tyr
            180                 185                 190
Val Gly Phe Ser Asp Gly Trp Gln Asp Leu Asn Gln His Gly Cys Leu
                195                 200                 205
Thr Trp Ser Tyr Gln Arg Ala Glu Asn Gly Asn Val Ala Leu Ser Ala
            210                 215                 220
Asp Leu Gln Asp Ala Ser Gly Leu Leu Ala Leu Gly Phe Ala Glu Asn
225                 230                 235                 240
Val Thr Gly Ala Gln Gly Leu Ala Arg Ala Ser Leu Ala Glu Gly Asp
                245                 250                 255
Glu Pro Ala Arg Arg Ala Phe Leu Tyr Ala Trp Glu Ala Trp Gly Ser
            260                 265                 270
Ala Leu Lys Leu Gly Gly Ser Thr Pro Glu Leu Glu Ala Glu Ala Leu
            275                 280                 285
Leu Ser Ala Thr Val Leu Lys Val His Glu Asp Arg Thr Tyr Pro Gly
        290                 295                 300
Ala Leu Val Ala Ser Leu Ser Ile Pro Trp Gly Asn Thr Thr Asp Thr
305                 310                 315                 320
Leu Gly Gly Tyr His Leu Val Trp Pro Arg Asp Ala Thr Leu Ala Ala
                325                 330                 335
Phe Ala Leu Leu Ala Cys Asn Gln Pro Glu Asp Ala Arg Arg Val Leu
            340                 345                 350
Ala Trp Phe Ile Ala Asn Gln Gln Pro Asp Gly His Trp Leu Gln Asn
            355                 360                 365
Tyr Tyr Pro Asp Gly Gln Asp Phe Trp His Gly Val Gln Leu Asp Glu
        370                 375                 380
Thr Ala Phe Pro Val Leu Leu Ala Ala Lys Leu Arg Glu Glu Gly Glu
385                 390                 395                 400
Pro Glu Leu Glu Gly Thr Arg Asp Met Val Arg Arg Ala Leu Ala Phe
                405                 410                 415
Val Ala Arg Thr Gly Pro Thr Ser Asp Gln Asp Arg Trp Glu Glu Asn
            420                 425                 430
Gln Gly Val Asn Pro Phe Thr Leu Ala Val Ala Ile Ala Ala Leu Val
            435                 440                 445
Ala Gly Ser Gly Trp Leu Glu Asn Glu Arg His Tyr Val Leu Ser
        450                 455                 460
Leu Ala Asp Asp Trp Asn Glu Arg Leu Glu Ser Leu Cys Tyr Val Thr
465                 470                 475                 480
Gly Thr Pro Leu Cys Arg Glu Leu Gly Val Gln Gly Tyr Tyr Val Arg
                485                 490                 495
Leu Ala Pro Pro Asp Arg Asp Gly Thr Leu Thr Gly Val Thr Leu
            500                 505                 510
Gln Asn Arg Gln Gly Lys Thr Val Glu Ala Ser Ala Leu Val Ser Leu
            515                 520                 525
Asp Phe Ser Tyr Leu Pro Arg Leu Gly Leu Arg Ser Ala Leu Asp Pro
        530                 535                 540
```

```
Arg Ile Arg Asp Thr Val Lys Val Val Asp His Leu Leu Ala Gln Lys
545                 550                 555                 560

Thr Pro Thr Gly Thr Phe Tyr His Arg Tyr Asn Gly Asp Gly Tyr Gly
                565                 570                 575

Glu His Glu Asp Gly Ala Pro Tyr Asp Gly Phe Val Gly Arg Leu
            580                 585                 590

Trp Pro Leu Leu Asn Gly Glu Arg Gly His Leu Ala Leu Gln Ala Gly
            595                 600                 605

Glu Asp Ala Ser Leu Tyr Leu Asp Ser Leu Leu Arg Cys Ala Gly Pro
            610                 615                 620

Gly Gly Leu Leu Pro Glu Gln Val Trp Asp Gly Pro Ile Pro Glu
625                 630                 635                 640

Arg Gly Leu Phe Pro Gly Arg Pro Asn Gly Ser Ala Met Pro Leu Leu
                645                 650                 655

Trp Ala His Ala Glu Phe Leu Lys Leu Leu His Thr Ala Gln Thr Gly
                660                 665                 670

Arg Pro Ala Glu Leu Leu Arg Glu Val Glu Glu Arg Tyr Arg Gln Pro
                675                 680                 685

Leu Pro Ala Gln Ala Arg His Trp Arg Pro Ala Ala Pro Val Pro Glu
                690                 695                 700

Leu Glu Pro Gly Leu Leu Leu Ile Glu Asp Asp Lys Pro Phe Leu
705                 710                 715                 720

Leu His Tyr Gly Phe Asp Gly Trp Gln Asn Pro Gln Asp Arg Gln Ala
                725                 730                 735

Leu Arg Leu Pro Phe Gly Leu Trp Gly Val Thr Phe Ser Pro Gly Glu
                740                 745                 750

Leu Gly Gln His His Thr Leu Asp Phe Thr Arg Gln Leu Ala Ala Gly
                755                 760                 765

Trp Glu Gly Gln Asp His His Ile Arg Leu His Glu Arg Ala Pro Lys
770                 775                 780

Val Ser Leu Thr Ala Gln Asn Gly
785                 790

<210> SEQ ID NO 59
<211> LENGTH: 2388
<212> TYPE: DNA
<213> ORGANISM: Deinococcus sp.
<220> FEATURE:
<221> NAME/KEY: misc_feature
<223> OTHER INFORMATION: Endocellulase processive derived from M1-3H
      (full sequence)

<400> SEQUENCE: 59
gtgaaactcg gcgaggacac gaccgccccg tacgagttca cggtgaacgc cgaccctggc      60
ctgaacggca cgcacgtcta ctccgcgcag gcggtggcgg cgacgcggc cgggatctcc     120 gcgccggtca gcgtgcagat ccgcatcgcg gacacccgca ccaccgaact gctcagcaac     180
ggggacttca gccagggcct gaaccctggg tggactgccg gaacggccgc cagcacgacc     240
ggcggtgaga cctgcctgaa catcacgcag ccgggcagca accctgggga cgtgctgttc     300
gggcagggcg gcgtgggcct gaacgagggc ggcacgtaca ccctgagctt cacggcgcgc     360
gccgcgcagc ccacgtcgtt caggacgctg ctgcagttcg acggcgcgcc gtacaccaac     420
tacttcgtgc aggacgcgga cgtgaccagc cagccgaaga ccttcacgtc cacgttcacg     480
atggcgcagc ccagtgacgc gaaggccgcg ttccagttcc agctgggcgc cagggccgcc     540
```

```
acgaccgtgt gcttcagccg catttcactg actggccctg ccttcggcag cgccgtgccc      600
gcctcgggtg cggacgacct gaagctggtg cggctcaacc agaccgggta cctgccggac      660
cggccgaaac tggcggccct gccgttcgac tcggaccggc cgctgccgtg gactctgctg      720
gacggcacgc gcacggtcgc cagtggcgtg acccgcgtgt tcggcgcgga cgccgcgtcc      780
ggcgagcacg tgcatcaggt ggacttcagt gccgtgaccg ccccggccga cgggctggtg      840
ctggacgtcg cgggtttccg cagccacccg ttccggatcg ggcgcgtgta cgacggcctg      900
aaacgcgacg cgctggcgta cttctaccac aaccgcagcg gcacgcccat caaggcgaag      960
tacgtcgggg acgcctgggc gcgcccggcc ggtcacgccg gaccagccc gaaccagggg     1020 gacacgcgcg tcagctgctt caagggcacc gatcaggccg gaacgtctg gcccggctgc      1080 gggtacgaac tggacgccag cggcggctgg tacgacgccg gggatcacgg gaagtacgtc     1140
gtgaacggcg gcgtgagcgt ctggacgctg ctgaacctcg ccgagcgggg cgcgcgcctg     1200
aacctcccgg acgcggacgg cagcctgaat atcccggaaa gcgggaacgg ccgcagcgac     1260
ctgctggacg aggtccgctg ggagctggac ttcatgctgc ggatgcaggt cccggatggg     1320
cagaccctgg tcctgccgcg cggcgaccag cgcggcgccc cgctgaccct gacgcccacc     1380 ccggcggcg ggctggtgca ccagaaactc acggacgtcg cctggaccgg cctgccgctg     1440
cgccccgatc aggatccgca gccgcgcgcg ctgtactacc ccacgaccgc cgcgaccctg     1500
aacctcgcgg gcgtggcggc gcagtgcgcc cgcgtgtacc gcgcctcgga cccggccttc     1560
gcggtccgct gcctgagcgc cgcgcgccgc gcgtggcagg ccgcgcgggc cgcgccggac     1620
gtgtacgcgt acgacctgtt cgtgggcggc ggcccgtacg acgatacgga cgtcagcgac     1680
gagttctact gggcggcggc ggaactgtac gccacgaccg gcgaggcggc gttcctggag     1740
gcgctgcggg ccagtccgct gttcctgcag atgcccgagg ggcgtgaact gggctggagt     1800
gacctgacgg cagcgggcac cctgacgctc gccagcgtgc ccacggcgct gcccggcgcg     1860
gacgtgcagc aggcccgcgc gaacgtcgtg cggcggcgc gggcgttccg ggacgcggca     1920
ggcacgcagg ggtaccgcct gccgatgacc ggcgccgagg ccacctgggg ctcgaacagt     1980
ggcgtgctga accgctcggt cgtgatgggc gccgcgtggg acttcacggg tgacgattcg     2040
ttcgtgaatg tcgtgctgga gggcctgaac tacctgctgg acgcaaccc gatggacaag     2100 tcgtacgtgt ccgggtacgg cgagcgtccg ctgctgaacc gcaccaccg cttctgggcg     2160 cggtcgctgg acgcggcgct gccccggccg ccgcgtgggg tggtgtcggg cggcccgaac     2220
agcgtgaact tcagtgatcc ggtcgcggcg aaactcaggg gccgctgcgt gggcctgcgc     2280
tgctacaccg acgacatcgg cgcgtacacc atgaacgagg tgaccatcaa ctggaacgcg     2340
ccgctggcgt gggtggcggc gttcgtggag cacagcaccc gacgctaa                 2388
```

<210> SEQ ID NO 60
<211> LENGTH: 795
<212> TYPE: PRT
<213> ORGANISM: Deinococcus sp.
<220> FEATURE:
<221> NAME/KEY: MISC_FEATURE
<223> OTHER INFORMATION: Endocellulase processive derived from
      M1-3H(full sequence)

<400> SEQUENCE: 60

Val Lys Leu Gly Glu Asp Thr Thr Ala Pro Tyr Glu Phe Thr Val Asn
1               5                   10                  15

Ala Asp Pro Gly Leu Asn Gly Thr His Val Tyr Ser Ala Gln Ala Val
            20                  25                  30

```
Ala Gly Asp Ala Ala Gly Ile Ser Ala Pro Val Ser Val Gln Ile Arg
         35                  40                  45

Ile Ala Asp Thr Arg Thr Thr Glu Leu Leu Ser Asn Gly Asp Phe Ser
 50                  55                  60

Gln Gly Leu Asn Pro Trp Trp Thr Ala Gly Thr Ala Ala Ser Thr Thr
 65              70                  75                  80

Gly Gly Glu Thr Cys Leu Asn Ile Thr Gln Pro Gly Ser Asn Pro Trp
                 85                  90                  95

Asp Val Leu Phe Gly Gln Gly Val Gly Leu Asn Glu Gly Gly Thr
                100                 105                 110

Tyr Thr Leu Ser Phe Thr Ala Arg Ala Ala Gln Pro Thr Ser Phe Arg
                115                 120                 125

Thr Leu Leu Gln Phe Asp Gly Ala Pro Tyr Thr Asn Tyr Phe Val Gln
        130                 135                 140

Asp Ala Asp Val Thr Ser Gln Pro Lys Thr Phe Thr Ser Thr Phe Thr
145                 150                 155                 160

Met Ala Gln Pro Ser Asp Ala Lys Ala Ala Phe Gln Phe Gln Leu Gly
                165                 170                 175

Ala Arg Ala Ala Thr Thr Val Cys Phe Ser Arg Ile Ser Leu Thr Gly
                180                 185                 190

Pro Ala Phe Gly Ser Ala Val Pro Ala Ser Gly Ala Asp Asp Leu Lys
                195                 200                 205

Leu Val Arg Leu Asn Gln Thr Gly Tyr Leu Pro Asp Arg Pro Lys Leu
        210                 215                 220

Ala Ala Leu Pro Phe Asp Ser Asp Arg Pro Leu Pro Trp Thr Leu Leu
225                 230                 235                 240

Asp Gly Thr Arg Thr Val Ala Ser Gly Val Thr Arg Val Phe Gly Ala
                245                 250                 255

Asp Ala Ala Ser Gly Glu His Val His Gln Val Asp Phe Ser Ala Val
                260                 265                 270

Thr Ala Pro Ala Asp Gly Leu Val Leu Asp Val Ala Gly Phe Arg Ser
        275                 280                 285

His Pro Phe Arg Ile Gly Arg Val Tyr Asp Gly Leu Lys Arg Asp Ala
        290                 295                 300

Leu Ala Tyr Phe Tyr His Asn Arg Ser Gly Thr Pro Ile Lys Ala Lys
305                 310                 315                 320

Tyr Val Gly Asp Ala Trp Ala Arg Pro Ala Gly His Ala Gly Thr Ser
                325                 330                 335

Pro Asn Gln Gly Asp Thr Arg Val Ser Cys Phe Lys Gly Thr Asp Gln
                340                 345                 350

Ala Gly Asn Val Trp Pro Gly Cys Gly Tyr Glu Leu Asp Ala Ser Gly
                355                 360                 365

Gly Trp Tyr Asp Ala Gly Asp His Gly Lys Tyr Val Val Asn Gly Gly
        370                 375                 380

Val Ser Val Trp Thr Leu Leu Asn Leu Ala Glu Arg Gly Ala Arg Leu
385                 390                 395                 400

Asn Leu Pro Asp Ala Asp Gly Ser Leu Asn Ile Pro Glu Ser Gly Asn
                405                 410                 415

Gly Arg Ser Asp Leu Leu Asp Glu Val Arg Trp Glu Leu Asp Phe Met
                420                 425                 430

Leu Arg Met Gln Val Pro Asp Gly Gln Thr Leu Val Leu Pro Arg Gly
        435                 440                 445
```

```
Asp Gln Arg Gly Ala Pro Leu Thr Leu Thr Pro Thr Pro Ala Gly Gly
    450                 455                 460
Leu Val His Gln Lys Leu Thr Asp Val Ala Trp Thr Gly Leu Pro Leu
465                 470                 475                 480
Arg Pro Asp Gln Asp Pro Gln Pro Arg Ala Leu Tyr Tyr Pro Thr Thr
                485                 490                 495
Ala Ala Thr Leu Asn Leu Ala Gly Val Ala Ala Gln Cys Ala Arg Val
                500                 505                 510
Tyr Arg Ala Ser Asp Pro Ala Phe Ala Val Arg Cys Leu Ser Ala Ala
                515                 520                 525
Arg Arg Ala Trp Gln Ala Ala Arg Ala Ala Pro Asp Val Tyr Ala Tyr
    530                 535                 540
Asp Leu Phe Val Gly Gly Pro Tyr Asp Asp Thr Asp Val Ser Asp
545                 550                 555                 560
Glu Phe Tyr Trp Ala Ala Ala Glu Leu Tyr Ala Thr Thr Gly Glu Ala
                565                 570                 575
Ala Phe Leu Glu Ala Leu Arg Ala Ser Pro Leu Phe Leu Gln Met Pro
                580                 585                 590
Glu Gly Arg Glu Leu Gly Trp Ser Asp Leu Thr Ala Ala Gly Thr Leu
    595                 600                 605
Thr Leu Ala Ser Val Pro Thr Ala Leu Pro Gly Ala Asp Val Gln Gln
    610                 615                 620
Ala Arg Ala Asn Val Val Ala Ala Ala Arg Ala Phe Arg Asp Ala Ala
625                 630                 635                 640
Gly Thr Gln Gly Tyr Arg Leu Pro Met Thr Gly Ala Glu Ala Thr Trp
                645                 650                 655
Gly Ser Asn Ser Gly Val Leu Asn Arg Ser Val Val Met Gly Ala Ala
                660                 665                 670
Trp Asp Phe Thr Gly Asp Asp Ser Phe Val Asn Val Leu Glu Gly
                675                 680                 685
Leu Asn Tyr Leu Leu Gly Arg Asn Pro Met Asp Lys Ser Tyr Val Ser
    690                 695                 700
Gly Tyr Gly Glu Arg Pro Leu Leu Asn Pro His His Arg Phe Trp Ala
705                 710                 715                 720
Arg Ser Leu Asp Ala Ala Leu Pro Gly Pro Arg Gly Val Val Ser
                725                 730                 735
Gly Gly Pro Asn Ser Val Asn Phe Ser Asp Pro Val Ala Ala Lys Leu
                740                 745                 750
Arg Gly Arg Cys Val Gly Leu Arg Cys Tyr Thr Asp Asp Ile Gly Ala
                755                 760                 765
Tyr Thr Met Asn Glu Val Thr Ile Asn Trp Asn Ala Pro Leu Ala Trp
    770                 775                 780
Val Ala Ala Phe Val Glu His Ser Thr Arg Arg
785                 790                 795

<210> SEQ ID NO 61
<211> LENGTH: 3063
<212> TYPE: DNA
<213> ORGANISM: Deinococcus sp.
<220> FEATURE:
<221> NAME/KEY: misc_feature
<223> OTHER INFORMATION: Alpha-amylase derived from M23-3A

<400> SEQUENCE: 61
atgaaacgtt tccagaaggt gggtcgcagt ggcgccctgg ccgtccttac gttggctctg    60
```

```
tccgcctgtg gcgtcttgaa ggcgcccgag acgggaggca acactcgtgc ctggcaggac    120
gaggtgatct acttcgccat gaccgaccgc ttcgccaacg ggaacccggc caacgacaac    180
ggcccgaacc gcaatgaggg cgaccgggcc gaccggacca acccgctcgg ctggcacggc    240
ggcgacttcg cggggctgaa ggcgaagatc gaggagggct atttcaagcg catgggcttt    300
acggccctct ggatcagccc ggtggtcctg caggttccgg ccatcgaggg cccgaagacc    360
gggccgaacg ccgggaagct cttcgcggga taccacggct actgggccga ggacttttc     420 aaggtagacc cacacttcgg cacgctggac gagtacaagt ccctcatcca gactgcgcac    480
aggaacggca tcaaggtgat tcaggacatt gtggtcaacc acgcgggcta cggcgccaca    540
ctcaccaaga ccaatcctga ctggtttcac acccaggctg aatgcgacgc cagcaccaac    600
aaacgggtgg actgtccgct ggcgggcctg cctgacttca gcaggagcg gcccgaggtc     660 acaacgtacc tgaacgactt cgtgaactcc tggcgcaagg aaaccggcat cgacgggctg    720
cggatcgaca ccatgcagca cgtctctgac agctactggc agcagttctt tgccgcgggt    780
gggccggggg accctttccaa gatctggtcg gtcgcgagg tgttcaacgg tgatccggcc     840
ttcctggccc actatatgga tgacctcgga tcgcccagcg tgttcgattt cgcgctgtac    900
ttcgccatca aggatggctt gtcgagtgcg cgcggcgacc taggacgctt ggccgacgtg    960
ttcgcgcggg atggtgcgta ccgggaccc acacggctga ccaccttcgt ggacaaccac    1020
gacgtgcccc gcttcgtgag cgaggtgcag gagcgcggcg gacagcggc gcaggcgaac    1080 gagcgccttg acctggccct cagtctgatc tatacctcgc gcggcacacc gagcgtgtac    1140
cagggcacgg agatcgcgca gcctggcttg ggcgaccct acaactacgc caccggccaa    1200
ggcaaccgcg aggacatgaa cttcggggcc ctctcgcaga gcagtatcga cgagcggctg    1260
gcagctctcg ccgcggcacg cgcgaagtac cgggcactca cacatggcgt gcagcaggag    1320
ctgtggcggc caaacggcgg ggcgcccatc ttcgcccacc gccggattgt cacggatggt    1380
caaggcggac agcccgtcgt cgtcgtgatc aacaacggcg acacgcccgt ggacctctcc    1440
actctgagcg ggggcggtat tccgctgctg gggaccttca gcgggacggc gctgacagaa    1500
attaccgggc gaaccagcga cctgagcgtg agcggcggcc aactcgtagg cacggttcct    1560
gcccgctccg cgcttgctgt cacggccccg gcgggcagcg gcagcacagg cacggtgaac    1620
cccaggctgc cggaggtgac ggatctcagt gcgaaggccg gagacagcgc cgtgcagctc    1680
acgtggacgg cctccacgga cctgaacgtc accggctgcc gcgtctacgc ccgcaccggg    1740
agcgggcagg aacggctcct caacttcgcg ccgctgccca aggaccagac cacgtacctc    1800
gccgcaggca ttccgaacga ccaggaaacg accttccggg tggtcacggt agacgcgcag    1860
ggcgccgaga gtcggggcgt cagcgtcaag gccacgccca gcagcaagaa cacggtcagg    1920
gtgactttca cggtggacgc ccgcagccag ggcaacggcc cgatcgagct gcgccgcttc    1980
gacacgggct cgcagcttga gtaccccatg acgcaggtga gccgcggcat ctggaagacg    2040
gcgattgacc tccccctctt ccgcgagatc aagtttaagt tcggcaacga cggacccgcc    2100
gccaagaaca gcggctacga ggcacccggc caacccgacc gcagctatgt ggtgggaaca    2160
aatcctaacg tctacaccgg cacctatgac tttattaccc agccggtgcc gcagaccacc    2220
atcgagggcc aagtcagagg agcgggcaat ccctcgcga atgcgttggt cgaagcggtg     2280
accgccaacc ccgacctgca ctatgcgatg acctttccgg acggcacata cacactgttt    2340
gttccggcag ggaccacac actgcaggcc aaggcaggcg gctacgtagc agccagccgg     2400
caggcgatct cgccggggac gggcgcagac ttcaacctgg cccaggacct gagcaccaag    2460
```

-continued

```
tacaccatcg acggcaacct ggccgactgg acggccccca aggtgacgct gcaaagcccg      2520
accgagggag gcttcgggcc cgacaacaat tggttgacac tccaggccga cagtgatgac      2580
cactatctgt acctcgcgta cacgtaccgg gtgaagggaa acagcgcgat cctgtacctg      2640
gacaccaaga tgggcggtgc ggcccaagcc gacaatttcg aggcttggaa gcgggcggcg      2700
accttcagtg ggagcatggg gggcgccgac gcctttgttg cgcggtacga aaaccagatg      2760
gctcaactga ggctgtttca gagcgatact gccacgcccg aggtcaacac gggcgactac      2820
aagtttgcag cgagcggtac cctgcccgag cagacggtgg aactggcgat cccgtggaca      2880
gcactcggcc tcagcgaaaa acctgcgaac ggtgtgaacg tggtgggtgg aattttcggt      2940
ggcgacggct acggcgcggg cgacatcgtg cccaatacca ccagtacacc ccccggtgcc      3000
aacaccattg aacggatgc cgaacagcgc cgggcaacct tcactcagcc cctcaacgtg      3060
agg                                                                     3063
```

<210> SEQ ID NO 62
<211> LENGTH: 1021
<212> TYPE: PRT
<213> ORGANISM: Deinococcus sp.
<220> FEATURE:
<221> NAME/KEY: MISC_FEATURE
<223> OTHER INFORMATION: Alpha-amylase derived from M23-3A

<400> SEQUENCE: 62

```
Met Lys Arg Phe Gln Lys Val Gly Arg Ser Gly Ala Leu Ala Val Leu
1               5                   10                  15

Thr Leu Ala Leu Ser Ala Cys Gly Val Leu Lys Ala Pro Glu Thr Gly
            20                  25                  30

Gly Asn Thr Arg Ala Trp Gln Asp Glu Val Ile Tyr Phe Ala Met Thr
        35                  40                  45

Asp Arg Phe Ala Asn Gly Asn Pro Ala Asn Asp Gly Pro Asn Arg
    50                  55                  60

Asn Glu Gly Asp Arg Ala Asp Arg Thr Asn Pro Leu Gly Trp His Gly
65                  70                  75                  80

Gly Asp Phe Ala Gly Leu Lys Ala Lys Ile Glu Glu Gly Tyr Phe Lys
                85                  90                  95

Arg Met Gly Phe Thr Ala Leu Trp Ile Ser Pro Val Val Leu Gln Val
            100                 105                 110

Pro Ala Ile Glu Gly Pro Lys Thr Gly Pro Asn Ala Gly Lys Leu Phe
        115                 120                 125

Ala Gly Tyr His Gly Tyr Trp Ala Glu Asp Phe Lys Val Asp Pro
    130                 135                 140

His Phe Gly Thr Leu Asp Glu Tyr Lys Ser Leu Ile Gln Thr Ala His
145                 150                 155                 160

Arg Asn Gly Ile Lys Val Ile Gln Asp Ile Val Asn His Ala Gly
                165                 170                 175

Tyr Gly Ala Thr Leu Thr Lys Thr Asn Pro Asp Trp Phe His Thr Gln
            180                 185                 190

Ala Glu Cys Asp Ala Ser Thr Asn Lys Arg Val Asp Cys Pro Leu Ala
        195                 200                 205

Gly Leu Pro Asp Phe Lys Gln Glu Arg Pro Glu Val Thr Thr Tyr Leu
    210                 215                 220

Asn Asp Phe Val Asn Ser Trp Arg Lys Glu Thr Gly Ile Asp Gly Leu
225                 230                 235                 240
```

-continued

```
Arg Ile Asp Thr Met Gln His Val Ser Asp Ser Tyr Trp Gln Gln Phe
                245                 250                 255
Phe Ala Ala Gly Gly Pro Gly Asp Pro Ser Lys Ile Trp Ser Val Gly
            260                 265                 270
Glu Val Phe Asn Gly Asp Pro Ala Phe Leu Ala His Tyr Met Asp Asp
        275                 280                 285
Leu Gly Ser Pro Ser Val Phe Asp Phe Ala Leu Tyr Phe Ala Ile Lys
    290                 295                 300
Asp Gly Leu Ser Ser Ala Arg Gly Asp Leu Arg Leu Ala Asp Val
305                 310                 315                 320
Phe Ala Arg Asp Gly Ala Tyr Arg Asp Pro Thr Arg Leu Thr Thr Phe
                325                 330                 335
Val Asp Asn His Asp Val Pro Arg Phe Val Ser Glu Val Gln Glu Arg
            340                 345                 350
Gly Gly Thr Ala Ala Gln Ala Asn Glu Arg Leu Asp Leu Ala Leu Ser
        355                 360                 365
Leu Ile Tyr Thr Ser Arg Gly Thr Pro Ser Val Tyr Gln Gly Thr Glu
    370                 375                 380
Ile Ala Gln Pro Gly Leu Gly Asp Pro Tyr Asn Tyr Ala Thr Gly Gln
385                 390                 395                 400
Gly Asn Arg Glu Asp Met Asn Phe Gly Ala Leu Ser Gln Ser Ser Ile
                405                 410                 415
Asp Glu Arg Leu Ala Ala Leu Ala Ala Arg Ala Lys Tyr Arg Ala
            420                 425                 430
Leu Thr His Gly Val Gln Gln Glu Leu Trp Arg Pro Asn Gly Gly Ala
        435                 440                 445
Pro Ile Phe Ala His Arg Arg Ile Val Thr Asp Gly Gln Gly Gln
    450                 455                 460
Pro Val Val Val Ile Asn Asn Gly Asp Thr Pro Val Asp Leu Ser
465                 470                 475                 480
Thr Leu Ser Gly Gly Ile Pro Leu Leu Gly Thr Phe Ser Gly Thr
                485                 490                 495
Ala Leu Thr Glu Ile Thr Gly Arg Thr Ser Asp Leu Ser Val Ser Gly
            500                 505                 510
Gly Gln Leu Val Gly Thr Val Pro Ala Arg Ser Ala Leu Ala Val Thr
        515                 520                 525
Ala Pro Ala Gly Ser Gly Ser Thr Gly Thr Val Asn Pro Arg Leu Pro
    530                 535                 540
Glu Val Thr Asp Leu Ser Ala Lys Ala Gly Asp Ser Ala Val Gln Leu
545                 550                 555                 560
Thr Trp Thr Ala Ser Thr Asp Leu Asn Val Thr Gly Cys Arg Val Tyr
                565                 570                 575
Ala Arg Thr Gly Ser Gly Gln Glu Arg Leu Leu Asn Phe Ala Pro Leu
            580                 585                 590
Pro Lys Asp Gln Thr Thr Tyr Leu Ala Ala Gly Ile Pro Asn Asp Gln
        595                 600                 605
Glu Thr Thr Phe Arg Val Val Thr Val Asp Ala Gln Gly Ala Glu Ser
    610                 615                 620
Arg Gly Val Ser Val Lys Ala Thr Pro Ser Ser Lys Asn Thr Val Arg
625                 630                 635                 640
Val Thr Phe Thr Val Asp Ala Arg Ser Gln Gly Asn Gly Pro Ile Glu
                645                 650                 655
Leu Arg Arg Phe Asp Thr Gly Ser Gln Leu Glu Tyr Pro Met Thr Gln
```

```
                    660                 665                 670
Val Ser Arg Gly Ile Trp Lys Thr Ala Ile Asp Leu Pro Leu Phe Arg
        675                 680                 685
Glu Ile Lys Phe Lys Phe Gly Asn Asp Gly Pro Ala Ala Lys Asn Ser
    690                 695                 700
Gly Tyr Glu Ala Pro Gly Gln Pro Asp Arg Ser Tyr Val Val Gly Thr
705                 710                 715                 720
Asn Pro Asn Val Tyr Thr Gly Thr Tyr Asp Phe Ile Thr Gln Pro Val
                725                 730                 735
Pro Gln Thr Thr Ile Glu Gly Gln Val Arg Gly Ala Gly Asn Pro Leu
            740                 745                 750
Ala Asn Ala Leu Val Glu Ala Val Thr Ala Asn Pro Asp Leu His Tyr
        755                 760                 765
Ala Met Thr Phe Pro Asp Gly Thr Tyr Thr Leu Phe Val Pro Ala Gly
    770                 775                 780
Thr His Thr Leu Gln Ala Lys Ala Gly Gly Tyr Val Ala Ala Ser Arg
785                 790                 795                 800
Gln Ala Ile Ser Pro Gly Thr Gly Ala Asp Phe Asn Leu Ala Gln Asp
                805                 810                 815
Leu Ser Thr Lys Tyr Thr Ile Asp Gly Asn Leu Ala Asp Trp Thr Ala
            820                 825                 830
Pro Lys Val Thr Leu Gln Ser Pro Thr Glu Gly Gly Phe Gly Pro Asp
        835                 840                 845
Asn Asn Trp Leu Thr Leu Gln Ala Asp Ser Asp Asp His Tyr Leu Tyr
    850                 855                 860
Leu Ala Tyr Thr Tyr Arg Val Lys Gly Asn Ser Ala Ile Leu Tyr Leu
865                 870                 875                 880
Asp Thr Lys Met Gly Gly Ala Ala Gln Ala Asp Asn Phe Glu Ala Trp
                885                 890                 895
Lys Arg Ala Ala Thr Phe Ser Gly Ser Met Gly Gly Ala Asp Ala Phe
            900                 905                 910
Val Ala Arg Tyr Glu Asn Gln Met Ala Gln Leu Arg Leu Phe Gln Ser
        915                 920                 925
Asp Thr Ala Thr Pro Glu Val Asn Thr Gly Asp Tyr Lys Phe Ala Ala
    930                 935                 940
Ser Gly Thr Leu Pro Glu Gln Thr Val Glu Leu Ala Ile Pro Trp Thr
945                 950                 955                 960
Ala Leu Gly Leu Ser Glu Lys Pro Ala Asn Gly Val Asn Val Val Gly
                965                 970                 975
Gly Ile Phe Gly Gly Asp Gly Tyr Gly Ala Gly Asp Ile Val Pro Asn
            980                 985                 990
Thr Thr Ser Thr Pro Pro Gly Ala  Asn Thr Ile Gly Thr  Asp Ala Glu
        995                 1000                1005
Gln Arg  Arg Ala Thr Phe Thr  Gln Pro Leu Asn Val  Arg
    1010                1015                1020

<210> SEQ ID NO 63
<211> LENGTH: 960
<212> TYPE: DNA
<213> ORGANISM: Deinococcus sp.
<220> FEATURE:
<221> NAME/KEY: misc_feature
<223> OTHER INFORMATION: Acetyl xylan esterase no. 1 derived from DRH-46

<400> SEQUENCE: 63
```

```
atggcttttt ttgacctgcc cctggaacag ctgaagacct accgtcctga aatccgctgc    60
ccagcagact ttgacgcttt ctggcagcag actttgcagg aagctgcaca gcatcccctg   120
aatgcccgtt ttgatgaggt gaagacacca ctccagaccc tcagggtttt tgatgtcacc   180
tttgcaggat ttgggggcca tgagatcaag gggtggttga tggttccgca caacctggag   240
ggtcctttc cctgtgtggt ggaattcatc ggttatggcg gaggacgggg agagcctgtg    300
gaccacctga cctacgccag tgcaggtcac gcccatctgg tcatggacac ccggggccag   360
ggcagcggat ggcgcaaggg ggatacccct gatccggtgg gttccgggcc tcagcaccca   420
ggcttcatga cccgtgggat cgaaacccca gaggcctatt attaccgccg ggtgttcacc   480
gatggggtga gggccgtgca ggcggcacag gcctctgaac tggtggaccc acagcgcatt   540
gctgttgccg gagaaagcca gggggcgggg attgcccttg cagttgctgc tttgagccat   600
caggtgaaac tcctgatgtc cgatgtgcct tttttgtgtc actttgagag ggccatcacc   660
ctcacggaca gcattcccta tgtggaaatc gcaaaccact gcgggtgca tcgggacagg    720
tgggagcagg ttctgggaac actggcttat tttgatggaa tgaattttgc ctcactgtgt   780
aaagtcccag ccctgttatc ggtggccctg atggaccaga cctgccctcc gagcacggtc   840
tttgctgctt tcaatcattt tgcaggtcca aaagaaatct gtgtttatcc attcaacaga   900
catgagggag gacagactgc acaattgctc cagcggctga aattttaca gcagcactgg    960
```

```
<210> SEQ ID NO 64
<211> LENGTH: 320
<212> TYPE: PRT
<213> ORGANISM: Deinococcus sp.
<220> FEATURE:
<221> NAME/KEY: MISC_FEATURE
<223> OTHER INFORMATION: Acetyl xylan esterase no. 1 derived from DRH-46

<400> SEQUENCE: 64
```

Met Ala Phe Phe Asp Leu Pro Leu Glu Gln Leu Lys Thr Tyr Arg Pro
1               5                   10                  15

Glu Ile Arg Cys Pro Ala Asp Phe Asp Ala Phe Trp Gln Gln Thr Leu
            20                  25                  30

Gln Glu Ala Ala Gln His Pro Leu Asn Ala Arg Phe Asp Glu Val Lys
        35                  40                  45

Thr Pro Leu Gln Thr Leu Arg Val Phe Asp Val Thr Phe Ala Gly Phe
    50                  55                  60

Gly Gly His Glu Ile Lys Gly Trp Leu Met Val Pro His Asn Leu Glu
65                  70                  75                  80

Gly Pro Phe Pro Cys Val Val Glu Phe Ile Gly Tyr Gly Gly Gly Arg
                85                  90                  95

Gly Glu Pro Val Asp His Leu Thr Tyr Ala Ser Ala Gly His Ala His
            100                 105                 110

Leu Val Met Asp Thr Arg Gly Gln Gly Ser Gly Trp Arg Lys Gly Asp
        115                 120                 125

Thr Pro Asp Pro Val Gly Ser Gly Pro Gln His Pro Gly Phe Met Thr
    130                 135                 140

Arg Gly Ile Glu Thr Pro Glu Ala Tyr Tyr Arg Arg Val Phe Thr
145                 150                 155                 160

Asp Gly Val Arg Ala Val Gln Ala Ala Gln Ala Ser Glu Leu Val Asp
                165                 170                 175

Pro Gln Arg Ile Ala Val Ala Gly Glu Ser Gln Gly Gly Gly Ile Ala
            180                 185                 190

```
Leu Ala Val Ala Ala Leu Ser His Gln Val Lys Leu Leu Met Ser Asp
            195                 200                 205

Val Pro Phe Leu Cys His Phe Glu Arg Ala Ile Thr Leu Thr Asp Ser
    210                 215                 220

Ile Pro Tyr Val Glu Ile Ala Asn His Leu Arg Val His Arg Asp Arg
225                 230                 235                 240

Trp Glu Gln Val Leu Gly Thr Leu Ala Tyr Phe Asp Gly Met Asn Phe
                245                 250                 255

Ala Ser Leu Cys Lys Val Pro Ala Leu Leu Ser Val Ala Leu Met Asp
            260                 265                 270

Gln Thr Cys Pro Pro Ser Thr Val Phe Ala Ala Phe Asn His Phe Ala
            275                 280                 285

Gly Pro Lys Glu Ile Cys Val Tyr Pro Phe Asn Arg His Glu Gly Gly
        290                 295                 300

Gln Thr Ala Gln Leu Leu Gln Arg Leu Lys Phe Leu Gln Gln His Trp
305                 310                 315                 320
```

<210> SEQ ID NO 65
<211> LENGTH: 966
<212> TYPE: DNA
<213> ORGANISM: Deinococcus sp.
<220> FEATURE:
<221> NAME/KEY: misc_feature
<223> OTHER INFORMATION: Acetyl xylan esterase no. 2 derived from DRH-46

<400> SEQUENCE: 65

```
atggctttct tgatcttcc tgtgaccgag ctggaacgct acctccctga ccgcaccgaa      60
cgccctgatt ttgatgcctt ctggcaaacc acccttgcag aggcccgcag ctttccactg     120
aatgccacct tcaccccgta tcccaccccc tttgagaccc tggagttctt cgatgtgacc     180
tacaggggtt acggcggcca ccccatcaaa ggctggtttg tgctgccaaa aaaccgttcg     240
gcagaaaaac tgccctgtgt ggtggaatac atcggttacg gtggaggacg ggggattcct     300
gcccactgga tgcactatgc cagtgcaggc tacgcccatc tgatcatgga cacccgtgga     360
cagggcagca gctggcgcac cggagacacc ccagatcctg aaggcacctc tccccacatt     420
cccggtttca tgacccaggg catcgacagg cccgaaacct actattaccg ccgtgtctac     480
accgatgctg tgcgtgctgt ggaagctgca cgcagtcacc cgcaagttga tccagagcgc     540
attgctgtgc tgggtggaag ccaggggga ggcatcacca tcgctgtggc cggactggac     600
cccacggtga tgctgtgct gcccgatgtg cctttcctct gccacttcga gcgtgccgtg     660
accatggtgg acagttaccc ctatcaggaa atcaccaatt acctgaaaat ccaccgccgc     720
aagatcgata cggtgttcca cacctcagt tactttgatg gcatgaacct ggcggcccgt     780
gccaaggccc cctccctgtt ttctgtggcc ctgatggact ccatttgccc gccctccacg     840
gtgtacgcgg ccttcaacca ttacgccggt gagaaaacca tccaggtgtg gcccttcaac     900
caccatgaag ggggagacat ggaccagacc atgctgcgac tggacttcct gcacaaaacc     960
ctgcgt                                                                966
```

<210> SEQ ID NO 66
<211> LENGTH: 322
<212> TYPE: PRT
<213> ORGANISM: Deinococcus sp.
<220> FEATURE:
<221> NAME/KEY: MISC_FEATURE
<223> OTHER INFORMATION: Acetyl xylan esterase no. 2 derived from DRH-46

<400> SEQUENCE: 66

```
Met Ala Phe Phe Asp Leu Pro Val Thr Glu Leu Arg Tyr Leu Pro
1               5                   10                  15

Asp Arg Thr Glu Arg Pro Asp Phe Asp Ala Phe Trp Gln Thr Thr Leu
            20                  25                  30

Ala Glu Ala Arg Ser Phe Pro Leu Asn Ala Thr Phe Thr Pro Tyr Pro
        35                  40                  45

Thr Pro Phe Glu Thr Leu Glu Phe Phe Asp Val Thr Tyr Arg Gly Tyr
    50                  55                  60

Gly Gly His Pro Ile Lys Gly Trp Phe Val Leu Pro Lys Asn Arg Ser
65                  70                  75                  80

Ala Glu Lys Leu Pro Cys Val Val Glu Tyr Ile Gly Tyr Gly Gly Gly
                85                  90                  95

Arg Gly Ile Pro Ala His Trp Met His Tyr Ala Ser Ala Gly Tyr Ala
            100                 105                 110

His Leu Ile Met Asp Thr Arg Gly Gln Gly Ser Ser Trp Arg Thr Gly
        115                 120                 125

Asp Thr Pro Asp Pro Glu Gly Thr Ser Pro His Ile Pro Gly Phe Met
    130                 135                 140

Thr Gln Gly Ile Asp Arg Pro Glu Thr Tyr Tyr Tyr Arg Arg Val Tyr
145                 150                 155                 160

Thr Asp Ala Val Arg Ala Val Glu Ala Ala Arg Ser His Pro Gln Val
                165                 170                 175

Asp Pro Glu Arg Ile Ala Val Leu Gly Gly Ser Gln Gly Gly Gly Ile
            180                 185                 190

Thr Ile Ala Val Ala Gly Leu Asp Pro Thr Val Asn Ala Val Leu Pro
        195                 200                 205

Asp Val Pro Phe Leu Cys His Phe Glu Arg Ala Val Thr Met Val Asp
    210                 215                 220

Ser Tyr Pro Tyr Gln Glu Ile Thr Asn Tyr Leu Lys Ile His Arg Arg
225                 230                 235                 240

Lys Ile Asp Thr Val Phe His Thr Leu Ser Tyr Phe Asp Gly Met Asn
                245                 250                 255

Leu Ala Ala Arg Ala Lys Ala Pro Ser Leu Phe Ser Val Ala Leu Met
            260                 265                 270

Asp Ser Ile Cys Pro Pro Ser Thr Val Tyr Ala Ala Phe Asn His Tyr
    275                 280                 285

Ala Gly Glu Lys Thr Ile Gln Val Trp Pro Phe Asn His His Glu Gly
290                 295                 300

Gly Asp Met Asp Gln Thr Met Leu Arg Leu Asp Phe Leu His Lys Thr
305                 310                 315                 320

Leu Arg
```

<210> SEQ ID NO 67
<211> LENGTH: 1491
<212> TYPE: DNA
<213> ORGANISM: Deinococcus sp.
<220> FEATURE:
<221> NAME/KEY: misc_feature
<223> OTHER INFORMATION: Arabinofuranosidase derived from DRH-46

<400> SEQUENCE: 67
atgaaaaaag cccagattct tcttgacacc cacagaacca tcagcgaaat cagccactac        60
atctttggtg gattcgccga gcacatgggc cgctgcatct acgagggcat ctacgacccc       120
caaagccctc tgagcgacga gaacggcatc cgcagggatg tgatggacgc cctgaaggaa       180

```
ctcaatttcc gttccatccg ttaccccggg ggcaacttcg tgtcagggta caactgggaa    240
gacggaattg gccccaggga aaaccgcccg gtcaagcgcg atctggcctg gaggagcatc    300
gaaaccaacc agtttggcac ggatgaattc atgaaggtct gcgctgaact gaagaccgaa    360
cccatgatgg ccgtgaacct gggcaccgga agtattcagg acgcggccaa catcgtcgaa    420
tactgcaacc tcgaaggcgg cacccattac agcgacctgc gcatcaaaaa cggtgctgaa    480
aaaccttatg gtgtgaagtt ctggtgtctg gggaacgaga tggatggtcc ctggcaggtg    540
ggacagcttt ctgcagagga ttacagtaag aaagccgtgc aggctgcaaa ggccatgaag    600
ctgatcgatc cttccattca actgattgcc tgcggttcct cctccagcct catgaactcc    660
taccccgagt gggaccgcat cgtgctggaa gagacctggg accagatcga ttacctctcg    720
atgcactact atgccagcaa ccgggaggag gacactgcca gttacctcgc ctatacccgt    780
gaattcgaag accacctgca aaccctggcc gccaccatcc gttacgtgaa agccaagaaa    840
cgcagccaga aagacgtgtt cctctcctgg gatgaatgga acgtctggta ccgcgaaatg    900
aacggcaacg gcgagtggca gcaggccccc cacatcctgg aagaggtcta caaccttgaa    960
gatgcgctgg tggtggccca gtggatgaat gtcctcctga gcacagcaa tgtgctgaag   1020 atggcctcca tcgcacaggt tgtcaatgtg atcgctccca tcatgaccag acgggatggc   1080
atgttcaaac agaccatcta ttatccttc ctggtgttca gcaaacacgc ttctggtcag   1140
gcgctcagcc tgcatgtggc ctccgaccag tacgagacga aaaaacacgg cctcgtgaac   1200
ctgctcgatg ccagtgccag ttttgatgcc agccagaacg aagggggctgt ttttctggtc   1260 aaccgcagcc aggatgaaga actcgaaacc gaaatcgtct ttcagggccg tgttcccact   1320
tccgtgcgcg tggcccacca gcttgctggc agcgaccccca agcccacaa ctccttcgag   1380 gagcctgaaa agctcaccct gcagacgatt gaagcagggg agatcaaaga cggcaaactc   1440
gtgctgaagc ttcctgccct gtccttttcg gcagtggtgc tggactacta a            1491
```

<210> SEQ ID NO 68
<211> LENGTH: 496
<212> TYPE: PRT
<213> ORGANISM: Deinococcus sp.
<220> FEATURE:
<221> NAME/KEY: MISC_FEATURE
<223> OTHER INFORMATION: Arabinofuranosidase derived from DRH-46

<400> SEQUENCE: 68

```
Met Lys Lys Ala Gln Ile Leu Leu Asp Thr His Arg Thr Ile Ser Glu
1               5                   10                  15

Ile Ser His Tyr Ile Phe Gly Gly Phe Ala Glu His Met Gly Arg Cys
                20                  25                  30

Ile Tyr Glu Gly Ile Tyr Asp Pro Gln Ser Pro Leu Ser Asp Glu Asn
            35                  40                  45

Gly Ile Arg Arg Asp Val Met Asp Ala Leu Lys Glu Leu Asn Phe Arg
        50                  55                  60

Ser Ile Arg Tyr Pro Gly Gly Asn Phe Val Ser Gly Tyr Asn Trp Glu
65                  70                  75                  80

Asp Gly Ile Gly Pro Arg Glu Asn Arg Pro Val Lys Arg Asp Leu Ala
                85                  90                  95

Trp Arg Ser Ile Glu Thr Asn Gln Phe Gly Thr Asp Glu Phe Met Lys
            100                 105                 110

Val Cys Ala Glu Leu Lys Thr Glu Pro Met Met Ala Val Asn Leu Gly
        115                 120                 125
```

Thr Gly Ser Ile Gln Asp Ala Ala Asn Ile Val Glu Tyr Cys Asn Leu
            130                 135                 140

Glu Gly Gly Thr His Tyr Ser Asp Leu Arg Ile Lys Asn Gly Ala Glu
145                 150                 155                 160

Lys Pro Tyr Gly Val Lys Phe Trp Cys Leu Gly Asn Glu Met Asp Gly
                165                 170                 175

Pro Trp Gln Val Gly Gln Leu Ser Ala Glu Asp Tyr Ser Lys Lys Ala
            180                 185                 190

Val Gln Ala Ala Lys Ala Met Lys Leu Ile Asp Pro Ser Ile Gln Leu
        195                 200                 205

Ile Ala Cys Gly Ser Ser Ser Leu Met Asn Ser Tyr Pro Glu Trp
    210                 215                 220

Asp Arg Ile Val Leu Glu Glu Thr Trp Asp Gln Ile Asp Tyr Leu Ser
225                 230                 235                 240

Met His Tyr Tyr Ala Ser Asn Arg Glu Glu Asp Thr Ala Ser Tyr Leu
                245                 250                 255

Ala Tyr Thr Arg Glu Phe Glu Asp His Leu Gln Thr Leu Ala Ala Thr
            260                 265                 270

Ile Arg Tyr Val Lys Ala Lys Arg Ser Gln Lys Asp Val Phe Leu
        275                 280                 285

Ser Trp Asp Glu Trp Asn Val Trp Tyr Arg Glu Met Asn Gly Asn Gly
    290                 295                 300

Glu Trp Gln Gln Ala Pro His Ile Leu Glu Glu Val Tyr Asn Leu Glu
305                 310                 315                 320

Asp Ala Leu Val Val Ala Gln Trp Met Asn Val Leu Leu Lys His Ser
                325                 330                 335

Asn Val Leu Lys Met Ala Ser Ile Ala Gln Val Val Asn Val Ile Ala
            340                 345                 350

Pro Ile Met Thr Arg Arg Asp Gly Met Phe Lys Gln Thr Ile Tyr Tyr
        355                 360                 365

Pro Phe Leu Val Phe Ser Lys His Ala Ser Gly Gln Ala Leu Ser Leu
    370                 375                 380

His Val Ala Ser Asp Gln Tyr Glu Thr Lys Lys His Gly Leu Val Asn
385                 390                 395                 400

Leu Leu Asp Ala Ser Ala Ser Phe Asp Ala Ser Gln Asn Glu Gly Ala
                405                 410                 415

Val Phe Leu Val Asn Arg Ser Gln Asp Glu Glu Leu Glu Thr Glu Ile
            420                 425                 430

Val Phe Gln Gly Arg Val Pro Thr Ser Val Arg Val Ala His Gln Leu
        435                 440                 445

Ala Gly Ser Asp Pro Lys Ala His Asn Ser Phe Glu Glu Pro Glu Lys
    450                 455                 460

Leu Thr Leu Gln Thr Ile Glu Ala Gly Glu Ile Lys Asp Gly Lys Leu
465                 470                 475                 480

Val Leu Lys Leu Pro Ala Leu Ser Phe Ser Ala Val Val Leu Asp Tyr
                485                 490                 495

<210> SEQ ID NO 69
<211> LENGTH: 2418
<212> TYPE: DNA
<213> ORGANISM: Deinococcus sp.
<220> FEATURE:
<221> NAME/KEY: misc_feature
<223> OTHER INFORMATION: Endocellulase derived from DRH-46

<400> SEQUENCE: 69

```
gtgtgcctgg agtgcttttt cagggtcctc caggcgttga aggccacacc tgtcctcctg      60
aggggccctt gttgcacctt caggaggttc aatcccatga tgccaacccc ttcaaaagtc     120
ctgcctgcca gtgtgctgct gatggtctcc ctgctgacca gctcctgtaa tctgttccag     180
ccacctgcac ccaactgcac ccccaagacc accggagcca ccgttccagc aggggactac     240
gatcctgcag caagtgaaaa agccttcccg gacctgctga ccacagctgc ccgcaaaccc     300
tcacaggccg agccctgca actcgtgcag caagactgca tggttacgct ggcagacagc     360
agcggcaaac ccatccagct tcgtggcatg agcacccacg gcctgcaatg gtacccggaa     420
atcgtcaatg acaatgcctt caaggccctg gccaacgact gggggtccaa tgtcttccgt     480
ctggccctgt acgtcggaga agggggatac gccaccaaac ccgaactgaa acaaaaagtc     540
attgaaggca ttgattttgc cattgccaac gacatgtacg tgattgtgga ctggcacgtg     600
catgcccctg cgacccccaa cgcagacgtg tacaccaatg ccaaaccgct ggagttcttc     660
aagtccatcg cccagaagta ccccaacaac aagcacatca tttacgaggt cgccaacgaa     720
cccaaccccg gtcaggctcc aggggtcagc aatgacgctg aaggctggaa gaagatcaag     780
tcctacgcag agcccatcat caagatgctg cgggacctgg gcaacaagaa catcgtgatt     840
gtcgggaccc ccaactggag ccagcgcccg gatctggctg ccgacaaccc catcaaagac     900
agtgccaccc tttacactgt gcacttctac accggcaccc acatgccctc caccaacctg     960
gcagaccggg gcaacgtgat gagcaatgcc cgttacgccc tggagcacgg tgtgggcgtg    1020
ttctccaccg agtgggggt cagcgaggcc agcggaaaca acggacccttt cctcaaagaa    1080
gccgacgtct ggctgcagtt cctcaacaaa cacaacatca gctgggtcaa ctggtctctc    1140
accaacaagg ccgagacttc tgcagccttc ctgccgttcc ccaaccagac cagccttgat    1200
cccggggcag acaggctgtg accccagc gagctcaccc tgtccgggga atacgttcgg      1260
gcgcgcatca aagggaccaa ataccagccc attgaccgca ctgccttcac tgaggtggcc    1320
ttcaattttg acaacgacac cacccagggt tttgccctga cccggacag tggagtcaaa     1380
gggatcacgg tcagcgcaga gaacaagatg ctgaaactca gcccccctgag cggaagcaat    1440
gacgtttcag caggcaactt ctgggccaac gcgcgcttct ctgcagatgg aaccagccag    1500
catcccaacc tgcggggtgc gaagagcatg agcatggatg tgtatgtgcc tgcccccacc    1560
aaagtctccg tggccgctgt gccccagagc agcaaggatg gctggaccaa ccctgcgcgt    1620
gctgtgatcg tgaacgcaga ccagtttgtg aaacaggcag atggcaagta caaagccacc    1680
gtcaccctgt ctgacgaaga tgctcccaac ctgaaactca ttgccgaaga tgagaccgac    1740
aatgtgctct cgaaccctgat cctcttcatt ggcaccgaga gccaggaagc caatgacacc    1800
gtgtggatcg acaacatcac cttctctggg gaccgtgtgg tggtccctgt ggaacatgat    1860
cccatcggca ccgccaccct gccctccaca tttgaagaca gcaccgcca gggctgggac      1920
tgggccggag aatctggcgt taaaactgca ctgaagatcc agaccgccaa tgcgtcaaaa    1980
gccctgtcct gggatgtcat ctaccctgat gtgaaacctg ccgatggctg ggcctctgct    2040
ccccgtctgg tgctggagaa atccaacctt cccgcggtg ccaacaagta cctcgctttc     2100
gacctgtacc tgaagccaga tcgggccagc aaagggaccc tctccgtcaa cctggctttt    2160
ggtcctccga gctggggta ctgggcacag gccagcgaga cgtcgacat cgacttgacc      2220
acgctggggg ccatgaccaa aactgccgat ggactgtacc gcattgcagg gaaattcgat    2280
ctggacaaga tcaatgacaa caaggtgatt gctgcagaca ctgttctggg caaaatcacc    2340
```

```
ctggtggtcg ccgatgtgaa cagcgattac gccgggaaga tgttcctgga caacgtgcgt    2400
ttcaccaacg aaccctaa                                                  2418
```

<210> SEQ ID NO 70
<211> LENGTH: 805
<212> TYPE: PRT
<213> ORGANISM: Deinococcus sp.
<220> FEATURE:
<221> NAME/KEY: MISC_FEATURE
<223> OTHER INFORMATION: Endocellulase derived from DRH-46

<400> SEQUENCE: 70

Val Cys Leu Glu Cys Phe Phe Arg Val Leu Gln Ala Leu Lys Ala Thr
1               5                   10                  15

Pro Val Leu Leu Arg Gly Pro Cys Cys Thr Phe Arg Arg Phe Asn Pro
            20                  25                  30

Met Met Pro Thr Pro Ser Lys Val Leu Pro Ala Ser Val Leu Leu Met
        35                  40                  45

Val Ser Leu Leu Thr Ser Ser Cys Asn Leu Phe Gln Pro Pro Ala Pro
    50                  55                  60

Asn Cys Thr Pro Lys Thr Thr Gly Ala Thr Val Pro Ala Gly Asp Tyr
65                  70                  75                  80

Asp Pro Ala Ala Ser Glu Lys Ala Phe Pro Asp Leu Leu Thr Thr Ala
                85                  90                  95

Ala Arg Lys Pro Ser Gln Ala Gly Ala Leu Gln Leu Val Gln Gln Asp
            100                 105                 110

Cys Met Val Thr Leu Ala Asp Ser Ser Gly Lys Pro Ile Gln Leu Arg
        115                 120                 125

Gly Met Ser Thr His Gly Leu Gln Trp Tyr Pro Glu Ile Val Asn Asp
    130                 135                 140

Asn Ala Phe Lys Ala Leu Ala Asn Asp Trp Gly Ser Asn Val Phe Arg
145                 150                 155                 160

Leu Ala Leu Tyr Val Gly Glu Gly Gly Tyr Ala Thr Lys Pro Glu Leu
                165                 170                 175

Lys Gln Lys Val Ile Glu Gly Ile Asp Phe Ala Ile Ala Asn Asp Met
            180                 185                 190

Tyr Val Ile Val Asp Trp His Val His Ala Pro Gly Asp Pro Asn Ala
        195                 200                 205

Asp Val Tyr Thr Asn Ala Lys Pro Leu Glu Phe Phe Lys Ser Ile Ala
    210                 215                 220

Gln Lys Tyr Pro Asn Asn Lys His Ile Ile Tyr Glu Val Ala Asn Glu
225                 230                 235                 240

Pro Asn Pro Gly Gln Ala Pro Gly Val Ser Asn Asp Ala Glu Gly Trp
                245                 250                 255

Lys Lys Ile Lys Ser Tyr Ala Glu Pro Ile Ile Lys Met Leu Arg Asp
            260                 265                 270

Leu Gly Asn Lys Asn Ile Val Ile Val Gly Thr Pro Asn Trp Ser Gln
        275                 280                 285

Arg Pro Asp Leu Ala Ala Asp Asn Pro Ile Lys Asp Ser Ala Thr Leu
    290                 295                 300

Tyr Thr Val His Phe Tyr Thr Gly Thr His Met Pro Ser Thr Asn Leu
305                 310                 315                 320

Ala Asp Arg Gly Asn Val Met Ser Asn Ala Arg Tyr Ala Leu Glu His
                325                 330                 335

```
Gly Val Gly Val Phe Ser Thr Glu Trp Val Ser Glu Ala Ser Gly
            340                 345                 350

Asn Asn Gly Pro Phe Leu Lys Glu Ala Asp Val Trp Leu Gln Phe Leu
            355                 360                 365

Asn Lys His Asn Ile Ser Trp Val Asn Trp Ser Leu Thr Asn Lys Ala
370                 375                 380

Glu Thr Ser Ala Ala Phe Leu Pro Phe Pro Asn Gln Thr Ser Leu Asp
385                 390                 395                 400

Pro Gly Ala Asp Arg Leu Trp Thr Pro Ser Glu Leu Thr Leu Ser Gly
                405                 410                 415

Glu Tyr Val Arg Ala Arg Ile Lys Gly Thr Lys Tyr Gln Pro Ile Asp
            420                 425                 430

Arg Thr Ala Phe Thr Glu Val Ala Phe Asn Phe Asp Asn Asp Thr Thr
            435                 440                 445

Gln Gly Phe Ala Leu Asn Pro Asp Ser Gly Val Lys Gly Ile Thr Val
            450                 455                 460

Ser Ala Glu Asn Lys Met Leu Lys Leu Ser Pro Leu Ser Gly Ser Asn
465                 470                 475                 480

Asp Val Ser Ala Gly Asn Phe Trp Ala Asn Ala Arg Phe Ser Ala Asp
                485                 490                 495

Gly Thr Ser Gln His Pro Asn Leu Arg Gly Ala Lys Ser Met Ser Met
            500                 505                 510

Asp Val Tyr Val Pro Ala Pro Thr Lys Val Ser Val Ala Ala Val Pro
            515                 520                 525

Gln Ser Ser Lys Asp Gly Trp Thr Asn Pro Ala Arg Ala Val Ile Val
530                 535                 540

Asn Ala Asp Gln Phe Val Lys Gln Ala Asp Gly Lys Tyr Lys Ala Thr
545                 550                 555                 560

Val Thr Leu Ser Asp Glu Asp Ala Pro Asn Leu Lys Leu Ile Ala Glu
                565                 570                 575

Asp Glu Thr Asp Asn Val Leu Ser Asn Leu Ile Leu Phe Ile Gly Thr
            580                 585                 590

Glu Ser Gln Glu Ala Asn Asp Thr Val Trp Ile Asp Asn Ile Thr Phe
            595                 600                 605

Ser Gly Asp Arg Val Val Val Pro Val Glu His Asp Pro Ile Gly Thr
610                 615                 620

Ala Thr Leu Pro Ser Thr Phe Glu Asp Ser Thr Arg Gln Gly Trp Asp
625                 630                 635                 640

Trp Ala Gly Glu Ser Gly Val Lys Thr Ala Leu Lys Ile Gln Thr Ala
                645                 650                 655

Asn Ala Ser Lys Ala Leu Ser Trp Asp Val Ile Tyr Pro Asp Val Lys
            660                 665                 670

Pro Ala Asp Gly Trp Ala Ser Ala Pro Arg Leu Val Leu Glu Lys Ser
            675                 680                 685

Asn Leu Thr Arg Gly Ala Asn Lys Tyr Leu Ala Phe Asp Leu Tyr Leu
690                 695                 700

Lys Pro Asp Arg Ala Ser Lys Gly Thr Leu Ser Val Asn Leu Ala Phe
705                 710                 715                 720

Gly Pro Pro Ser Leu Gly Tyr Trp Ala Gln Ala Ser Glu Asn Val Asp
                725                 730                 735

Ile Asp Leu Thr Thr Leu Gly Ala Met Thr Lys Thr Ala Asp Gly Leu
            740                 745                 750

Tyr Arg Ile Ala Gly Lys Phe Asp Leu Asp Lys Ile Asn Asp Asn Lys
```

-continued

```
        755                 760                 765

Val Ile Ala Ala Asp Thr Val Leu Gly Lys Ile Thr Leu Val Val Ala
    770                 775                 780

Asp Val Asn Ser Asp Tyr Ala Gly Lys Met Phe Leu Asp Asn Val Arg
785                 790                 795                 800

Phe Thr Asn Glu Pro
                805
```

<210> SEQ ID NO 71
<211> LENGTH: 1329
<212> TYPE: DNA
<213> ORGANISM: Deinococcus sp.
<220> FEATURE:
<221> NAME/KEY: misc_feature
<223> OTHER INFORMATION: Alpha-Glucuronidase derived from DRH-46

<400> SEQUENCE: 71

```
atgtcccgca accccgtgat cacctttatt ggcgctggca gcaccgtgtt tgccaagaac      60
ctcctcaccg acatcctcag ctttcccgag ctctcaggtg cagaaatccg actgtacgac     120
atcaacgagg agcgcctgaa gaccagtgag gtggtggccc agaggctcgc ccagaccctc     180
ggcattcagc ccaccattgt ctccaccctt gaccgggacc gtgctttaga cggggcagat     240
tacgccatca acatgatcca ggtgggtggg taccagcctg ccaccgtcac cgacttcgag     300
attcccaaaa aatacggcct gagacagacc atcgcagaca ccctcgggat gggtggcatc     360
atgcgtgccc tgcgcaccat tccggtgttc ctggacatgg cccgtgacat ggaacgcctg     420
tgccccgatg tgacccacct gaactacgtc aaccccatgg tcatgaactg ctgggccctc     480
aacaaagcca caaagatcaa aaccatcgga ctgtgccaca gcgtgcagca cacggcccag     540
gaactggcca atgatctggg cattcctgtg gaggagatca actatgtggc cgcaggcatc     600
aaccacatgg cgttctattt gaagtttgag cgggatggag aagacctcta cccccgcctg     660
caagacattg cccgcacagg aaaaatgccc gactggaaca gggtgcgcta cgaaatgctg     720
acccgtcttg gttacttcgt caccgagtcc agcgaacact tctccgagta cgtgccttac     780
ttcatcaaag agaagcaccc cgaactcatc gaccgattca acattcccct ggatgagtac     840
ccccgccgct gtgtgaacca gatcgcaggc tgggaagacc tcagaaagca gctggaagac     900
cccagccacc ccatggaagt gcaccgcagt gtggaatacg ggtccctgat catccacagc     960
ctggaaaccg gaattccccg ggtggtctac ggcaacgtgc aaaacgacca cctcatcgaa    1020
aacctgccgc tggactgttg tgtggaagtt cccgtgctgg tggacaagaa tggcctgcaa    1080
cccacccgca ttggcaagat tcctccacaa ctcgccgccc tgatgcagac caacatcaac    1140
gtgcagtccc tgaccgtgga agccgccctg accggcaaga aagagcacat ctatcacgcc    1200
gccatgctgg acccccacac cagcaccgaa ctcaccctgg acgaaatctg gtccctggtg    1260
gatgacctcc tggaagccca caggggctgg attcccgatc acttcctcaa agagcctgtg    1320
ctgtcctaa                                                            1329
```

<210> SEQ ID NO 72
<211> LENGTH: 442
<212> TYPE: PRT
<213> ORGANISM: Deinococcus sp.
<220> FEATURE:
<221> NAME/KEY: MISC_FEATURE
<223> OTHER INFORMATION: Alpha-Glucuronidase derived from DRH-46

<400> SEQUENCE: 72
```
Met Ser Arg Asn Pro Val Ile Thr Phe Ile Gly Ala Gly Ser Thr Val
 1               5                  10                  15

Phe Ala Lys Asn Leu Leu Thr Asp Ile Leu Ser Phe Pro Glu Leu Ser
                20                  25                  30

Gly Ala Glu Ile Arg Leu Tyr Asp Ile Asn Glu Glu Arg Leu Lys Thr
                35                  40                  45

Ser Glu Val Val Ala Gln Arg Leu Ala Gln Thr Leu Gly Ile Gln Pro
     50                  55                  60

Thr Ile Val Ser Thr Leu Asp Arg Asp Arg Ala Leu Asp Gly Ala Asp
 65                  70                  75                  80

Tyr Ala Ile Asn Met Ile Gln Val Gly Gly Tyr Gln Pro Ala Thr Val
                85                  90                  95

Thr Asp Phe Glu Ile Pro Lys Lys Tyr Gly Leu Arg Gln Thr Ile Ala
                100                 105                 110

Asp Thr Leu Gly Met Gly Gly Ile Met Arg Ala Leu Arg Thr Ile Pro
                115                 120                 125

Val Phe Leu Asp Met Ala Arg Asp Met Glu Arg Leu Cys Pro Asp Val
                130                 135                 140

Thr His Leu Asn Tyr Val Asn Pro Met Val Met Asn Cys Trp Ala Leu
145                 150                 155                 160

Asn Lys Ala Thr Lys Ile Lys Thr Ile Gly Leu Cys His Ser Val Gln
                165                 170                 175

His Thr Ala Gln Glu Leu Ala Asn Asp Leu Gly Ile Pro Val Glu Glu
                180                 185                 190

Ile Asn Tyr Val Ala Ala Gly Ile Asn His Met Ala Phe Tyr Leu Lys
                195                 200                 205

Phe Glu Arg Asp Gly Glu Asp Leu Tyr Pro Arg Leu Gln Asp Ile Ala
                210                 215                 220

Arg Thr Gly Lys Met Pro Asp Trp Asn Arg Val Arg Tyr Glu Met Leu
225                 230                 235                 240

Thr Arg Leu Gly Tyr Phe Val Thr Glu Ser Ser Glu His Phe Ser Glu
                245                 250                 255

Tyr Val Pro Tyr Phe Ile Lys Glu Lys His Pro Glu Leu Ile Asp Arg
                260                 265                 270

Phe Asn Ile Pro Leu Asp Glu Tyr Pro Arg Arg Cys Val Asn Gln Ile
                275                 280                 285

Ala Gly Trp Glu Asp Leu Arg Lys Gln Leu Glu Asp Pro Ser His Pro
                290                 295                 300

Met Glu Val His Arg Ser Val Glu Tyr Gly Ser Leu Ile Ile His Ser
305                 310                 315                 320

Leu Glu Thr Gly Ile Pro Arg Val Val Tyr Gly Asn Val Gln Asn Asp
                325                 330                 335

His Leu Ile Glu Asn Leu Pro Leu Asp Cys Cys Val Glu Val Pro Val
                340                 345                 350

Leu Val Asp Lys Asn Gly Leu Gln Pro Thr Arg Ile Gly Lys Ile Pro
                355                 360                 365

Pro Gln Leu Ala Ala Leu Met Gln Thr Asn Ile Asn Val Gln Ser Leu
                370                 375                 380

Thr Val Glu Ala Ala Leu Thr Gly Lys Lys Glu His Ile Tyr His Ala
385                 390                 395                 400

Ala Met Leu Asp Pro His Thr Ser Thr Glu Leu Thr Leu Asp Glu Ile
                405                 410                 415

Trp Ser Leu Val Asp Asp Leu Leu Glu Ala His Arg Gly Trp Ile Pro
```

```
                      420                 425                 430
Asp His Phe Leu Lys Glu Pro Val Leu Ser
            435                 440

<210> SEQ ID NO 73
<211> LENGTH: 25
<212> TYPE: PRT
<213> ORGANISM: Deinococcus sp.

<400> SEQUENCE: 73

Met Lys Arg Ser Lys Thr His Leu Ala Val Val Gly Leu Gly Leu Leu
1               5                   10                  15

Ala Leu Leu Gly Ser Cys Gly Gln Ser
            20                  25

<210> SEQ ID NO 74
<211> LENGTH: 19
<212> TYPE: PRT
<213> ORGANISM: Deinococcus sp.
<220> FEATURE:
<221> NAME/KEY: MISC_FEATURE
<222> LOCATION: (1)..(19)
<223> OTHER INFORMATION: a mature form of alpha-amylase of SEQ ID NO:
      3 without signal peptide

<400> SEQUENCE: 74

Met Arg Arg Leu Pro Leu Leu Ala Ala Leu Leu Ala Ser Leu Ala Gly
1               5                   10                  15

Ala Gln Ala

<210> SEQ ID NO 75
<211> LENGTH: 28
<212> TYPE: PRT
<213> ORGANISM: Deinococcus sp.
<220> FEATURE:
<221> NAME/KEY: MISC_FEATURE
<222> LOCATION: (1)..(28)
<223> OTHER INFORMATION: a mature form of alpha-amylase of SEQ ID NO:
      62 without signal peptide

<400> SEQUENCE: 75

Met Lys Arg Phe Gln Lys Val Gly Arg Ser Gly Ala Leu Ala Val Leu
1               5                   10                  15

Thr Leu Ala Leu Ser Ala Cys Gly Val Leu Lys Ala
            20                  25
```